United States Patent
Fox et al.

(10) Patent No.: US 9,783,814 B2
(45) Date of Patent: Oct. 10, 2017

(54) GENETIC REDUCTION OF MALE FERTILITY IN PLANTS

(71) Applicant: PIONEER HI BRED INTERNATIONAL INC, Johnston, IA (US)

(72) Inventors: Tim Fox, Des Moines, IA (US); Dale F Loussaert, Clive, IA (US); Jeffrey Schussler, Marion, IA (US); Juan Pablo San Martin Toloza, Cedar Rapids, IA (US); Bo Shen, Johnston, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 362 days.

(21) Appl. No.: 14/384,854

(22) PCT Filed: Mar. 12, 2013

(86) PCT No.: PCT/US2013/030559
§ 371 (c)(1),
(2) Date: Sep. 12, 2014

(87) PCT Pub. No.: WO2013/138358
PCT Pub. Date: Sep. 19, 2013

(65) Prior Publication Data
US 2015/0167013 A1  Jun. 18, 2015

Related U.S. Application Data

(60) Provisional application No. 61/610,252, filed on Mar. 13, 2012.

(51) Int. Cl.
*A01H 1/02* (2006.01)
*C12N 15/82* (2006.01)
*C07K 14/415* (2006.01)

(52) U.S. Cl.
CPC .......... *C12N 15/8231* (2013.01); *A01H 1/02* (2013.01); *C07K 14/415* (2013.01); *C12N 15/8245* (2013.01); *C12N 15/8247* (2013.01); *C12N 15/8251* (2013.01); *C12N 15/8259* (2013.01); *C12N 15/8261* (2013.01); *C12N 15/8273* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| 5,478,369 | A | * | 12/1995 | Albertsen | A01H 1/02 |
| | | | | | 47/DIG. 1 |
| 5,689,049 | A | | 11/1997 | Cigan et al. | |
| 5,750,867 | A | | 5/1998 | Williams et al. | |
| 6,399,856 | B1 | | 6/2002 | Cigan et al. | |
| 7,517,975 | B2 | | 4/2009 | Albertsen et al. | |
| 7,563,947 | B2 | | 7/2009 | Ito et al. | |
| 7,592,508 | B1 | | 9/2009 | Chen et al. | |
| 7,612,251 | B2 | | 11/2009 | Albertsen et al. | |
| 7,612,255 | B2 | | 11/2009 | Gressel et al. | |
| 7,667,093 | B2 | | 2/2010 | Maliga et al. | |
| 7,705,215 | B1 | | 4/2010 | Adams et al. | |
| 7,723,576 | B2 | | 5/2010 | Hawkes et al. | |
| 7,728,194 | B2 | | 6/2010 | Kim et al. | |
| 7,741,541 | B2 | | 6/2010 | Bisht et al. | |
| 7,759,543 | B2 | | 7/2010 | Albertsen et al. | |
| 7,759,546 | B2 | | 7/2010 | Scott et al. | |
| 7,875,764 | B2 | | 1/2011 | Wu et al. | |
| 7,888,550 | B2 | | 2/2011 | Albertsen et al. | |
| 7,888,551 | B2 | | 2/2011 | Albertsen et al. | |
| 7,893,317 | B2 | | 2/2011 | Albertsen et al. | |
| 7,893,318 | B2 | | 2/2011 | Albertsen et al. | |
| 7,910,802 | B2 | | 3/2011 | Albertsen et al. | |
| 7,915,478 | B2 | | 3/2011 | Albertsen et al. | |
| 7,919,676 | B2 | | 4/2011 | Albertsen et al. | |
| 7,951,997 | B2 | | 5/2011 | Huang et al. | |
| 7,973,152 | B2 | | 7/2011 | Albertsen et al. | |
| 7,982,109 | B2 | | 7/2011 | Komori et al. | |
| 8,013,218 | B2 | | 9/2011 | Wu et al. | |
| 8,030,548 | B2 | | 10/2011 | Sodhi et al. | |
| 8,058,505 | B2 | | 11/2011 | Horiuchi et al. | |
| 8,158,850 | B2 | | 4/2012 | Feng et al. | |
| 8,178,750 | B2 | | 5/2012 | Albertsen et al. | |
| 8,293,970 | B2 | | 10/2012 | Albertsen et al. | |
| 8,334,430 | B2 | | 12/2012 | Allen et al. | |

(Continued)

FOREIGN PATENT DOCUMENTS

EP    0465024 A1    1/1992
WO    92/13957 A1   8/1992

(Continued)

OTHER PUBLICATIONS

Albertsen et al. Maize Genetics Cooperative Newsletter 67: 51-52 (1993).*
von Heijne, G. Nucleic Acids Research 14(11): 4683-4690 (1986).*
Albertsen et al. Maize Genetics Cooperative Newsletter 62: 70 (1988).*
Albertsen et al. Maize Genetics Cooperative Newsletter 66: 49 (1992).*
Albertsen et al. Maize Genetics Cooperative Newsletter 64: 52 (1990).*
Sep. 16, 2014 International Preliminary Report on Patentability PCT/US2013/030406.
Uniprot Database Accession Number: Q9ATN1; "Aquaporin NIP3-1" Jun. 1, 2001.
Uniprot Database Accession No. Q9SBW9; "Anther specific protein (LTP-like protein)" May 1, 2000.Lauga et al XP002697369.

(Continued)

*Primary Examiner* — David T Fox
(74) *Attorney, Agent, or Firm* — Pioneer HI-Bred Intl., Inc.

(57) ABSTRACT

Genetic male sterile plants are provided in which complementing constructs result in suppression of a parental phenotype in the progeny. Methods to generate and maintain such plants and methods of use of said plants, are provided, including use of parental plants to produce sterile plants for hybrid seed production.

10 Claims, 21 Drawing Sheets

(56) References Cited

U.S. PATENT DOCUMENTS

| | | |
|---|---|---|
| 8,361,929 B2 | 1/2013 | Higashitani et al. |
| 8,378,171 B2 | 2/2013 | Conner et al. |
| 8,399,255 B2 | 3/2013 | Rudrabhatla et al. |
| 8,476,493 B2 | 7/2013 | Rottmann et al. |
| 8,604,281 B2 | 12/2013 | Werner et al. |
| 8,614,367 B2 | 12/2013 | Wu et al. |
| 8,624,086 B2 | 1/2014 | Parish et al. |
| 8,642,836 B2 | 2/2014 | Hawkes et al. |
| 8,648,228 B2 | 2/2014 | Albertsen et al. |
| 8,710,301 B2 | 4/2014 | Sawant et al. |
| 8,748,698 B2 | 6/2014 | Tanaka |
| 8,754,292 B2 | 6/2014 | Albertsen et al. |
| 8,847,014 B2 | 9/2014 | Albertsen et al. |
| 2007/0277269 A1 | 11/2007 | Alexandrov et al. |
| 2009/0271897 A1 | 10/2009 | Gibson et al. |
| 2011/0271399 A1 | 11/2011 | Cerney et al. |
| 2013/0205439 A1 | 8/2013 | Rooney et al. |
| 2014/0259208 A1 | 9/2014 | Dirks et al. |
| 2014/0289895 A1 | 9/2014 | Cigan et al. |

FOREIGN PATENT DOCUMENTS

| | | |
|---|---|---|
| WO | WO9218625 A1 | 10/1992 |
| WO | WO9302197 A1 | 2/1993 |
| WO | WO9704116 A1 | 2/1997 |
| WO | WO0100834 A1 | 1/2001 |
| WO | WO0164926 A2 | 9/2001 |
| WO | WO2008112970 A2 | 9/2008 |
| WO | WO2009124282 A1 | 10/2009 |
| WO | WO2011090752 A1 | 7/2011 |
| WO | WO2013138289 A3 | 9/2013 |
| WO | WO2013138354 A1 | 9/2013 |
| WO | WO2013138358 A1 | 9/2013 |
| WO | WO2013138363 A2 | 9/2013 |

OTHER PUBLICATIONS

EPO Exam Report, Issued Sep. 25, 2013, Application #PCT/US2013-030406.

Chen, et al.; "CaMF2, an anther-specific lipid transfer protein (LTP) gene, affects pollen development in Capsicum annuum L.," Plant Science; (2011) 181:439-448.

Gillikin, et al.; "A Defective Signal Peptide Tethers the floury-2 Zein to the Endoplasmic Reticulum Membrane," Plant Physiol; (1997) 114:345-352.

Kaul; "Male Sterility in Plants," Higher Plants; (1988) 11:278-287.

Kim, et al.; "A Defective Signal Peptide in a 19-kD a-Zein Protein Causes the Unfolded Protein Response and an Opague Endosperm Phenotype in the Maize De-B30 Mutant," Plant Physiology; (2004) 134:380-387.

Vitale, et al.; "The Endoplasmic Reticulum—Gateway of the Secretory Pathway," The Plant Cell; (1999) 11:615-628.

Chaudhury, "Nuclear Genes Controlling Male Fertility," The Plant Cell; (1993) 5:1277-1283.

Chaubal, et al.; "Two male-sterile mutants of Zea mays (Poaceae) with an extra cell division in the anther wall," American Journal of Botany; (2000) 87(8):1193-1201.

Duvick, "Cytoplasmic pollen sterility in corn," Science; (1965) 13:1-56.

Kaser-Schneider, "Physiological and agronomic traits of cytoplasmic male sterility in maize (Zea mays, L.) and its molecular discrimination," XP002698812, (2002) 7-89.

Tian, "Characterization of a male sterile related gene BcMF15 from Brassica campestris ssp. chinensis" Mol Biol Rep (2007) 36:307-314.

Jun. 28, 2013 ISR and Written Opinion 4597-PCT-PCT/US2013/030554.

Sep. 2, 2013 ISR and Written Opinion 4239-PCT-PCT/US2013/030567.

Sep. 2, 2013 ISR and Written Opinion 4264-PCT-PCT/US2013-030559.

Jan. 10, 2013 ISR and Written Opinion 4168-PCT-PCT/US2013/030406.

Chinwuba et al, "Interaction of detasseling, sterility, and spacing on yields of maize hybrids" Crop Science (1961) 1:4:279-280.

Sanford et al, "Influence of male-sterility on nitrogen utilization in corn, Zea mays L" Agronomy Journal, American Society of Agronomy, Inc. US (1965) 57:6:580-583.

Seyedin et al, "Auxin levels in tassels of maize Zea-mays cultivars differing in tolerance to high populations densities" Canadian Journal of Plant Science (1980) 60:4:1427-1430.

Criswell, et al.; "Effect of Cytoplasmic Male Sterility on Accumulation and Translocation of C-labelled Assimilates in Corn," Crop Science; (1974) 14:252-254.

Skibbe, et al. "Male Sterility in Maize" Maydica 50 (2005):367-376.

Arnevik, et al, US Statutory Invention Registration USH2258H1, Jun. 7, 2011.

Gomes, et al.; "Aquaporins are multifunctional water and solute transporters highly divergent in living organisms," Biochem. Biophys. Acta; (2009) 1788:1213-1228.

EMBL Accession No. AC215675, (Sep. 2013).

EMBL Accession No. AC202971, (Sep. 2014).

* cited by examiner

```
                                                   1                                                                        50
(SEQ ID NO: 108)Arabidopsis1  ------------------------MVSLKSLAAA----------------ILVAMFLATG--PTVLAQ-
(SEQ ID NO: 109)Brassica      ------------------------MEFLKSFTT----------------ILFVMFLAMSALETVPMVRAQ-
(SEQ ID NO: 110)Ricinus1      ------------------MAALRSLIALSSQAALLLLVLALAMQTHL-VHSQT---
(SEQ ID NO: 111)Ricinus2      ------------------MAAPKFLQAALLLLLIAVAVQTQE-AQSQT----
(SEQ ID NO: 112)Populus       ------------------MAALKSLSSPVAVLLLLTALAVQTQL-AHSQQ--
       (SEQ ID NO: 113)Silene ------------------MANNMKSAT----FCKATWAIFIVALAILVQLKGSEAQAG-
(SEQ ID NO: 114)Lilium1       ------------------MASMKSLAT----AILVVLLIAALS---REGRSQ-
(SEQ ID NO: 115)Lilium2       ------------------MASMKSLAT----AILVVLLLAALS---REGRSQ-
(SEQ ID NO: 116)Lilium3       ------------------MAAVKFLVC----SVLIVVLATQS----EIGLAQ-
(SEQ ID NO: 117)Oryza1        ------------------MAASKGNAA----AAACALVLVLLAVGA-----EAQGG
       (SEQ ID NO: 10 )Zea1   ------------------MALEAATAP----RALLAACLVLLVLGGGTGPSSVLRGA
(SEQ ID NO: 14 )ms44dom       ------------------MALEAATAP----RALLAACLVLLVLGGSTGPSSVLRGA
(SEQ ID NO: 118)Sorghum       ------------MAALEAATTSTVP----RALLAACLVLLVLGG--GPSSSVQAQ
(SEQ ID NO: 119)Hordeum       ------------------MAPSTVP----RALLAVSLVLLVAGG-LGPAAEAQRP
(SEQ ID NO: 120)Brachypodium  ------------------MAPPRMS----KGIQVMVAVAEAQQR---------
       (SEQ ID NO: 121)Zea2   MTATTTTAAGGAXVQPRG-----LPAALSLLLLVLAAGLGGGAEAQQ-
(SEQ ID NO: 122)Oryza2        ------------------MAVT----RTALIVVLVAGAMTMTMRGAEAQQP-
(SEQ ID NO: 123)Antirrhinum   ------------------MAAMKSIVP------LVMLTVLVAQSQL-ITQSEAQ-
(SEQ ID NO: 124)Capsicum      ------------------MADVKSS----VVSLFLLGLLVVLQSGV-IECQP-Q-
(SEQ ID NO: 125)Solanum       ------------------MASVKSSSSSSSSFISLLLLILLVIVLQSQV-IECQPQQ-
       (SEQ ID NO: 126)Arabidopsis2 ------MAASSKYSSMSFMKVAMMVALVLVVAATV-VDGQS--
(SEQ ID NO: 127)Glycine       ------------------MAASPKS----LLSLILLLLVVAHGTQI-AMAQSS--
(SEQ ID NO: 128)Medicago      ------------------MAGPVSM----RCQVALVLVLVVALGTKM-EMGEAQT-
       (SEQ ID NO: 129)Vitis  ------------MAAARSLFSLRFRATLLLVVALVARTQM-AWSQPS--
```

Figure 2A

```
                                                                                        100
(SEQ ID NO: 108)Arabidopsis1  -------QCRDELSNVQVCAPLLLPGA----VNPAANSNCCAALQATNKDCL
(SEQ ID NO: 109)Brassica      -------QCLDNLSNMQVCAPLVLPGA----VNPAPNSNCCIALQATNKDCI
(SEQ ID NO: 110)Ricinus1      -------CQNQLNSLNVCAPLVLPGA----ANTSPNAECCNALESVQMDCI
(SEQ ID NO: 111)Ricinus2      -------CPSQLNSLNVCAPFVVPGA----TNTNPNAECCSALQSVEHDCL
(SEQ ID NO: 112)Populus       -------CTSQLNNLNVCAPFVVPGA----ANTNPNAECCNALEAVQHDCL
(SEQ ID NO: 113)Silene        -------GCASQLGNLNVCAPYVVPGA----VNTNPSQECCAALSGVNHDCM
(SEQ ID NO: 114)Lilium1       -------NCSAAIGELMTCGPYVLPG-----NNGAPSEQCCSALRAVNHGCL
(SEQ ID NO: 115)Lilium2       -------NCSAAIGELMTCGPYVLPG-----NNGAPSEQCCSALRAVNHGCL
(SEQ ID NO: 116)Lilium3       -------NCSAAIGGLMSCGPYVLPG-----NQLTPSTQCCSAIQAVNHGCL
(SEQ ID NO: 117)Oryza1        G------GGECVPQLNRLLACRAYAVPG-----AGDPSAECCSALSSISQGCA
       (SEQ ID NO: 10)Zea1    GAQAGGQCIPQLNRLLACRAYLVPG-------APDSADCCSALSAVSHECA
(SEQ ID NO: 14)ms44dom         GTQAGGQCLPQLNGLLACRAYLVPG-------APDSADCCSALSAVSHECA
(SEQ ID NO: 118)Sorghum       G--GGGLCLPQLNGLLACRAYLVPG-------APDSADCCSALSAVSHECA
(SEQ ID NO: 119)Hordeum       G------ECVPQLNRLLACRAYLVPG-------AADPSAECCGALSSISRDCA
(SEQ ID NO: 120)Brachypodium  -------ECVPQLNRLLACRAYLAAPGAA--AAAPSAECCGALAGISRECA
       (SEQ ID NO: 121)Zea2   -------TCAGQLRGLAPCLRYSVPPLPGQVPPAPGPECCSALGAVSRDCA
       (SEQ ID NO: 122)Oryza2 -------SCAAQLTQLAPCARVGVAPAPGQPLPAPPAECCSALGAVSHDCA
(SEQ ID NO: 123)Antirrhinum   -------TCSASLANLNACAPFVVLG----AATTPSSDCCTALQSVDHECL
(SEQ ID NO: 124)Capsicum      -------ICNPSLTSLNVCAPFVVPG----AP-SASAECCTALQSINHGCM
(SEQ ID NO: 125)Solanum       -------SCTASLTGLNVCAPFLVPG----SP-TASTECCNAVQSINHDCM
(SEQ ID NO: 126)Arabidopsis2  -------CNAQLSTLNVCGEFVVPGA----DRTNPSAECCNALEAVPNECL
(SEQ ID NO: 127)Glycine       -------TCTTQLSELNVCAPFVVPG----VNTNPSSRCCNALQAVDRDCL
(SEQ ID NO: 128)Medicago      -------TCPTQLSNLNVCAPFVVPGS---PNTNPSPDCCTALQSTNPDCL
(SEQ ID NO: 129)Vitis         -------ACSTQLNNLSVCAPFVVPGA---PDSTPSADCCTALQTIDDACM
```

Figure 2B

```
                                                                                                    141
(SEQ ID NO: 108)Arabidopsis1    CNRLRAATTLTSLCNLPSFDCGKMIHRLKPFLLDFYKLFHQ
(SEQ ID NO: 109)Brassica        CNALRAATTFTTTCNLPSLDCGIT-----------------
(SEQ ID NO: 110)Ricinus1        CNTLRIAGRLPSLCNLSPINCGN------------------
(SEQ ID NO: 111)Ricinus2        CNTLRIAARLPSQCNLAPVNCGNW-----------------
(SEQ ID NO: 112)Populus         CSTLQISSRLPSQCNLPPLTCGN------------------
      (SEQ ID NO: 113)Silene    CNTLRVASQLPSSCNLAALNCGN------------------
(SEQ ID NO: 114)Lilium1         CETINIISSLPDHCSLPAVNCAA------------------
(SEQ ID NO: 115)Lilium2         CETINIISSLPDHCSLPAVNCAS------------------
(SEQ ID NO: 116)Lilium3         CETINIISSLPGHCSLPPVSCGTA-----------------
(SEQ ID NO: 117)Oryza1          CSAISIMNSLPSRCHLSQINCSA------------------
      (SEQ ID NO: 10 )Zea1      CSTMGIINSLPGRCHLAQANCSA------------------
(SEQ ID NO: 14 )ms44dom         CSTMGIINSLPGRCHLAQANCSA------------------
(SEQ ID NO: 118)Sorghum         CSTMGIINSLPGRCNLAQVNCSA------------------
(SEQ ID NO: 119)Hordeum         CSTMGIINSLPSRCNIGQVNCSA------------------
(SEQ ID NO: 120)Brachypodium    CSTMAIINSIPSRCGVSQVNCTASSTSTCA-----------
      (SEQ ID NO: 121)Zea2      CGTFSIINSLPAKCGLPPVSCQ-------------------
      (SEQ ID NO: 122)Oryza2    CGTLDIINSLPAKCGLPRVTCQ-------------------
(SEQ ID NO: 123)Antirrhinum     CNTLRIASRVPAQCNLPPLSCGGKLSWTNC-----------
(SEQ ID NO: 124)Capsicum        CDTMRIAAQIPAQCNLPPLSCAAN-----------------
(SEQ ID NO: 125)Solanum         CNTMRIAAQIPAQCNLPPLSCSAN-----------------
(SEQ ID NO: 126)Arabidopsis2    CNTFRIASRLPSRCNIPTLSCS-------------------
(SEQ ID NO: 127)Glycine         CSTIRIASQLPSQCQTPSLGCSAN-----------------
(SEQ ID NO: 128)Medicago        CNTLRIASQLTSQCNLPSFGCVLN-----------------
      (SEQ ID NO: 129)Vitis     CSTLRIASRLPSHCNLTPVTCDVNA----------------
```

Figure 2C

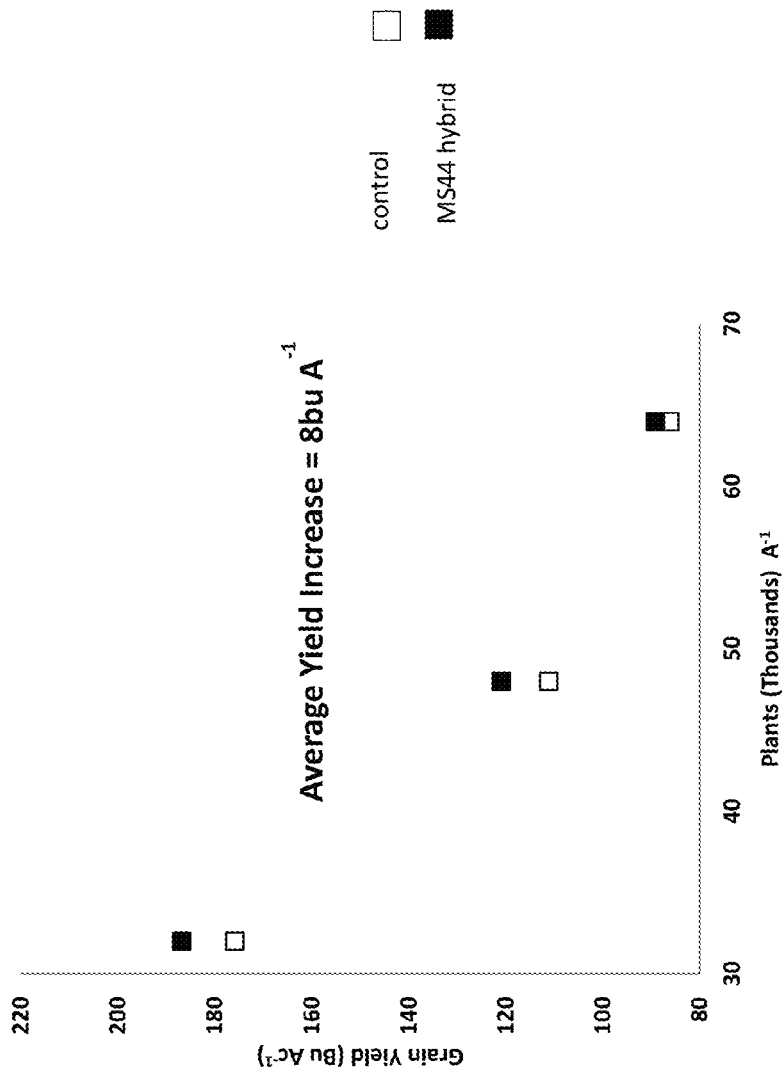

FIGURE 15B

```
                                                                             63
(SEQ ID NO: 14)MS44dom         MA-LEEAAT----APRALLAACLVLLLVLGGSTGPSS-VLRGAGTQAGGQ---CLPQLNRLLACRAY
(SEQ ID NO:153)MS44-2629       MA-LEEAAT----APRALLAACLVLLLVLGGSTGPSS-VLRGAGVQAGGQ---CLPQLNRLLACRAY
(SEQ ID NO: 10)ms44            MA-LEEAAT----APRALLAACLVLLLVLGGSTGPSS-VLRGAGAQAGGQ---CLPQLNRLLACRAY
(SEQ ID NO:118)SorghumMS44     MAALEAATTSTVPRALLAACLVLLLVLG--GPSSSV----QAQGGGGL-CLPQLNGLLACRAY
(SEQ ID NO:119)BarleyMS44      MAPS----T---VPRALLAVSLVLIVAGG-LGP-------AAEAQRPGE--CVPQLNRLLACRAY
(SEQ ID NO:130)WheatMs44       MAPS----T---FPRALLAVSLVLLVVGG-LGP-------AAEAQPPGR--CVPQLNRLLACRAY
(SEQ ID NO:117)RiceMs44        MAASK-------GNAAAAACALVLVLLAVGA---------EAQGGGGECVPQLNRLLACRAY 110
(SEQ ID NO: 14)MS44dom         LVPGAPDPSADCCSALSAVSHECACSTMGIINSLPGRCHLAQANCSA
(SEQ ID NO:153)MS44-2629       LVPGAPDPSADCCSALSAVSHECACSTMGIINSLPGRCHLAQANCSA
(SEQ ID NO: 10)ms44            LVPGAPDPSADCCSALSAVSHECACSTMGIINSLPGRCHLAQANCSA
(SEQ ID NO:118)SorghumMS44     LVPGAPDPSADCCSALSAVSHECACSTMGIINSLPGRCNLAQVNCSA
(SEQ ID NO:119)BarleyMS44      LVPGAADPSAECCGALSSISRDCACSTMGIINSLPSRCNIGQVNCSA
(SEQ ID NO:130)WheatMs44       LVPGAADPSADCCSALSSISRDCACSTMGIINSLPSRCNIGQVNCSA
(SEQ ID NO:117)RiceMs44        AVPGAGDPSAECCSALSSISQGCACSAISIMNSLPSRCHLSQINCSA
```

FIGURE 16

GENETIC REDUCTION OF MALE FERTILITY IN PLANTS

CROSS REFERENCE

This application is a U.S. National Stage application under 35 USC §371 of international application PCT/US13/30559 filed Mar. 12, 2013, which claims priority to and the benefit of US provisional patent application 61/610,252 filed Mar. 13, 2012, the disclosures of which are hereby incorporated by reference.

FIELD

The disclosure relates generally to the field of molecular biology, specifically the modulation of plant fertility to improve plant stress tolerance.

BACKGROUND

The domestication of many plants has correlated with dramatic increases in yield. Most phenotypic variation occurring in natural populations is continuous and is affected by multiple gene influences. The identification of specific genes responsible for the dramatic differences in yield in domesticated plants has become an important focus of agricultural research.

Plants allocate photosynthates, mineral nutrients, and other growth components among various plant tissues during the developmental life cycle. In maize, for example, ear and tassel are specific female and male inflorescence structures that share certain developmental processes and compete with each other for required nutrients. Tassel apical dominance may limit ear growth and grain yield potential in the maize plants-methods and compositions to improve grain yield are disclosed herein.

SUMMARY

A method for increasing yield or maintaining yield stability in a plant, the method includes reducing male fertility and thereby increasing nutrient allocation to a female reproductive tissue during concurrent male and female tissue development. In an embodiment, the male fertility is reduced in the plant by altering the expression or activity of a genetic male fertility gene. In an embodiment, the plant is grown under abiotic stress. In an embodiment, the nutrient limited is nitrogen. In an embodiment, the plant with reduced male fertility has as an agronomic parameter selected from the group consisting of increased SPAD value, increased silk emergence, increased ear length, increased ear width, increased seed number per ear, increased seed weight per ear, and seed with increased embryo size. In an embodiment, the plant is grown under a drought stress. In an embodiment, the drought tolerance of the plant is improved by male sterility.

A method for increasing yield or maintaining yield stability in a maize plant, the method includes reducing male fertility and thereby increasing nutrient allocation to a female reproductive tissue during concurrent male and female tissue development. In an embodiment, the plant includes a mutation in a nuclear gene that results in dominant genetic male sterility.

In an embodiment, the male fertility of the plants disclosed herein is reduced by the expression of a polynucleotide encoding a polypeptide of SEQ ID NOS: 14 or 153. In an embodiment, the polynucleotide is selected from the group consisting of SEQ ID NOS: 13, 15, and 152.

In an embodiment, the male fertility is reduced by expressing a tassel suppressing nucleic acid under a regulatory element selected from the group consisting of SEQ ID NOS: 64-106, 134, 137, 142, 143, 144, 149 and 150.

In an embodiment, the male fertility is reduced by expressing a nucleic acid suppressing the expression of a polynucleotide encoding an amino acid sequence of SEQ ID NO: 156 under a regulatory element selected from the group consisting of SEQ ID NOS: 64-106, 134, 137, 142, 143, 144, 149 and 150.

In an embodiment, the male fertility is reduced by the expression of a nucleic acid encoding a polypeptide having a mutation corresponding to amino acid position 37 of SEQ ID NO: 14, wherein the polypeptide is selected from the group consisting of SEQ ID NOS: 14, 108-130. In an embodiment, the mutation results in an improper processing of the signal peptide.

In an embodiment, the plant exhibiting reduced male fertility is a maize non-transgenic plant. In an embodiment, the female tissue development is ear development in maize.

In an embodiment, the mutation resulting in reduced male fertility is engineered in an endogenous fertility gene of the plant.

A method of increasing maize yield in a field having a first population of maize plants, the method includes growing a population of maize plants in the field, wherein the maize plants exhibit dominant male sterility due to the presence of a polypeptide comprising the amino acid sequence of SEQ ID NO: 14 or a homolog thereof and wherein the field further comprises a second population of maize plants that produce an effective amount of pollen to fertilize the first population of maize plants in the field, thereby increasing the yield compared to a control field that does not contain the first population of plants. In an embodiment, the first population of plants includes about 50% to about 90% of the maize plants in the field. In an embodiment, the first population of plants includes about 80% of the maize plants in the field. In an embodiment, the first population of plants includes about 75% of the maize plants in the field. In an embodiment, the first population of plants includes about 85% of the maize plants in the field. In an embodiment, the first population of plants includes about 70% of the maize plants in the field. In an embodiment, the first population of plants includes about 95% of the maize plants in the field. In an embodiment, the resulting progeny is fertile.

A population of maize plants grown in a field, wherein the population of maize plants includes a first sub-population that has reduced male fertility and a second sub-population that exhibits normal male fertility, wherein the population of maize plants results in increased grain yield compared to a control population of plants. In an embodiment, seeds are produced from the maize plants, wherein the seeds produce plants that are fertile.

An isolated nucleic acid molecule having a polynucleotide which initiates transcription in a plant cell and comprises a sequence selected from the group consisting of:
  a. promoter region of SEQ ID NO: 13 and 62, SEQ ID NOS: 64-106, 134, 137, 142, 143, 144, 149 and 150;
  b. at least 100 contiguous nucleotides of SEQ ID NOS: 13, 62, 64-106, 134, 137, 142, 143, 144, 149 and 150; and
  c. a nucleotide sequence having at least 70% sequence identity to the full length of SEQ ID NOS: 13, 62, 64-106, 134, 137, 142, 143, 144, 149 and 150.

An expression cassette has a polynucleotide that initiates transcription as disclosed herein and is operably linked to a polynucleotide of interest. In an embodiment, a vector includes the expression cassette described herein. In an embodiment, a plant cell has stably incorporated into its genome the expression cassette described herein. In an embodiment, the plant cell is from a monocot. In an embodiment, monocot is maize, barley, wheat, oat, rye, sorghum or rice.

In an embodiment, a plant having stably incorporated into its genome the expression cassettes described herein are included. In an embodiment, the plant is a monocot. In an embodiment, the plant is maize, barley, wheat, oat, rye, sorghum, or rice.

A transgenic seed of the plant described herein are disclosed. In an embodiment, a polynucleotide that encodes a gene product that confers pathogen or insect resistance are disclosed.

In an embodiment, the plant further includes a polynucleotide that encodes a polypeptide involved in nutrient uptake, nitrogen use efficiency, drought tolerance, root strength, root lodging resistance, soil pest management, corn root worm resistance, carbohydrate metabolism, protein metabolism, fatty acid metabolism or phytohormone biosynthesis.

An unit of maize seeds that includes a proportion of male sterile seeds that are transgenic and a proportion of male fertile seeds that are transgenic, wherein the proportion of the male sterile transgenic seeds ranges from about 50% to about 95% to the total maize seeds in the unit. In an embodiment, an unit is a bag of maize seeds.

A seed blend of maize seeds that includes a proportion of male sterile seeds that are transgenic and a proportion of male fertile seeds that are transgenic, wherein the proportion of the male sterile transgenic seeds ranges from about 50% to about 95% to the total maize seeds in the unit. In an embodiment, the seed blend is in a bag of maize seeds. In an embodiment, the male sterile seeds are in a separate bag. In an embodiment, the male sterile seeds are blended in the same bag with the male fertile seeds.

In an embodiment, the male fertility gene encodes a protein of SEQ ID NO: 10. In an embodiment, the male fertility gene includes a nucleotide sequence of SEQ ID NO: 13. In an embodiment, the male fertility gene encodes a polypeptide of SEQ ID NO: 14.

In an embodiment, the reduction of male fertility or rendering the plant male sterile is effected by a single nucleotide substitution from G to an A at position 118 relative to the first Met codon of SEQ ID NO: 13, resulting in an amino acid change at amino acid 37, from Alanine to Threonine in the predicted protein. In an embodiment, the reduction of male fertility or rendering the plant male sterile is effected by a single nucleotide substitution from C to a T at position 119 relative to the first Met codon of SEQ ID NO: 152, resulting in an amino acid change at amino acid 37, from Alanine to Valine in the predicted protein. In an embodiment, the dominant male fertility gene is operably linked to promoter selected from the group consisting of: inducible promoter, tissue preferred promoter, temporally regulated promoter or an element thereof. For example, the promoter preferentially drives expression in male reproductive tissue.

In an embodiment, the male fertility is reduced in the female plant (e.g., a female inbred line) of a breeding pair.

In an embodiment, a plant or a cell or a seed or a progeny thereof that includes the reduced male fertility sequence encoding amino acid sequence 43-101 of SEQ ID NO: 10 in its genome and wherein the expression of the male fertility gene confers the dominant male sterility trait.

An isolated nucleic acid molecule includes a polynucleotide capable of initiating transcription in a plant cell and includes a sequence selected from the group consisting of: SEQ ID NO: 15; at least 100 contiguous nucleotides of SEQ ID NO: 15 and a sequence having at least 70% sequence identity to the full length of SEQ ID NO: 15. In an embodiment, an expression cassette or a vector includes SEQ ID NO: 15 disclosed herein operably linked to a polynucleotide of interest.

Suitable plants for the materials and methods disclosed herein include e.g., corn, sorghum, canola, wheat, barley, rye, triticale, rice, sugar cane, turfgrass, pearl millet, soybeans, cotton.

In an embodiment, a plant with reduced fertility or any other trait disclosed herein optionally exhibits one or more polynucleotides conferring the following phenotype or trait of interest: nutrient uptake, nitrogen use efficiency, drought tolerance, root strength, root lodging resistance, soil pest management, corn root worm resistance, herbicide tolerance, disease resistance, insect resistance, carbohydrate metabolism, protein metabolism, fatty acid metabolism or phytohormone biosynthesis.

A method of increasing yield or maintaining yield stability in plants includes reducing male reproductive tissue development by expressing a transgene under the control of a male reproductive tissue preferred promoter; and increasing nutrient allocation to female reproductive tissue during concurrent male and female tissue development.

In an embodiment, the male reproductive tissue is tassel. In an embodiment, the male reproductive tissue development is decreased by the expression of a gene operably linked to a promoter comprising at least 100 contiguous nucleotides of a sequence selected from the list SEQ ID NO: 64-106. Subsets of the promoter sequences disclosed herein e.g., SEQ ID NOS: 64-70; 70-75; 75-80; 85-90; 90-95; 100-106 are also suitable for driving tissue-preferred expression of the polynucleotides of interest disclosed herein.

In an embodiment, a plant or a plant cell or a seed that transgenically expresses a polynucleotide of interest (e.g., Ms44 having the dominant male sterility mutation) under the control of a tassel-preferred promoter disclosed herein exhibit improved agronomic parameters such as increased nutrient allocation to ears during reproductive development.

An isolated nucleic acid molecule comprising a polynucleotide which initiates transcription in a plant cell and comprises a sequence selected from the group consisting of:
  a sequence selected from SEQ ID NO: 64-106;
  at least 100 contiguous nucleotides of a sequence selected from SEQ ID NO: 64-106 and
  a sequence having at least 70% to about 95% sequence identity to the full length of a sequence selected from SEQ ID NO: 64-106 or to sub-promoter regions thereof.

In an embodiment, a plant or a plant cell or a seed that transgenically expresses a polynucleotide of interest (e.g., RNAi suppression sequence targeting a polynucleotide involved in tassel development) under the control of a tassel-preferred promoter disclosed herein exhibits increased agronomic parameters such as improved nutrient allocation to ears during reproductive development.

A method of increasing yield or maintaining yield stability in plants includes reducing male fertility and increasing nutrient allocation to female reproductive tissue during concurrent male and female tissue development. In an embodiment, the male fertility is reduced in a plant by altering expression of a genetic male fertility gene. In an embodiment, the plant is grown under stress. In an embodiment, the plant is grown under nutrient limiting conditions, e.g., reduced available nitrogen.

In an embodiment, the plants with reduced male fertility and wherein the nutrient is allocated more to female reproductive tissue during concurrent male and female tissue development exhibits one or more of the following agronomically relevant parameters: increased SPAD value; increased silk emergence; increased ear length; increased ear width; increased seed number per ear; increased seed weight per ear and increased embryo size.

In an embodiment, the plants with reduced male fertility and wherein the nutrient is allocated more to female reproductive tissue during concurrent male and female tissue are grown under drought stress. In an embodiment, drought tolerance of the plants is improved by male sterility.

An isolated nucleic acid molecule comprising a polynucleotide which initiates transcription in a plant cell in a tissue preferred manner and includes a sequence from:
  SEQ ID NOS: 13, 62 and 64-106;
    at least 100 contiguous nucleotides of SEQ ID NOS: 13, 62 and 64-106 and
    a sequence having at least 70% sequence identity to the full length of SEQ ID NOS: 13, 62 and 64-106.

In an embodiment, a method of increasing yield stability in plants under stress includes expressing an element that affect male fertility under a tassel preferred promoter disclosed herein and thereby reducing the competition for nutrients during the reproductive development phase of the plant and wherein the yield is increased.

A method of increasing yield or maintaining yield stability in plants under nitrogen limiting conditions and/or normal nitrogen conditions includes reducing male reproductive tissue development and increasing nutrient allocation to female reproductive tissue during concurrent male and female tissue development.

In an embodiment, the male reproductive tissue is tassel and the male reproductive tissue development is decreased by reducing the expression of a NIP3-1 or a NIP3-1-like protein. In an embodiment, NIP3-1 protein has an amino acid sequence of SEQ ID NO: 156. The male reproductive tissue development is decreased by increasing the expression of SEQ ID NO: 63.

In an embodiment, the male reproductive tissue development is decreased by affecting the function of a gene involved in tassel formation, e.g., tassel-less gene.

In an embodiment, the male reproductive tissue development is decreased in a plant transformed with an expression cassette that targets the suppression of a gene encoding amino acid sequence of SEQ ID NO: 156 or a sequence that is at least 70% or 80% or 85% or 90% or 95% identical to SEQ ID NO: 156. Plants with native mutations in the Tls1 allele are also disclosed herein.

In an embodiment, a promoter preferentially drives expression of a gene of interest in male reproductive tissue. In an embodiment, the promoter is a tissue-specific promoter, a constitutive promoter or an inducible promoter. In an embodiment, the tissue-preferred promoter is a tassel specific promoter.

An isolated nucleic acid molecule comprising a polynucleotide that includes a sequence selected from the group consisting of: SEQ ID NO: 63; at least 100 contiguous nucleotides of SEQ ID NO: 63 and a sequence having at least 70% sequence identity to the full length of SEQ ID NO: 63. An isolated nucleic acid molecule comprising a polynucleotide that encodes the TLS1 protein comprising an amino acid sequence of SEQ ID NO: 156 or a sequence that is at least 70% or 80% or 85% or 90% or 95% identical to SEQ ID NO: 156.

A method for producing male sterile hybrid seeds includes transforming a female inbred line that is heterozygous for dominant male sterility with a gene construct that includes an element that suppresses the dominant male sterility phenotype, a second element that disrupts pollen function, and optionally a selectable marker, wherein expressing the construct in the inbred line renders the line male fertile. In an embodiment, this method further includes self-pollinating these male fertile plants and producing homozygous progeny that are dominant male sterile. The method further includes identifying those seeds having the homozygous dominant male sterility genotypes the female inbred line; optionally increasing female inbred line by crossing with the transgenic maintainer line, resulting in 100% homozygous dominant male sterile seed without the construct; and crossing progeny from the dominant male sterile seed with a male parent to produce hybrids that are heterozygous for dominant male sterility and display the dominant male sterile phenotype.

In an embodiment, the dominant male sterility phenotype is conferred by a polynucleotide sequence that includes at least 100 consecutive nucleotides of SEQ ID NO: 15 and further comprises a codon at positions 109 through 111, which encodes a Threonine instead of an Alanine at position 37 of SEQ ID NO: 14 (the amino acid sequence encoded by SEQ ID NO: 15).

In an embodiment, the suppression element includes a promoter inverted repeat sequence specific to SEQ ID NO: 15. In an embodiment, the inverted repeat sequence includes a functional fragment of at least 100 consecutive nucleotides of the SEQ ID NO: 15. In an embodiment, the suppression element is a RNAi construct designed to suppress the expression of the dominant Ms44 gene in the male sterile female inbred line. In an embodiment, the suppression element is a genetic suppressor that acts in a dominant fashion to suppress the dominant phenotype of Ms44 mutation in a plant. Optionally, if the endogenous normal ms44 is also suppressed by the suppression element, the construct may include an element that restores the normal function of the ms44 gene, e.g., ms44 gene under the control of its own promoter or a heterologous promoter.

In an embodiment, a plant or a plant cell or a seed or a progeny of the plant derived from the methods disclosed herein is disclosed.

In an embodiment, a method for producing hybrid seeds includes expressing in a female inbred a dominant male sterility gene operably linked to a heterologous promoter amenable to inverted-repeat inactivation; pollinating the male sterile plant with pollen from a male fertile plant containing an inverted repeat specific to the heterologous promoter. In an embodiment, the pollen comprises the inverted repeat specific to the heterologous promoter with inverted repeat inactivation specificity. In an embodiment, the dominant male sterility gene is linked to a rice 5126 promoter.

In an embodiment, the dominant male sterility gene used in the context of hybrid seed production is any gene that acts in a dominant manner to achieve male sterility and optionally is amenable to suppression to maintain the male sterile female inbred line. In an embodiment, the dominant male sterility gene is selected from the group comprising: barnase, DAM methylase, MS41 and MS42.

BRIEF DESCRIPTION OF THE DRAWINGS

FIG. 2—Alignment of MS44 related sequences (FIG. 2 A-C). The identical residues are in bold and all similar residues are underlined and italicized.

4A—A female inbred line heterozygous for dominant male sterility is transformed with a gene construct that comprises an element that suppresses the dominant male sterility, a second element that disrupts pollen function, and optionally a selectable marker. Expression of this construct in the inbred line renders the plants male fertile.

4B—The plants are self-pollinated to produce seed.

4C and 4D—Seeds or progeny plants are genotyped to identify those which are homozygous for dominant male sterility.

4E—The female inbred line can be increased by crossing it with the transgenic maintainer line, resulting in 100% homozygous dominant male sterile seed.

4F—Dominant male-sterile plants are pollinated by a second inbred to produce hybrids that are heterozygous for dominant male sterility and exhibit the dominant male sterile phenotype.

Figure 5A:
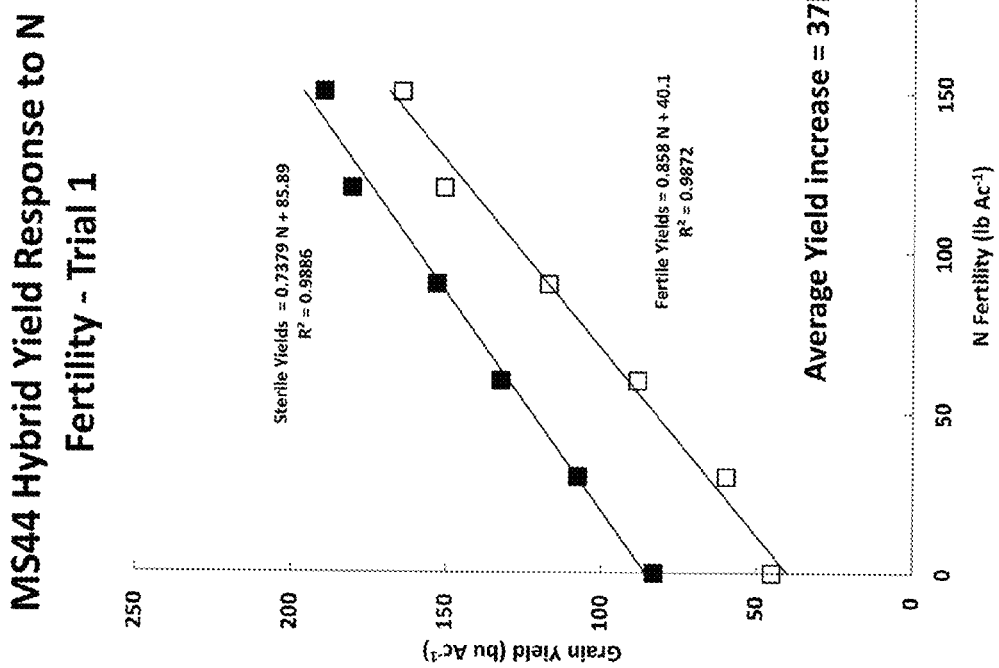
Figure 5B:
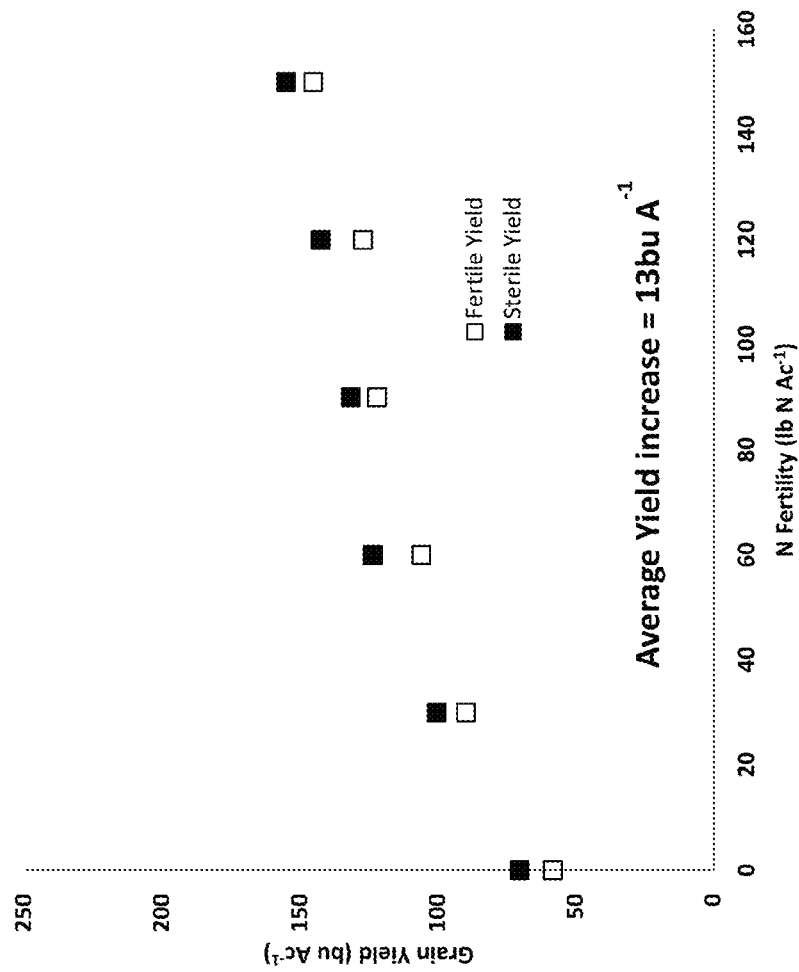

FIG. 5-FIG. 5A shows MS44 hybrid yield response to N fertility—Trial 1. FIG. 5B shows MS44 hybrid yield response to N fertility—Trial 2.

Figure 6:
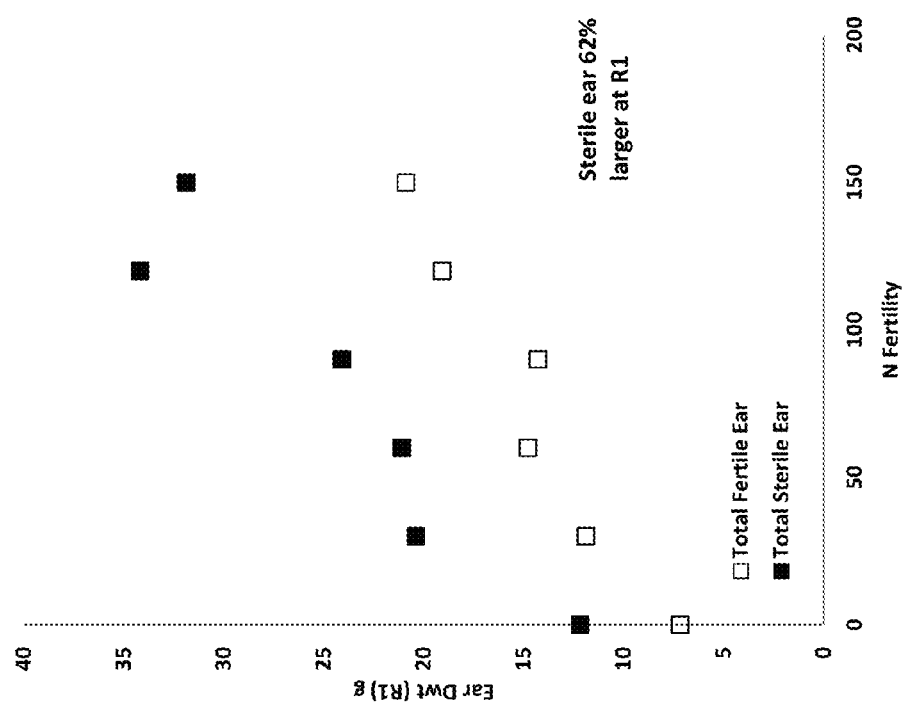

FIG. 6 shows MS44 hybrid ear dry weight (R1) as compared to wild-type.

Figure 7A:
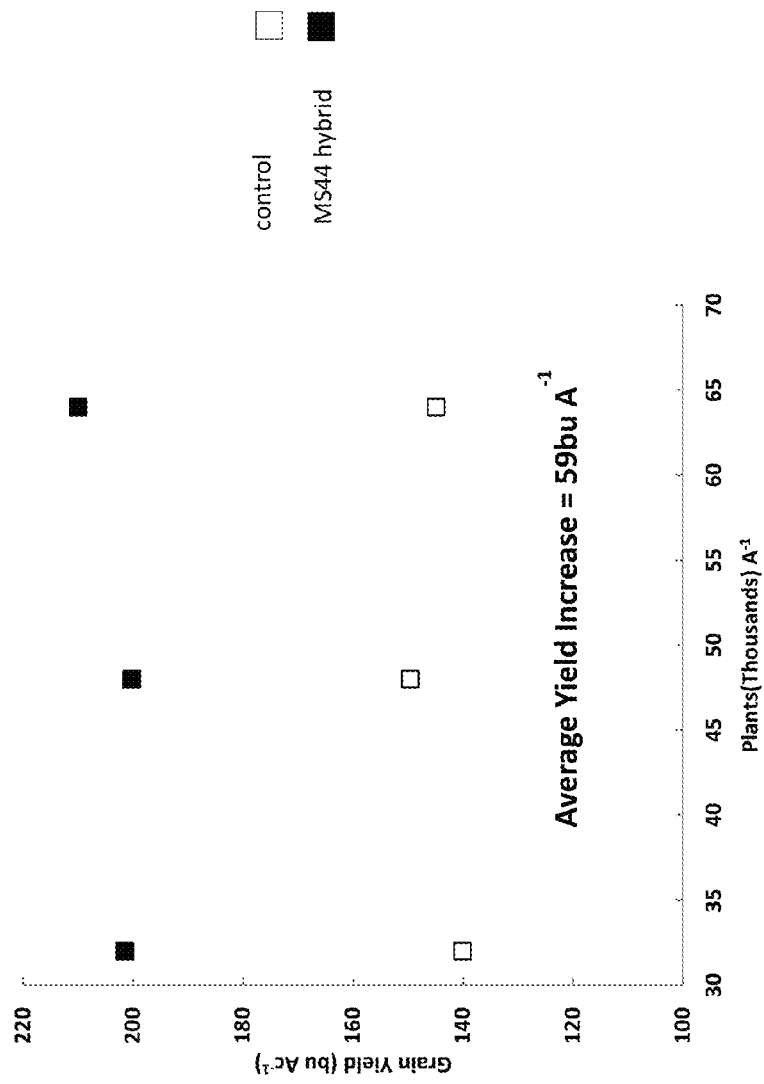

FIG. 7—FIG. 7A shows MS44 hybrid yield response to plant population—Trial 1. FIG. 7B shows MS44 hybrid yield response to plant population—Trial 2.

Figure 8:
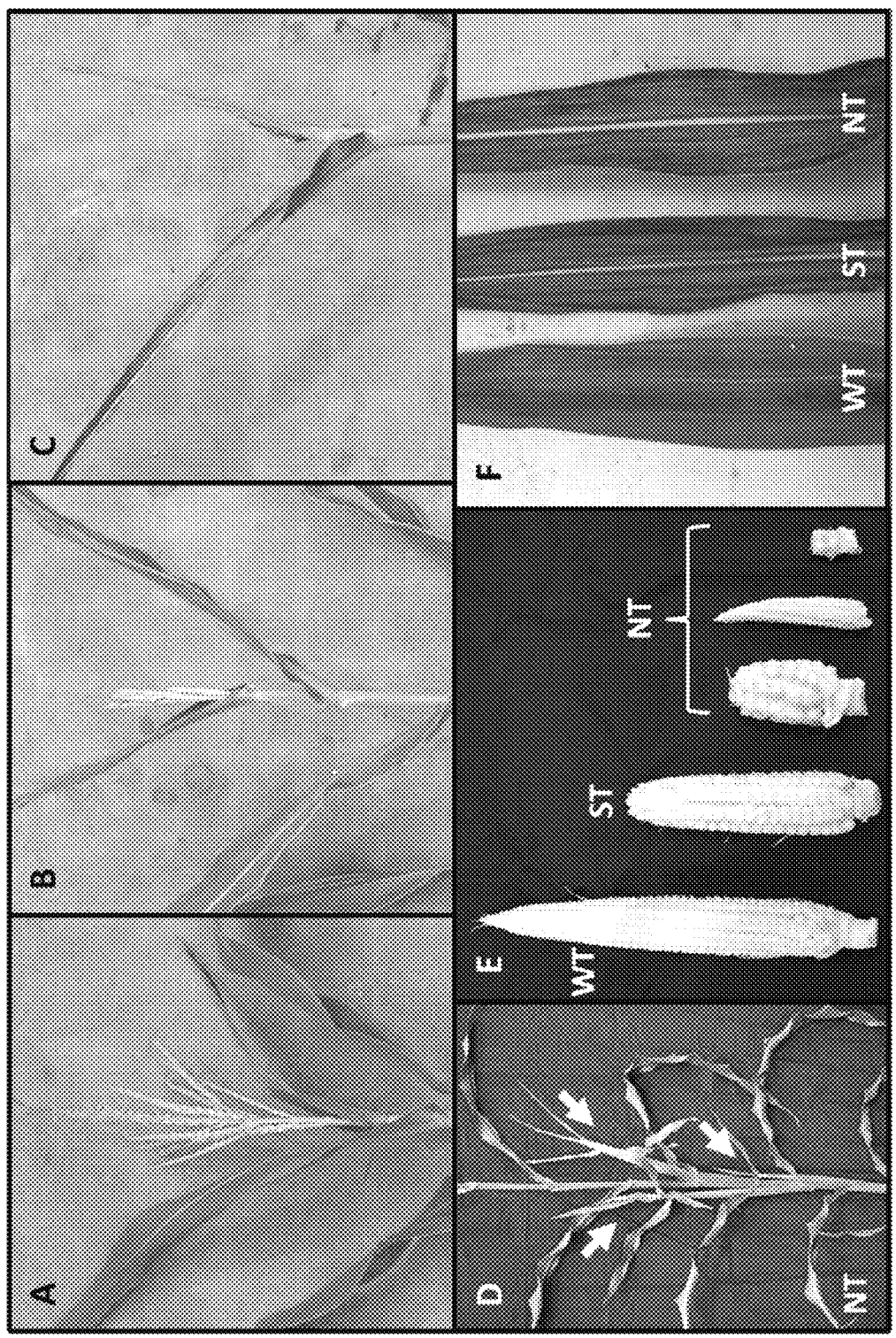

FIG. 8 shows the tls1 mutant phenotype. A) Tassel from a wild type plant. B) Homozygous tls1 plant with a small tassel phenotype. C) Homozygous tls1 plant with no tassel. D) Plants with most severe phenotypes tend to have multiple ears with long husks and no silk emergence (arrows). E) Range of ear phenotypes. F) Range of leaf phenotypes. WT=homozygous wild type plant; ST=homozygous tls1 plant with a small tassel; NT=homozygous tls1 plant with no tassel.

Figure 9:
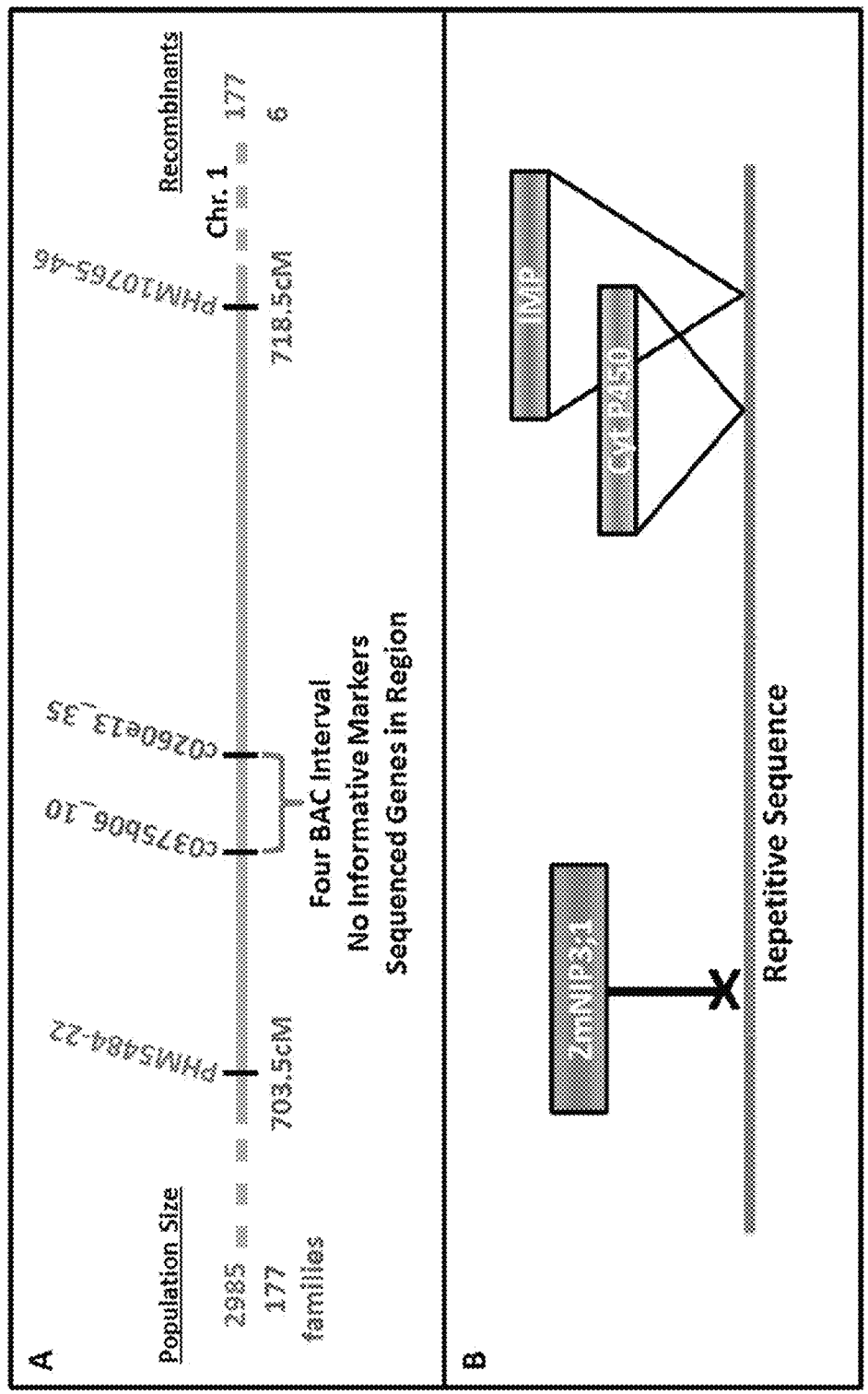

FIG. 9 shows the map-based cloning of tls1.

Figure 10:
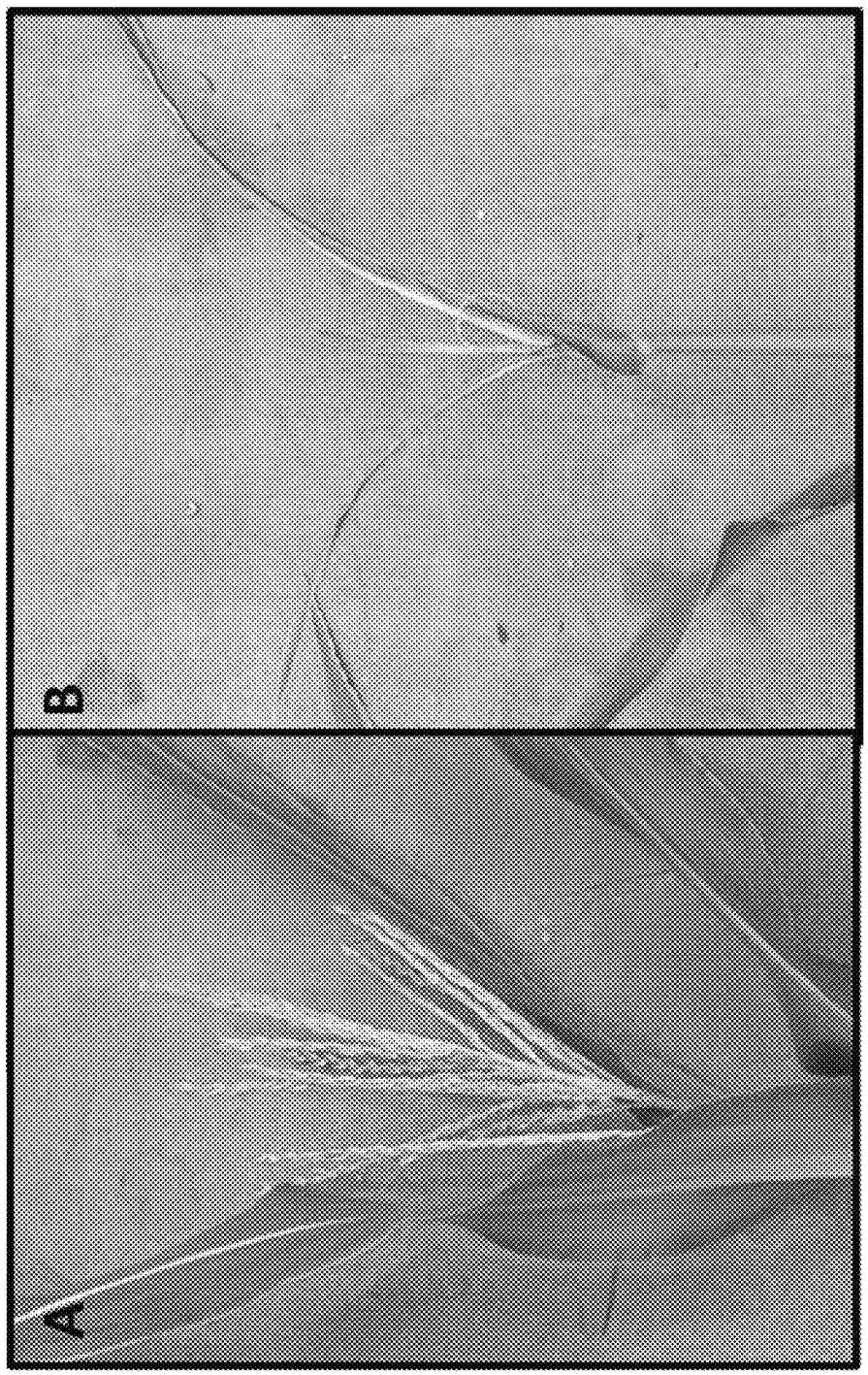

FIG. 10 shows tls1 candidate gene validation. Knockout of ZmNIP3-1 results in tls1 phenotype. FIG. 10A Wild type plant with intact ZmNIP3-1. FIG. 10B Plant with Mu-insertion in ZmNIP3.1 exhibits tls1 phenotype.

Figure 11:
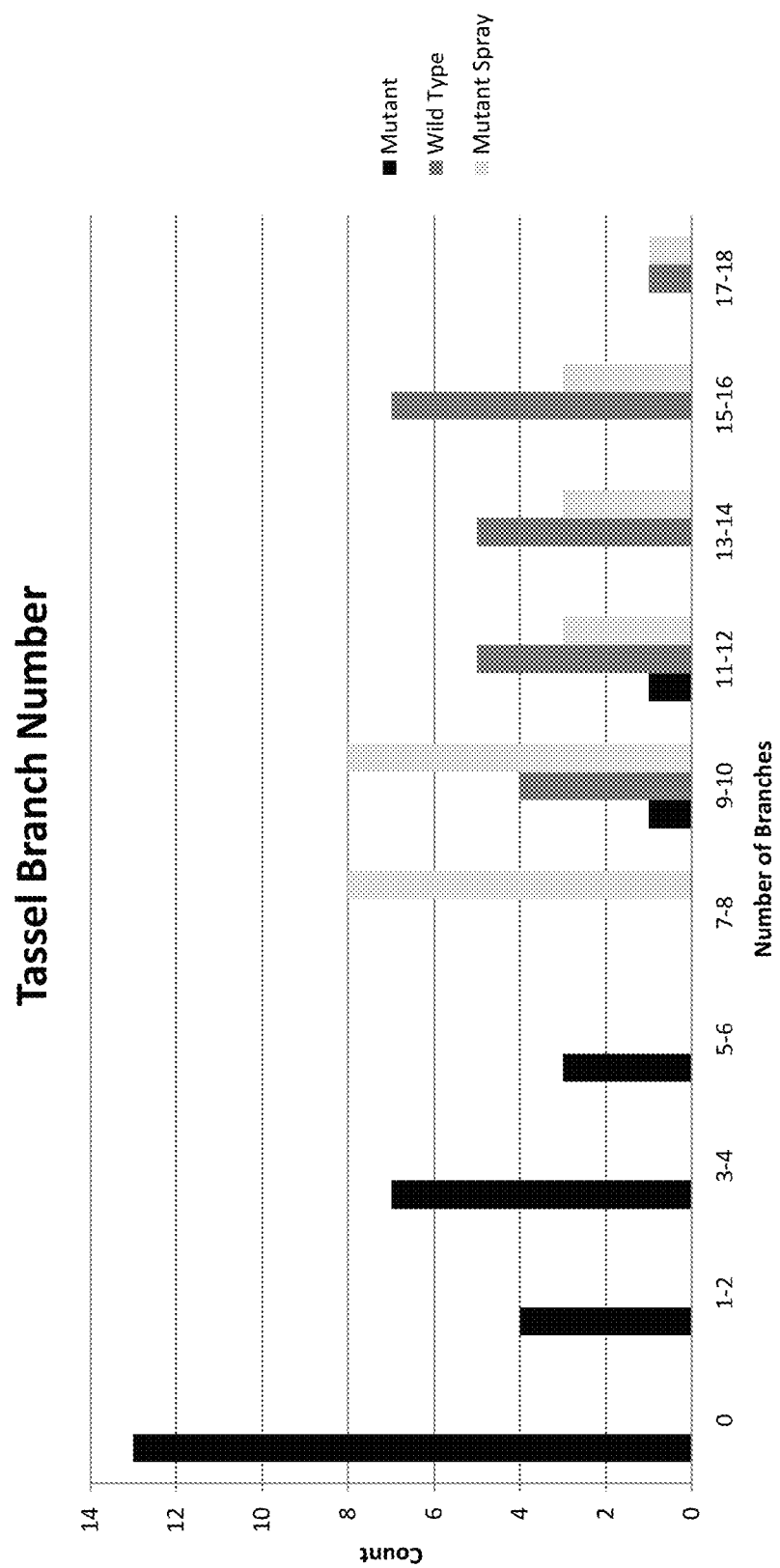

FIG. 11 shows the tassel branch number in mutant, wild-type and mutant sprayed with boron.

Figure 12:
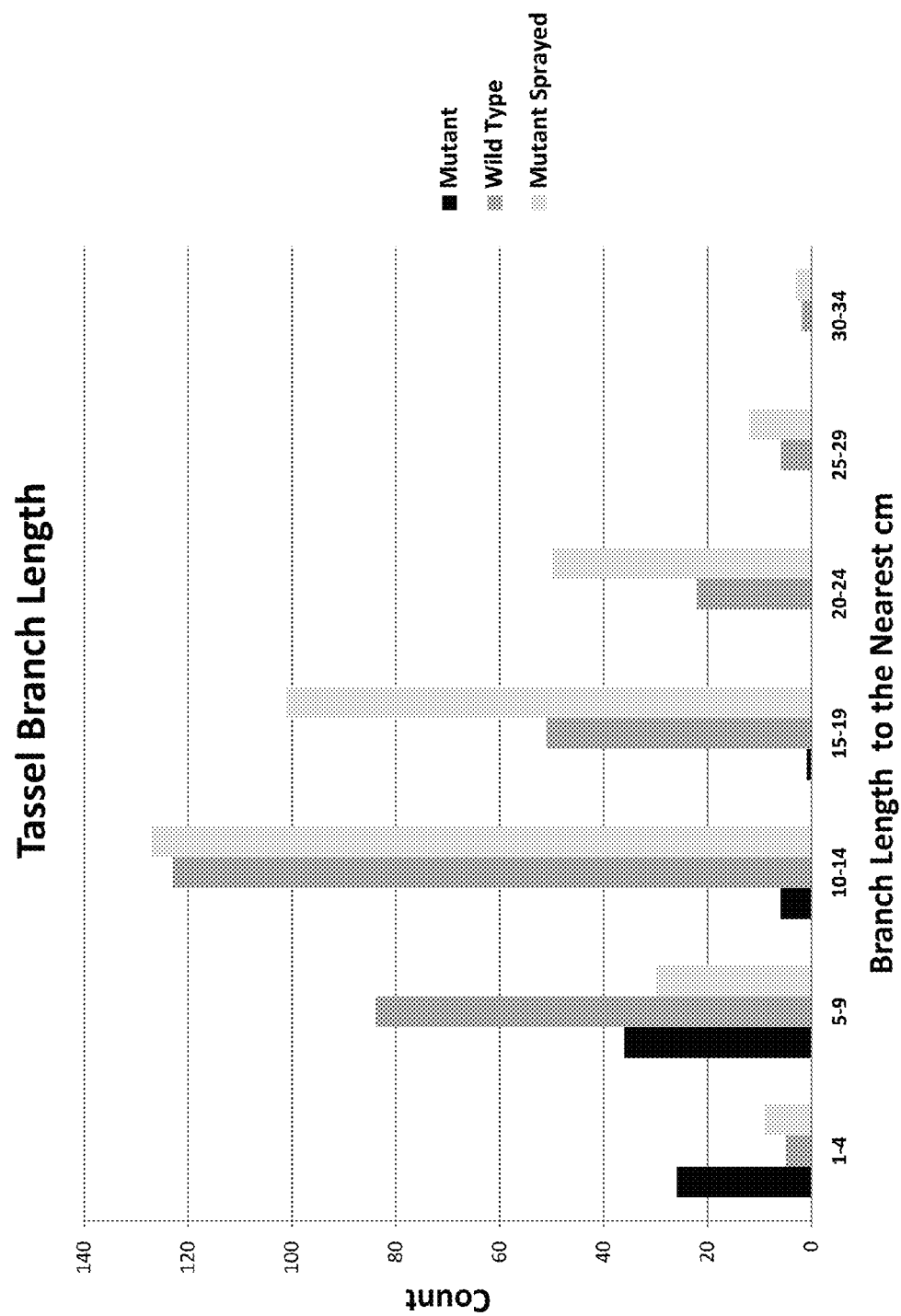

FIG. 12 shows the tassel branch length in mutant, wild-type and mutant sprayed with boron.

Figure 13:
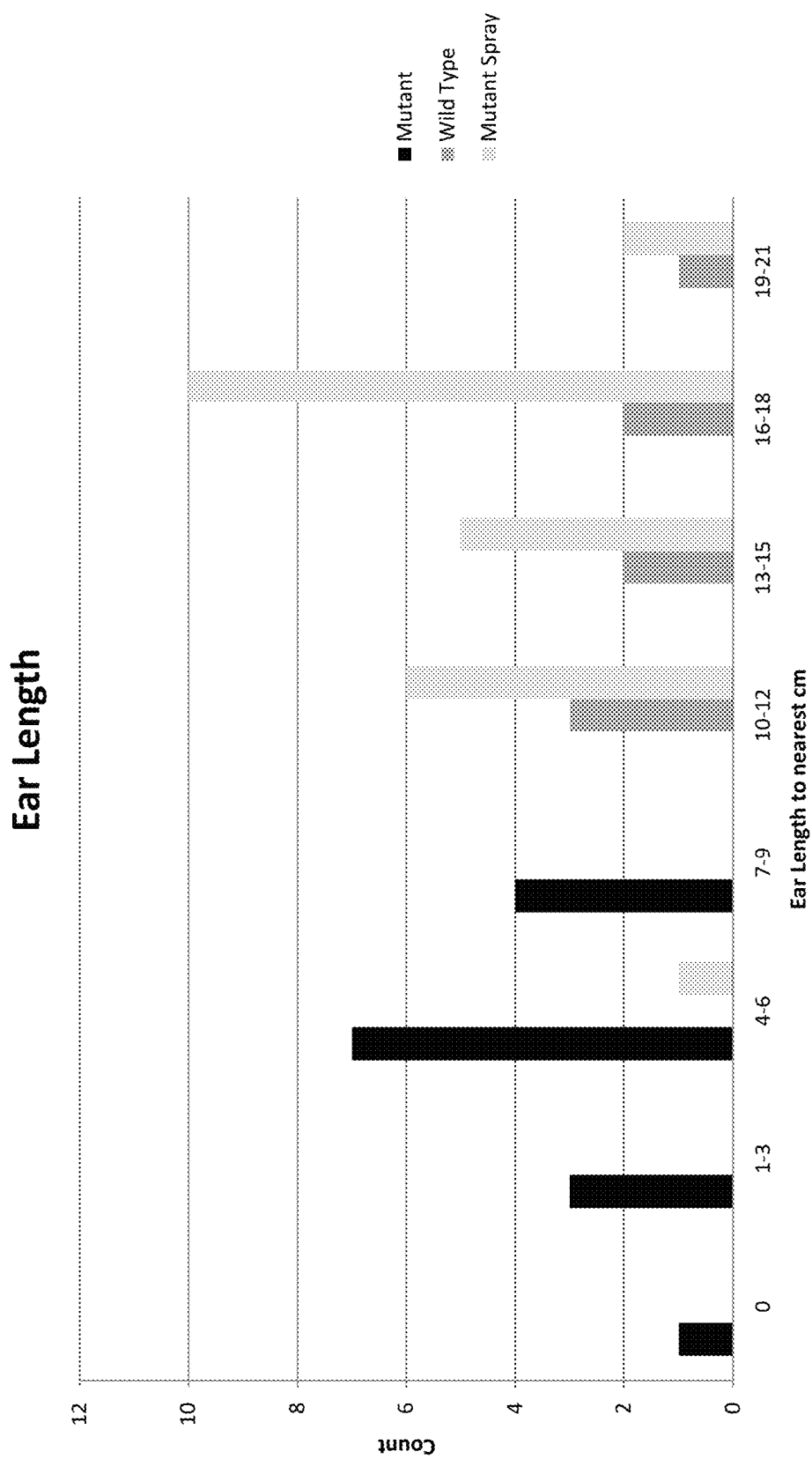

FIG. 13 shows the ear length in mutant, wild-type and mutant sprayed with boron.

Figure 14:
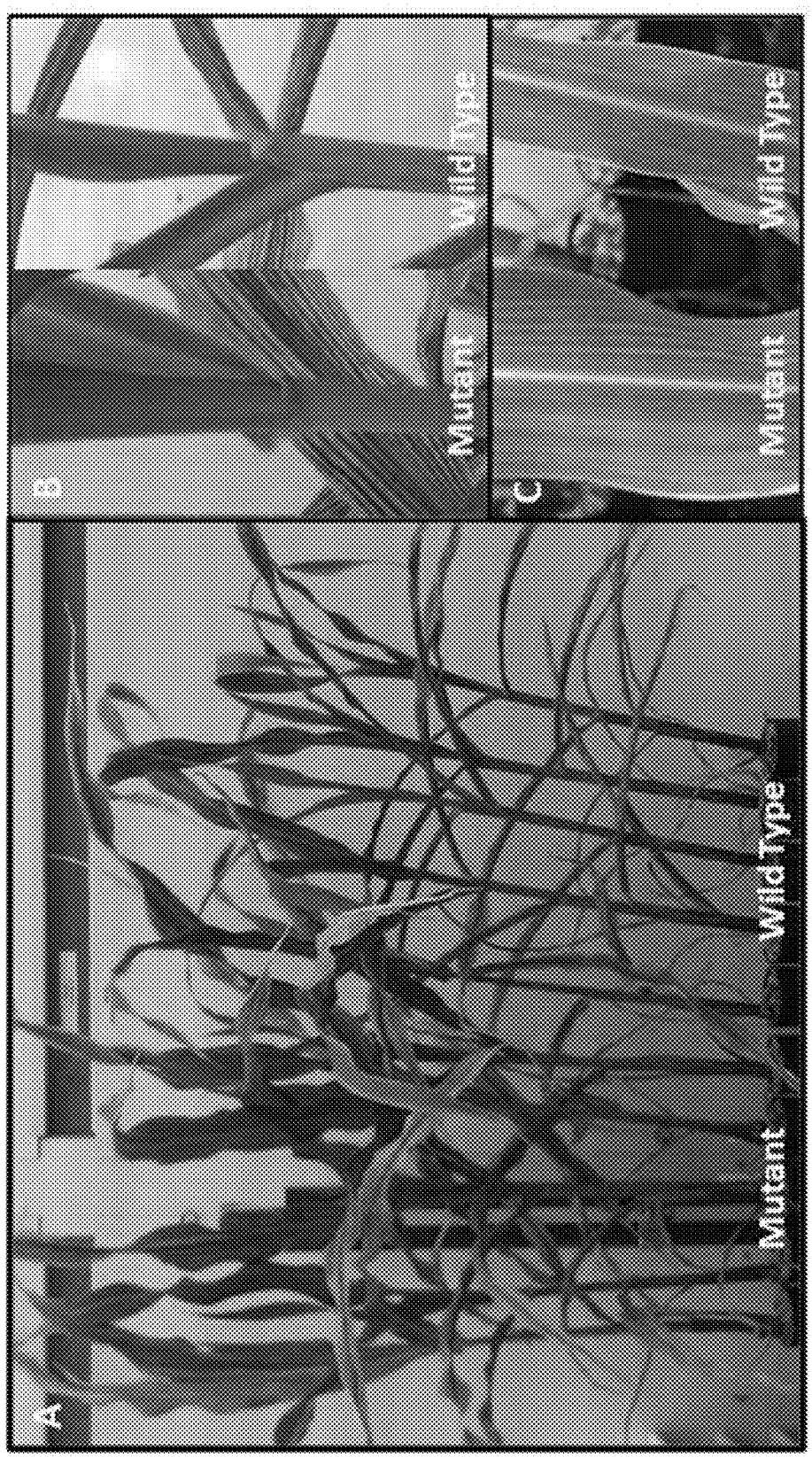

FIG. 14 shows that tls1 plants are less susceptible to boron-toxic conditions of 50 ppm boron. FIG. 14A Side-by-side of homozygous tls1 and wild type plants with mutant plants appearing taller and larger. FIG. 14B In wild type plants, the node of the second youngest fully expanded leaf extends above the node of the youngest fully expanded leaf, whereas mutant plants appear normal. FIG. 14C Youngest fully expanded leaf of mutant is broader than wild type.

Figure 15:
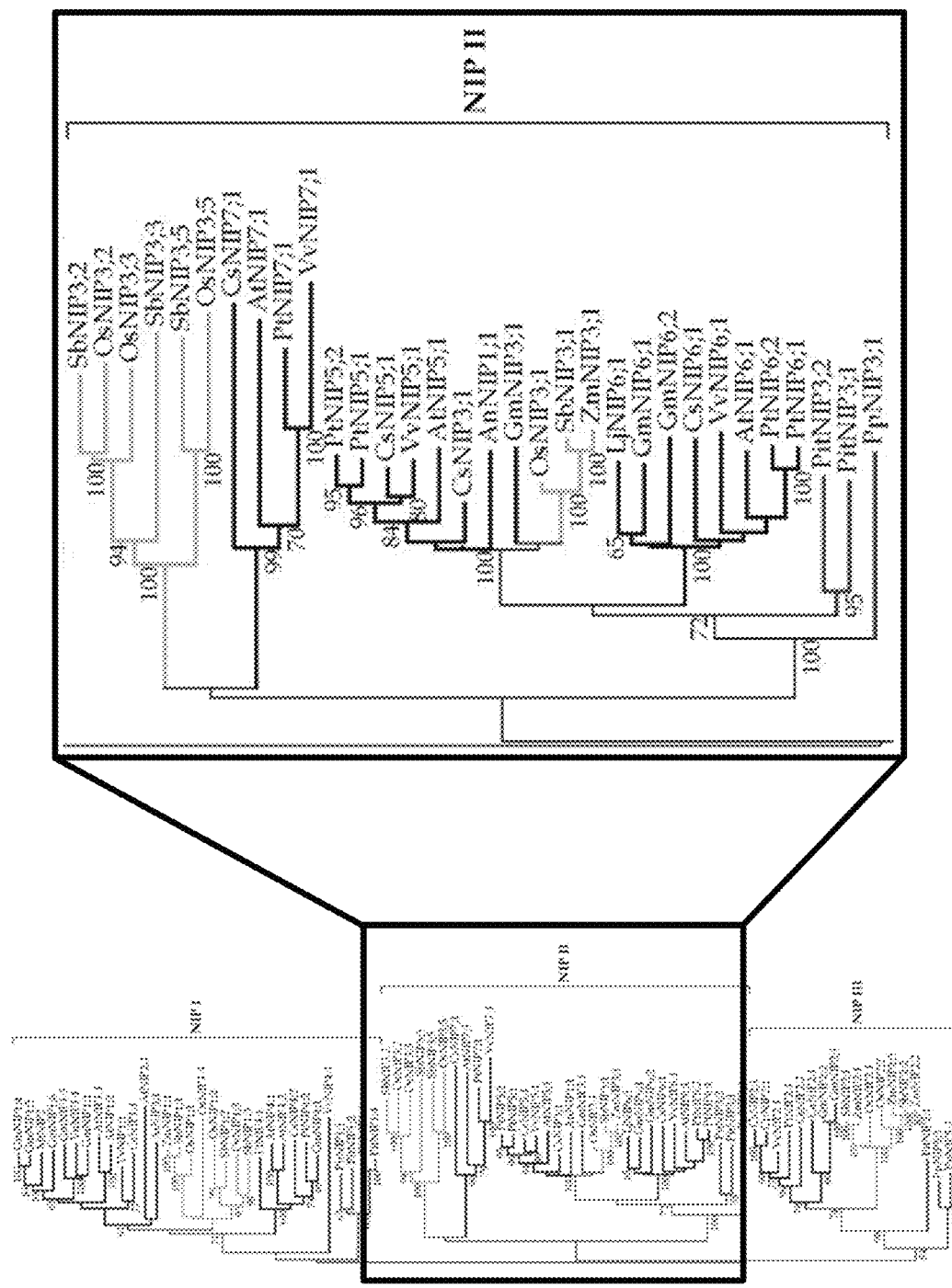
Figure 15B:
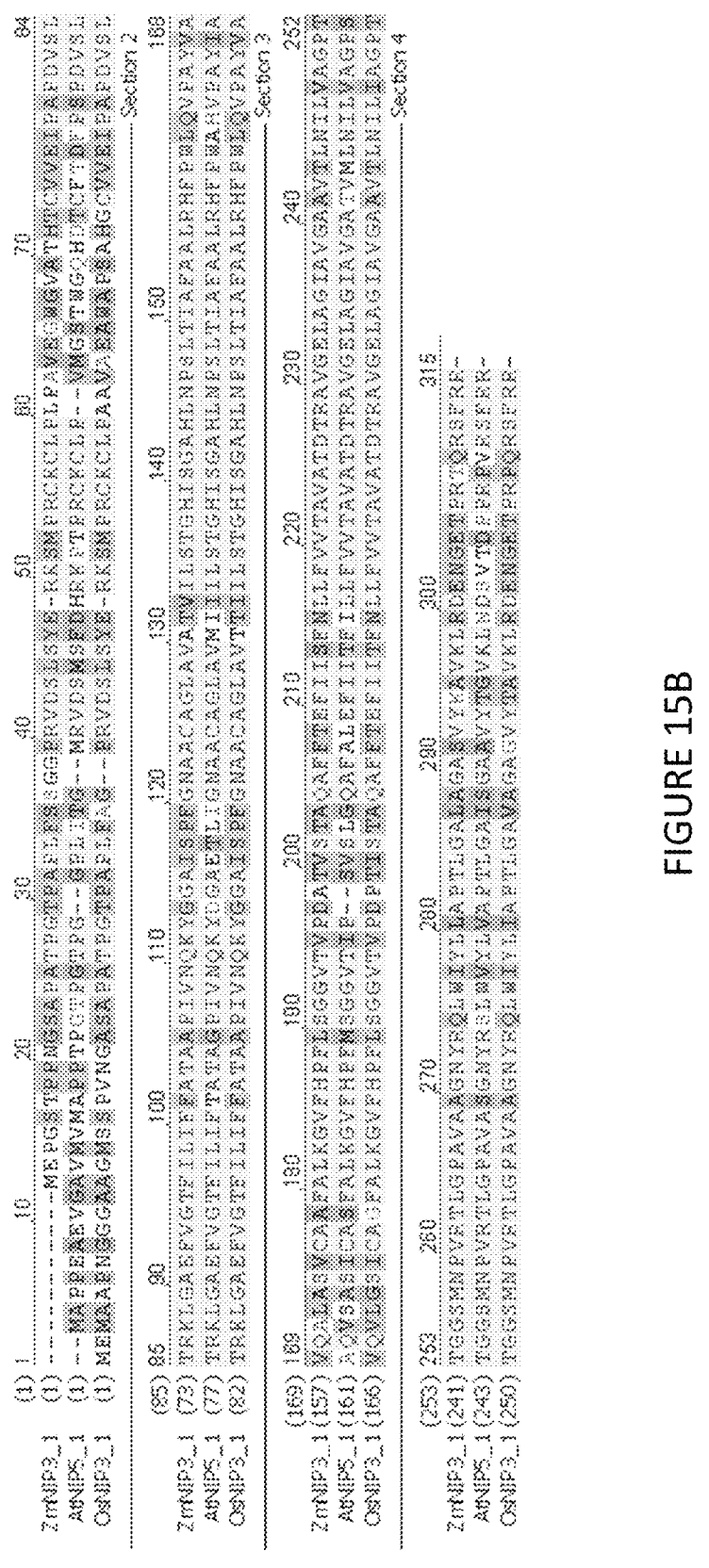

FIG. 15 shows ZmNIP3-1 is similar to boron channel proteins. FIG. 15A Phylogenetic tree shows ZmNIP3.1 (SEQ ID NO: 156) is closely related to OsNIP3.1 and AtNIP5.1 (highlighted), which have been characterized as boron channel proteins. FIG. 15B Alignment of protein sequences highlighted in FIG. 15A; ZmNIP3.1 is 84.4 and 67.3 percent identical to OsNIP3.1 (SEQ ID NO: 155) and AtNIP5.1 (SEQ ID NO: 154) respectively.

FIG. 16—Ms44 sequences from selected species. In this alignment, the amino acid mutation for the Ms44 Dominant polypeptide sequence is indicated in bold and underlined in position 42, as T in the MS44dom allele (SEQ ID NO: 14) or V in the Ms44-2629 allele (SEQ ID NO: 153), where all other sequences have A at that position.

DETAILED DESCRIPTION

The content and disclosures of PCT application PCT/US2013/30406 filed Mar. 12, 2013 and PCT application PCT/US2013/30455 filed Mar. 12, 2013, are incorporated herein by reference in their entireties. The methods and embodiments thereof related to male fertility are herein incorporated by reference.

Nitrogen utilization efficiency (NUE) genes affect yield and have utility for improving the use of nitrogen in crop plants, especially maize. Increased nitrogen use efficiency can result from enhanced uptake and assimilation of nitrogen fertilizer and/or the subsequent remobilization and reutilization of accumulated nitrogen reserves, as well as increased tolerance of plants to stress situations such as low nitrogen environments. The genes can be used to alter the genetic composition of the plants, rendering them more productive with current fertilizer application standards or maintaining their productive rates with significantly reduced fertilizer or reduced nitrogen availability. Improving NUE in corn would increase corn harvestable yield per unit of input nitrogen fertilizer, both in developing nations where access to nitrogen fertilizer is limited and in developed nations where the level of nitrogen use remains high. Nitrogen utilization improvement also allows decreases in on-farm input costs, decreased use and dependence on the non-renewable energy sources required for nitrogen fertilizer production and reduces the environmental impact of nitrogen fertilizer manufacturing and agricultural use.

Methods and compositions for improving plant yield are provided. In some embodiments, plant yield is improved under stress, particularly abiotic stress, such as nitrogen limiting conditions. Methods of improving plant yield include inhibiting the fertility of the plant. The male fertility of a plant can be inhibited using any method known in the art, including but not limited to the disruption of a tassel development gene, or a decrease in the expression of the gene through the use of co-suppression, antisense or RNA silencing or interference. Other male sterile plants can be achieved by using genetic male sterile mutants.

Inhibiting the male fertility in a plant can improve the nitrogen stress tolerance of the plant and such plants can maintain their productive rates with significantly less nitrogen fertilizer input and/or exhibit enhanced uptake and assimilation of nitrogen fertilizer and/or remobilization and reutilization of accumulated nitrogen reserves. In addition to an overall increase in yield, the improvement of nitrogen stress tolerance through the reduction in male fertility can also result in increased root mass and/or length, increased ear, leaf, seed and/or endosperm size, and/or improved standability. Accordingly, in some embodiments, the methods further comprise growing said plants under nitrogen limiting conditions and optionally selecting those plants exhibiting greater tolerance to the low nitrogen levels.

Further, methods and compositions are provided for improving yield under abiotic stress, which include evaluating the environmental conditions of an area of cultivation for abiotic stressors (e.g., low nitrogen levels in the soil) and planting seeds or plants having reduced male fertility, in stressful environments.

Constructs and expression cassettes comprising nucleotide sequences that can efficiently reduce male fertility are also provided herein.

Additional methods include but are not limited to:

A method of increasing yield by increasing one or more yield components in a plant includes reducing male fertility by affecting the expression or activity of a nuclear encoded component in the plant, and growing the plant under plant growing conditions, wherein the component exhibits a dominant phenotype. In an embodiment, the nuclear encoded component is a male fertility gene or a male sterility gene that has a dominant phenotype. Optionally, the male fertility gene or the male sterility gene is a transgene.

The developing female reproductive structure competes with male reproductive structures for nitrogen, carbon and other nutrients during development of these reproductive structures. This is demonstrated in quantifying the nitrogen budget of developing maize ears and tassels when the plants are grown in increasing levels of nitrogen fertilizer. When maize is grown under lower nitrogen fertility levels the nitrogen budget of the ear is negative, or during development the ear loses nitrogen to other parts of the plant when nitrogen is limiting. The nitrogen budget of the ear improves as the amount of nitrogen fertilizer provided to the plant increases until the ear maintains a positive increase in nitrogen through to silk emergence. In contrast, the tassel maintains a positive nitrogen budget irrespective of the level of nitrogen fertility in which the plant is grown. The tassel and ear compete for nitrogen during reproductive development and the developing tassel dominates over the developing ear. The ear and tassel likely compete for a number of nutrients during development and the competition becomes more severe under stress conditions. The ear is in competition with the tassel during reproductive development prior to anthesis reducing the ability of the developing ear to accumulate nutrients under stress resulting in a smaller, less developed ear with fewer kernels. More severe, extended stress can result in failure of the ear to exert silks and produce grain. Genetic reduction in male fertility would reduce the nutrient requirement for tassel is development resulting in improved ear development at anthesis. Genetic male sterile and fertile sibs were grown in varying levels of nitrogen fertility and sampled at ~50% pollen shed. Male sterile plants produced larger ears under both nitrogen fertility levels. The proportion of male sterile plants with emerged silks was also greater than the fertile sib plants. Though the biomass (total above ground plant dry weight minus the ear dry weight) was greater in the higher nitrogen fertility grown plants, there was no effect of male sterility on biomass. This shows the positive effect of male sterility is specifically on the ability of the plant to produce a heavier more fully developed (silks) ear without affecting overall vegetative growth.

Yield experiments with genetic male sterile derived hybrids have not been done because, until recently, there has been no reasonable method of producing hybrid seed using this source of male sterility. Since most genetic male steriles are recessive, producing male sterile hybrids would require the source of male sterility to be backcrossed into both parents of the hybrid. The female parent would have to be homozygous recessive (male sterile) and the male parent would have to be heterozygous (male fertile) for the hybrid to segregate 1:1 for male sterility. In contrast, MS44, a dominant genetic male sterile, only needs to be backcrossed into the female parent to produce hybrid seed segregating 1:1 for male sterility. Dominant male sterility is especially useful in polyploid plants such as wheat, where maintenance of homozygous recessive sterility is more complex.

Figure 1:
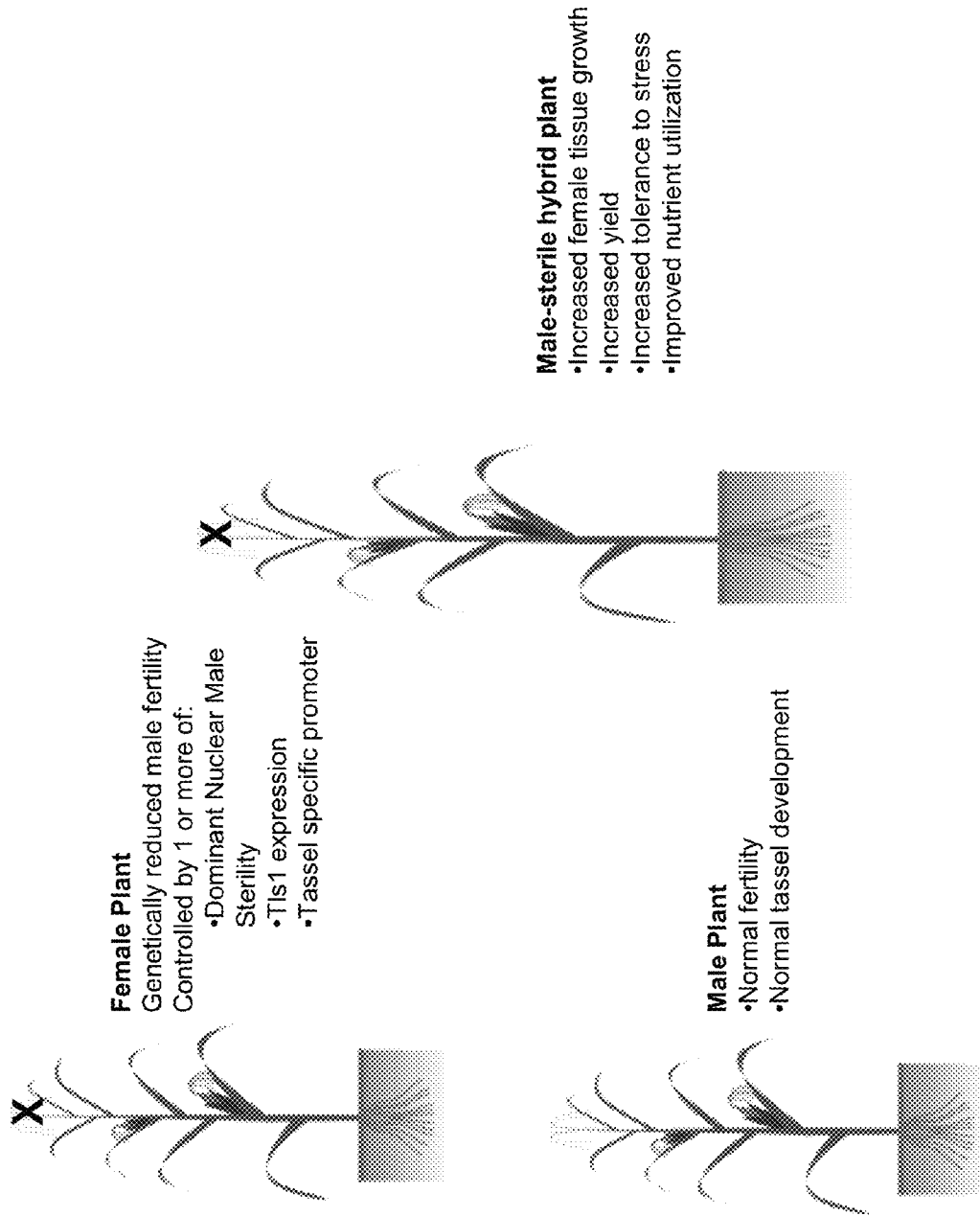
FIG. 1—Diagram of Genetic Dominant Male Sterility system to produce a male-sterile hybrid plant. Genetic reduction of male fertility in a plant, which may utilize one or more of a dominant nuclear male-sterile gene, a tassel-specific or tassel-preferred promoter, and a tassel-specific or tassel-preferred gene, has been found to increase ear tissue development, improve nutrient utilization in the growing plant, increase stress tolerance, and/or increase seed metrics, ultimately leading to improved yield.

The process of expressing a dominant genetic male sterile gene in a plant, optionally combined with tassel tissue specific/preferred promoters and tassel specific genes, has been found to increase ear tissue development, improve nutrient utilization in the growing plant and increase seed metrics, ultimately leading to improved yield. (FIG. 1)

Genetic male sterility is much more likely to produce a yield response because pollen development fails much earlier in genetic male sterile mutants than in CMS derived sterility. Most genetic male sterile mutants fail shortly after pollen tetrad release (Albertson and Phillips, (1981) *Can. J. Genet. Cytol.* 23:195-208) which occurs during very early stages of female (ear) development. CMS derived male sterility is not determined until 10 days prior to anthesis as judged by the environmental interactions associated with CMS stability (Weider, et al., (2009) *Crop Sci.* 49:77-84). The bulk of ear development would have already occurred prior to 10 days before anthesis providing little relief from tassel competition during ear development. Whereas, early failure of genetic male sterility would be one method of reducing competition for nutrients of the developing ear with tassel development when the ear is in early stages of development. Yield improvements associated with male sterile hybrids vectored through improved ear development are very consistent with the reduction in competition of ear development with tassel development.

The yield response to N fertility was tested in restored (male fertile) and non-restored (male sterile) cytoplasmic male sterile (CMS) hybrids. One hybrid became male fertile due to environmental conditions during flowering and the other hybrid showed no significant yield effects due to male sterility. Male sterility determined via cytoplasmic genes is not generally established until very late in tassel and ear development, as judged by the environmental interactions associated with CMS stability. The bulk of ear development has already occurred before CMS male sterility is set (10 days before anthesis) providing little relief from tassel competition during ear development. Most genetic male sterile mutants fail shortly after pollen tetrad release which is during very early stages of female (ear) development. Thus tassel development in a genetic male sterile would be reduced during the entire ear developmental timeframe and compete less with ear development. Genetic male sterile mutants are not significantly affected by environmental conditions.

Relieving competition between developing tassel and ear could also be achieved by chemically induced male sterility. A combination of unique chemicals and genetic manipulation could also induce male sterility. Herbicide tolerance modified by promoters with less efficacy in male reproductive tissue or the use of pro-gametocides (Dotson, et al., (1996) *The Plant Journal* 10:383-392) and (Mayer and Jefferson, (2004) Molecular Methods for Hybrid Rice Production. A report for the Rural Industries Research and Development Corporation) to release male inhibitors in a tissue specific manner would also be effective means of practicing this disclosure.

In a number of circumstances, a particular plant trait is expressed by maintenance of a homozygous recessive condition. Difficulties arise in maintaining the homozygous condition when a transgenic restoration gene must be used for maintenance. For example, the MS45 gene in maize (U.S. Pat. No. 5,478,369) has been shown to be critical to male fertility. Plants heterozygous or hemizygous for the dominant MS45 allele are fully fertile due to the sporophytic nature of the MS45 fertility trait. A natural mutation in the MS45 gene, designated ms45, imparts a male sterility phenotype to plants when this mutant allele is in the homozygous state. This sterility can be reversed (i.e., fertility restored) when the non-mutant form of the gene is introduced into the plant, either through normal crossing or transgenic complementation methods. However, restoration of fertility by crossing removes the desired homozygous recessive condition, and both methods restore full male fertility and prevent maintenance of pure male sterile maternal lines.

A method to maintain the desired homozygous recessive condition is described in U.S. Pat. Nos. 7,696,405 and 7,517,975, where a maintainer line is used to cross onto homozygous recessive male sterile siblings. The maintainer line is in the desired homozygous recessive condition for male sterility but also contains a hemizygous transgenic construct consisting of a dominant male fertility gene to complement the male sterility condition; a pollen ablation gene, which prevents the transfer through pollen of the transgenic construct to the male sterile sibling but allows for the transfer of the recessive male sterile allele through the non-transgenic pollen grains and a seed marker gene which allows for the sorting of transgenic maintainer seeds or plants and transgenic-null male sterile seeds or plants.

Seed Production Technology (SPT) provides methods to maintain the homozygous recessive condition of a male-sterility gene in a plant. See, for example, U.S. Pat. No. 7,696,405. SPT utilizes a maintainer line that is the pollen source for fertilization of its homozygous-recessive male-sterile siblings. The maintainer line is in the desired homozygous recessive condition for male sterility but also contains a hemizygous transgenic construct (the "SPT construct"). In certain embodiments the SPT construct comprises the following three elements: (1) a dominant male-fertility gene to complement the male-sterile recessive condition; (2) a gene encoding a product which interferes with the formation, function, or dispersal of male gametes and (3) a marker gene which allows for the sorting of transgenic maintainer seeds/plants from those which lack the transgene. Interference with pollen formation, function or dispersal prevents the transfer through pollen of the transgenic construct; functional pollen lacks the transgene. Resulting seeds produce plants which are male-sterile. These male-sterile inbred plants are then used in hybrid production by pollinating with a male parent, which may be an unrelated inbred line homozygous for the dominant allele of the male-fertility gene. Resulting hybrid seeds produce plants which are male-fertile.

Figure 3:
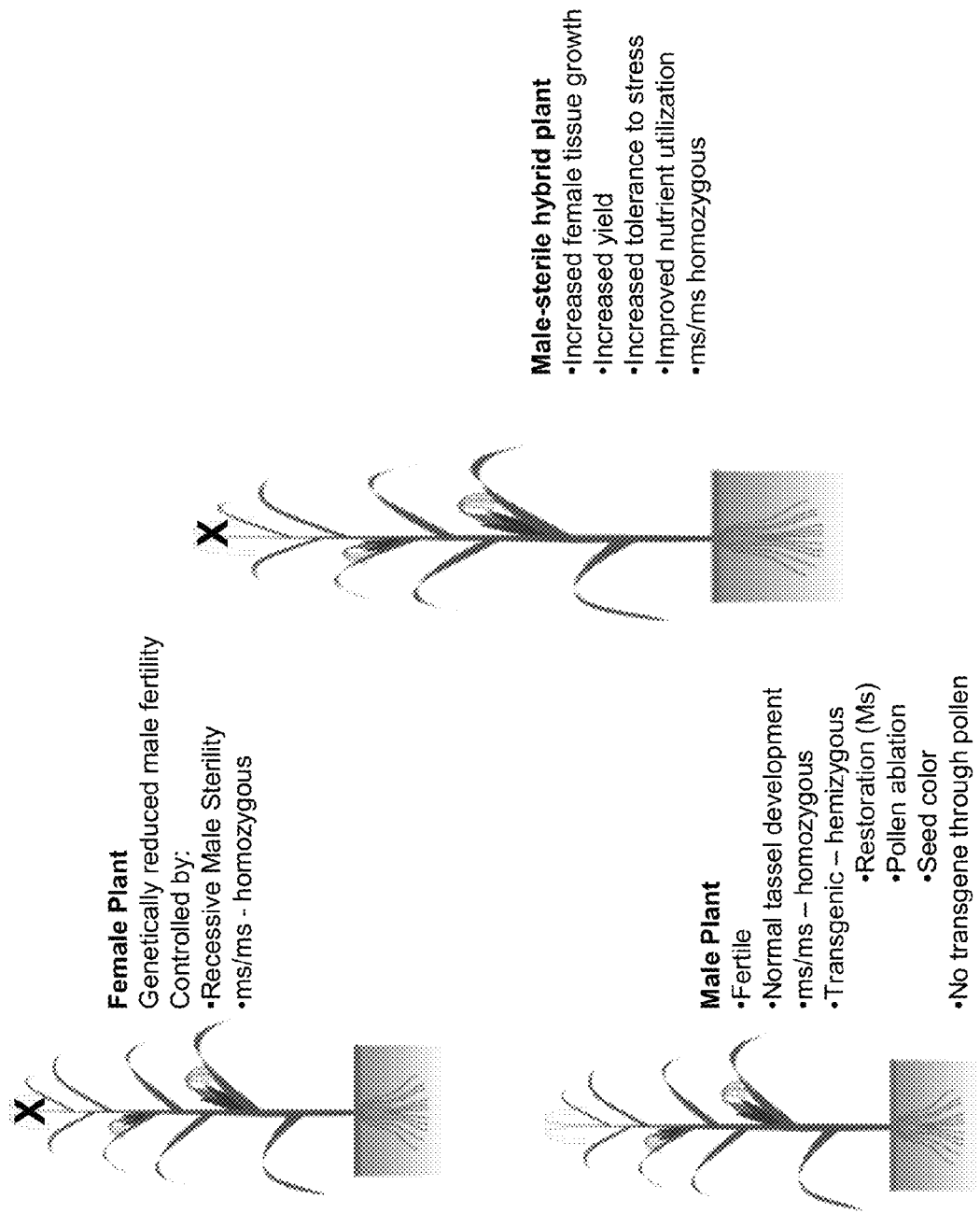
FIG. 3—Diagram of method to produce a male-sterile hybrid plant using a recessive male-sterile gene. Both the female parent and the male parent have the homozygous recessive alleles which confer sterility. However, the male parent carries the restorer allele within a construct which prevents transmission of the restorer allele through pollen. Resulting hybrid seed produce a male-sterile hybrid plant.

To create hybrid male sterile progeny, the male parent would serve as the maintainer line to cross onto male sterile female inbreds, (increased using a separate female maintainer line), to give fully male sterile hybrid plants. See, for example, FIG. 3.

The use of a dominant approach is another method to achieve male sterility. In many regards a dominant male sterility approach has advantages over the use of recessive male sterility because only a single copy of the dominant gene is required for full sterility. However, if methods are not available to create a homozygous dominant male sterile line, then resulting progeny will segregate 50% for male sterility. This situation can be alleviated by transgenically linking a screenable or selectable marker to the dominant male sterility gene and screening or selecting progeny seeds or plants carrying the marker. For a dominant male sterile allele, linked genetic markers or a linked phenotype could be employed to sort progeny. Methods describing a reversible dominant male sterility system are described in U.S. Pat. No. 5,962,769 where a chemical is applied to dominant male sterile plants, which reverses the phenotype and results in male fertility, allowing for self pollinations so that homozygous dominant male sterile plants can be obtained. Other methods for creating a homozygous dominant male sterile plant could be envisioned using an inducible promoter controlling a gene that represses or interferes with function of the dominant male sterile gene. The plant is constitutively sterile, becoming fertile only when the promoter is induced, allowing for expression of the repressor which disrupts the dominant male sterile gene function. A repressor might be an antisense gene, RNAi, an inverted repeat that targets either the dominant male sterile gene itself or its promoter or a gene product that is capable of binding or inactivating the dominant male sterile gene product.

Another approach to produce 100% male sterility in progeny from dominant male sterility would use auto splicing protein sequences. An auto splicing protein sequence is a segment of a protein that is able to excise itself and rejoin the remaining portion/s with a peptide bond. Auto splicing protein sequences can self splice and relegate the remaining portions in both cis and trans states. A dominant male sterile gene could be modified such that the regions coding for the N and C protein regions are separated into different transgenic constructs, coupled with a sequence coding for an auto splicing protein sequence. A plant containing a single construct would be male fertile since the protein is truncated and non-functional, which allows for self fertilization to create a homozygous plant. Plants homozygous for the N-DMS-N-auto splicing protein sequence can then be crossed with plants homozygous for the C-auto splicing protein sequence-C-DMS protein. All of the progeny from this cross would be male sterile through the excision of each auto splicing protein sequence and the relegation of the N and C sequences to create a functional dominant male sterile protein.

A series of field experiments were used to quantify the yield response of genetic male sterility under a variety of environmental variables. There were two variables used: nitrogen fertilizer rate, and plant density, to subject the plants to various degrees of stress. This continuum of stress treatments allowed for clear separation of plant performance due to greater assimilate partitioning to ears of the genetic male sterile plants. These methods were used to quantify and demonstrate positive yield effects in a representative crop canopy environment in the field. These data validated earlier individual plant responses measured in greenhouse studies.

Male sterility is manifested in the changes in development of specific plant tissues. Maize ear and tassel are both inflorescence structures that share common development processes and are controlled by a common set of genes. The tissues compete with each other for the required nutrients. Tassel however has the advantage of apical dominance over the ear, which is unfavorable to ear growth and yield potential in the maize plants. Reducing the tassel apical dominance could be used to divert more resource to the ear growth, kernel number or size and ultimately can lead to increased grain yield.

There are multiple approaches to reducing the competition of the tassel, such as male sterility, tassel size reduction, or tassel elimination (a tasseless maize plant). While genetic mutations (mutants) of genes such as male sterility genes can be used to reduce the competition of the tassel with ear, transgenic manipulation offers alternatives or enabling tools for this purpose. As genes that are involved in tassel development are often involved in ear development, reducing tassel development by interrupting these genes may also affect the ear development. The tasseless gene (Tsl1) mutation is an example, in which the tasseless plant is also earless. To enable tassel growth reduction without interfering with the ear development, a tassel-specific promoter is needed to target the gene disruption in the tassel tissues only.

All references referred to are incorporated herein by reference.

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

The practice of the present disclosure will employ, unless otherwise indicated, conventional techniques of botany, microbiology, tissue culture, molecular biology, chemistry, biochemistry and recombinant DNA technology, which are within the skill of the art.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present disclosure, the following terms will be employed and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS) and strand displacement amplification (SDA). See, e.g., *Diagnostic Molecular Microbiology: Principles and Applications*, Persing, et al., eds., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen. Microbiol.* 139:425-32) can be modified to yield a functionally identical molecule. Accordingly, each silent variation of a nucleic acid, which encodes a polypeptide of the present disclosure, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity or ligand/receptor binding is generally at least 30%, 40%, 50%, 60%, 70%, 80% or 90%, preferably 60-90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V) and
6) Phenylalanine (F), Tyrosine (Y), Tryptophan (W).

See also, Creighton, *Proteins*, W.H. Freeman and Co. (1984).

As used herein, "consisting essentially of" means the inclusion of additional sequences to an object polynucleotide or polypeptide where the additional sequences do not materially affect the basic function of the claimed polynucleotide or polypeptide sequences.

The term "construct" is used to refer generally to an artificial combination of polynucleotide sequences, i.e. a combination which does not occur in nature, normally comprising one or more regulatory elements and one or more coding sequences. The term may include reference to expression cassettes and/or vector sequences, as is appropriate for the context.

A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed. A control plant may also be a plant transformed with an alternative down-regulation construct.

By "encoding" or "encoded," with respect to a specified nucleic acid, is meant comprising the information for translation into the specified protein. A nucleic acid encoding a protein may comprise non-translated sequences (e.g., introns) within translated regions of the nucleic acid or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolum* (Yamao, et al., (1985) *Proc. Natl. Acad. Sci. USA* 82:2306-9) or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present disclosure may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference). Thus, the maize preferred codon for a particular amino acid might be derived from known gene sequences from maize. Maize codon usage for 28 genes from maize plants is listed in Table 4 of Murray, et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived or, if from the same species, one or both are substantially modified from their original form. A heterologous protein may originate from a foreign species or, if from the same species, is substantially modified from its original form by deliberate human intervention.

By "host cell" is meant a cell, which comprises a heterologous nucleic acid sequence of the disclosure, which contains a vector and supports the replication and/or expression of the expression vector. Host cells may be prokaryotic cells such as *E. coli*, or eukaryotic cells such as yeast, insect, plant, amphibian or mammalian cells. Preferably, host cells are monocotyledonous or dicotyledonous plant cells, including but not limited to maize, sorghum, sunflower, soybean, wheat, alfalfa, rice, cotton, canola, barley, millet and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

The terms "isolated" refers to material, such as a nucleic acid or a protein, which is substantially or essentially free from components which normally accompany or interact with it as found in its naturally occurring environment. The terms "non-naturally occurring"; "mutated", "recombinant"; "recombinantly expressed"; "heterologous" or "heterologously expressed" are representative biological materials that are not present in its naturally occurring environment.

The term "NUE nucleic acid" means a nucleic acid comprising a polynucleotide ("NUE polynucleotide") encoding a full length or partial length polypeptide.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, (1987) *Guide To Molecular Cloning Techniques*, from the series *Methods in Enzymology*, vol. 152, Academic Press, Inc., San Diego, Calif.; Sambrook, et al., (1989) *Molecular Cloning: A Laboratory Manual*, $2^{nd}$ ed., vols. 1-3; and *Current Protocols in Molecular Biology*, Ausubel, et al., eds, Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA corresponding to the second sequence. Generally, operably linked means that the nucleic acid sequences being linked are contiguous and, where necessary, to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen and microspores. The class of plants, which can be used in the methods of the disclosure, is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium* and *Triticum*. A particularly preferred plant is *Zea mays*.

As used herein, "yield" may include reference to bushels per acre of a grain crop at harvest, as adjusted for grain moisture (15% typically for maize, for example) and the volume of biomass generated (for forage crops such as alfalfa and plant root size for multiple crops). Grain moisture is measured in the grain at harvest. The adjusted test weight of grain is determined to be the weight in pounds per bushel, adjusted for grain moisture level at harvest. Biomass is measured as the weight of harvestable plant material generated.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Examples are promoters that preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter which is active in essentially all tissues of a plant, under most environmental conditions and states of development or cell differentiation.

The term "polypeptide" refers to one or more amino acid sequences. The term is also inclusive of fragments, variants, homologs, alleles or precursors (e.g., preproproteins or proproteins) thereof. A "NUE protein" comprises a polypeptide. Unless otherwise stated, the term "NUE nucleic acid" means a nucleic acid comprising a polynucleotide ("NUE polynucleotide") encoding a polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.*, 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier, New York (1993); and *Current Protocols in Molecular Biology*, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to:

CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG® programs (Accelrys, Inc., San Diego, Calif.).). The CLUSTAL program is well described by Higgins and Sharp, (1988) *Gene* 73:237-44; Higgins and Sharp, (1989) *CABIOS* 5:151-3; Corpet, et al., (1988) *Nucleic Acids Res.* 16:10881-90; Huang, et al., (1992) *Computer Applications in the Biosciences* 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) *CABIOS* 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, *Current Protocols in Molecular Biology*, Chapter 19, Ausubel et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.* 17:149-63) and XNU (Claverie and States, (1993) *Comput. Chem.* 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

TABLE 1

| SEQ ID NUMBER | POLYNUCLEO-TIDE/POLYPEPTIDE | IDENTITY |
| --- | --- | --- |
| SEQ ID NO: 1 | Polynucleotide | Primer |
| SEQ ID NO: 2 | Polynucleotide | Primer |
| SEQ ID NO: 3 | Polynucleotide | Primer |
| SEQ ID NO: 4 | Polynucleotide | Primer |
| SEQ ID NO: 5 | Polynucleotide | Primer |
| SEQ ID NO: 6 | Polynucleotide | Primer |
| SEQ ID NO: 7 | Polynucleotide | Primer |
| SEQ ID NO: 8 | Polynucleotide | Primer |
| SEQ ID NO: 9 | Polynucleotide | ms44 wildtype genomic |
| SEQ ID NO: 10 | Polypeptide | ms44 wildtype protein |
| SEQ ID NO: 11 | Polynucleotide | Primer |
| SEQ ID NO: 12 | Polynucleotide | Primer |
| SEQ ID NO: 13 | Polynucleotide | MS44 mutant allele dominant genomic seq |
| SEQ ID NO: 14 | Polynucleotide | MS44 dominant protein |
| SEQ ID NO: 15 | Polynucleotide | MS44 dom CDS |
| SEQ ID NO: 16 | Polypeptide | Arabidopsis thaliana |
| SEQ ID NO: 17 | Polypeptide | Oryza sativa |
| SEQ ID NO: 18 | Polypeptide | Lilium longiflorum |
| SEQ ID NO: 19 | Polypeptide | Zea mays YY1 |
| SEQ ID NO: 20 | Polypeptide | Hordeum vulgare |
| SEQ ID NO: 21 | Polypeptide | Oryza brachyantha |
| SEQ ID NO: 22 | Polypeptide | Zea mays anther specific |
| SEQ ID NO: 23 | Polypeptide | Sorghum bicolor |
| SEQ ID NO: 24 | Polypeptide | Lilium longiflorum |
| SEQ ID NO: 25 | Polypeptide | Lilium longiflorum |
| SEQ ID NO: 26 | Polypeptide | Brassica rapa |
| SEQ ID NO: 27 | Polypeptide | Silene latiflia |
| SEQ ID NO: 28 | Polynucleotide | Primer |
| SEQ ID NO: 29 | Polynucleotide | Primer |
| SEQ ID NO: 30 | Polynucleotide | Primer |
| SEQ ID NO: 31 | Polynucleotide | Primer |
| SEQ ID NO: 32 | Polynucleotide | Primer |
| SEQ ID NO: 33 | Polynucleotide | Primer |
| SEQ ID NO: 34 | Polynucleotide | Primer |
| SEQ ID NO: 35 | Polynucleotide | Primer |
| SEQ ID NO: 36 | Polynucleotide | Primer |
| SEQ ID NO: 37 | Polynucleotide | Primer |
| SEQ ID NO: 38 | Polynucleotide | Primer |
| SEQ ID NO: 39 | Polynucleotide | Primer |
| SEQ ID NO: 40 | Polynucleotide | Primer |
| SEQ ID NO: 41 | Polynucleotide | Primer |
| SEQ ID NO: 42 | Polynucleotide | Primer |
| SEQ ID NO: 43 | Polynucleotide | Primer |

TABLE 1-continued

| SEQ ID NUMBER | POLYNUCLEO-TIDE/POLYPEPTIDE | IDENTITY |
| --- | --- | --- |
| SEQ ID NO: 44 | Polynucleotide | Primer |
| SEQ ID NO: 45 | Polynucleotide | Primer |
| SEQ ID NO: 46 | Polynucleotide | Primer |
| SEQ ID NO: 47 | Polynucleotide | Primer |
| SEQ ID NO: 48 | Polynucleotide | Primer |
| SEQ ID NO: 49 | Polynucleotide | Primer |
| SEQ ID NO: 50 | Polynucleotide | Primer |
| SEQ ID NO: 51 | Polynucleotide | Primer |
| SEQ ID NO: 52 | Polynucleotide | Primer |
| SEQ ID NO: 53 | Polynucleotide | Primer |
| SEQ ID NO: 54 | Polynucleotide | Primer |
| SEQ ID NO: 55 | Polynucleotide | Primer |
| SEQ ID NO: 56 | Polynucleotide | Primer |
| SEQ ID NO: 57 | Polynucleotide | Primer |
| SEQ ID NO: 58 | Polynucleotide | Primer |
| SEQ ID NO: 59 | Polynucleotide | Primer |
| SEQ ID NO: 60 | Polynucleotide | Primer |
| SEQ ID NO: 61 | Polynucleotide | Primer |
| SEQ ID NO: 62 | Polynucleotide | tls1 genomic |
| SEQ ID NO: 63 | Polynucleotide | tls1 CDS |
| SEQ ID NO: 64 | Polynucleotide | Tassel preferred promoter |
| SEQ ID NO: 65 | Polynucleotide | Tassel preferred promoter |
| SEQ ID NO: 66 | Polynucleotide | Tassel preferred promoter |
| SEQ ID NO: 67 | Polynucleotide | Tassel preferred promoter |
| SEQ ID NO: 68 | Polynucleotide | Tassel preferred promoter |
| SEQ ID NO: 69 | Polynucleotide | Tassel preferred promoter |
| SEQ ID NO: 70 | Polynucleotide | Tassel preferred promoter |
| SEQ ID NO: 71 | Polynucleotide | Tassel preferred promoter |
| SEQ ID NO: 72 | Polynucleotide | Tassel preferred promoter |
| SEQ ID NO: 73 | Polynucleotide | Tassel preferred promoter |
| SEQ ID NO: 74 | Polynucleotide | Tassel preferred promoter |
| SEQ ID NO: 75 | Polynucleotide | Tassel preferred promoter |
| SEQ ID NO: 76 | Polynucleotide | Tassel preferred promoter |
| SEQ ID NO: 77 | Polynucleotide | Tassel preferred promoter |
| SEQ ID NO: 78 | Polynucleotide | Tassel preferred promoter |
| SEQ ID NO: 79 | Polynucleotide | Tassel preferred promoter |
| SEQ ID NO: 80 | Polynucleotide | Tassel preferred promoter |
| SEQ ID NO: 81 | Polynucleotide | Tassel preferred promoter |
| SEQ ID NO: 82 | Polynucleotide | Tassel preferred promoter |
| SEQ ID NO: 83 | Polynucleotide | Tassel preferred promoter |
| SEQ ID NO: 84 | Polynucleotide | Tassel preferred promoter |
| SEQ ID NO: 85 | Polynucleotide | Tassel preferred promoter |
| SEQ ID NO: 86 | Polynucleotide | Tassel preferred promoter |
| SEQ ID NO: 87 | Polynucleotide | Tassel preferred promoter |
| SEQ ID NO: 88 | Polynucleotide | Tassel preferred promoter |
| SEQ ID NO: 89 | Polynucleotide | Tassel preferred promoter |
| SEQ ID NO: 90 | Polynucleotide | Tassel preferred promoter |
| SEQ ID NO: 91 | Polynucleotide | Tassel preferred promoter |
| SEQ ID NO: 92 | Polynucleotide | Tassel preferred promoter |
| SEQ ID NO: 93 | Polynucleotide | Tassel preferred promoter |
| SEQ ID NO: 94 | Polynucleotide | Tassel preferred promoter |
| SEQ ID NO: 95 | Polynucleotide | Tassel preferred promoter |
| SEQ ID NO: 96 | Polynucleotide | Tassel preferred promoter |
| SEQ ID NO: 97 | Polynucleotide | Tassel preferred promoter |
| SEQ ID NO: 98 | Polynucleotide | Tassel preferred promoter |
| SEQ ID NO: 99 | Polynucleotide | Tassel preferred promoter |
| SEQ ID NO: 100 | Polynucleotide | Tassel preferred promoter |
| SEQ ID NO: 101 | Polynucleotide | Tassel preferred promoter |
| SEQ ID NO: 102 | Polynucleotide | Tassel preferred promoter |
| SEQ ID NO: 103 | Polynucleotide | Tassel preferred promoter |
| SEQ ID NO: 104 | Polynucleotide | Tassel preferred promoter |
| SEQ ID NO: 105 | Polynucleotide | Tassel preferred promoter |
| SEQ ID NO: 106 | Polynucleotide | Tassel preferred promoter |
| SEQ ID NO: 156 | Polypeptide | tls1 protein |
| SEQ ID NO: 108 | Polypeptide | Arabidopsis thaliana |
| SEQ ID NO: 109 | Polypeptide | Brassica napus |
| SEQ ID NO: 110 | Polypeptide | Ricinus communis |
| SEQ ID NO: 111 | Polypeptide | Ricinus communis |
| SEQ ID NO: 112 | Polypeptide | Populus trichocarpa |
| SEQ ID NO: 113 | Polypeptide | Silene latifolia |
| SEQ ID NO: 114 | Polypeptide | Lilium longiflorum |
| SEQ ID NO: 115 | Polypeptide | Lilium longiflorum |
| SEQ ID NO: 116 | Polypeptide | Lilium longiflorum |
| SEQ ID NO: 117 | Polypeptide | Oryza sativa |
| SEQ ID NO: 118 | Polypeptide | Sorghum bicolor |
| SEQ ID NO: 119 | Polypeptide | Hordeum vulgare |
| SEQ ID NO: 120 | Polypeptide | Brachypodium distachyon |

TABLE 1-continued

| SEQ ID NUMBER | POLYNUCLEO-TIDE/POLYPEPTIDE | IDENTITY |
| --- | --- | --- |
| SEQ ID NO: 121 | Polypeptide | Zea mays |
| SEQ ID NO: 122 | Polypeptide | Oryza sativa |
| SEQ ID NO: 123 | Polypeptide | Antirrhinum majus |
| SEQ ID NO: 124 | Polypeptide | Capsicum annuum |
| SEQ ID NO: 125 | Polypeptide | Solanum lycopersicum |
| SEQ ID NO: 126 | Polypeptide | Arabidopsis thaliana |
| SEQ ID NO: 127 | Polypeptide | Glycine max |
| SEQ ID NO: 128 | Polypeptide | Medicago truncatula |
| SEQ ID NO: 129 | Polypeptide | Vitis vinifera |
| SEQ ID NO: 130 | Polypeptide | Triticum sp. |

Construction of Nucleic Acids

The isolated nucleic acids of the present disclosure can be made using (a) standard recombinant methods, (b) synthetic techniques or combinations thereof. In some embodiments, the polynucleotides of the present disclosure will be cloned, amplified or otherwise constructed from a fungus or bacteria.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) Nucleic Acids Res. 15:8125) and the 5<G> 7 methyl GpppG RNA cap structure (Drummond, et al., (1985) Nucleic Acids Res. 13:7375). Negative elements include stable intramolecular 5' UTR stem-loop structures (Muesing, et al., (1987) Cell 48:691) and AUG sequences or short open reading frames preceded by an appropriate AUG in the 5' UTR (Kozak, supra, Rao, et al., (1988) Mol. and Cell. Biol. 8:284). Accordingly, the present disclosure provides 5' and/or 3' UTR regions for modulation of translation of heterologous coding sequences.

Further, the polypeptide-encoding segments of the polynucleotides of the present disclosure can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present disclosure can be analyzed statistically using commercially available software packages such as "Codon Preference" available from the University of Wisconsin Genetics Computer Group. See, Devereaux, et al., (1984) Nucleic Acids Res. 12:387-395) or MacVector 4.1 (Eastman Kodak Co., New Haven, Conn.). Thus, the present disclosure provides a codon usage frequency characteristic of the coding region of at least one of the polynucleotides of the present disclosure. The number of polynucleotides (3 nucleotides per amino acid) that can be used to determine a codon usage frequency can be any integer from 3 to the number of polynucleotides of the present disclosure as provided herein. Optionally, the polynucleotides will be full-length sequences. An exemplary number of sequences for statistical analysis can be at least 1, 5, 10, 20, 50 or 100.

Sequence Shuffling

The present disclosure provides methods for sequence shuffling using polynucleotides of the present disclosure, and compositions resulting therefrom. Sequence shuffling is described in PCT Publication Number 1996/19256. See also, Zhang, et al., (1997) Proc. Natl. Acad. Sci. USA 94:4504-9 and Zhao, et al., (1998) Nature Biotech 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation or other expression property of a gene or transgene, a replicative element, a protein-binding element or the like, such as any feature which confers a selectable or detectable property. In some embodiments, the selected characteristic will be an altered $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present disclosure further provides recombinant expression cassettes comprising a nucleic acid of the present disclosure. A nucleic acid sequence coding for the desired polynucleotide of the present disclosure, for example a cDNA or a genomic sequence encoding a polypeptide long enough to code for an active protein of the present disclosure, can be used to construct a recombinant expression cassette which can be introduced into the desired host cell. A recombinant expression cassette will typically comprise a polynucleotide of the present disclosure operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present disclosure in essentially all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of Agrobacterium tumefaciens, the Smas promoter, the cinnamyl alcohol dehydrogenase promoter (U.S. Pat. No. 5,683,439), the Nos promoter, the rubisco promoter, the GRP1-8 promoter, the 35S promoter from cauliflower mosaic virus (CaMV), as described in Odell, et al., (1985) Nature 313:810-2; rice actin (McElroy, et al., (1990) Plant Cell 163-171); ubiquitin (Christensen, et al., (1992) Plant Mol. Biol. 12:619-632 and Christensen, et al., (1992) Plant

*Mol. Biol.* 18:675-89); pEMU (Last, et al., (1991) *Theor. Appl. Genet.* 81:581-8); MAS (Velten, et al., (1984) *EMBO J.* 3:2723-30) and maize H3 histone (Lepetit, et al., (1992) *Mol. Gen. Genet.* 231:276-85 and Atanassvoa, et al., (1992) *Plant Journal* 2(3):291-300); ALS promoter, as described in PCT Application Number WO 1996/30530 and other transcription initiation regions from various plant genes known to those of skill. For the present disclosure ubiquitin is the preferred promoter for expression in monocot plants.

Alternatively, the plant promoter can direct expression of a polynucleotide of the present disclosure in a specific tissue or may be otherwise under more precise environmental or developmental control. Such promoters may be "inducible" promoters. Environmental conditions that may effect transcription by inducible promoters include pathogen attack, anaerobic conditions or the presence of light. Examples of inducible promoters are the Adh1 promoter, which is inducible by hypoxia or cold stress, the Hsp70 promoter, which is inducible by heat stress and the PPDK promoter, which is inducible by light. Diurnal promoters that are active at different times during the circadian rhythm are also known (US Patent Application Publication Number 2011/0167517, incorporated herein by reference).

Examples of promoters under developmental control include promoters that initiate transcription only, or preferentially, in certain tissues, such as leaves, roots, fruit, seeds or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The polyadenylation region can be derived from a variety of plant genes, or from T-DNA. The 3' end sequence to be added can be derived from, for example, the nopaline synthase or octopine synthase genes or alternatively from another plant gene or less preferably from any other eukaryotic gene. Examples of such regulatory elements include, but are not limited to, 3' termination and/or polyadenylation regions such as those of the *Agrobacterium tumefaciens* nopaline synthase (nos) gene (Bevan, et al., (1983) *Nucleic Acids Res.* 12:369-85); the potato proteinase inhibitor II (PINII) gene (Keil, et al., (1986) *Nucleic Acids Res.* 14:5641-50 and An, et al., (1989) *Plant Cell* 1:115-22) and the CaMV 19S gene (Mogen, et al., (1990) *Plant Cell* 2:1261-72).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, (1988) *Mol. Cell Biol.* 8:4395-4405; Callis, et al., (1987) *Genes Dev.* 1:1183-200). Such intron enhancement of gene expression is typically greatest when placed near the 5' end of the transcription unit. Use of maize introns Adh1-S intron 1, 2 and 6, the Bronze-1 intron are known in the art. See generally, *The Maize Handbook*, Chapter 116, Freeling and Walbot, eds., Springer, New York (1994).

Plant signal sequences, including, but not limited to, signal-peptide encoding DNA/RNA sequences which target proteins to the extracellular matrix of the plant cell (Dratewka-Kos, et al., (1989) *J. Biol. Chem.* 264:4896-900), such as the *Nicotiana plumbaginifolia* extension gene (DeLoose, et al., (1991) *Gene* 99:95-100); signal peptides which target proteins to the vacuole, such as the sweet potato sporamin gene (Matsuka, et al., (1991) *Proc. Natl. Acad. Sci. USA* 88:834) and the barley lectin gene (Wilkins, et al., (1990) *Plant Cell*, 2:301-13); signal peptides which cause proteins to be secreted, such as that of PRIb (Lind, et al., (1992) *Plant Mol. Biol.* 18:47-53) or the barley alpha amylase (BAA) (Rahmatullah, et al., (1989) *Plant Mol. Biol.* 12:119 and hereby incorporated by reference) or signal peptides which target proteins to the plastids such as that of rapeseed enoyl-Acp reductase (Verwaert, et al., (1994) *Plant Mol. Biol.* 26:189-202) are useful in the disclosure.

The vector comprising the sequences from a polynucleotide of the present disclosure will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. Enzymol.* 153:253-77. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA*, 86:8402-6. Another useful vector herein is plasmid pBI101.2 that is available from CLONTECH Laboratories, Inc. (Palo Alto, Calif.).

Expression of Proteins in Host Cells

Using the nucleic acids of the present disclosure, one may express a protein of the present disclosure in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present disclosure. No attempt to describe in detail the various methods known for the expression of proteins in prokaryotes or eukaryotes will be made.

In brief summary, the expression of isolated nucleic acids encoding a protein of the present disclosure will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences and promoters useful for regulation of the expression of the DNA encoding a protein of the present disclosure. To obtain high level expression of a cloned gene, it is desirable to construct expression vectors which contain, at the minimum, a strong promoter, such as ubiquitin, to direct transcription, a ribosome binding site for translational initiation and a transcription/translation terminator. Constitutive promoters are classified as providing for a range of constitutive expression. Thus, some are weak constitutive promoters and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level," or about 1/10 transcripts to about 1/100 transcripts to about 1/1,000 transcripts.

One of skill would recognize that modifications could be made to a protein of the present disclosure without diminishing its biological activity. Some modifications may be made to facilitate the cloning, expression or incorporation of the targeting molecule into a fusion protein. Such modifications are well known to those of skill in the art and include, for example, a methionine added at the amino terminus to provide an initiation site or additional amino acids (e.g., poly His) placed on either terminus to create conveniently located restriction sites or termination codons or purification sequences.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198: 1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present disclosure are available using *Bacillus* sp. and *Salmonella* (Palva, et al., (1983) *Gene* 22:229-35; Mosbach, et al., (1983) *Nature* 302:543-5). The pGEX-4T-1 plasmid vector from Pharmacia is the preferred *E. coli* expression vector for the present disclosure.

Expression in Eukaryotes

A variety of eukaryotic expression systems such as yeast, insect cell lines, plant and mammalian cells, are known to those of skill in the art. As explained briefly below, the present disclosure can be expressed in these eukaryotic systems. In some embodiments, transformed/transfected plant cells, as discussed infra, are employed as expression systems for production of the proteins of the instant disclosure.

Synthesis of heterologous proteins in yeast is well known. Sherman, et al., (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase and an origin of replication, termination sequences and the like as desired.

A protein of the present disclosure, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present disclosure can also be ligated to various expression vectors for use in transfecting cell cultures of, for instance, mammalian, insect or plant origin. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present disclosure are available, for instance, from the American Type Culture Collection Catalogue of Cell Lines and Hybridomas ($7^{th}$ ed., 1992).

Appropriate vectors for expressing proteins of the present disclosure in insect cells are usually derived from the SF9 baculovirus. Suitable insect cell lines include mosquito larvae, silkworm, armyworm, moth and *Drosophila* cell lines such as a Schneider cell line (see, e.g., Schneider, (1987) *J. Embryol. Exp. Morphol.* 27:353-65).

As with yeast, when higher animal or plant host cells are employed, polyadenlyation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) *J. Virol.* 45:773-81). Additionally, gene sequences to control replication in the host cell may be incorporated into the vector such as those found in bovine papilloma virus type-vectors (Saveria-Campo, "Bovine Papilloma Virus DNA a Eukaryotic Cloning Vector," in *DNA Cloning: A Practical Approach*, vol. II, Glover, ed., IRL Press, Arlington, Va., pp. 213-38 (1985)).

In addition, the NUE gene placed in the appropriate plant expression vector can be used to transform plant cells. The polypeptide can then be isolated from plant callus or the transformed cells can be used to regenerate transgenic plants. Such transgenic plants can be harvested, and the appropriate tissues (seed or leaves, for example) can be subjected to large scale protein extraction and purification techniques.

Plant Transformation Methods

Numerous methods for introducing foreign genes into plants are known and can be used to insert an NUE polynucleotide into a plant host, including biological and physical plant transformation protocols. See, e.g., Miki et al., "Procedure for Introducing Foreign DNA into Plants," in *Methods in Plant Molecular Biology and Biotechnology*, Glick and Thompson, eds., CRC Press, Inc., Boca Raton, pp. 67-88 (1993). The methods chosen vary with the host plant and include chemical transfection methods such as calcium phosphate, microorganism-mediated gene transfer such as *Agrobacterium* (Horsch, et al., (1985) *Science* 227:1229-31), electroporation, micro-injection and biolistic bombardment.

Expression cassettes and vectors and in vitro culture methods for plant cell or tissue transformation and regeneration of plants are known and available. See, e.g., Gruber, et al., "Vectors for Plant Transformation," in *Methods in Plant Molecular Biology and Biotechnology*, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) *Biotechniques* 4:320-334 and U.S. Pat. No. 6,300,543), electroporation (Riggs, et al., (1986) *Proc. Natl. Acad. Sci. USA* 83:5602-5606, direct gene transfer (Paszkowski et al., (1984) *EMBO J.* 3:2717-2722) and ballistic particle acceleration (see, for example, Sanford, et al., U.S. Pat. No. 4,945,050; WO 1991/10725 and McCabe, et al., (1988) *Biotechnology* 6:923-926). Also see, Tomes, et al., "Direct DNA Transfer into Intact Plant Cells Via Microprojectile Bombardment". pp. 197-213 in *Plant Cell, Tissue and Organ Culture, Fundamental Methods*. eds. Gamborg and Phillips. Springer-Verlag Berlin Heidelberg New York, 1995; U.S. Pat. No. 5,736,369 (meristem); Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); WO 91/10725 (maize); Klein, et al., (1988) *Plant Physiol.* 91:440-444 (maize); Fromm, et al., (1990) *Biotechnology* 8:833-839 and Gordon-Kamm, et al., (1990) *Plant Cell* 2:603-618 (maize); Hooydaas-Van Slogteren and Hooykaas, (1984) *Nature* (London) 311:763-764; Bytebierm, et al., (1987) *Proc. Natl. Acad. Sci. USA* 84:5345-5349 (Liliaceae); De Wet, et al., (1985) In *The Experimental Manipulation of Ovule Tissues*, ed. G. P. Chapman, et al., pp. 197-209. Longman, N Y (pollen); Kaeppler, et al., (1990) *Plant Cell Reports* 9:415-418 and Kaeppler, et al., (1992) *Theor. Appl. Genet.* 84:560-566 (whisker-mediated transformation); U.S. Pat. No. 5,693,512 (sonication); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotech.* 14:745-750; *Agrobacterium* mediated maize transformation (U.S. Pat. No. 5,981,840); silicon carbide whisker methods (Frame, et al., (1994) *Plant J.* 6:941-948); laser methods (Guo, et al., (1995) *Physiologia Plantarum* 93:19-24); sonication methods (Bao, et al., (1997) *Ultrasound in Medicine & Biology* 23:953-959; Finer and Finer, (2000) *Lett Appl Microbiol.* 30:406-10; Amoah, et al., (2001) *J Exp Bot* 52:1135-42); polyethylene glycol methods (Krens, et al., (1982) *Nature* 296:72-77); protoplasts of monocot and dicot cells can be transformed using electroporation (Fromm, et al., (1985) *Proc. Natl. Acad. Sci. USA* 82:5824-5828) and microinjection (Crossway, et al., (1986) *Mol. Gen. Genet.* 202:179-185), all of which are herein incorporated by reference.

*Agrobacterium*-Mediated Transformation

The most widely utilized method for introducing an expression vector into plants is based on the natural transformation system of *Agrobacterium*. *A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) *Crit. Rev. Plant Sci.* 10:1. Descriptions of the *Agrobacterium* vector systems and methods for *Agrobacterium*-mediated gene transfer are provided in Gruber, et al., supra; Miki, et al., supra and Moloney, et al., (1989) *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) *Science* 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993 and Simpson, et al., (1986) *Plant Mol. Biol.* 6:403-15 (also referenced in the '306 patent), all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. Several other transgenic plants are also contemplated by the present disclosure including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledonous plants, some gymnosperms and a few monocotyledonous plants (e.g., certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. EP Patent Application Number 604 662 A1 discloses a method for transforming monocots using *Agrobacterium*. EP Patent Application Number 672 752 A1 discloses a method for transforming monocots with *Agrobacterium* using the scutellum of immature embryos. Ishida, et al., discuss a method for transforming maize by exposing immature embryos to *A. tumefaciens* (*Nature Biotechnology* 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) *Theor. Appl. Genet.* 69:235-40; U.S. Pat. No. 4,658,082; Simpson, et al., supra and U.S. patent application Ser. Nos. 913,913 and 913,914, both filed Oct. 1, 1986, as referenced in U.S. Pat. No. 5,262,306, issued Nov. 16, 1993, the entire disclosures therein incorporated herein by reference.

Direct Gene Transfer

Despite the fact that the host range for *Agrobacterium*-mediated transformation is broad, some major cereal crop species and gymnosperms have generally been recalcitrant to this mode of gene transfer, even though some success has recently been achieved in rice (Hiei, et al., (1994) *The Plant Journal* 6:271-82). Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) *Part. Sci. Technol.* 5:27; Sanford, (1988) *Trends Biotech* 6:299; Sanford, (1990) *Physiol. Plant* 79:206 and Klein, et al., (1992) *Biotechnology* 10:268).

Another method for physical delivery of DNA to plants is sonication of target cells as described in Zang, et al., (1991) *BioTechnology* 9:996. Alternatively, liposome or spheroplast fusions have been used to introduce expression vectors into plants. See, e.g., Deshayes, et al., (1985) *EMBO J.* 4:2731 and Christou, et al., (1987) *Proc. Natl. Acad. Sci. USA* 84:3962. Direct uptake of DNA into protoplasts using $CaCl_2$ precipitation, polyvinyl alcohol, or poly-L-ornithine has also been reported. See, e.g., Hain, et al., (1985) *Mol. Gen. Genet.* 199:161 and Draper, et al., (1982) *Plant Cell Physiol.* 23:451.

Electroporation of protoplasts and whole cells and tissues has also been described. See, e.g., Donn, et al., (1990) Abstracts of the *VIIth Int'l. Congress on Plant Cell and Tissue Culture IAPTC*, A2-38, p. 53; D'Halluin, et al., (1992) *Plant Cell* 4:1495-505 and Spencer, et al., (1994) *Plant Mol. Biol.* 24:51-61.

Reducing the Activity and/or Level of a Polypeptide

Methods are provided to reduce or eliminate the activity of a polypeptide of the disclosure by transforming a plant cell with an expression cassette that expresses a polynucleotide that inhibits the expression of the polypeptide. The polynucleotide may inhibit the expression of the polypeptide directly, by preventing transcription or translation of the messenger RNA, or indirectly, by encoding a polypeptide that inhibits the transcription or translation of a gene encoding polypeptide. Methods for inhibiting or eliminating the expression of a gene in a plant are well known in the art and any such method may be used in the present disclosure to inhibit the expression of polypeptide.

In accordance with the present disclosure, the expression of polypeptide is inhibited if the protein level of the polypeptide is less than 70% of the protein level of the same polypeptide in a plant that has not been genetically modified or mutagenized to inhibit the expression of that polypeptide. In particular embodiments of the disclosure, the protein level of the polypeptide in a modified plant according to the disclosure is less than 60%, less than 50%, less than 40%, less than 30%, less than 20%, less than 10%, less than 5% or less than 2% of the protein level of the same polypeptide in a plant that is not a mutant or that has not been genetically modified to inhibit the expression of that polypeptide. The expression level of the polypeptide may be measured directly, for example, by assaying for the level of polypeptide expressed in the plant cell or plant, or indirectly, for example, by measuring the nitrogen uptake activity of the polypeptide in the plant cell or plant or by measuring the phenotypic changes in the plant. Methods for performing such assays are described elsewhere herein.

In other embodiments of the disclosure, the activity of the polypeptides is reduced or eliminated by transforming a plant cell with an expression cassette comprising a polynucleotide encoding a polypeptide that inhibits the activity of a polypeptide. The enhanced nitrogen utilization activity of a polypeptide is inhibited according to the present disclosure if the activity of the polypeptide is less than 70% of the activity of the same polypeptide in a plant that has not been modified to inhibit the activity of that polypeptide. In particular embodiments of the disclosure, the activity of the polypeptide in a modified plant according to the disclosure is less than 60%, less than 50%, less than 40%, less than 30%, less than 20%, less than 10% or less than 5% of the activity of the same polypeptide in a plant that that has not been modified to inhibit the expression of that polypeptide. The activity of a polypeptide is "eliminated" according to the disclosure when it is not detectable by the assay methods described elsewhere herein. Methods of determining the alteration of nitrogen utilization activity of a polypeptide are described elsewhere herein.

In other embodiments, the activity of a polypeptide may be reduced or eliminated by disrupting the gene encoding the polypeptide. The disclosure encompasses mutagenized plants that carry mutations in genes, where the mutations reduce expression of the gene or inhibit the nitrogen utilization activity of the encoded polypeptide.

Thus, many methods may be used to reduce or eliminate the activity of a polypeptide. In addition, more than one method may be used to reduce the activity of a single polypeptide.

1. Polynucleotide-Based Methods:

In some embodiments of the present disclosure, a plant is transformed with an expression cassette that is capable of expressing a polynucleotide that inhibits the expression of a polypeptide of the disclosure. The term "expression" as used herein refers to the biosynthesis of a gene product, including the transcription and/or translation of said gene product. For example, for the purposes of the present disclosure, an expression cassette capable of expressing a polynucleotide that inhibits the expression of at least one polypeptide is an expression cassette capable of producing an RNA molecule that inhibits the transcription and/or translation of at least one polypeptide of the disclosure. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a polypeptide are given below.

i. Sense Suppression/Cosuppression

In some embodiments of the disclosure, inhibition of the expression of a polypeptide may be obtained by sense suppression or cosuppression. For cosuppression, an expression cassette is designed to express an RNA molecule corresponding to all or part of a messenger RNA encoding a polypeptide in the "sense" orientation. Over expression of the RNA molecule can result in reduced expression of the native gene. Accordingly, multiple plant lines transformed with the cosuppression expression cassette are screened to identify those that show the desired degree of inhibition of polypeptide expression.

The polynucleotide used for cosuppression may correspond to all or part of the sequence encoding the polypeptide, all or part of the 5' and/or 3' untranslated region of a polypeptide transcript or all or part of both the coding sequence and the untranslated regions of a transcript encoding a polypeptide. In some embodiments where the polynucleotide comprises all or part of the coding region for the polypeptide, the expression cassette is designed to eliminate the start codon of the polynucleotide so that no protein product will be translated.

Cosuppression may be used to inhibit the expression of plant genes to produce plants having undetectable protein levels for the proteins encoded by these genes. See, for example, Broin, et al., (2002) *Plant Cell* 14:1417-1432. Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington, (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763 and U.S. Pat. Nos. 5,034,323, 5,283,184 and 5,942,657, each of which is herein incorporated by reference. The efficiency of cosuppression may be increased by including a poly-dT region in the expression cassette at a position 3' to the sense sequence and 5' of the polyadenylation signal. See, US Patent Application Publication Number 2002/0048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See U.S. Pat. Nos. 5,283,184 and 5,034,323, herein incorporated by reference.

ii. Antisense Suppression

In some embodiments of the disclosure, inhibition of the expression of the polypeptide may be obtained by antisense suppression. For antisense suppression, the expression cassette is designed to express an RNA molecule complementary to all or part of a messenger RNA encoding the polypeptide. Over expression of the antisense RNA molecule can result in reduced expression of the target gene. Accordingly, multiple plant lines transformed with the antisense suppression expression cassette are screened to identify those that show the desired degree of inhibition of polypeptide expression.

The polynucleotide for use in antisense suppression may correspond to all or part of the complement of the sequence encoding the polypeptide, all or part of the complement of the 5' and/or 3' untranslated region of the target transcript or all or part of the complement of both the coding sequence and the untranslated regions of a transcript encoding the polypeptide. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, US Patent Application Publication Number 2002/0048814, herein incorporated by reference.

iii. Double-Stranded RNA Interference

In some embodiments of the disclosure, inhibition of the expression of a polypeptide may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the desired degree of inhibition of polypeptide expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743 and WO 1999/49029, WO 1999/53050, WO 1999/61631 and WO 2000/49035, each of which is herein incorporated by reference.

iv. Hairpin RNA Interference and Intron-Containing Hairpin RNA Interference

In some embodiments of the disclosure, inhibition of the expression of a polypeptide may be obtained by hairpin RNA (hpRNA) interference or intron-containing hairpin RNA (ihpRNA) interference. These methods are highly efficient at inhibiting the expression of endogenous genes. See, Waterhouse and Helliwell, (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Alternatively, the base-paired stem region may correspond to a portion of a promoter sequence controlling expression of the gene whose expression is to be inhibited. Thus, the base-paired stem region of the molecule generally determines the specificity of the RNA interference. hpRNA molecules are highly efficient at inhibiting the expression of endogenous genes and the RNA interference they induce is inherited by subsequent generations of plants. See, for example, Chuang and Meyerowitz, (2000) *Proc. Natl. Acad. Sci. USA* 97:4985-4990; Stoutjesdijk, et al., (2002) *Plant Physiol.* 129:1723-1731 and Waterhouse and Helliwell, (2003) *Nat. Rev. Genet.* 4:29-38. Methods for using hpRNA interference to inhibit or silence the expression of genes are described, for example, in Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini et al., *BMC Biotechnology* 3:7 and US Patent Application Publication Number 2003/0175965, each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse, (2001) *Curr. Opin. Plant Biol.* 5:146-150; Waterhouse and Helliwell, (2003) *Nat. Rev. Genet.* 4:29-38; Helliwell and Waterhouse, (2003) *Methods* 30:289-295 and US Patent Application Publication Number 2003/0180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 2002/00904; Mette, et al., (2000) *EMBO J* 19:5194-5201; Matzke, et al., (2001) *Curr. Opin. Genet. Devel.* 11:221-227; Scheid, et al., (2002) *Proc. Natl. Acad. Sci., USA* 99:13659-13662; Aufsaftz, et al., (2002) *Proc. Nat'l. Acad. Sci.* 99(4):16499-16506; Sijen, et al., *Curr. Biol.* (2001) 11:436-440), herein incorporated by reference.

v. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the polypeptide). Methods of using amplicons to inhibit the expression of endogenous plant genes are described, for example, in Angell and Baulcombe, (1997) *EMBO J.* 16:3675-3684, Angell and Baulcombe, (1999) *Plant J.* 20:357-362 and U.S. Pat. No. 6,646,805, each of which is herein incorporated by reference.

vi. Ribozymes

In some embodiments, the polynucleotide expressed by the expression cassette of the disclosure is catalytic RNA or has ribozyme activity specific for the messenger RNA of the polypeptide. Thus, the polynucleotide causes the degradation of the endogenous messenger RNA, resulting in reduced expression of the polypeptide. This method is described, for example, in U.S. Pat. No. 4,987,071, herein incorporated by reference.

vii. Small Interfering RNA or Micro RNA

In some embodiments of the disclosure, inhibition of the expression of a polypeptide may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier, et al., (2003) *Nature* 425:257-263, herein incorporated by reference.

For miRNA interference, the expression cassette is designed to express an RNA molecule that is modeled on an endogenous miRNA gene. For example, the miRNA gene encodes an RNA that forms a hairpin structure containing a 22-nucleotide sequence that is complementary to another endogenous gene (target sequence). For suppression of NUE expression, the 22-nucleotide sequence is selected from a NUE transcript sequence and contains 22 nucleotides of said NUE sequence in sense orientation and 21 nucleotides of a corresponding antisense sequence that is complementary to the sense sequence. A fertility gene, whether endogenous or exogenous, may be an miRNA target. miRNA molecules are highly efficient at inhibiting the expression of endogenous genes, and the RNA interference they induce is inherited by subsequent generations of plants.

2. Polypeptide-Based Inhibition of Gene Expression

In one embodiment, the polynucleotide encodes a zinc finger protein that binds to a gene encoding a polypeptide, resulting in reduced expression of the gene. In particular embodiments, the zinc finger protein binds to a regulatory region of a NUE gene. In other embodiments, the zinc finger protein binds to a messenger RNA encoding a polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US Patent Application Publication Number 2003/0037355, each of which is herein incorporated by reference.

3. Polypeptide-Based Inhibition of Protein Activity

In some embodiments of the disclosure, the polynucleotide encodes an antibody that binds to at least one polypeptide and reduces the enhanced nitrogen utilization activity of the polypeptide. In another embodiment, the binding of the antibody results in increased turnover of the antibody-NUE complex by cellular quality control mechanisms. The expression of antibodies in plant cells and the inhibition of molecular pathways by expression and binding of antibodies to proteins in plant cells are well known in the art. See, for example, Conrad and Sonnewald, (2003) *Nature Biotech.* 21:35-36, incorporated herein by reference.

4. Gene Disruption

In some embodiments of the present disclosure, the activity of a polypeptide is reduced or eliminated by disrupting the gene encoding the polypeptide. The gene encoding the polypeptide may be disrupted by any method known in the art. For example, in one embodiment, the gene is disrupted by transposon tagging. In another embodiment, the gene is disrupted by mutagenizing plants using random or targeted mutagenesis and selecting for plants that have reduced nitrogen utilization activity.

i. Transposon Tagging

In one embodiment of the disclosure, transposon tagging is used to reduce or eliminate the activity of one or more polypeptide. Transposon tagging comprises inserting a transposon within an endogenous NUE gene to reduce or eliminate expression of the polypeptide. "NUE gene" is intended to mean the gene that encodes a polypeptide according to the disclosure.

In this embodiment, the expression of one or more polypeptide is reduced or eliminated by inserting a transposon within a regulatory region or coding region of the gene encoding the polypeptide. A transposon that is within an exon, intron, 5' or 3' untranslated sequence, a promoter or any other regulatory sequence of a NUE gene may be used to reduce or eliminate the expression and/or activity of the encoded polypeptide.

Methods for the transposon tagging of specific genes in plants are well known in the art. See, for example, Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928). In addition, the TUSC process for selecting Mu insertions in selected genes has been described in Bensen, et al., (1995) *Plant Cell* 7:75-84; Mena, et al., (1996) *Science* 274:1537-1540 and U.S. Pat. No. 5,962,764, each of which is herein incorporated by reference.

ii. Mutant Plants with Reduced Activity

Additional methods for decreasing or eliminating the expression of endogenous genes in plants are also known in the art and can be similarly applied to the instant disclosure. These methods include other forms of mutagenesis, such as ethyl methanesulfonate-induced mutagenesis, deletion mutagenesis and fast neutron deletion mutagenesis used in a reverse genetics sense (with PCR) to identify plant lines in which the endogenous gene has been deleted. For examples of these methods see, Ohshima, et al., (1998) *Virology* 243:472-481; Okubara, et al., (1994) *Genetics* 137:867-874 and Quesada, et al., (2000) *Genetics* 154:421-436, each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant disclosure. See, McCallum, et al., (2000) *Nat. Biotechnol.* 18:455-457, herein incorporated by reference.

Mutations that impact gene expression or that interfere with the function (enhanced nitrogen utilization activity) of the encoded protein are well known in the art. Insertional mutations in gene exons usually result in null-mutants. Mutations in conserved residues are particularly effective in inhibiting the activity of the encoded protein. Conserved residues of plant polypeptides suitable for mutagenesis with the goal to eliminate activity have been described. Such mutants can be isolated according to well-known procedures and mutations in different NUE loci can be stacked by genetic crossing. See, for example, Gruis, et al., (2002) *Plant Cell* 14:2863-2882.

In another embodiment of this disclosure, dominant mutants can be used to trigger RNA silencing due to gene inversion and recombination of a duplicated gene locus. See, for example, Kusaba, et al., (2003) *Plant Cell* 15:1455-1467.

The disclosure encompasses additional methods for reducing or eliminating the activity of one or more polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984, each of which are herein incorporated by reference. See also, WO 1998/49350, WO 1999/07865, WO 1999/25821 and Beetham, et al., (1999) *Proc. Natl. Acad. Sci. USA* 96:8774-8778, each of which is herein incorporated by reference.

iii. Modulating Nitrogen Utilization Activity

In specific methods, the level and/or activity of a NUE regulator in a plant is decreased by increasing the level or activity of the polypeptide in the plant. The increased expression of a negative regulatory molecule may decrease the level of expression of downstream one or more genes responsible for an improved NUE phenotype.

Methods for increasing the level and/or activity of polypeptides in a plant are discussed elsewhere herein. Briefly, such methods comprise providing a polypeptide of the disclosure to a plant and thereby increasing the level and/or activity of the polypeptide. In other embodiments, a NUE nucleotide sequence encoding a polypeptide can be provided by introducing into the plant a polynucleotide comprising a NUE nucleotide sequence of the disclosure, expressing the NUE sequence, increasing the activity of the polypeptide and thereby decreasing the number of tissue cells in the plant or plant part. In other embodiments, the NUE nucleotide construct introduced into the plant is stably incorporated into the genome of the plant.

In other methods, the growth of a plant tissue is increased by decreasing the level and/or activity of the polypeptide in the plant. Such methods are disclosed in detail elsewhere herein. In one such method, a NUE nucleotide sequence is introduced into the plant and expression of said NUE nucleotide sequence decreases the activity of the polypeptide and thereby increasing the tissue growth in the plant or plant part. In other embodiments, the NUE nucleotide construct introduced into the plant is stably incorporated into the genome of the plant.

As discussed above, one of skill will recognize the appropriate promoter to use to modulate the level/activity of a NUE in the plant. Exemplary promoters for this embodiment have been disclosed elsewhere herein.

In other embodiments, such plants have stably incorporated into their genome a nucleic acid molecule comprising a NUE nucleotide sequence of the disclosure operably linked to a promoter that drives expression in the plant cell.

iv. Modulating Root Development

Methods for modulating root development in a plant are provided. By "modulating root development" is intended any alteration in the development of the plant root when compared to a control plant. Such alterations in root development include, but are not limited to, alterations in the growth rate of the primary root, the fresh root weight, the extent of lateral and adventitious root formation, the vasculature system, meristem development or radial expansion.

Methods for modulating root development in a plant are provided. The methods comprise modulating the level and/or activity of the polypeptide in the plant. In one method, a NUE sequence of the disclosure is provided to the plant. In another method, the NUE nucleotide sequence is provided by introducing into the plant a polynucleotide comprising a NUE nucleotide sequence of the disclosure, expressing the NUE sequence and thereby modifying root development. In still other methods, the NUE nucleotide construct introduced into the plant is stably incorporated into the genome of the plant.

In other methods, root development is modulated by altering the level or activity of the polypeptide in the plant. A change in activity can result in at least one or more of the following alterations to root development, including, but not limited to, alterations in root biomass and length.

As used herein, "root growth" encompasses all aspects of growth of the different parts that make up the root system at different stages of its development in both monocotyledonous and dicotyledonous plants. It is to be understood that enhanced root growth can result from enhanced growth of one or more of its parts including the primary root, lateral roots, adventitious roots, etc.

Methods of measuring such developmental alterations in the root system are known in the art. See, for example, US Patent Application Publication Number 2003/0074698 and Werner, et al., (2001) *PNAS* 18:10487-10492, both of which are herein incorporated by reference.

As discussed above, one of skill will recognize the appropriate promoter to use to modulate root development in the plant. Exemplary promoters for this embodiment include constitutive promoters and root-preferred promoters. Exemplary root-preferred promoters have been disclosed elsewhere herein.

Stimulating root growth and increasing root mass by decreasing the activity and/or level of the polypeptide also finds use in improving the standability of a plant. The term "resistance to lodging" or "standability" refers to the ability of a plant to fix itself to the soil. For plants with an erect or semi-erect growth habit, this term also refers to the ability to maintain an upright position under adverse (environmental) conditions. This trait relates to the size, depth and morphology of the root system. In addition, stimulating root growth and increasing root mass by altering the level and/or activity of the polypeptide also finds use in promoting in vitro propagation of explants.

Furthermore, higher root biomass production due to activity has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

Accordingly, the present disclosure further provides plants having modulated root development when compared to the root development of a control plant. In some embodiments, the plant of the disclosure has an increased level/activity of the polypeptide of the disclosure and has enhanced root growth and/or root biomass. In other embodiments, such plants have stably incorporated into their genome a nucleic acid molecule comprising a NUE nucleotide sequence of the disclosure operably linked to a promoter that drives expression in the plant cell.

v. Modulating Shoot and Leaf Development

Methods are also provided for modulating shoot and leaf development in a plant. By "modulating shoot and/or leaf development" is intended any alteration in the development of the plant shoot and/or leaf. Such alterations in shoot and/or leaf development include, but are not limited to, alterations in shoot meristem development, in leaf number, leaf size, leaf and stem vasculature, internode length and leaf senescence. As used herein, "leaf development" and "shoot development" encompasses all aspects of growth of the different parts that make up the leaf system and the shoot system, respectively, at different stages of their development, both in monocotyledonous and dicotyledonous plants. Methods for measuring such developmental alterations in the shoot and leaf system are known in the art. See, for example, Werner, et al., (2001) *PNAS* 98:10487-10492 and US Patent Application Publication Number 2003/0074698, each of which is herein incorporated by reference.

The method for modulating shoot and/or leaf development in a plant comprises modulating the activity and/or level of a polypeptide of the disclosure. In one embodiment, a NUE sequence of the disclosure is provided. In other embodiments, the NUE nucleotide sequence can be provided by introducing into the plant a polynucleotide comprising a NUE nucleotide sequence of the disclosure, expressing the NUE sequence and thereby modifying shoot and/or leaf development. In other embodiments, the NUE nucleotide construct introduced into the plant is stably incorporated into the genome of the plant.

In specific embodiments, shoot or leaf development is modulated by altering the level and/or activity of the polypeptide in the plant. A change in activity can result in at least one or more of the following alterations in shoot and/or leaf development, including, but not limited to, changes in leaf number, altered leaf surface, altered vasculature, internodes and plant growth and alterations in leaf senescence when compared to a control plant.

As discussed above, one of skill will recognize the appropriate promoter to use to modulate shoot and leaf development of the plant. Exemplary promoters for this embodiment include constitutive promoters, shoot-preferred promoters, shoot meristem-preferred promoters and leaf-preferred promoters. Exemplary promoters have been disclosed elsewhere herein.

Increasing activity and/or level in a plant results in altered internodes and growth. Thus, the methods of the disclosure find use in producing modified plants. In addition, as discussed above, activity in the plant modulates both root and shoot growth. Thus, the present disclosure further provides methods for altering the root/shoot ratio. Shoot or leaf development can further be modulated by altering the level and/or activity of the polypeptide in the plant.

Accordingly, the present disclosure further provides plants having modulated shoot and/or leaf development when compared to a control plant. In some embodiments, the plant of the disclosure has an increased level/activity of the polypeptide of the disclosure. In other embodiments, the plant of the disclosure has a decreased level/activity of the polypeptide of the disclosure.

vi. Modulating Reproductive Tissue Development

Methods for modulating reproductive tissue development are provided. In one embodiment, methods are provided to modulate floral development in a plant. By "modulating floral development" is intended any alteration in a structure of a plant's reproductive tissue as compared to a control plant in which the activity or level of the polypeptide has not been modulated. "Modulating floral development" further includes any alteration in the timing of the development of a plant's reproductive tissue (i.e., a delayed or an accelerated timing of floral development) when compared to a control plant in which the activity or level of the polypeptide has not been modulated. Macroscopic alterations may include changes in size, shape, number or location of reproductive organs, the developmental time period that these structures form or the ability to maintain or proceed through the flowering process in times of environmental stress. Microscopic alterations may include changes to the types or shapes of cells that make up the reproductive organs.

The method for modulating floral development in a plant comprises modulating activity in a plant. In one method, a NUE sequence of the disclosure is provided. A NUE nucleotide sequence can be provided by introducing into the plant a polynucleotide comprising a NUE nucleotide sequence of the disclosure, expressing the NUE sequence and thereby modifying floral development. In other embodiments, the NUE nucleotide construct introduced into the plant is stably incorporated into the genome of the plant.

In specific methods, floral development is modulated by increasing the level or activity of the polypeptide in the plant. A change in activity can result in at least one or more of the following alterations in floral development, including, but not limited to, altered flowering, changed number of flowers, modified male sterility and altered seed set, when compared to a control plant. Inducing delayed flowering or inhibiting flowering can be used to enhance yield in forage crops such as alfalfa. Methods for measuring such developmental alterations in floral development are known in the art. See, for example, Mouradov, et al., (2002) *The Plant Cell* S111-S130, herein incorporated by reference.

As discussed above, one of skill will recognize the appropriate promoter to use to modulate floral development of the plant. Exemplary promoters for this embodiment include constitutive promoters, inducible promoters, shoot-preferred promoters and inflorescence-preferred promoters.

In other methods, floral development is modulated by altering the level and/or activity of the NUE sequence of the disclosure. Such methods can comprise introducing a NUE nucleotide sequence into the plant and changing the activity of the polypeptide. In other methods, the NUE nucleotide construct introduced into the plant is stably incorporated into the genome of the plant. Altering expression of the NUE sequence of the disclosure can modulate floral development during periods of stress. Such methods are described elsewhere herein. Accordingly, the present disclosure further provides plants having modulated floral development when compared to the floral development of a control plant. Compositions include plants having an altered level/activity of the polypeptide of the disclosure and having an altered floral development. Compositions also include plants having a modified level/activity of the polypeptide of the disclosure wherein the plant maintains or proceeds through the flowering process in times of stress.

Methods are also provided for the use of the NUE sequences of the disclosure to increase seed size and/or weight. The method comprises increasing the activity of the NUE sequences in a plant or plant part, such as the seed. An increase in seed size and/or weight comprises an increased size or weight of the seed and/or an increase in the size or weight of one or more seed part including, for example, the embryo, endosperm, seed coat, aleurone or cotyledon.

As discussed above, one of skill will recognize the appropriate promoter to use to increase seed size and/or seed weight. Exemplary promoters of this embodiment include constitutive promoters, inducible promoters, seed-preferred promoters, embryo-preferred promoters and endosperm-preferred promoters.

The method for altering seed size and/or seed weight in a plant comprises increasing activity in the plant. In one embodiment, the NUE nucleotide sequence can be provided by introducing into the plant a polynucleotide comprising a NUE nucleotide sequence of the disclosure, expressing the NUE sequence and thereby decreasing seed weight and/or size. In other embodiments, the NUE nucleotide construct introduced into the plant is stably incorporated into the genome of the plant.

It is further recognized that increasing seed size and/or weight can also be accompanied by an increase in the speed of growth of seedlings or an increase in early vigor. As used herein, the term "early vigor" refers to the ability of a plant to grow rapidly during early development, and relates to the successful establishment, after germination, of a well-developed root system and a well-developed photosynthetic apparatus. In addition, an increase in seed size and/or weight can also result in an increase in plant yield when compared to a control.

Accordingly, the present disclosure further provides plants having an increased seed weight and/or seed size when compared to a control plant. In other embodiments, plants having an increased vigor and plant yield are also provided. In some embodiments, the plant of the disclosure has a modified level/activity of the polypeptide of the disclosure and has an increased seed weight and/or seed size. In other embodiments, such plants have stably incorporated into their genome a nucleic acid molecule comprising a NUE nucleotide sequence of the disclosure operably linked to a promoter that drives expression in the plant cell.

vii. Method of Use for NUE Polynucleotide, Expression Cassettes, and Additional Polynucleotides The nucleotides, expression cassettes and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics and commercial products. Genes of interest include, generally, those involved in oil, starch, carbohydrate or nutrient metabolism as well as those affecting kernel size, sucrose loading and the like.

In certain embodiments the nucleic acid sequences of the present disclosure can be used in combination ("stacked") with other polynucleotide sequences of interest in order to create plants with a desired phenotype. The combinations generated can include multiple copies of any one or more of the polynucleotides of interest. The polynucleotides of the present disclosure may be stacked with any gene or combination of genes to produce plants with a variety of desired trait combinations, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165:99-106 and WO 1998/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present disclosure can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 1994/11516)); modified starches (e.g., ADPG pyrophosphorylases (AGPase), starch synthases (SS), starch branching enzymes (SBE) and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present disclosure with polynucleotides affecting agronomic traits such as male sterility (e.g., see, U.S. Pat. No. 5,583,210), stalk strength, flowering time or transformation technology traits such as cell cycle regulation or gene targeting (e.g., WO 1999/61619; WO 2000/17364; WO 1999/25821), the disclosures of which are herein incorporated by reference.

Transgenic plants comprising or derived from plant cells or native plants with reduced male fertility of this disclosure can be further enhanced with stacked traits, e.g., a crop plant having an enhanced trait resulting from expression of DNA disclosed herein in combination with herbicide tolerance and/or pest resistance traits. For example, plants with reduced male fertility can be stacked with other traits of agronomic interest, such as a trait providing herbicide resistance and/or insect resistance, such as using a gene from *Bacillus thuringensis* to provide resistance against one or more of lepidopteran, coliopteran, homopteran, hemiopteran and other insects. Known genes that confer tolerance to herbicides such as e.g., auxin, HPPD, glyphosate, dicamba, glufosinate, sulfonylurea, bromoxynil and norflurazon herbicides can be stacked either as a molecular stack or a breeding stack with plants expressing the traits disclosed herein. Polynucleotide molecules encoding proteins involved in herbicide tolerance include, but are not limited to, a polynucleotide molecule encoding 5-enolpyruvylshikimate-3-phosphate synthase (EPSPS) disclosed in U.S. Pat. Nos. 39,247; 6,566,587 and for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Pat. Nos. 7,622,641; 7,462,481; 7,531,339; 7,527,955; 7,709,709; 7,714,188 and 7,666,643, also for providing glyphosate tolerance; dicamba monooxygenase disclosed in U.S. Pat. No. 7,022,896 and WO 2007/146706 A2 for providing dicamba tolerance; a polynucleotide molecule encoding AAD12 disclosed in US Patent Application Publication Number 2005/731044 or WO 2007/053482 A2 or encoding AAD1 disclosed in US Patent Application Publication Number 2011/0124503 A1 or U.S. Pat. No. 7,838,733 for providing tolerance to auxin herbicides (2,4-D); a polynucleotide molecule encoding hydroxyphenylpyruvate dioxygenase (HPPD) for providing tolerance to HPPD inhibitors (e.g., hydroxyphenylpyruvate dioxygenase) disclosed in e.g., U.S. Pat. No. 7,935,869; US Patent Application Publication Numbers 2009/0055976 A1 and 2011/0023180 A1, each publication is herein incorporated by reference in its entirety.

Other examples of herbicide-tolerance traits that could be combined with the traits disclosed herein include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616 and 5,879,903. Plants containing an exogenous phosphinothricin acetyltransferase can exhibit improved tolerance to glufosinate herbicides, which inhibit the enzyme glutamine synthase. Other examples of herbicide-tolerance traits include those conferred by polynucleotides conferring altered protoporphyrinogen oxidase (protox) activity, as described in U.S. Pat. Nos. 6,288,306 B1; 6,282,837 B1 and 5,767,373 and international publication WO 2001/12825. Plants containing such polynucleotides can exhibit improved tolerance to any of a variety of herbicides which target the protox enzyme (also referred to as "protox inhibitors")

In one embodiment, sequences of interest improve plant growth and/or crop yields. For example, sequences of interest include agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias, et al., (1996) *Plant Cell* 8:1533-44); AKT1, a component of the potassium uptake apparatus in *Arabidopsis*, (Spalding, et al., (1999) *J Gen Physiol* 113:909-18); RML genes which activate cell division cycle in the root apical cells (Cheng, et al., (1995) *Plant Physiol* 108:881); maize glutamine synthetase genes (Sukanya, et al., (1994) *Plant Mol Biol* 26:1935-46) and hemoglobin (Duff, et al., (1997) *J. Biol. Chem* 27:16749-16752, Arredondo-Peter, et al., (1997) *Plant Physiol.* 115:1259-1266; Arredondo-Peter, et al., (1997) *Plant Physiol* 114:493-500 and references sited therein). The sequence of interest may also be useful in expressing antisense nucleotide sequences of genes that that negatively affects root development.

Additional, agronomically important traits such as oil, starch and protein content can be genetically altered in addition to using traditional breeding methods. Modifications include increasing content of oleic acid, saturated and unsaturated oils, increasing levels of lysine and sulfur, providing essential amino acids and also modification of starch. Hordothionin protein modifications are described in U.S. Pat. Nos. 5,703,049, 5,885,801, 5,885,802 and 5,990,389, herein incorporated by reference. Another example is lysine and/or sulfur rich seed protein encoded by the soybean 2S albumin described in U.S. Pat. No. 5,850,016 and the chymotrypsin inhibitor from barley described in Williamson, et al., (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. patent application Ser. No. 08/740,682, filed Nov. 1, 1996, and WO 1998/20133, the disclosures of which are herein incorporated by reference. Other proteins include methionine-rich plant proteins such as from sunflower seed (Lilley, et al., (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen, et al., (1986) *J. Biol. Chem.* 261:6279; Kirihara, et al., (1988) *Gene* 71:359, both of which are herein incorporated by reference) and rice (Musumura, et al., (1989) *Plant Mol. Biol.* 12:123, herein incorporated by reference). Other agronomically important genes encode latex, Floury 2, growth factors, seed storage factors and transcription factors.

Insect resistance genes may encode resistance to pests that have great yield drag such as rootworm, cutworm, European Corn Borer and the like. Such genes include, for example, *Bacillus thuringiensis* toxic protein genes (U.S. Pat. Nos. 5,366,892; 5,747,450; 5,736,514; 5,723,756; 5,593,881 and Geiser, et al., (1986) *Gene* 48:109) and the like.

Genes encoding disease resistance traits include detoxification genes, such as against fumonosin (U.S. Pat. No. 5,792,931); avirulence (avr) and disease resistance (R) genes (Jones, et al., (1994) *Science* 266:789; Martin, et al., (1993) *Science* 262:1432 and Mindrinos, et al., (1994) *Cell* 78:1089) and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802 and 5,990,389.

Commercial traits can also be encoded on a gene or genes that could increase for example, starch for ethanol production or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase) and acetoacetyl-CoA reductase (see, Schubert, et al., (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones and the like. The level of proteins, particularly modified proteins having improved amino acid distribution to improve the nutrient value of the plant, can be increased. This is achieved by the expression of such proteins having enhanced amino acid content.

The promoter, which is operably linked to the nucleotide sequence, can be any promoter that is active in plant cells, particularly a promoter that is active (or can be activated) in reproductive tissues of a plant (e.g., stamens or ovaries). As such, the promoter can be, for example, a constitutively active promoter, an inducible promoter, a tissue-specific promoter or a developmental stage specific promoter. Also, the promoter of the first exogenous nucleic acid molecule can be the same as or different from the promoter of the second exogenous nucleic acid molecule.

In general, a promoter is selected based, for example, on whether endogenous fertility genes to be inhibited are male fertility genes or female fertility genes. Thus, where the endogenous genes to be inhibited are male fertility genes (e.g., a BS7 gene and an SB200 gene), the promoter can be a stamen specific and/or pollen specific promoter such as an MS45 gene promoter (U.S. Pat. No. 6,037,523), a 5126 gene promoter (U.S. Pat. No. 5,837,851), a BS7 gene promoter (WO 2002/063021), an SB200 gene promoter (WO 2002/26789), a TA29 gene promoter (*Nature* 347:737 (1990)), a PG47 gene promoter (U.S. Pat. No. 5,412,085; U.S. Pat. No. 5,545,546; *Plant J* 3(2):261-271 (1993)) an SGB6 gene promoter (U.S. Pat. No. 5,470,359) a G9 gene promoter (U.S. Pat. Nos. 5,837,850 and 5,589,610) or the like, such that the hpRNA is expressed in anther and/or pollen or in tissues that give rise to anther cells and/or pollen, thereby reducing or inhibiting expression of the endogenous male fertility genes (i.e., inactivating the endogenous male fertility genes). In comparison, where the endogenous genes to be inhibited are female fertility genes, the promoter can be an ovary specific promoter, for example. However, as disclosed herein, any promoter can be used that directs expression in the tissue of interest, including, for example, a constitutively active promoter such as an ubiquitin promoter, which generally effects transcription in most or all plant cells.

Genome Editing and Induced Mutagenesis

In general, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" meganucleases produced to modify plant genomes (see, e.g., WO 2009/114321; Gao, et al., (2010) *Plant Journal* 1:176-187). Another site-directed engineering is through the use of zinc finger domain recognition coupled with the restriction properties of restriction enzyme. See, e.g., Urnov, et al., (2010) *Nat Rev Genet.* 11(9):636-46; Shukla, et al., (2009) *Nature* 459(7245):437-41.

"TILLING" or "Targeting Induced Local Lesions IN Genomics" refers to a mutagenesis technology useful to generate and/or identify and to eventually isolate mutagenised variants of a particular nucleic acid with modulated expression and/or activity (McCallum, et al., (2000), *Plant Physiology* 123:439-442; McCallum, et al., (2000) *Nature Biotechnology* 18:455-457 and Colbert, et al., (2001) *Plant Physiology* 126:480-484).

TILLING combines high density point mutations with rapid sensitive detection of the mutations. Typically, ethylmethanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes. Methods for TILLING are well known in the art (U.S. Pat. No. 8,071,840).

Other mutagenic methods can also be employed to introduce mutations in the MS44 gene. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

Embodiments of the disclosure reflect the determination that the genotype of an organism can be modified to contain dominant suppressor alleles or transgene constructs that suppress (i.e., reduce, but not ablate) the activity of a gene, wherein the phenotype of the organism is not substantially affected.

In some embodiments, the present disclosure is exemplified with respect to plant fertility and more particularly with respect to plant male fertility.

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor relative to the hybrid plants. For example, female selfed plants of maize are identified by their less vigorous appearance for vegetative and/or reproductive characteristics, including shorter plant height, small ear size, ear and kernel shape, cob color or other characteristics. Selfed lines also can be identified using molecular marker analyses (see, e.g., Smith and Wych, (1995) *Seed Sci. Technol.* 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. The present disclosure contributes to this goal, for example by providing plants that, when crossed, generate male sterile progeny, which can be used as female parental plants for generating hybrid plants.

A large number of genes have been identified as being tassel preferred in their expression pattern using traditional methods and more recent high-throughput methods. The correlation of function of these genes with important biochemical or developmental processes that ultimately lead to fertile pollen is arduous when approaches are limited to classical forward or reverse genetic mutational analysis. As disclosed herein, suppression approaches in maize provide an alternative rapid means to identify genes that are directly related to pollen development in maize. As used herein, the term "endogenous", when used in reference to a gene, means a gene that is normally present in the genome of cells of a specified organism and is present in its normal state in the cells (i.e., present in the genome in the state in which it normally is present in nature). The term "exogenous" is used herein to refer to any material that is introduced into a cell. The term "exogenous nucleic acid molecule" or "transgene" refers to any nucleic acid molecule that either is not normally present in a cell genome or is introduced into a cell. Such exogenous nucleic acid molecules generally are recombinant nucleic acid molecules, which are generated using recombinant DNA methods as disclosed herein or otherwise known in the art. In various embodiments, a transgenic non-human organism as disclosed herein, can contain, for example, a first transgene and a second transgene. Such first and second transgenes can be introduced into a cell, for example, a progenitor cell of a transgenic organism, either as individual nucleic acid molecules or as a single unit (e.g., contained in different vectors or contained in a single vector, respectively). In either case, confirmation may be made that a cell from which the transgenic organism is to be derived contains both of the transgenes using routine and well-known methods such as expression of marker genes or nucleic acid hybridization or PCR analysis. Alternatively, or additionally, confirmation of the presence of transgenes may occur later, for example, after regeneration of a plant from a putatively transformed cell.

Promoters useful for expressing a nucleic acid molecule of interest can be any of a range of naturally-occurring promoters known to be operative in plants or animals, as desired. Promoters that direct expression in cells of male or female reproductive organs of a plant are useful for generating a transgenic plant or breeding pair of plants of the disclosure. The promoters useful in the present disclosure can include constitutive promoters, which generally are active in most or all tissues of a plant; inducible promoters, which generally are inactive or exhibit a low basal level of expression and can be induced to a relatively high activity upon contact of cells with an appropriate inducing agent; tissue-specific (or tissue-preferred) promoters, which generally are expressed in only one or a few particular cell types (e.g., plant anther cells) and developmental- or stage-specific promoters, which are active only during a defined period during the growth or development of a plant. Often promoters can be modified, if necessary, to vary the expression level. Certain embodiments comprise promoters exogenous to the species being manipulated. For example, the Ms45 gene introduced into ms45ms45 maize germplasm may be driven by a promoter isolated from another plant species; a hairpin construct may then be designed to target the exogenous plant promoter, reducing the possibility of hairpin interaction with non-target, endogenous maize promoters.

Exemplary constitutive promoters include the 35S cauliflower mosaic virus (CaMV) promoter promoter (Odell, et al., (1985) *Nature* 313:810-812), the maize ubiquitin promoter (Christensen, et al., (1989) *Plant Mol. Biol.* 12:619-632 and Christensen, et al., (1992) *Plant Mol. Biol.* 18:675-689); the core promoter of the Rsyn7 promoter and other constitutive promoters disclosed in WO 1999/43838 and U.S. Pat. No. 6,072,050; rice actin (McElroy, et al., (1990) *Plant Cell* 2:163-171); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026); rice actin promoter (U.S. Pat. No. 5,641,876; WO 2000/70067), maize histone promoter (Brignon, et al., (1993) *Plant Mol Bio* 22(6):1007-1015; Rasco-Gaunt, et al., (2003) *Plant Cell Rep.* 21(6):569-576) and the like. Other constitutive promoters include, for example, those described in U.S. Pat. Nos. 5,608,144 and 6,177,611 and PCT Publication Number WO 2003/102198.

Tissue-specific, tissue-preferred or stage-specific regulatory elements further include, for example, the AGL8/FRUITFULL regulatory element, which is activated upon floral induction (Hempel, et al., (1997) *Development* 124:3845-3853); root-specific regulatory elements such as the regulatory elements from the RCP1 gene and the LRP1 gene (Tsugeki and Fedoroff, (1999) *Proc. Natl. Acad., USA* 96:12941-12946; Smith and Fedoroff, (1995) *Plant Cell* 7:735-745); flower-specific regulatory elements such as the regulatory elements from the LEAFY gene and the APETALA1 gene (Blazquez, et al., (1997) *Development* 124:3835-3844; Hempel, et al., supra, 1997); seed-specific regulatory elements such as the regulatory element from the oleosin gene (Plant, et al., (1994) *Plant Mol. Biol.* 25:193-205) and dehiscence zone specific regulatory element. Additional tissue-specific or stage-specific regulatory elements include the Zn13 promoter, which is a pollen-specific promoter (Hamilton, et al., (1992) *Plant Mol. Biol.* 18:211-218); the UNUSUAL FLORAL ORGANS (UFO) promoter, which is active in apical shoot meristem; the promoter active in shoot meristems (Atanassova, et al., (1992) *Plant J.* 2:291), the cdc2 promoter and cyc07 promoter (see, for example, Ito, et al., (1994) *Plant Mol. Biol.* 24:863-878; Martinez, et al., (1992) *Proc. Natl. Acad. Sci., USA* 89:7360); the meristematic-preferred meri-5 and H3 promoters (Medford, et al., (1991) *Plant Cell* 3:359; Terada, et al., (1993) *Plant J.* 3:241); meristematic and phloem-preferred promoters of Myb-related genes in barley (Wissenbach, et al., (1993) *Plant J.* 4:411); *Arabidopsis* cyc3aAt and cyc1At (Shaul, et al., (1996) *Proc. Natl. Acad. Sci.* 93:4868-4872); *C. roseus* cyclins CYS and CYM (Ito, et al., (1997) *Plant J.* 11:983-992); and *Nicotiana* CyclinB1 (Trehin, et al., (1997) *Plant Mol. Biol.* 35:667-672); the promoter of the APETALA3 gene, which is active in floral meristems (Jack, et al., (1994) *Cell* 76:703; Hempel, et al., supra, 1997); a promoter of an agamous-like (AGL) family member, for example, AGL8, which is active in shoot meristem upon the transition to flowering (Hempel, et al., supra, 1997); floral abscission zone promoters; L1-specific promoters; the ripening-enhanced tomato polygalacturonase promoter (Nicholass, et al., (1995) *Plant Mol. Biol.* 28:423-435), the E8 promoter (Deikman, et al., (1992) *Plant Physiol.* 100:2013-2017) and the fruit-specific 2A1 promoter, U2 and U5 snRNA promoters from maize, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, and the like. Additional tissue-specific promoters can be isolated using well known methods (see, e.g., U.S. Pat. No. 5,589,379). Shoot-preferred promoters include shoot meristem-preferred promoters such as promoters disclosed in Weigel, et al., (1992) *Cell* 69:843-859 (Accession Number M91208); Accession Number AJ131822; Accession Number Z71981; Accession Number AF049870 and shoot-preferred promoters disclosed in McAvoy, et al., (2003) *Acta Hort.* (ISHS) 625:379-385. Inflorescence-preferred promoters include the promoter of chalcone synthase (Van der Meer, et al., (1992) *Plant J.* 2(4):525-535), anther-specific LAT52 (Twell, et al., (1989) *Mol. Gen. Genet.* 217:240-245), pollen-specific Bp4 (Albani, et al., (1990) *Plant Mol Biol.* 15:605, maize pollen-specific gene Zm13 (Hamilton, et al., (1992) *Plant Mol. Biol.* 18:211-218; Guerrero, et al., (1993) *Mol. Gen. Genet.* 224:161-168), microspore-specific promoters such as the apg gene promoter (Twell, et al., (1993) *Sex. Plant Reprod.* 6:217-224) and tapetum-specific promoters such as the TA29 gene promoter (Mariani, et al., (1990) *Nature* 347:737; U.S. Pat. No. 6,372,967) and other stamen-specific promoters such as the MS45 gene promoter, 5126 gene promoter, BS7 gene promoter, PG47 gene promoter (U.S. Pat. No. 5,412,085; U.S. Pat. No. 5,545,546; *Plant J* 3(2): 261-271 (1993)), SGB6 gene promoter (U.S. Pat. No. 5,470,359), G9 gene promoter (U.S. Pat. No. 5,8937,850; U.S. Pat. No. 5,589,610), SB200 gene promoter (WO 2002/26789), or the like (see, Example 1). Tissue-preferred promoters of interest further include a sunflower pollen-expressed gene SF3 (Baltz, et al., (1992) *The Plant Journal* 2:713-721), *B. napus* pollen specific genes (Arnoldo, et al., (1992) *J. Cell. Biochem*, Abstract Number Y101204). Tissue-preferred promoters further include those reported by Yamamoto, et al., (1997) *Plant J.* 12(2):255-265 (psaDb); Kawamata, et al., (1997) *Plant Cell Physiol.* 38(7):792-803 (PsPAL1); Hansen, et al., (1997) *Mol. Gen Genet.* 254(3):337-343 (ORF13); Russell, et al., (1997) *Transgenic Res.* 6(2):157-168 (waxy or ZmGBS; 27 kDa zein, ZmZ27; osAGP; osGT1); Rinehart, et al., (1996) *Plant Physiol.* 112(3):1331-1341 (FbI2A from cotton); Van Camp, et al., (1996) *Plant Physiol.* 112(2):525-535 (*Nicotiana* SodA1 and SodA2); Canevascini, et al., (1996) *Plant Physiol.* 112(2):513-524 (*Nicotiana* ltp1); Yamamoto, et al., (1994) *Plant Cell Physiol.* 35(5):773-778 (*Pinus* cab-6 promoter); Lam, (1994) *Results Probl. Cell Differ.* 20:181-196; Orozco, et al., (1993) *Plant Mol Biol.* 23(6):1129-1138 (spinach rubisco activase (Rca)); Matsuoka, et al., (1993) *Proc Natl. Acad. Sci. USA* 90(20):9586-9590 (PPDK promoter) and Guevara-Garcia, et al., (1993) *Plant J.* 4(3):495-505 (*Agrobacterium* pmas promoter). A tissue-specific promoter that is active in cells of male or female reproductive organs can be particularly useful in certain aspects of the present disclosure.

"Seed-preferred" promoters include both "seed-developing" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message), cZ19B1 (maize 19 kDa zein), milps (myo-inositol-1-phosphate synthase); see, WO 2000/11177 and U.S. Pat. No.

6,225,529. Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 2000/12733 and U.S. Pat. No. 6,528,704, where seed-preferred promoters from end1 and end2 genes are disclosed. Additional embryo specific promoters are disclosed in Sato, et al., (1996) *Proc. Natl. Acad. Sci.* 93:8117-8122 (rice homeobox, OSH1) and Postma-Haarsma, et al., (1999) *Plant Mol. Biol.* 39:257-71 (rice KNOX genes). Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 (barley DOF); Opsahl-Ferstad, et al., (1997) *Plant J* 12:235-46 (maize Esr) and Wu, et al., (1998) *Plant Cell Physiology* 39:885-889 (rice GIuA-3, GluB-1, NRP33, RAG-1).

An inducible regulatory element is one that is capable of directly or indirectly activating transcription of one or more DNA sequences or genes in response to an inducer. The inducer can be a chemical agent such as a protein, metabolite, growth regulator, herbicide or phenolic compound or a physiological stress, such as that imposed directly by heat, cold, salt, or toxic elements or indirectly through the action of a pathogen or disease agent such as a virus or other biological or physical agent or environmental condition. A plant cell containing an inducible regulatory element may be exposed to an inducer by externally applying the inducer to the cell or plant such as by spraying, watering, heating or similar methods. An inducing agent useful for inducing expression from an inducible promoter is selected based on the particular inducible regulatory element. In response to exposure to an inducing agent, transcription from the inducible regulatory element generally is initiated de novo or is increased above a basal or constitutive level of expression. Typically the protein factor that binds specifically to an inducible regulatory element to activate transcription is present in an inactive form which is then directly or indirectly converted to the active form by the inducer. Any inducible promoter can be used in the instant disclosure (See, Ward, et al., (1993) *Plant Mol. Biol.* 22:361-366).

Examples of inducible regulatory elements include a metallothionein regulatory element, a copper-inducible regulatory element or a tetracycline-inducible regulatory element, the transcription from which can be effected in response to divalent metal ions, copper or tetracycline, respectively (Furst, et al., (1988) *Cell* 55:705-717; Mett, et al., (1993) *Proc. Natl. Acad. Sci., USA* 90:4567-4571; Gatz, et al., (1992) *Plant J.* 2:397-404; Roder, et al., (1994) *Mol. Gen. Genet.* 243:32-38). Inducible regulatory elements also include an ecdysone regulatory element or a glucocorticoid regulatory element, the transcription from which can be effected in response to ecdysone or other steroid (Christopherson, et al., (1992) *Proc. Natl. Acad. Sci., USA* 89:6314-6318; Schena, et al., (1991) *Proc. Natl. Acad. Sci. USA* 88:10421-10425; U.S. Pat. No. 6,504,082); a cold responsive regulatory element or a heat shock regulatory element, the transcription of which can be effected in response to exposure to cold or heat, respectively (Takahashi, et al., (1992) *Plant Physiol.* 99:383-390); the promoter of the alcohol dehydrogenase gene (Gerlach, et al., (1982) *PNAS USA* 79:2981-2985; Walker, et al., (1987) *PNAS* 84(19):6624-6628), inducible by anaerobic conditions; and the light-inducible promoter derived from the pea rbcS gene or pea psaDb gene (Yamamoto, et al., (1997) *Plant J.* 12(2):255-265); a light-inducible regulatory element (Feinbaum, et al., (1991) *Mol. Gen. Genet.* 226:449; Lam and Chua, (1990) *Science* 248:471; Matsuoka, et al., (1993) *Proc. Natl. Acad. Sci. USA* 90(20):9586-9590; Orozco, et al., (1993) *Plant Mol. Bio.* 23(6):1129-1138), a plant hormone inducible regulatory element (Yamaguchi-Shinozaki, et al., (1990) *Plant Mol. Biol.* 15:905; Kares, et al., (1990) *Plant Mol. Biol.* 15:225), and the like. An inducible regulatory element also can be the promoter of the maize In2-1 or In2-2 gene, which responds to benzenesulfonamide herbicide safeners (Hershey, et al., (1991) *Mol. Gen. Gene.* 227:229-237; Gatz, et al., (1994) *Mol. Gen. Genet.* 243:32-38) and the Tet repressor of transposon Tn10 (Gatz, et al., (1991) *Mol. Gen. Genet.* 227:229-237). Stress inducible promoters include salt/water stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423:324-328), ci7 (Kirch, et al., (1997) *Plant Mol Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57), rd29 (Kasuga, et al., (1999) *Nature Biotechnology* 18:287-291); osmotic inducible promoters, such as Rab17 (Vilardell, et al., (1991) *Plant Mol. Biol.* 17:985-93) and osmotin (Raghothama, et al., (1993) *Plant Mol Biol* 23:1117-28) and heat inducible promoters, such as heat shock proteins (Barros, et al., (1992) *Plant Mol.* 19:665-75; Marrs, et al., (1993) *Dev. Genet.* 14:27-41), smHSP (Waters, et al., (1996) *J. Experimental Botany* 47:325-338) and the heat-shock inducible element from the parsley ubiquitin promoter (WO 03/102198). Other stress-inducible promoters include rip2 (U.S. Pat. No. 5,332, 808 and US Patent Application Publication Number 2003/0217393) and rd29a (Yamaguchi-Shinozaki, et al., (1993) *Mol. Gen. Genetics* 236:331-340). Certain promoters are inducible by wounding, including the *Agrobacterium* pmas promoter (Guevara-Garcia, et al., (1993) *Plant J.* 4(3):495-505) and the *Agrobacterium* ORF13 promoter (Hansen, et al., (1997) *Mol. Gen. Genet.* 254(3):337-343).

Additional regulatory elements active in plant cells and useful in the methods or compositions of the disclosure include, for example, the spinach nitrite reductase gene regulatory element (Back, et al., (1991) *Plant Mol. Biol.* 17:9); a gamma zein promoter, an oleosin ole16 promoter, a globulin I promoter, an actin I promoter, an actin cI promoter, a sucrose synthetase promoter, an INOPS promoter, an EXM5 promoter, a globulin2 promoter, a b-32, ADPG-pyrophosphorylase promoter, an LtpI promoter, an Ltp2 promoter, an oleosin ole17 promoter, an oleosin ole18 promoter, an actin 2 promoter, a pollen-specific protein promoter, a pollen-specific pectate lyase gene promoter or PG47 gene promoter, an anther specific RTS2 gene promoter, SGB6 gene promoter, or G9 gene promoter, a tapetum specific RAB24 gene promoter, an anthranilate synthase alpha subunit promoter, an alpha zein promoter, an anthranilate synthase beta subunit promoter, a dihydrodipicolinate synthase promoter, a Thi I promoter, an alcohol dehydrogenase promoter, a cab binding protein promoter, an H3C4 promoter, a RUBISCO SS starch branching enzyme promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphate-1-phosphotransferase promoter, a beta-ketoacyl-ACP synthase promoter, a 33 kDa photosystem 11 promoter, an oxygen evolving protein promoter, a 69 kDa vacuolar ATPase subunit promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, a chalcone synthase promoter, a zein promoter, a globulin-1 promoter, an auxin-binding protein promoter, a UDP glucose flavonoid glycosyl-transferase gene promoter, an NTI promoter, an actin promoter and an opaque 2 promoter.

Plants suitable for purposes of the present disclosure can be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis thaliana* and woody plants such as coniferous and deciduous trees. Thus, a transgenic plant or genetically modified plant cell of the disclosure can be an angiosperm or gymnosperm.

Angiosperms are divided into two broad classes based on the number of cotyledons, which are seed leaves that generally store or absorb food; a monocotyledonous angiosperm has a single cotyledon and a dicotyledonous angiosperm has two cotyledons. Angiosperms produce a variety of useful products including materials such as lumber, rubber and paper; fibers such as cotton and linen; herbs and medicines such as quinine and vinblastine; ornamental flowers such as roses and where included within the scope of the present disclosure, orchids and foodstuffs such as grains, oils, fruits and vegetables. Angiosperms encompass a variety of flowering plants, including, for example, cereal plants, leguminous plants, oilseed plants, hardwood trees, fruit-bearing plants and ornamental flowers, which general classes are not necessarily exclusive. Cereal plants, which produce an edible grain, include, for example, corn, rice, wheat, barley, oat, rye, orchardgrass, guinea grass and sorghum. Leguminous plants include members of the pea family (Fabaceae) and produce a characteristic fruit known as a legume. Examples of leguminous plants include, for example, soybean, pea, chickpea, moth bean, broad bean, kidney bean, lima bean, lentil, cowpea, dry bean and peanut, as well as alfalfa, birdsfoot trefoil, clover and sainfoin. Oilseed plants, which have seeds that are useful as a source of oil, include soybean, sunflower, rapeseed (canola) and cottonseed. Angiosperms also include hardwood trees, which are perennial woody plants that generally have a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut, sequoia and willow. Trees are useful, for example, as a source of pulp, paper, structural material and fuel.

Angiosperms produce seeds enclosed within a mature, ripened ovary. An angiosperm fruit can be suitable for human or animal consumption or for collection of seeds to propagate the species. For example, hops are a member of the mulberry family that are prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, lily, tulip and chrysanthemum, snapdragon, camellia, carnation and petunia plants and can include orchids. It will be recognized that the present disclosure also can be practiced using gymnosperms, which do not produce seeds in a fruit.

Homozygosity is a genetic condition existing when identical alleles reside at corresponding loci on homologous chromosomes. Heterozygosity is a genetic condition existing when different alleles reside at corresponding loci on homologous chromosomes. Hemizygosity is a genetic condition existing when there is only one copy of a gene (or set of genes) with no allelic counterpart on the sister chromosome.

The plant breeding methods used herein are well known to one skilled in the art. For a discussion of plant breeding techniques, see, Poehlman, (1987) *Breeding Field Crops* AVI Publication Co., Westport Conn. Many of the plants which would be most is preferred in this method are bred through techniques that take advantage of the plant's method of pollination.

Backcrossing methods may be used to introduce a gene into the plants. This technique has been used for decades to introduce traits into a plant. An example of a description of this and other plant breeding methodologies that are well known can be found in references such as Plant Breeding Methodology, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

By transgene, it is meant any nucleic acid sequence which is introduced into the genome of a cell by genetic engineering techniques. A transgene may be a native DNA sequence or a heterologous DNA sequence (i.e., "foreign DNA"). The term native DNA sequence refers to a nucleotide sequence which is naturally found in the cell but that may have been modified from its original form.

Certain constructs described herein comprise an element which interferes with formation, function, or dispersal of male gametes. By way of example but not limitation, this can include use of genes which express a product cytotoxic to male gametes (See for example, U.S. Pat. Nos. 5,792,853; 5,689,049; PCT/EP89/00495); inhibit product formation of another gene important to male gamete function or formation (see, U.S. Pat. Nos. 5,859,341; 6,297,426); combine with another gene product to produce a substance preventing gene formation or function (see, U.S. Pat. Nos. 6,162,964; 6,013,859; 6,281,348; 6,399,856; 6,248,935; 6,750,868; 5,792,853); are antisense to or cause co-suppression of a gene critical to male gamete function or formation (see, U.S. Pat. Nos. 6,184,439; 5,728,926; 6,191,343; 5,728,558; 5,741,684); interfere with expression through use of hairpin formations (Smith, et al., (2000) *Nature* 407:319-320; WO 1999/53050 and WO 1998/53083) or the like. Many nucleotide sequences are known which inhibit pollen formation or function and any sequences which accomplish this function will suffice. A discussion of genes which can impact proper development or function is included at U.S. Pat. No. 6,399,856 and includes dominant negative genes such as cytotoxin genes, methylase genes and growth-inhibiting genes. Dominant negative genes include diphtheria toxin A-chain gene (Czako and An, (1991) *Plant Physiol.* 95:687-692. and Greenfield, et al., (1983) *PNAS* 80:6853, Palmiter, et al., (1987) *Cell* 50:435); cell cycle division mutants such as CDC in maize (Colasanti, et al., (1991) *PNAS* 88:3377-3381); the WT gene (Farmer, et al., (1994) *Hum. Mol. Genet.* 3:723-728) and P68 (Chen, et al., (1991) *PNAS* 88:315-319).

Further examples of so-called "cytotoxic" genes are discussed supra and can include, but are not limited to pectate lyase gene pelE, from Erwinia chrysanthermi (Kenn, et al., (1986) *J. Bacteroil* 168:595); T-urf13 gene from cms-T maize mitochondrial genomes (Braun, et al., (1990) *Plant Cell* 2:153; Dewey, et al., (1987) *PNAS* 84:5374); CytA toxin gene from *Bacillus thuringiensis Israeliensis* that causes cell membrane disruption (McLean, et al., (1987) *J. Bacteriol* 169:1017, U.S. Pat. No. 4,918,006); DNAses, RNAses, (U.S. Pat. No. 5,633,441); proteases or genes expressing antisense RNA. A suitable gene may also encode a protein involved in inhibiting pistil development, pollen stigma interactions, pollen tube growth or fertilization or a combination thereof. In addition genes that either interfere with the normal accumulation of starch in pollen or affect osmotic balance within pollen may also be suitable. These may include, for example, the maize alpha-amylase gene, maize beta-amylase gene, debranching enzymes such as Sugary1 and pullulanase, glucanase and SacB.

In an illustrative embodiment, the DAM-methylase gene is used, discussed supra and at U.S. Pat. Nos. 5,792,852 and 5,689,049, the expression product of which catalyzes methylation of adenine residues in the DNA of the plant. In another embodiment, an .alpha.-amylase gene can be used with a male tissue-preferred promoter. During the initial germinating period of cereal seeds, the aleurone layer cells will synthesize .alpha.-amylase, which participates in hydrolyzing starch to form glucose and maltose, so as to provide the nutrients needed for the growth of the germ (Rogers and Milliman, (1984) *J. Biol. Chem.* 259(19):12234-12240; Rogers, (1985) *J. Biol. Chem.* 260:3731-3738). In an embodiment, the .alpha.-amylase gene used can be the *Zea mays* .alpha.-amylase-1 gene. See, for example, Young, et al., *Plant Physiol.* 105(2):759-760 and GenBank Accession Numbers L25805, GI:426481 See, also, U.S. Pat. No. 8,013,218. Sequences encoding .alpha.-amylase are not typically found in pollen cells and when expression is directed to male tissue, the result is a breakdown of the energy source for the pollen grains and repression of pollen function.

One skilled in this area readily appreciates the methods described herein are particularly applicable to any other crops which have the potential to outcross. By way of example, but not limitation it can include maize, soybean, sorghum or any plant with the capacity to outcross.

The disclosure contemplates the use of promoters providing tissue-preferred expression, including promoters which preferentially express to the gamete tissue, male or female, of the plant. The disclosure does not require that any particular gamete tissue-preferred promoter be used in the process, and any of the many such promoters known to one skilled in the art may be employed. By way of example, but not limitation, one such promoter is the 5126 promoter, which preferentially directs expression of the gene to which it is linked to male tissue of the plants, as described in U.S. Pat. Nos. 5,837,851 and 5,689,051. Other examples include the MS45 promoter described at U.S. Pat. No. 6,037,523, SF3 promoter described at U.S. Pat. No. 6,452,069, the BS92-7 or BS7 promoter described at WO 2002/063021, the SBMu200 promoter described at WO 2002/26789, a SGB6 regulatory element described at U.S. Pat. No. 5,470,359 and TA39 (Koltunow, et al., (1990) *Plant Cell* 2:1201-1224; Goldberg, et al., (1993) *Plant Cell* 5:1217-1229 and U.S. Pat. No. 6,399,856. See, also, Nadeau, et al., (1996) *Plant Cell* 8(2):213-39 and Lu, et al., (1996) *Plant Cell* 8(12):2155-68.

Using well-known techniques, additional promoter sequences may be isolated based on their sequence homology. In these techniques, all or part of a known promoter sequence is used as a probe which selectively hybridizes to other sequences present in a population of cloned genomic DNA fragments (i.e. genomic libraries) from a chosen organism. Methods that are readily available in the art for the hybridization of nucleic acid sequences may be used to obtain sequences which correspond to these promoter sequences in species including, but not limited to, maize (corn; *Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals and conifers. Preferably, plants include maize, soybean, sunflower, safflower, canola, wheat, barley, rye, alfalfa and sorghum.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g., Innis, et al., (1990) *PCR Protocols, A Guide to Methods and Applications*, eds., Academic Press).

In general, sequences that correspond to a promoter sequence of the present disclosure and hybridize to a promoter sequence disclosed herein will be at least 50% homologous, 55% homologous, 60% homologous, 65% homologous, 70% homologous, 75% homologous, 80% homologous, 85% homologous, 90% homologous, 95% homologous and even 98% homologous or more with the disclosed sequence.

Fragments of a particular promoter sequence disclosed herein may operate to promote the pollen-preferred expression of an operably-linked isolated nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequences disclosed herein. The nucleotides of such fragments will usually comprise the TATA recognition sequence of the particular promoter sequence. Such fragments can be obtained by use of restriction enzymes to cleave the naturally-occurring promoter sequences disclosed herein; by synthesizing a nucleotide sequence from the naturally-occurring DNA sequence or through the use of PCR technology. See particularly, Mullis, et al., (1987) *Methods Enzymol.* 155:335-350 and Erlich, ed. (1989) *PCR Technology* (Stockton Press, New York). Again, variants of these fragments, such as those resulting from site-directed mutagenesis, are encompassed by the compositions of the present disclosure.

Thus, nucleotide sequences comprising at least about 20 contiguous nucleotides of the sequences set forth in SEQ ID NO: 64-106 are encompassed. These sequences can be isolated by hybridization, PCR, and the like. Such sequences encompass fragments capable of driving pollen-preferred expression, fragments useful as probes to identify similar sequences, as well as elements responsible for temporal or tissue specificity.

Biologically active variants of the promoter sequence are also encompassed by the compositions of the present disclosure. A regulatory "variant" is a modified form of a promoter wherein one or more bases have been modified, removed or added. For example, a routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3',4-base overhangs. Timed digests of a clone with this enzyme produce unidirectional nested deletions.

One example of a regulatory sequence variant is a promoter formed by causing one or more deletions in a larger promoter. Deletion of the 5' portion of a promoter up to the TATA box near the transcription start site may be accomplished without abolishing promoter activity, as described by Zhu, et al., (1995) *The Plant Cell* 7:1681-89. Such variants should retain promoter activity, particularly the ability to drive expression in specific tissues. Biologically active variants include, for example, the native regulatory sequences of the disclosure having one or more nucleotide substitutions, deletions or insertions. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

The nucleotide sequences for the pollen-preferred promoters disclosed in the present disclosure, as well as variants and fragments thereof, are useful in the genetic manipulation of any plant when operably linked with an isolated nucleotide sequence whose expression is to be controlled to achieve a desired phenotypic response.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences claimed herein can be operably linked to antisense DNA sequences to reduce or inhibit expression of a native or exogenous protein in the plant.

Regulation of male fertility is necessarily measured in terms of its effect on individual cells. For example, suppression in 99.99% of pollen grains is required to achieve reliable sterility for commercial use. However, successful suppression or restoration of expression of other traits may be accomplished with lower stringency. Within a particular tissue, for example, expression in 98%, 95%, 90%, 80% or fewer cells may result in the desired phenotype. Further, for modification of assimilate partitioning and/or reduced competition for nitrogen between male and female reproductive structures, suppression of male fertility by 50% or even less may be effective and desirable.

EXAMPLES

Example 1: Ms44 Isolation and Characterization

The dominant male sterile gene, Ms44, arose through a seed based EMS mutagenesis treatment of the W23 maize line and was found to be tightly linked to the C2 locus on chromosome 4 (Linkage between Ms44 and C2, Albertsen and Trimnell, (1992). *MNL* 66:49). A map-based cloning approach was undertaken to identify the Ms44 gene. An initial population of 414 individuals was used to rough map Ms44 to chromosome 4. An additional population of 2686 individuals was used for fine mapping. Marker Lab genotyping narrowed the region of the mutation to a 0.43 cM interval on chromosome 4.

Additional markers were developed for fine mapping using the 39 recombinants. The Ms44 mutation was mapped to ~80 kb region between markers made from the sequences AZM5_9212 (five recombinants) and AZM5_2221 (2 recombinants).

Primers AZM5_9212 For4 (SEQ ID NO: 1) and AZM5_9212 Rev4 (SEQ ID NO: 2) were used for an initial round of PCR followed by a second round of PCR using the primers AZM5_9212 ForNest4 (SEQ ID NO: 3) and AZM5_9212 RevNest4 (SEQ ID NO: 4). The PCR product was digested with MspI and the banding pattern was analyzed to determine the genotypes at this locus.

Primers AZM5_2221 For3 (SEQ ID NO: 5) and AZM5_2221 Rev3 (SEQ ID NO: 6) were used for an initial round of PCR followed by a second round of PCR using the primers AZM5_2221 ForNest3 (SEQ ID NO: 7) and AZM5_2221 RevNest3 (SEQ ID NO: 8). The PCR product was digested with BsgI and the banding pattern was analyzed to determine the genotypes at this locus.

Within the ~80 kb Ms44 interval, a sequencing gap between BACs was present. The gap was sequenced and, within this region, a gene, pco641570, was identified. The first Met codon is found at nucleotide 1201, with a 101 bp intron at nucleotides 1505-1605 and the stop codon ending at nucleotide 1613 (SEQ ID NO: 9). The gene has an open reading frame of 312 bp which codes for a predicted protein of 104 amino acids (including the stop codon) (SEQ ID NO: 10). The predicted protein has homology to a variety of proteins and contains the InterProscan accession domain IPR003612, a domain found in plant lipid transfer protein/seed storage/trypsin-alpha amylase inhibitors. A secretory signal sequence (SSS) cleavage site was predicted, using SigCleave analysis, at amino acid 23. (von Heijne, G. "A new method for predicting signal sequence cleavage sites" Nucleic Acids Res.: 14:4683 (1986). Improved prediction of signal peptides: SignalP 3.0, Bendtsen J D, Nielsen H, von Heijne G, Brunak S., J Mol Biol. 2004 Jul. 16; 340(4):783-95. Von Heijne, G. "Sequence Analysis in Molecular Biology: Treasure Trove or Trivial Pursuit" Acad. Press (1987) 113-117. See also the SIGCLEAVE program in the EMBOSS (European Molecular Biology Open Software Site) suite of applications online.)

However, SigCleave analysis of ms44 orthologs in related moncot species reveals another potential cleavage site between amino acids 37 and 38. The protein is cysteine rich and BlastP analysis shows the highest homology to plant anther or tapetum specific genes such as the Lims or A9 genes. (The characterization of tapetum-specific cDNAs isolated from a *Lilium henryi* L. meiocyte subtractive cDNA library. Crossley, et al., (1995) *Planta*. 196(3):523-529. The isolation and characterization of the tapetum-specific *Arabidopsis thaliana* A9 gene. Paul, et al., (1992) *Plant Mol Biol*. 19(4):611-22.).

RT-PCR analysis was performed on developing anther and leaf cDNAs to assess the expression of the ms44 gene. Ms44 specific primers pco641570-5' (SEQ ID NO: 11) and pco641570-3'-2 (SEQ ID NO: 12) were used in an RT-PCR reaction with cDNA template from 0.5 mm, 1.0 mm, 1.5 mm and 2.0 mm anthers; anthers at pollen mother cell (PMC), Quartet, early uninucleate and binucleate stages of microspore/pollen development and leaf. Genomic DNA was also used as a template. Expression of ms44 begins early at the PMC stage and continues through quartet and early nucleate microspore stages but is absent by the binucleate stage of pollen development. No expression was detected in leaves.

The pco641570 gene was sequenced from the Ms44 mutant. The first Met codon is found at nucleotide 1222, with a 101 bp intron at nucleotides 1526-1626 and the stop codon ends at nucleotide 1634 (SEQ ID NO: 13). The sequence analysis revealed a nucleotide change which results in a translational change from an Alanine to a Threonine residue at amino acid 37 in the predicted protein (SEQ ID NO: 14). This nucleotide change also created a BsmF1 restriction site in the mutant allele which is not found in the wildtype, which allows for distinguishing the two alleles by amplification of both Ms44 alleles by PCR and subsequent digestion of the products by BsmF1.

MsD-2629 is another dominant male sterile mutant found in maize and was also generated through EMS mutagenesis. This mutant was mapped and found to reside on chromosome 4 very near the Ms44 gene. To determine whether MsD-2629 was an allele of Ms44, the Ms44 gene was PCR amplified and sequenced from MsD-2629 male sterile plants. Two different alleles were found through sequencing. One was a wild-type allele and the second allele had a single nucleotide change (SEQ ID NO: 152) which results in a translational change from the same Alanine residue as Ms44, but to a Valine at amino acid 37 in the predicted protein (SEQ ID NO:153). This allele was found in all MsD-2629 male sterile plants tested and was not present in male fertile siblings. The MsD-2629 mutant represents a second Ms44 allele and was designated Ms44-2629.

Both Ms44 mutations affect the same Alanine residue at position 37 and that amino acid is implicated through SignalCleave analysis as being the possible −1 SS cleavage site, in vitro transcription/translation (TnT) reactions (EasyXpress Insect Kit II, Qiagen, Cat #32561) were performed to assess cleavage of Ms44 protein variants that had been engineered with various amino acid substitutions based on conservation of amino acids around SS cleavage sites (Patterns of Amino Acids near Signal-Sequence Cleavage Sites. Gunnar Von Heijne (1983) *Eur. J. Biochem*. 133,17-21). The in vitro TnT assay showed that the wild-type ms44 protein (−1 Ala) is processed to a smaller mature form, whereas the mutant Ms44 (−1 Thr) is not. The Ms44-2629 protein (−1 Val) is not processed, nor is a +1 Pro, but a control −1 Gly protein is processed normally (FIG. 16) This result confirms that the SS cleavage site is between amino acid 37 and 38.

To confirm that this mutation was responsible for the dominant male sterile phenotype, the genomic region was cloned for this allele, containing approximately 1.2 Kb of upstream sequence (putative promoter) and about 0.75 KB of sequence downstream of the stop codon. This genomic sequence was sub-cloned into a transformation vector and designated, PHP42163. The vector was used to transform maize plants through *Agrobacterium* mediated transformation. Thirty six T0 plants were grown to maturity and tassels were phenotyped for the presence or absence of pollen. Thirty four of the thirty six plants were completely male sterile. DNA from these transgenic plants were genotyped using primers pco641570-5' (SEQ ID NO: 11) and pco641570-3'-2 (SEQ ID NO: 12) in a PCR reaction and then digested with BsmF1 and run on a 1% agarose gel. All thirty-four of the male sterile plants contained the mutant Ms44 allele as evidenced by the presence of two smaller bands produced by BsmF1 digestion. The remaining two male fertile plants were found by genotyping, not to contain the Ms44 allele and most likely arose through some rearrangement in the vector during transformation. This confirms that the single nucleotide change in the Ms44 allele results in a dominant male sterile phenotype.

The point mutation in the Ms44 gene changes a codon from an Ala to a Thr, with a second allele having an Ala to Val change. The affected amino acid is proposed to be at the −1 position of the SS cleavage site and the two mutations abolish SS cleavage of MS44 as shown by in vitro TnT assays. Without being bound to any theory, the dominance of the mutation may be due to a defect in protein processing through the endoplasmic reticulum (ER) and not due to a functional role of the ms44 gene product as a lipid transfer protein. Since the MS44 protein is cysteine rich, an ER-tethered Ms44 protein may cross-link through disulfide bridges and inhibit overall protein processing in the anther that is ultimately required for male fertility.

Example 2: Tassel Preferred Promoter Identification

In transgenics, one can stack a vector of tassel-preferred promoter driven negative genes, or male sterility mutants, with other vectors that enhance vegetative or ear growth. The combination of tassel reduction and enhancement of other organs can be effective in diverting nutrients to the ear to achieve yield gain.

Tassel-preferred promoters can be used to target silencing of the Tls1 gene in the tassel to knock down or knock-out the function of the gene in this tissue. This will eliminate the tassel, while the gene function in the ear remains intact. Use of the tassel-preferred promoters is not limited to Tls1 gene, it can be applied to driving any gene expression in tassel tissues that deliver a negative effect on tissue growth, for example to affect anther, pollen, or any cells that eventually interfere male fertility. Tassel-preferred promoter candidates are identified based upon their native expression patterns, cloned and are tested in transgenic plants to confirm their tassel-specificity.

In an embodiment, tassel-preferred promoters can also be used to express or suppress a gene, whereby the expression or suppression results in enhanced tassel development.

Example 3: tls1 Mutant Identification and Characterization

The tassel-less (tls1) mutant was described and mapped on the long arm of chromosome 1 (Albertsen, et al., (1993) *Maize Genetics Newsletter* 67:51-52). A small F2 population of 75 individuals, generated by crossing homozygous tls1 plants (background unknown) to Mo17, was genotyped to confirm the previously identified tls1 position. The mutation was found to be located between two SNP markers, MZA5484-22 and MZA10765-46. These markers were used to screen for recombinants in a larger F2 population of 2985 individuals. All the recombinants were selected for self-pollination and 177 F3 ears were harvested. 177 F3 families were grown in rows in the field. Phenotypes for all the individuals in rows were taken to determine each F2 line as homozygous wild-type, heterozygous or homozygous tls1. Leaf punches from 8 individuals of each F3 family were pooled together for genotyping. Using these lines, tls1 was confirmed to be between markers MZA5484 and MZA10765, which were converted to CAPS markers.

Primers MZA5484-F768 (SEQ ID NO: 28) and MZA5484-R (SEQ ID NO: 29) were used to amplify the MZA5484 locus. The PCR product was digested with MwoI and the banding pattern was analyzed to determine the genotypes at this locus.

Primers MZA10765-F429 (SEQ ID NO: 30) and MZA10765-R1062 (SEQ ID NO: 31) were used to amplify the MZA10765 locus. The PCR product was digested with BslI and the banding pattern was analyzed to determine the genotypes at this locus.

Additional markers were used to fine map the tls1 mutation with the 177 F3 families. These markers were developed from DuPont proprietary sequences of known map positions, BAC-end sequences, and other low copy regions. The tls1 mutation was eventually mapped between markers c0375b06_10 and c0260e13_35.

Primers c0375b06_10-For (SEQ ID NO: 32) and c0375b16_10-Rev (SEQ ID NO: 33) were used to amplify the c0375b06_10 locus. PCR product for this reaction was used as template for a second reaction using the primers c0375b06_10-ForNest (SEQ ID NO: 34) and c0375b06_10-RevNest (SEQ ID NO: 35). This PCR product was digested with MboII and the banding pattern was analyzed to determine the genotypes at this locus.

Primers c0260e13_35-For (SEQ ID NO: 36) and c0260e13_35-Rev (SEQ ID NO: 37) were used to amplify the c0260e13_35 locus. PCR product for this reaction was used as template for a second reaction using the primers c0260e13_35-ForNest (SEQ ID NO: 38) and c0260e13_35-RevNest (SEQ ID NO: 39). This PCR product was digested with HphI and the banding pattern was analyzed to determine the genotypes at this locus.

The physical interval between the flanking markers c0375b06_10 and c0260e13_35 contained approximately four sequenced BAC clones based on the B73 physical map. Sequencing low copy regions within this interval revealed a very low level of polymorphism and the few markers available co-segregated with the tls1 phenotype. All the annotated genes in this interval were sequenced to identify the causative mutation. One gene, annotated as NOD26-like integral membrane protein/aquaporin/ZmNIP3-1 (hereafter known as NIP3-1) (SEQ ID NO: 62—Genomic Sequence from B73; SEQ ID NO: 63—CDS from B73, SEQ ID NO: 156 NIP3-1 protein), was unable to be amplified in homozygous tls1 individuals but could be amplified in homozygous wild-type and heterozygous lines.

Primer pairs c0297o12_75-For (SEQ ID NO: 40) and c0297o12_75-Rev (SEQ ID NO: 41), c0297o12_76-For (SEQ ID NO: 44) and c0297o12_76-Rev (SEQ ID NO: 45), c0297o12_77-For (SEQ ID NO: 48) and c0297o12_77-Rev (SEQ ID NO: 49), c0297o12_78-For (SEQ ID NO: 52) and c0297o12_78-Rev (SEQ ID NO: 53) were used to amplify the genomic region spanning NIP3-1. PCR products from these reactions were used as templates for second reactions using the corresponding primer pairs: c0297o12_75-ForNest (SEQ ID NO: 42) and c0297o12_75-RevNest (SEQ ID NO: 43), c0297o12_76-ForNest (SEQ ID NO: 46) and c0297o12_76-RevNest (SEQ ID NO: 47), c0297o12_77-ForNest (SEQ ID NO: 50) and c0297o12_77-RevNest (SEQ ID NO: 51), c0297o12_78-ForNest (SEQ ID NO: 54) and c0297o12_78-RevNest (SEQ ID NO: 55).

A BAC library was constructed from homozygous tls1 plants in order to determine the nature of the mutation. Sequencing BAC clones covering the tls1 locus revealed a deletion of approximately 6.6 kb in comparison to the B73 reference genome, corresponding to the NIP3-1 region. In addition, approximately 9 kb of repetitive sequence was present in its place. Therefore, the tls1 phenotype is likely due to the deletion of NIP3-1 in homozygous mutant plants.

Candidate Gene Validation

TUSC lines with Mutator (Mu) insertions in the NIP3.1 were identified to validate the candidate gene. Two independent TUSC lines, put-tls1-P30D5 and put-tls1-P177F10, were confirmed by PCR and sequencing to have Mu insertions within NIP3-1.

NIP3-1 specific primers DO143578 (SEQ ID NO: 56), DO143579 (SEQ ID NO: 57), DO143584 (SEQ ID NO: 58), or DO143583 (SEQ ID NO: 59) were used in combination with the Mu-specific primer, MuExt22D (SEQ ID NO: 60) to amplify the NIP3-1 and Mutator junction regions. PCR products from these reactions were used as templates for second reactions using the same NIP3-1 specific primers in combination with another Mu-specific primer, MuInt19 (SEQ ID NO: 61). The PCR product was run on a gel, the major bands excised, DNA extracted using a Gel Purification Kit (Qiagen) and sequenced. Sequencing results were BLASTed to confirm the Mu insertion in NIP3-1.

The TUSC lines mentioned above, which contained a Mu insertion in NIP3-1, were used in an allelism test. The TUCS lines which were heterozygous for the Mu insertion were used to pollinate heterozygous F3 plants at the tls1 locus. The resulting progenies were phenotyped and genotyped. Plants were genotyped as described below:

To confirm that a progeny from the allelism test contained a Mu insertion in NIP3-1, c0297o12_75-Rev (SEQ ID NO: 41), c0297o12_76-For (SEQ ID NO: 44), c0297o12_76-Rev (SEQ ID NO: 45), c0297o12_77-For (SEQ ID NO: 48), c0297o12_77-Rev (SEQ ID NO: 49), DO143583 (SEQ ID NO: 59) and DO143584 (SEQ ID NO: 58) were used in combination with the Mu-specific primer, MuExt22D (SEQ ID NO: 60). PCR products from these reactions were used as templates for second reactions using c0297o12_75-RevNest (SEQ ID NO: 43), c0297o12_76-ForNest (SEQ ID NO: 46), c0297o12_76-RevNest (SEQ ID NO: 47), c0297o12_77-ForNest (SEQ ID NO: 50), c0297o12_77-RevNest (SEQ ID NO: 51), DO143583 (SEQ ID NO: 59) and DO143584 (SEQ ID NO: 58) respectively in combination with the Mu-specific primer, MuInt19 (SEQ ID NO: 61). A positive PCR product indicated the presence of a Mu insertion.

To determine if a progeny from the allelism test inherited the wild-type or the reference tls1 allele, c0297o12_75-For (SEQ ID NO: 40) was used in combination with c0297o12_75-Rev (SEQ ID NO: 41) and c0297o12_77-For (SEQ ID NO: 48) was used in combination with c0297o12_77-Rev (SEQ ID NO: 49). PCR products from these reactions were used as templates for second reactions using c0297o12_75-ForNest (SEQ ID NO: 42) in combination with c0297o12_75-RevNest (SEQ ID NO: 43) and c0297o12_77-ForNest (SEQ ID NO: 50) in combination with c0297o12_77-RevNest (SEQ ID NO: 51), respectively.

The phenotyping results from the allelism test were compared with the genotyping results. Individuals without a Mu insertion were wild-type. Of the individuals that contained a Mu insertion, those that contained the wild-type allele of NIP3-1 had a wild-type phenotype while those that had the mutant allele of NIP3-1 mostly had a tls1 phenotype. The few aberrations were attributed to the incomplete penetrance of the tsl1 phenotype, which has been observed in the original description of the tls1 mutant (*MNL* 67:51-52) and in the current study.

Example 4: Low Nitrogen Seedling Assay Protocol

Seeds produced by transgenic plants are separated into transgene (heterozygous) and null seed using a seed color marker. Two different random assignments of treatments are made to each block of 54 pots, arranged as 6 rows of 9 columns and using 9 replicates of all treatments. In one case, null seed of 5 events of the same construct are mixed and used as control for comparison of the 5 positive events in this block, making up 6 treatment combinations in each block. In the second case, 3 transgenic positive treatments and their corresponding nulls are randomly assigned to the 54 pots of the block, making 6 treatment combinations for each block, containing 9 replicates of all treatment combinations. In the first case transgenic parameters are compared to a bulked construct null; in the second case, transgenic parameters are compared to the corresponding event null. In cases where there are 10, 15 or 20 events in a construct, the events are assigned in groups of 5 events, the variances calculated for each block of 54 pots, but the block null means are pooled across blocks before mean comparisons are made.

Two seeds of each treatment are planted in 4-inch-square pots containing TURFACE®-MVP on 8-inch, staggered centers and watered four times each day with a solution containing the following nutrients:

| | | | |
|---|---|---|---|
| 1 mM CaCl2 | 2 mM MgSO4 | 0.5 mM KH2PO4 | 83 ppm Sprint330 |
| 3 mM KCl | 1 mM KNO3 | 1 uM ZnSO4 | 1 uM MnCl2 |
| 3 uM H3BO3 | 1 uM MnCl2 | 0.1 uM CuSO4 | 0.1 uM NaMoO4 |

After emergence the plants are thinned to one seed per pot. Treatments routinely are planted on a Monday, emerge the following Friday and are harvested 18 days after planting. At harvest, plants are removed from the pots and the Turface® washed from the roots. The roots are separated from the shoot, placed in a paper bag and dried at 70° C. for 70 hr. The dried plant parts (roots and shoots) are weighed and placed in a 50 ml conical tube with approximately 20 5/32 inch steel balls and ground by shaking in a paint shaker. Approximately, 30 mg of the ground tissue (weight recorded for later adjustment) is hydrolyzed in 2 ml of 20% $H_2O_2$ and 6M $H_2SO_4$ for 30 min at 170° C. After cooling, water is added to 20 ml, mixed thoroughly and a 50 µl aliquot removed and added to 950 µl 1M $Na_2CO_3$. The ammonia in this solution is used to estimate total reduced plant nitrogen by placing 100 µl of this solution in individual wells of a 96 well plate followed by adding 50 µl of OPA solution. Fluorescence, excitation=360 nM/emission=530 nM, is determined and compared to $NH_4Cl$ standards dissolved in a similar solution and treated with OPA solution.

OPA solution—5 µl Mercaptoethanol+1 ml OPA stock solution (make fresh, daily) OPA stock—50 mg o-phthadialdehyde (OPA—Sigma #P0657) dissolved in 1.5 ml methanol+4.4 ml 1M Borate buffer pH9.5 (3.09 g $H_3BO_4$+1 g NaOH in 50 ml water)+0.55 ml 20% SDS (make fresh weekly)

Using these data the following parameters are measured and means are compared to null mean parameters using a Student's t test:
Total Plant Biomass
Root Biomass
Shoot Biomass
Root/Shoot Ratio
Plant N concentration
Total Plant N Variance is calculated within each block using a nearest neighbor calculation as well as by Analysis of Variance (ANOV) using a completely random design (CRD) model. An overall treatment effect for each block was calculated using an F statistic by dividing overall block treatment mean square by the overall block error mean square.

Example 5: Screening of Gaspe Bay Flint Derived Maize Lines Under Nitrogen Limiting Conditions Transgenic plants will contain two or three doses of Gaspe Flint-3 with one dose of GS3 (GS3/(Gaspe-3)2× or GS3/(Gaspe-3)3×) and will segregate 1:1 for a dominant transgene. Plants will be planted in TURFACE®, a commercial potting medium and watered four times each day with 1 mM $KNO_3$ growth medium and with 2 mM $KNO_3$ or higher, growth medium. Control plants grown in 1 mM $KNO_3$ medium will be less green, produce less biomass and have a smaller ear at anthesis. Results are analyzed for statistical significance.

Expression of a transgene will result in plants with improved plant growth in 1 mM $KNO_3$ when compared to a transgenic null. Thus biomass and greenness will be monitored during growth and compared to a transgenic null. Improvements in growth, greenness and ear size at anthesis will be indications of increased nitrogen utilization efficiency.

Example 6: Assays to Determine Alterations of Root Architecture in Maize

Transgenic maize plants are assayed for changes in root architecture at seedling stage, flowering time or maturity. Assays to measure alterations of root architecture of maize plants include, but are not limited to the methods outlined below. To facilitate manual or automated assays of root architecture alterations, corn plants can be grown in clear pots.

1) Root mass (dry weights). Plants are grown in Turface®, a growth medium that allows easy separation of roots. Oven-dried shoot and root tissues are weighed and a root/shoot ratio calculated.
2) Levels of lateral root branching. The extent of lateral root branching (e.g., lateral root number, lateral root length) is determined by sub-sampling a complete root system, imaging with a flat-bed scanner or a digital camera and analyzing with WinRHIZO™ software (Regent Instruments Inc.).
3) Root band width measurements. The root band is the band or mass of roots that forms at the bottom of greenhouse pots as the plants mature. The thickness of the root band is measured in mm at maturity as a rough estimate of root mass.
4) Nodal root count. The number of crown roots coming off the upper nodes can be determined after separating the root from the support medium (e.g., potting mix). In addition the angle of crown roots and/or brace roots can be measured. Digital analysis of the nodal roots and amount of branching of nodal roots form another extension to the aforementioned manual method.

All data taken on root phenotype are subjected to statistical analysis, normally a t-test to compare the transgenic roots with those of non-transgenic sibling plants. One-way ANOVA may also be used in cases where multiple events and/or constructs are involved in the analysis.

Example 7: NUE Assay of Plant Growth

Seeds of *Arabidopsis thaliana* (control and transgenic line), ecotype Columbia, are surface sterilized (Sánchez, et al., 2002) and then plated on to Murashige and Skoog (MS) medium containing 0.8% (w/v) Bacto™-Agar (Difco). Plates are incubated for 3 days in darkness at 4° C. to break dormancy (stratification) and transferred thereafter to growth chambers (Conviron, Manitoba, Canada) at a temperature of 20° C. under a 16-h light/8-h dark cycle. The average light intensity is 120 µE/m2/s. Seedling are grown for 12 days and then transferred to soil based pots. Potted plants are grown on a nutrient-free soil LB2 Metro-Mix® 200 (Scott's Sierra Horticultural Products, Marysville, Ohio, USA) in individual 1.5-in pots (*Arabidopsis* system; Lehle Seeds, Round Rock, Tex., USA) in growth chambers, as described above. Plants are watered with 0.6 or 6.5 mM potassium nitrate in the nutrient solution based on Murashige and Skoog (MS free Nitrogen) medium. The relative humidity is maintained around 70%. 16-18 days later plant shoots are collected for evaluation of biomass and SPAD readings.

Example 8: *Agrobacterium* Mediated Transformation into Maize

Maize plants can be transformed to overexpress a nucleic acid sequence of interest in order to examine the resulting phenotype.

*Agrobacterium*-mediated transformation of maize is performed essentially as described by Zhao, et al., (2006) *Meth. Mol. Biol.* 318:315-323 (see, also, Zhao, et al., (2001) *Mol. Breed.* 8:323-333 and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation
    Immature embryos are dissected from caryopses and placed in a 2 mL microtube containing 2 mL PHI-A medium.

2. *Agrobacterium* Infection and Co-Cultivation of Embryos
    2.1 Infection Step
    PHI-A medium is removed with 1 mL micropipettor and 1 mL Agrobacterium suspension is added. Tube is gently inverted to mix. The mixture is incubated for 5 min at room temperature.
    2.2 Co-Culture Step
    The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for 3 days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events
    To each plate of PHI-D medium in a 100×15 mm Petri dish, 10 embryos are transferred, maintaining orientation, and the dishes are sealed with Parafilm®. The plates are incubated in darkness at 28° C. Actively growing putative events, as pale yellow embryonic tissue are expected to be visible in 6-8 weeks. Embryos that produce no events may be brown and necrotic, and little friable tissue growth is evident. Putative transgenic embryonic tissue is subcultured to fresh PHI-D plates at 2-3 week intervals, depending on growth rate. The events are recorded.

4. Regeneration of T0 Plants
    Embryonic tissue propagated on PHI-D medium is sub-cultured to PHI-E medium (somatic embryo maturation medium); in 100×25 mm Petri dishes and incubated at 28° C., in darkness, until somatic embryos mature, for about 10-18 days. Individual, matured somatic embryos with well-defined scutellum and coleoptile are transferred to PHI-F embryo germination medium and incubated at 28° C. in the light (about 80 µE from cool white or equivalent fluorescent lamps). In 7-10 days, regenerated plants, about 10 cm tall, are potted in horticultural mix and hardened-off using standard horticultural methods.

Media for Plant Transformation
1. PHI-A: 4 g/L CHU basal salts, 1.0 mUL 1000× Eriksson's vitamin mix, 0.5 mg/L thiamin HCL, 1.5 mg/L 2,4-D, 0.69 g/L L-proline, 68.5 g/L sucrose, 36 g/L glucose, pH 5.2. Add 100 µM acetosyringone, filter-sterilized before using.
2. PHI-B: PHI-A without glucose, increased 2,4-D to 2 mg/L, reduced sucrose to 30 g/L and supplemented with 0.85 mg/L silver nitrate (filter-sterilized), 3.0 g/L Gelrite®, 100 µM acetosyringone (filter-sterilized), pH 5.8.
3. PHI-C: PHI-B without Gelrite® and acetosyringone, reduced 2,4-D to 1.5 mg/L and supplemented with 8.0 g/L agar, 0.5 g/L Ms-morpholino ethane sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, cat. no. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.

6. PHI-F: PHI-E without zeatin, IAA, ABA; sucrose reduced to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm, et al., (1990) *Bio/Technology* 8:833-839).

Phenotypic analysis of transgenic T0 plants and T1 plants can be performed.

T1 plants can be analyzed for phenotypic changes. Using image analysis T1 plants can be analyzed for phenotypical changes in plant area, volume, growth rate and color analysis at multiple times during growth of the plants. Alteration in root architecture can be assayed as described herein.

Subsequent analysis of alterations in agronomic characteristics can be done to determine whether plants containing the nucleic acid sequence of interest have an improvement of at least one agronomic characteristic, when compared to the control (or reference) plants that have not been so transformed. The alterations may also be studied under various environmental conditions.

Expression constructs containing the nucleic acid sequence of interest that result in a significant alteration in root and/or shoot biomass, improved green color, larger ear at anthesis or yield will be considered evidence that the nucleic acid sequence of interest functions in maize to alter nitrogen use efficiency.

Example 9: Electroporation of *Agrobacterium tumefaciens* LBA4404

Electroporation competent cells (40 µl), such as *Agrobacterium tumefaciens* LBA4404 (containing PHP10523), are thawed on ice (20-30 min). PHP10523 contains VIR genes for T-DNA transfer, an *Agrobacterium* low copy number plasmid origin of replication, a tetracycline resistance gene and a cos site for in vivo DNA biomolecular recombination. Meanwhile the electroporation cuvette is chilled on ice. The electroporator settings are adjusted to 2.1 kV.

A DNA aliquot (0.5 µL JT (U.S. Pat. No. 7,087,812) parental DNA at a concentration of 0.2 µg-1.0 µg in low salt buffer or twice distilled $H_2O$) is mixed with the thawed *Agrobacterium* cells while still on ice. The mix is transferred to the bottom of electroporation cuvette and kept at rest on ice for 1-2 min. The cells are electroporated (Eppendorf electroporator 2510) by pushing "Pulse" button twice (ideally achieving a 4.0 msec pulse). Subsequently 0.5 ml 2×YT medium (or SOCmedium) are added to cuvette and transferred to a 15 ml Falcon tube. The cells are incubated at 28-30° C., 200-250 rpm for 3 h.

Aliquots of 250 µl are spread onto #30B (YM+50 µg/mL Spectinomycin) plates and incubated 3 days at 28-30° C. To increase the number of transformants one of two optional steps can be performed:

Option 1: Overlay plates with 30 µl of 15 mg/ml Rifampicin. LBA4404 has a chromosomal resistance gene for Rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on AB minimal medium plus 50 mg/mL Spectinomycin plates (#12S medium) for isolation of single colonies. The plates are incubated at 28° C. for 2-3 days.

A single colony for each putative co-integrate is picked and inoculated with 4 ml #60A with 50 mg/l Spectinomycin. The mix is incubated for 24 h at 28° C. with shaking. Plasmid DNA from 4 ml of culture is isolated using Qiagen Miniprep+optional PB wash. The DNA is eluted in 30 µl. Aliquots of 2 µl are used to electroporate 20 µl of DH10b+20 µl of dd $H_2O$ as per above.

Optionally a 15 µl aliquot can be used to transform 75-100 µl of Invitrogen™ Library Efficiency DH5a. The cells are spread on LB medium plus 50 mg/mL Spectinomycin plates (#34T medium) and incubated at 37° C. overnight.

Three to four independent colonies are picked for each putative co-integrate and inoculated 4 ml of 2×YT (#60A) with 50 µg/ml Spectinomycin. The cells are incubated at 37° C. overnight with shaking.

The plasmid DNA is isolated from 4 ml of culture using QlAprep® Miniprep with optional PB wash (elute in 50 µl) and 8 µl are used for digestion with SalI (using JT parent and PHP10523 as controls).

Three more digestions using restriction enzymes BamHI, EcoRI and HindIII are performed for 4 plasmids that represent 2 putative co-integrates with correct SalI digestion pattern (using parental DNA and PHP10523 as controls). Electronic gels are recommended for comparison.

Example 10: Particle-Mediated Bombardment for Transformation of Maize

A vector can be transformed into embryogenic maize callus by particle bombardment, generally as described by Tomes, et al., Plant Cell, Tissue and Organ Culture: Fundamental Methods, Eds. Gamborg and Phillips, Chapter 8, pgs. 197-213 (1995) and as briefly outlined below. Transgenic maize plants can be produced by bombardment of embryogenically responsive immature embryos with tungsten particles associated with DNA plasmids. The plasmids typically comprise or consist of a selectable marker and an unselected structural gene, or a selectable marker and a polynucleotide sequence or subsequence, or the like.

Preparation of Particles

Fifteen mg of tungsten particles (General Electric), 0.5 to 1.8µ, preferably 1 to 1.8µ, and most preferably 1µ, are added to 2 ml of concentrated nitric acid. This suspension is sonicated at 0° C. for 20 minutes (Branson Sonifier Model 450, 40% output, constant duty cycle). Tungsten particles are pelleted by centrifugation at 10000 rpm (Biofuge) for one minute and the supernatant is removed. Two milliliters of sterile distilled water are added to the pellet and brief sonication is used to resuspend the particles. The suspension is pelleted, one milliliter of absolute ethanol is added to the pellet and brief sonication is used to resuspend the particles. Rinsing, pelleting and resuspending of the particles are performed two more times with sterile distilled water and finally the particles are resuspended in two milliliters of sterile distilled water. The particles are subdivided into 250-µl aliquots and stored frozen.

Preparation of Particle-Plasmid DNA Association

The stock of tungsten particles are sonicated briefly in a water bath sonicator (Branson Sonifier Model 450, 20% output, constant duty cycle) and 50 µl is transferred to a microfuge tube. The vectors are typically cis: that is, the selectable marker and the gene (or other polynucleotide sequence) of interest are on the same plasmid.

Plasmid DNA is added to the particles for a final DNA amount of 0.1 to 10 µg in 10 µL total volume and briefly sonicated. Preferably, 10 µg (1 µg/µL in TE buffer) total DNA is used to mix DNA and particles for bombardment.

Fifty microliters (50 μL) of sterile aqueous 2.5 M CaCl$_2$ are added and the mixture is briefly sonicated and vortexed. Twenty microliters (20 μL) of sterile aqueous 0.1 M spermidine are added and the mixture is briefly sonicated and vortexed. The mixture is incubated at room temperature for 20 minutes with intermittent brief sonication. The particle suspension is centrifuged and the supernatant is removed. Two hundred fifty microliters (250 μL) of absolute ethanol are added to the pellet, followed by brief sonication. The suspension is pelleted, the supernatant is removed and 60 μl of absolute ethanol are added. The suspension is sonicated briefly before loading the particle-DNA agglomeration onto macrocarriers.

Preparation of Tissue

Immature embryos of maize are the target for particle bombardment-mediated transformation. Ears from F1 plants are selfed or sibbed and embryos are aseptically dissected from developing caryopses when the scutellum first becomes opaque. This stage occurs about 9 13 days post-pollination and most generally about 10 days post-pollination, depending on growth conditions. The embryos are about 0.75 to 1.5 millimeters long. Ears are surface sterilized with 20 50% Clorox® for 30 minutes, followed by three rinses with sterile distilled water.

Immature embryos are cultured with the scutellum oriented upward, on embryogenic induction medium comprised of N6 basal salts, Eriksson vitamins, 0.5 mg/l thiamine HCl, 30 gm/l sucrose, 2.88 gm/l L-proline, 1 mg/l 2,4-dichlorophenoxyacetic acid, 2 gm/l Gelrite® and 8.5 mg/l AgNO$_3$, Chu, et al., (1975) *Sci. Sin.* 18:659; Eriksson, (1965) *Physiol. Plant* 18:976. The medium is sterilized by autoclaving at 121° C. for 15 minutes and dispensed into 100×25 mm Petri dishes. AgNO$_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos display this response, but most commonly, the embryogenic response frequency is about 80%.

When the embryogenic response is observed, the embryos are transferred to a medium comprised of induction medium modified to contain 120 gm/l sucrose. The embryos are oriented with the coleorhizal pole, the embryogenically responsive tissue, upwards from the culture medium. Ten embryos per Petri dish are located in the center of a Petri dish in an area about 2 cm in diameter. The embryos are maintained on this medium for 3 to 16 hours, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 μl are deposited on macrocarriers and the ethanol is allowed to evaporate. The macrocarrier is accelerated onto a stainless-steel stopping screen by the rupture of a polymer diaphragm (rupture disk). Rupture is affected by pressurized helium. The velocity of particle-DNA acceleration is determined based on the rupture disk breaking pressure. Rupture disk pressures of 200 to 1800 psi are used, with 650 to 1100 psi being preferred and about 900 psi being most highly preferred. Multiple disks are used to affect a range of rupture pressures.

The shelf containing the plate with embryos is placed 5.1 cm below the bottom of the macrocarrier platform (shelf #3).

To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A Petri dish with the target embryos is placed into the vacuum chamber and located in the projected path of accelerated particles. A vacuum is created in the chamber, preferably about 28 in Hg. After operation of the device, the vacuum is released and the Petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCl, 30 gm/l sucrose, 1 mg/l 2,4-dichlorophenoxyacetic acid, 2 gm/l Gelrite®, 0.85 mg/l Ag NO$_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferates from a fraction of the bombarded embryos. Putative transgenic tissue is rescued and that tissue derived from individual embryos is considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the coding and non-coding portion of the plasmid. Embryogenic tissue with amplifiable sequence is advanced to plant regeneration.

For regeneration of transgenic plants, embryogenic tissue is subcultured to a medium comprising MS salts and vitamins (Murashige and Skoog, (1962) *Physiol. Plant* 15:473), 100 mg/l myo-inositol, 60 gm/l sucrose, 3 gm/l Gelrite®, 0.5 mg/l zeatin, 1 mg/l indole-3-acetic acid, 26.4 ng/l cis-trans-abscissic acid and 3 mg/l bialaphos in 100×25 mm Petri dishes and is incubated in darkness at 28° C. until the development of well-formed, matured somatic embryos is seen. This requires about 14 days. Well-formed somatic embryos are opaque and cream-colored and are comprised of an identifiable scutellum and coleoptile. The embryos are individually subcultured to a germination medium comprising MS salts and vitamins, 100 mg/l myo-inositol, 40 gm/l sucrose and 1.5 gm/l Gelrite® in 100×25 mm Petri dishes and incubated under a 16 hour light:8 hour dark photoperiod and 40 meinsteinsm sec from cool-white fluorescent tubes. After about 7 days, the somatic embryos germinate and produce a well-defined shoot and root. The individual plants are subcultured to germination medium in 125×25 mm glass tubes to allow further plant development. The plants are maintained under a 16 hour light:8 hour dark photoperiod and 40 meinsteinsm sec from cool-white fluorescent tubes. After about 7 days, the plants are well-established and are transplanted to horticultural soil, hardened off and potted into commercial greenhouse soil mixture and grown to sexual maturity in a greenhouse. An elite inbred line is used as a male to pollinate regenerated transgenic plants.

Example 11: Soybean Embryo Transformation

Soybean embryos are bombarded with a plasmid comprising a preferred promoter operably linked to a heterologous nucleotide sequence comprising a polynucleotide sequence or subsequence, as follows. To induce somatic embryos, cotyledons of 3 5 mm in length are dissected from surface-sterilized, immature seeds of the soybean cultivar A2872, then cultured in the light or dark at 26° C. on an appropriate agar medium for six to ten weeks. Somatic embryos producing secondary embryos are then excised and placed into a suitable liquid medium. After repeated selection for clusters of somatic embryos that multiply as early, globular-staged embryos, the suspensions are maintained as described below.

Soybean embryogenic suspension cultures can be maintained in 35 ml liquid media on a rotary shaker, 150 rpm, at 26° C. with fluorescent lights on a 16:8 hour day/night schedule. Cultures are sub-cultured every two weeks by inoculating approximately 35 mg of tissue into 35 ml of liquid medium.

Soybean embryogenic suspension cultures may then be transformed by the method of particle gun bombardment (Klein, et al., (1987) Nature (London) 327:70-73, U.S. Pat. No. 4,945,050). A DuPont Biolistic™ PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188) and the 3' region of the nopaline synthase gene from the T-DNA of the Ti plasmid of Agrobacterium tumefaciens. The expression cassette of interest, comprising the preferred promoter and a heterologous polynucleotide, can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M) and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300 400 mg of a two-week-old suspension culture is placed in an empty 60×5 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 12: Ear Development at Varying Nitrogen Levels Sterile vs Fertile

Male sterility would reduce the nutrient requirement for tassel development resulting in improved ear development at anthesis. In this experiment male sterile sibs were grown in varying levels of nitrogen fertility and sampled at ~50% pollen shed. Male sterile plants produced larger ears under both nitrogen fertility levels. The proportion of male sterile plants with emerged silks was also greater than the fertile sib plants. Though the biomass (total above ground plant minus the ear dry weight) was greater in the higher nitrogen fertility grown plants there was no effect of male sterility on biomass. This shows the positive effect of male sterility is specifically on the ability of the plant to produce a heavier more fully developed (silks) ear without affecting overall vegetative growth.

Example 13: Nitrogen Budget Study

A study was undertaken, quantifying the nitrogen budget of developing maize ears and tassels when the plants are grown in increasing levels of nitrogen fertilizer. When maize is grown under lower nitrogen fertility levels the nitrogen budget of the ear is negative, or during development the ear loses nitrogen to other parts of the plant when nitrogen is limiting. The nitrogen budget of the ear improves as the amount of nitrogen fertilizer provided to the plant increases until the ear maintains a positive increase in nitrogen through to silk emergence. In contrast, the tassel maintains a positive nitrogen budget irrespective of the level of fertility in which the plant is grown. This result clearly shows that the tassel and ear compete for nitrogen during reproductive development and that the developing tassel dominates over the developing ear. Yield improvements associated with male sterile hybrids vectored through improved ear development are very consistent with the reduction in competition of ear development with tassel development.

Example 14: Field Experiments with Male Sterile Plants

Genetic male sterile hybrids also perform better in field experiments. Two field experiments were performed. In one experiment nitrogen fertilizer was varied with male sterile and male fertile hybrids segregating within each nitrogen fertility. Plant population density was varied in the second experiment, again, with male sterile and male fertile hybrids segregating within plant population densities. The experimental design of both experiments was a split plot. Nitrogen fertilizer rate was the main plot in the multiple rate nitrogen experiment and male sterile or male fertile was the sub plot. In the population experiment plant population was the main plot and male sterility or male fertility was the sub plot. The nitrogen fertilizer rates used in the multiple N experiment were 0, 30, 60, 90, 120 and 150 units (lbs acre) applied at V3 stage of development. The plant population used in the nitrogen multiple rate experiment was 32,000 plant $acre^{-1}$ whereas 32,000, 48,000 and 64,000 plant $acre^{-1}$ densities were used in the plant population study. The N fertility regime in the population study was 180 units N $acre^{-1}$ pre-plant for all populations followed by 95 units N $acre^{-1}$ side dressed at V6 (275 total units N $acre^{-1}$) in all plots. The 48,000 plant $acre^{-1}$ plots were supplemented with an additional 50 unit of N $acre^{-1}$ 10 days prior to flowering (325 total units N $acre^{-1}$) and the 64,000 plant $acre^{-1}$ plots were supplemented with an additional 100 units of N acre$^{-1}$ 10 days prior to flowering (375 total units N acre$^{-1}$).

Significant effects of male sterility were observed in both experiments. A significant effect of nitrogen fertility on yield was also observed but there was no significant effect of population density on yield. Results are presented below for each experiment.

Multiple N Experiment

The overall significance level (P>F) of each parameter was analyzed. Overall male sterile plants had statistically significantly (P>F<0.001) greater grain yield, number of ears plot$^{-1}$, higher SPAD, more silks, had longer and wider ears and more kernels ear$^{-1}$. These parameters also varied significantly with N fertility. There was a significant N fertility×male sterile/fertile interaction in ears plot$^{-1}$ and kernels ear$^{-1}$. This was due to the fact that fertile plants ear number plot$^{-1}$ increased with increased N fertility whereas the sterile plants had a constant number of ears plot$^{-1}$ across all of the N fertility levels. Silk number and kernels ear had significant treatment interactions and were likely due to a steeper rate of increase in silk number with N fertility in the male sterile plants than in the male fertile plants. The difference in yield between male fertile and male sterile plants was much greater at low N than at higher N levels. At 0 N acre$^{-1}$ the difference between male sterile and male fertile plants was 84% whereas the difference in yield between male sterile and male fertile plants was 15% at 150 lb acre$^{-1}$ N rate. In a hybrid trial involving MS44 mutants, an average increase of about 37 bu acre$^{-1}$ was observed. In another hybrid trial, the average increase was 13 bu acre$^{-1}$. (FIGS. 5A-5B).

SPAD was significantly different in response to N fertility and in response to male sterility but the response to N fertility of male sterile and male fertile plants was parallel indicating SPAD could not account for the difference in yield between male sterile and male fertile plants in response to N fertility.

Kernel number of male sterile and male fertile plants in response to N fertility showed different slopes, similarly as in the male sterile and male fertile yield response to N fertility which might suggest the increase in yield of male sterile plants might be related to increased kernel number. Differences in yield between male sterile and male fertile hybrids across N fertilities could nearly be accounted for by the sum of the differences in ears plot$^{-1}$ and kernels ear$^{-1}$ between male sterile and male fertile hybrids across N fertilities. These data are in agreement with the hypothesis that ear development is less encumbered by tassel development in male sterile plants resulting in more fully developed ears (kernels ear$^{-1}$) with a greater success rate of ear production (ear plot$^{-1}$) under low N. In one of the hybrid trials, the ear dry weight increased about 62% compared to the ear from normal fertile plants.

Population/Male Sterility Experiment

The genetic male sterile hybrid also responded better than the male fertile hybrid in the population stress experiment. Though there was no effect of population stress on grain yield, the genetic male sterile hybrid outperformed the male fertile hybrid by 40% (59 bu acre$^{-1}$) in all populations tested (see, FIG. 7A). In addition, in a separate trial, an average increase of about 8 bu acre$^{-1}$ was observed (see, FIG. 7B).

Example 15: Characterization of tls1 Gene and Utilization for Yield Enhancement

Phenotype of the tls1 mutant is shown in FIG. 8. A positional cloning approach was undertaken to clone tls1 (FIG. 9). The tls1 region was roughly mapped on Chr1 using 75 individuals from a tls1×Mo17 F2 population. A) The first round of fine mapping. tls1 was narrowed to a 15 cM region using 2985 F2 individuals. The resulting 177 recombinants were selfed and the progeny from each line were pooled together for further fine mapping. The 177 F3 families were used to narrow the tls1 interval to a four BAC region, containing no additional informative markers. The genes in the four BAC interval were sequenced and the only obvious difference was that ZmNIP3;1 could not be PCR amplified in the mutant. A BAC library from homozygous tls1 plants was created and BACs spanning the ZmNIP3;1 gene were sequenced to determine the nature of the mutation. B) BAC sequencing results. ZmNIP3;1 is missing in the mutant and in its place is ~9 kb of repetitive sequence. The closest neighboring genes, cytochrome P450 and IMP dehydrogenase, are indicated. FIGS. 2A and 2B are not drawn to scale. Sequence analysis of NIP3-1 from maize revealed a high level of similarity to NIP5;1 from *Arabidopsis* (AtNIP5;1) and NIP3;1 from rice (OsNIP3;1) and phylogenetic studies showed that they are closely related proteins in the NIP II subgroup (Liu, et al., (2009) *BCM Genomics* 10:1471-2164). (FIG. 15). These results indicate that NIP3-1 in maize is involved in boron uptake, and boron is needed for reproductive development.

Studies can be performed which manipulate the expression of tls1 in the development of hybrid maize for yield improvement under normal and stress conditions (e.g., nitrogen and water stress). NIP3-1 would be down-regulated in a tissue-specific manner (i.e., in the tassel), resulting in plants with no tassels that do not exhibit any of the other pleotropic effects associated with boron deficiency (e.g., underdeveloped ears). In this case, the resources that would be needed for tassel development may be allocated to the ear and shading effects from tassels would be minimized, resulting in an increased yield over other male sterility techniques in which a tassel is present. This same approach may be applied to any genes involved in the transport of boron.

tls1 Mutant Phenotype Rescued with Boron Application

Wild type and mutant plants from the F2 mapping population of tls1×Mo17 were planted. Half of the mutant and wild type plants were treated once a week from ~V2 to ~V6 stage with a foliar boron spray consisting of 0.0792% $B_2O_2$ and 0.0246% elemental Boron. It was observed that the mutant plants treated with the boron spray exhibited an increased number of tassel branches, which were longer and reminiscent of wild type in comparison to the untreated mutant plants. In addition, ears of the treated mutant plants appeared to be recovered as well. Wild type plants treated with boron had no discernable difference from untreated wild type plants. Recovered mutant plants were self-pollinated for a progeny test.

Progeny from self ing the recovered mutant plants were planted along with wild type for a control. Half the mutant progeny was treated with the boron spray as described above and half were left untreated. Tassel branch number (FIG. 11), branch length (FIG. 12) and ear length (FIG. 13) were measured from 24 wild type plants, 26 mutant plants treated with the boron spray and 29 untreated mutant plants. In comparison to the untreated mutant plants, mutant plants treated with the boron spray exhibited an increased number of tassel branches, increased tassel branch length, and an increased ear length similar to wild type plants (FIGS. 11-13). In addition, the observation that the progeny of recovered mutant plants still display the tls1 phenotype when left untreated indicates that the effects of treating with the boron spray are not transmitted to subsequent generations.

tls1 Mutant are More Tolerant to Boron Toxicity

Preliminary results indicate that the tls1 mutant may be more tolerant of boron toxic conditions than wild type plants. Wild type and mutant plants were grown hydroponically using Hoagland media containing either a normal Boron concentration (0.5 ppm) or 50 ppm of Boron. At ~V7 stage, mutant and wild type plants grown under normal Boron conditions were indistinguishable (FIG. 14). However, when grown in 50 ppm of Boron, mutant plants appeared larger overall and had wider leaves. In addition, in wild type plants grown in 50 ppm Boron, the node of the second youngest fully expanded leaf extended above the node of the youngest fully expanded leaf, while the mutant plants appeared normal.

Mutant Rescue and Seed Production by Boron Application

Homozygous tls1 plants have reduced tassel growth or substantially lack functional tassel for normal ear development. Therefore, the quantity of seeds from tls1 mutant plants or plants with reduced tassel development due to a deficiency in boron uptake are not to the levels needed for large-scale seed production. Because exogenous boron application rescues tassle development and growth in the tls1 mutant background, boron application is an option to increase seed production from tls1 plants. Depending on the need and the mode of application, exogenous boron (e.g., as a foliar spray) can be applied at various stages of reproductive growth (e.g., V2-V12 or V2-V8) and with varying levels of boron (e.g., 10-1000 ppm). In an embodiment, boron application can coincide with the transition from vegetative to reproductive state, e.g., V4-V5 depending on plant growing conditions.

Alleles of tls1

Based on the disclosure and guidance provided herein, additional weaker or stronger alleles of tls1 are obtained by performing available screens, e.g., through Targeting Induced Local Lesions in Genomes (TILLING), McCallum, et al., (2000) *Nat Biotechnol* 18:455-457. Additional alleles of Tls1 can include those variants that completely block boron transport resulting in substantial loss of tassel growth and development and those variants that result in for example, 10%, 20%, 30%, 40%, 50%, 60%, 70%, 80%, 90% or 95% reduction in tassel development as evidenced by the reduced pollen production or other suitable parameter known to those or ordinary skill in the art.

Example 16: Field Experiments on Reduced Male Fertility Plants with Drought Stress Treatments The effect of reduced male fertility on yield of maize grown under drought stress conditions evaluated in a field study. The field study was conducted in a managed stress field environment. The field location receives little or no rainfall during the growing season, allowing for the imposition of drought stress by removing the irrigation at various stages of development. This field location has no insect or disease pressure to interfere with the interpretation of hybrid performance under drought.

Male sterile and fertile versions of a single hybrid are planted in 10 replicates of a split plot design using standard planting practices. Plants were thinned to a standard density so that plant water use plot should be uniform. A stress treatment was imposed by eliminating irrigation from the plots beginning at the V8 stage of development. The plants continued to utilize the water that remained in the soil profile. After approximately 3 weeks, plant water deficits occurred, as indicated by leaf rolling and decreased plant growth. Plants remained under this water deficit condition until approximately 2 weeks after flowering, when the drought-stressed plots were fully rewatered. Thus the total duration of the stress treatment was about 5-6 weeks, bracketing the flowering period of development.

Maize is extremely sensitive to drought stress during the flowering period. Typically, development of the ears, exsertion of the silks and pollination of the ovaries are all inhibited by drought stress. The sensitivity of these processes is a major factor in reducing yield under drought stress. Alleviation of this sensitivity is an effective method of improving drought stress in maize. Male sterile plants will partition more assimilates to the ear during this critical period, thus making them more tolerant to this stress. The male sterile plants will exsert silks more rapidly, resulting in more efficient pollination of those ovaries, and a higher final kernel number plant$^{-1}$. The improvement of this critical reproductive process results in greater yield at harvest.

In this study, the data confirmed that drought tolerance was improved by reduced male fertility. The yield of the Male Sterile plants in the stress treatment was 106.7 bu acre$^{-1}$, while the yield of the Male Fertile plants in the stress treatment was 62.6 bu acre$^{-1}$. Total kernel number ear$^{-1}$ in the Male Sterile plants was 204.3, vs. 130.2 for the Male Fertile plants, confirming that ear development and kernel set under stress was improved in the Male Sterile plants.

Example 17: Creation of Male-Sterile Hybrid Progeny

A method for production of male-sterile hybrid plants is provided. In the hybrid production field, in one embodiment, female parent (male-sterile) plants of inbred A, homozygous recessive for a male-fertility gene, are fertilized by plants of inbred B. Inbred B is similarly homozygous recessive for the male-fertility gene; however Inbred B is hemizygous for a heterologous construct. This construct comprises (a) the dominant allele of the male-fertility gene, which complements the recessive genotype and restores fertility to inbred B; (b) a genetic element which results in disruption of the formation, function, or dispersal of pollen; (c) optionally, a marker gene, which may be a marker expressed in seed. As a result, seed produced on Inbred A are homozygous recessive for the male-fertility gene and will produce male-sterile progeny. These progeny are non-transgenic with respect to the described construct, because element "b" prevents transmission of the construct through pollen. See, for example, FIG. 3.

Because these hybrid plants are male-sterile, it is necessary to provide a pollinator. For planting of these hybrid seed in a grain-production field, it is practical to blend the hybrid seed with pollinator seed. The pollinator seed will be present in the minimum amount necessary to achieve adequate pollination of a substantial portion of the plants produced from the blended seed. Preferably, at least 1% to 50%, more preferably less than 25%, most preferably less than 15% of the blend (by weight) will be pollinator seed. Especially preferred is a blend wherein the pollinator seed is present in an amount of about 1% to 10% by weight. A substantial portion would be about 90% of the plants produced, more preferably about 95%, most preferably about 98% or more of the plants produced by the blend.

Example 18: Creation of Hybrid Male-Sterile Progeny Using Dominant Ms44

Figure 4:
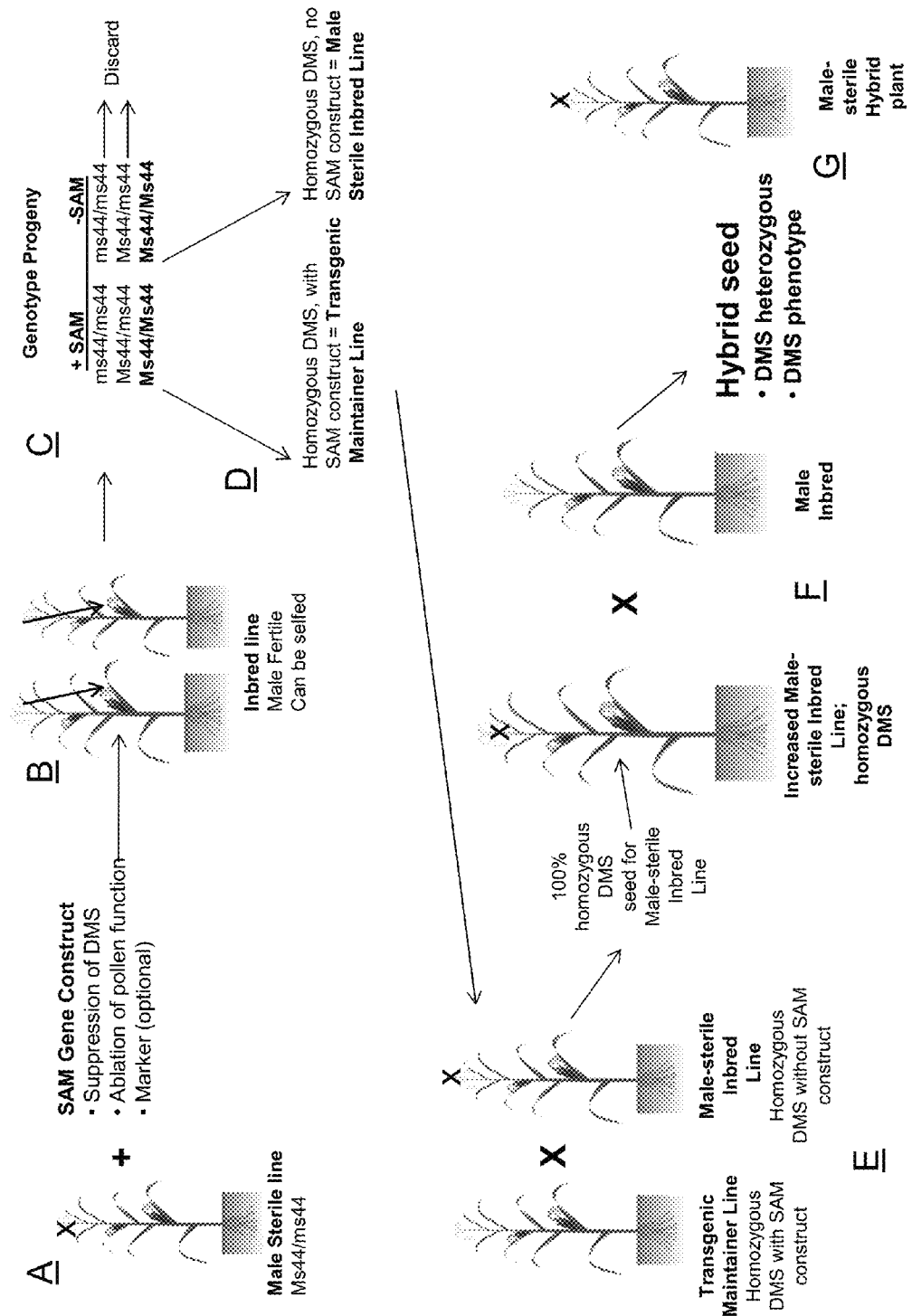
FIG. 4—Diagram of method for producing male sterile hybrid seeds using a dominant male-sterility gene.

In this example, the cloned dominant male-sterile gene Ms44 is used to produce male-sterile hybrid plants. See, FIG. 4, for example. A female inbred containing Ms44 in the heterozygous state is transformed with a heterologous SAM construct that comprises (1) a Suppression element, for example an inverted repeat (IR) engineered to the Ms44 promoter or Ms44 coding region; (2) a pollen Ablation gene which results in disruption of the formation, function, or dispersal of pollen; (3) a Marker gene, which may be a seed color gene. The suppression element disrupts the transcription or translation of the dominant Ms44 allele, such that the otherwise male-sterile plant is male-fertile and can be selfed. Because element 2 prevents transgene transmission through pollen, the resulting progeny on the ear will segregate 50:50 with respect to the hemizygous SAM construct and 25% of all the progeny will be homozygous for the Ms44 dominant allele. Seeds comprising the SAM construct can be identified by presence of the marker. Progeny from these seed can be genotyped to identify homozygous Ms44 progeny with the SAM construct; these are referred to as the maintainer line. Homozygous Ms44 progeny without the SAM construct are referred to as the male sterile female inbred (or "male-sterile inbred" line).

Male-sterile inbred seed can be increased by crossing the maintainer line onto male sterile female inbred lines. The resulting progeny are male-sterile homozygous Ms44 female inbreds, because the SAM construct is not passed through pollen to progeny. In this way the transgenic maintainer line is used to maintain, propagate, or increase the male sterile plants.

In a hybrid production cross, the male inbred crosses normally onto this male-sterile female inbred line, and no detasseling is required. However, because the Ms44 gene is a dominant male-sterile gene and is homozygous in the female inbred, 100% of the hybrid seed will contain a dominant Ms44 allele and plants produced from those seed will be male-sterile.

When this hybrid seed is planted in a grain-production field, it is practical to blend it with seed of a pollinator. The pollinator seed is present in the minimum necessary amount sufficient to permit adequate pollination of the plants produced from the blend. Preferably, at least 1% to 50%, more preferably less than 25%, most preferably less than 15%, of the blend (by weight) will be pollinator seed. Especially preferred is a blend wherein the pollinator seed is present in an amount of about 1-10% by weight. The pollinator seed should be present in the blend only in an amount sufficient to pollinate a substantial portion of the plants produced by the blend. A substantial portion would be about 90% of the plants produced, more preferably about 95%, most preferably about 98% or more of the plants produced by the blend.

Alternatively, pollinator blends in the hybrid grain crop could be predetermined in the seed production field by blending heterozygous MS44 female inbred parent with the homozygous MS44 female inbred parent. Since half of the progeny produced from a heterozygous dominant male sterile cross will segregate as male fertile, the proportion of pollinator in the hybrid grain crop can be pre-set by blending twice the proportion of heterozygous MS44 female inbred as the desired proportion of male fertile pollinators in the hybrid grain crop. If a final proportion of male fertile pollinator of 10% is desired then 20% of the seed production female could be blended as heterozygous MS44 female inbred. Any proportion of pollinator in the hybrid grain crop up to 50% can be produced in this fashion. The heterozygous MS44 female parent can be produced by crossing the homozygous MS44 inbred with wild type version of the same inbred. All of the progeny from this cross will be heterozygous MS44 and male sterile to effect cross pollination in the seed production field.

Alternatively, the dominant Ms44 gene could be introduced transgenically, operably linked to a heterologous promoter that is amenable to IR inactivation but expresses, such that dominant male sterility is achieved. This would ensure that the native ms44 expression is not inhibited by the IR. The rice5126 promoter may be appropriate, since it has an expression pattern that is similar to that of the ms44 gene and it has been utilized for promoter IR inactivation successfully.

This approach has applications not only for yield gain during stress but is also useful for any crop that can outcross to weedy species, such as sorghum, by reducing the propensity for outcrossing and minimizing the risk of adventitious presence. For example, the biofuels industry is utilizing enzymes transgenically to aid in the digestibility of substrates (i.e.cellulose) used in ethanol production. Linking these types of transgenes to the Ms44 gene would prevent outcrossing through pollen in a production field. One or more dominant traits could be linked to Ms44 to prevent an unintentional outcross to weedy species.

Example 19: Dominant Male Sterility in Hybrids

The dominant male sterility (DMS) gene Ms44 is introgressed into a female inbred maize line. Since this gene acts dominantly, selfing of these lines is not possible and the mutation will segregate 50:50 in resulting outcrossed progeny. Linked genetic markers may be employed to identify those plants containing the DMS gene so that the maize male inbred line can be used to cross specifically to those plants to create F1 hybrid seed. Again this hybrid seed will segregate 50% for male sterility. Ms41 and Ms42 are other known DMS mutants that are dominant in maize. (Liu and Cande, (1992) *MNL* 66:25-26; and Albertsen, et al., (1993) *MNL* 67:64)

An alternative approach is to use a transgenic Ms44 gene for dominant sterility. This gene would be linked to a seed marker gene and transformed into a female inbred line. Seed from this line could then be sorted based on the presence of the seed marker gene to ensure a pure population of Ms44 male sterile progeny from the female line. These progeny would then be crossed with a male inbred in a hybrid production field to yield 50% male sterility in the resultant hybrid progeny.

Example 20: Variants of Disclosed Sequences

Additional MS44 mutant sequences can be generated by known means including but not limited to truncations and point mutations. These variants can be assessed for their impact on male fertility by using standard transformation, regeneration, and evaluation protocols.

A. Variant Nucleotide Sequences That Do Not Alter the Encoded Amino Acid Sequence The disclosed nucleotide sequences are used to generate variant nucleotide sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO. These functional variants are generated using a standard codon table. While the nucleotide sequence of the variants is altered, the amino acid sequence encoded by the open reading frames does not change. These variants are associated with component traits that determine biomass production and quality. The ones that show association are then used as markers to select for each component traits.

B. Variant Nucleotide Sequences in the Non-Coding Regions

The disclosed nucleotide sequences are used to generate variant nucleotide sequences having the nucleotide sequence of the 5'-untranslated region, 3'-untranslated region or promoter region that is approximately 70%, 75%, 80%, 85%, 90% and 95% identical to the original nucleotide sequence of the corresponding SEQ ID NO. These variants are then associated with natural variation in the germplasm for component traits related to biomass production and quality. The associated variants are used as marker haplotypes to select for the desirable traits.

C. Variant Amino Acid Sequences of Disclosed Polypeptides

Variant amino acid sequences of the disclosed polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using a protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method. These variants are then associated with natural variation in the germplasm for component traits related to biomass production and quality. The associated variants are used as marker haplotypes to select for the desirable traits.

D. Additional Variant Amino Acid Sequences of Disclosed Polypeptides

In this example, artificial protein sequences are created having 80%, 85%, 90% and 95% identity relative to the reference protein sequence. This latter effort requires identifying conserved and variable regions in an alignment and then the judicious application of an amino acid substitutions table. These parts will be discussed in more detail below.

Largely, the determination of which amino acid sequences are altered is made based on the conserved regions among disclosed protein or among the other disclosed polypeptides. Based on the sequence alignment, the various regions of the disclosed polypeptide that can likely be altered are represented in lower case letters, while the conserved regions are represented by capital letters. It is recognized that conservative substitutions can be made in the conserved regions below without altering function. In addition, one of skill will understand that functional variants of the disclosed sequence of the disclosure can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the disclosed polypeptides are generating having about 80%, 85%, 90% and 95% amino acid identity to the starting unaltered ORF nucleotide sequence.

E. Variant Amino Acid Sequences of Disclosed Polypeptides that Interfere with Signal Peptide Processing Variant amino acid sequences of the disclosed polypeptides are generated. In this example, one or more amino acids are altered. Specifically, the N-terminal secretory signal sequence (SS) is reviewed to determine the possible amino acid(s) alteration. The selection of the amino acid to change is made by predicting the SS cleavage site using available prediction programs such as SignalP (von Heijne, G. "A new method for predicting signal sequence cleavage sites" Nucleic Acids Res.: 14:4683 (1986). Improved prediction of signal peptides: SignalP 3.0, Bendtsen J D, Nielsen H, von Heijne G, Brunak S., *J Mol Biol.* 2004 Jul. 16; 340(4):783-95.) An amino acid is selected that is deemed to be necessary for proper protein processing and secretion. Secretory proteins are synthesized on ribosomes bound to the rough ER. In the plant cell, the signal sequence, a sequence of hydrophobic amino acids usually at the N-terminus, is bound by a signal-recognition particle (SRP), which in turn is bound by an SRP receptor on the rough ER membrane. The SRP directs the binding of the ribosome to the ER membrane, as well as threading the protein through the transmembrane channel, called the translocon, where it is processed into its mature form by signal peptidase cleavage of the SS. An amino acid change that disrupts SRP binding or signal peptidase cleavage could inhibit the normal processing and secretion of the protein. For the Ms44 protein these types of amino acid substitutions would lead to a dominant male sterility phenotype.

All publications and patent applications in this specification are indicative of the level of ordinary skill in the art to which this disclosure pertains. All publications and patent applications are herein incorporated by reference to the same extent as if each individual publication or patent application was specifically and individually indicated by reference.

The disclosure has been described with reference to various specific and preferred embodiments and techniques. However, it should be understood that many variations and modifications may be made while remaining within the spirit and scope of the disclosure.

What is claimed is:

1. A method for increasing yield or maintaining yield stability in a population of hybrid maize plants in a field, in the absence of detasseling, the method comprising:
   growing a population of male sterile hybrid maize plants that comprise a dominant mutation in a polynucleotide encoding a polypeptide comprising an amino acid sequence that is at least 95% identical to SEQ ID NO:14 or SEQ ID NO:153, the mutation causing male sterility, wherein said encoded polypeptide comprises Threonine or Valine corresponding to amino acid 37 of either SEQ ID NOs:14 or 153,
   wherein the population of male sterile hybrid maize plants are produced from a male sterile female maize plant containing the mutation, said male sterile female maize plant resulting from a fertile female inbred maize plant homozygous for the mutation,
   thereby increasing the yield compared to a control field that does not contain the male sterile hybrid maize plants.

2. The method of claim 1, wherein the population of hybrid maize plants is grown under abiotic stress.

3. The method of claim 1, wherein the population of hybrid maize plants is grown under a nitrogen limited condition.

4. The method of claim 1, wherein the population of hybrid maize plants has as an agronomic parameter selected from the group consisting of increased silk emergence, increased ear length, increased ear width, increased seed number per ear, increased seed weight per ear, and seed with increased embryo size.

5. The method of claim 1, wherein the polynucleotide comprises a mutation G to an A at position 118 relative to the first Met codon of SEQ ID NO: 13, resulting in an amino acid change at amino acid 37, from Alanine to Threonine that results in dominant genetic male sterility.

6. The method of claim 1, wherein the polynucleotide encodes a polypeptide comprising the amino acid sequence of SEQ ID NO:14 or SEQ ID NO:153.

7. The method of claim 1, wherein the polynucleotide is either SEQ ID NO:13 or SEQ ID NO:15.

8. The method of claim 1, wherein the mutation is introduced into an endogenous polynucleotide of the plant.

9. A method of increasing maize yield in a field comprising a first population of hybrid maize plants which exhibit dominant male sterility conferred by a dominant mutation, in the absence of detasseling, the method comprising:
   growing a population of maize plants in the field, wherein the hybrid maize plants exhibiting dominant male sterility comprise a polynucleotide which comprises said mutation, said polynucleotide encoding a polypeptide comprising the amino acid sequence of either SEQ ID NO:14 or SEQ ID NO:153, or an amino acid sequence that is at least 95% identical to either SEQ ID NO:14 or SEQ ID NO:153, said polypeptide comprising Threonine or Valine corresponding to position 37 of SEQ ID NO:14 or SEQ ID NO:153, and wherein
   (a) the field further comprises a second population of maize plants that produce an effective amount of pollen to fertilize the first population of maize plants in the field, and
   (b) the hybrid maize plants are produced from a male sterile female maize plant containing the mutation, said male sterile female maize plant resulting from a fertile female inbred line homozygous for the mutation,
   thereby increasing the yield compared to a control field that does not contain the first population of plants.

10. The method of claim 9, wherein the first population of plants is selected from the group consisting of maize plant populations which:
   a. comprises about 50% to about 90% of the maize plants in the field,
   b. comprises about 80% of the maize plants in the field,
   c. comprises about 75% of the maize plants in the field,
   d. comprises about 85% of the maize plants in the field, and
   e. comprises about 70% of the maize plants in the field.

* * * * *

```
                         SEQUENCE LISTING

<160> NUMBER OF SEQ ID NOS: 156

<210> SEQ ID NO 1
<211> LENGTH: 22
<212> TYPE: DNA
<213> ORGANISM: artificial sequence
<220> FEATURE:
<223> OTHER INFORMATION: primer

<400> SEQUENCE: 1
cagtcctgct cggagcttgc tt                                          22

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
accgaaggat gcctgggaat                                             20

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
caacgagagc gaggagacga                                             20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
gaacttgacc ttgacgcgga                                             20

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5
agttgttgtg cttgaagtac ttggg                                       25

<210> SEQ ID NO 6
<211> LENGTH: 25
<212> TYPE: DNA
<213> ORGANISM: artificial sequence
```

```
<220> FEATURE:
<223> OTHER INFORMATION: primer

<400> SEQUENCE: 6
ggtcataggc tttcaagtgt acaca                                          25

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
ccacacgatg aaggcagacc                                                20

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
aaacagtgca gcatcgccaa                                                20

<210> SEQ ID NO 9
<211> LENGTH: 2213
<212> TYPE: DNA
<213> ORGANISM: Zea mays

<400> SEQUENCE: 9
catcggtcgt cggactctta atagccggct ttaggatatt gtccggggag atatcggtgt    60
gatctttaga accggccatt tgatggcctg agttttagta gatctagaca catttcccca   120
acggagtcgc caaaaagtgt gttggcgccg atccaggcgc gaaacactgg agatggaccg   180
tttggcggtg ttctctgcgg aggtgaggac ggtccgcgac ctggcgcagc agcgactctc   240
ctctacgtgt gtccggacgg tccgcgtctg gggctcggac ggtccgcgat ggcgcagagg   300
gtcttcttct tcgcagccga cctagatctc gcctcccggg agggaccccg tcggggagga   360
gagattgtag ggtgtgtctt ggcgtcgaca ggccacacaa tacgcctcta gtcgacgtag   420
agccgaagag aggtgaagga ttgaggtaga aggaggctaa acttgggcta aactagaact   480
actgctaatg cataaggtaa aaacgagaag tggacttcat ttgatcgatt gtggaaggtt   540
taatcgactg tagccccttta tctatataaa ggggaggtat ggacccgtta caagccgttt   600
cccgagctaa tctcacggtt ttagttaata atcctgcga gaaactcgga actctaactg    660
attctactca tgcgcgaacc attcgtgccg ccaccgctgc ccgtccggct acgctcagtt   720
aaccctgtgt tgtgcgctgt gatttggtgg catataaaac cacatttgca ataaaatt     780 gtagggatt aacataccaa gtgctgcgga aaggaatcgt tttcggagga cccaaaatta    840
aagaggcaga tgctagagct cgtccagctc agcgctgagc acctgtgttg tcttcctcgt   900
ccacgccggc ggagatgaac ggcaacaaag gcggaaaggc cgagacgctg agctcaagga   960
cgtgacaccg cgcgtacctc gcgttcagtt ggctcacaca acagcagctc gctcgcccca  1020
agctcccgcg tcctgatccg taggtgagcc atgcaaaggt cgccgcgcgc cctgatccat  1080
tgcacccttc aaagctcgaa cctacaaata gcgtgcacca ggcatcctgg ccacacccac  1140
acagcaagcc agcagagcag aaagcagccg cagccccagc ccccacaaga cgaggcaaca  1200
```

```
atggcgctag aagcagccac cgcccccgc gcactcctcg ccgcgtgcct cgtcctgctg    1260
gtcctcggcg gcggcaccgg cccgtcgtcg gtgctgcgcg gcgccggggc gcaggccggc    1320
gggcagtgcc tgccgcagct gaaccgcctc ctggcgtgcc gcgcgtacct ggtgcccggc    1380
gcgccggacc ccagcgcgga ctgctgcagc gcgctgagcg ccgtgtcgca cgagtgcgcc    1440
tgcagcacca tgggcatcat caacagcctg cccggccggt gccacctcgc ccaagccaac    1500
tgctgtaagc ttgtagccag gccgcaacgg cttcgtctct tcatctcggt gctatgctaa    1560
gcttattaat cttatgtttt cctgcggttc gtgttcacca tgcagccgct tgaagcaggg    1620
acctggcacg cgtgctgcaa tggatggcag gaggggagag gaataagaag tgtttccatt    1680
tcacagtgag agcagtcgag ctccaacgtt gtcgtcgtcg tcgtcttctt cttttgatat    1740
tcagactctg tcttgcggtc tatatcatca gcataataat aataaaataa gtaaaaccaa    1800
accatgcatg accatgctat acatgttgcg agttccagcg agacggttaa ctataatgac    1860
tgcaacaaag gattctgttc gttttgacac gtgatcacgt aagaataccg ctcaggagac    1920
caacacggat ggtctaaacc actatctcca agtaaaacca tactcaagtc ttaaaaccgc    1980
aagagctaca gttgttctga aatctgaatg tagaactgcc catctgcaca gtcagatcga    2040
aacacctccg tttcagagca cagaagatgg cgacgggatc tctagagatc agtaatcatt    2100
caaccgctgc agtattttca tgaacacacg ccaggcacga tctaaatgac cgattttata    2160
agtgcatata ctactcgacc ataactccag aaccttgtac tctacgcaga cag           2213
```

<210> SEQ ID NO 10
<211> LENGTH: 103
<212> TYPE: PRT
<213> ORGANISM: Zea mays

<400> SEQUENCE: 10

```
Met Ala Leu Glu Ala Ala Thr Ala Pro Arg Ala Leu Leu Ala Ala Cys
1               5                   10                  15

Leu Val Leu Val Leu Gly Gly Ser Thr Gly Pro Ser Ser Val Leu
            20                  25                  30

Arg Gly Ala Gly Ala Gln Ala Gly Gly Gln Cys Leu Pro Gln Leu Asn
        35                  40                  45

Arg Leu Leu Ala Cys Arg Ala Tyr Leu Val Pro Gly Ala Pro Asp Pro
    50                  55                  60

Ser Ala Asp Cys Cys Ser Ala Leu Ser Ala Val Ser His Glu Cys Ala
65                  70                  75                  80

Cys Ser Thr Met Gly Ile Ile Asn Ser Leu Pro Gly Arg Cys His Leu
                85                  90                  95

Ala Gln Ala Asn Cys Ser Ala
            100
```

<210> SEQ ID NO 11
<211> LENGTH: 25
<212> TYPE: DNA
<213> ORGANISM: artificial sequence
<220> FEATURE:
<223> OTHER INFORMATION: primer

<400> SEQUENCE: 11

```
gagatgaacg gcaacaaagg cggaa                                           25
```

<210> SEQ ID NO 12
<211> LENGTH: 25
<212> TYPE: DNA

<213> ORGANISM: artificial sequence
<220> FEATURE:
<223> OTHER INFORMATION: primer

<400> SEQUENCE: 12
atagcaccga gatgaagaga cgaag           25

<210> SEQ ID NO 13
<211> LENGTH: 2356
<212> TYPE: DNA
<213> ORGANISM: Zea mays

<400> SEQUENCE: 13

| | | | | | |
|---|---|---|---|---|---|
| aattcgccct | tgttgttgc | tcatcggtcg | tcggactctt | aatagccggc | tttaggatat | 60 |
| tgtccgggga | gatatcggtg | tgatctttag | aaccggccat | ttgatggcct | gagttttagt | 120 |
| agatctagac | acatttcccc | aacggagtcg | ccaaaaagtg | tgttggcgcc | gatccaggcg | 180 |
| cgaaacactg | gagatggacc | gtttggcggt | gttctctgcg | gaggtgagga | cggtccgcga | 240 |
| cctggcgcag | cagcgactct | cctctacgtg | tgtccggacg | gtccgcgtct | ggggctcgga | 300 |
| cggtccgcga | tggcgcagag | ggtcttcttc | ttcgcagccg | acctagatct | cgcctcccgg | 360 |
| gagggacccc | gtcggggagg | agagattgta | gggtgtgtct | tggcgtcgac | aggccacaca | 420 |
| atacgcctct | agtcgacgta | gagccgaaga | gaggtgaagg | attgaggtag | aaggaggcta | 480 |
| aacttgggct | aaactagaac | tactgctaat | gcataaggta | aaaacgagaa | gtggacttca | 540 |
| tttgatcgat | tgtggaaggt | ttaatcgact | gtagcccttt | atctatataa | aggggaggta | 600 |
| tggacccgtt | acaagcygtt | tcccgagcta | atctcacggt | tttagttaat | aaatcctgcg | 660 |
| agaaactcgg | aactctaact | gattctactc | atgcgcgaac | cattcgtgcc | gccaccgctg | 720 |
| cccgtccggc | tacgctcagt | taaccctgtg | ttgtgcgctg | tgatttggtg | gcatataaaa | 780 |
| ccacatttgc | aataaaaatt | tgtagggatt | taacatacca | agtgctgcgg | aaaggaatcg | 840 |
| ttttcggagg | acccaaaatt | aaagaggcag | atgctagagc | tcgtccagct | cagcgctgag | 900 |
| cacctgtgtt | gtcttcctcg | tccacgccgg | cggagatgaa | cggcaacaaa | ggcggaaagg | 960 |
| ccgagacgct | gagctcaagg | acgtgacacc | gcgcgtacct | cgcgttcagt | tggctcacac | 1020 |
| aacagcagct | cgctcgcccc | aagctcccgc | gtcctgatcc | gtaggtgagc | catgcaaagg | 1080 |
| tcgccgcgcg | ccctgatcca | ttgcacccctt | caaagctcga | acctacaaat | agcgtgcacc | 1140 |
| aggcatcctg | gccacaccca | cacagcaagc | cagcagagca | gaaagcagcc | gcagccccag | 1200 |
| cccccacaag | acgaggcaac | aatggcgcta | gaagcagcca | ccgcccccg | cgcactcctc | 1260 |
| gccgcgtgcc | tcgtcctgct | ggtcctcggc | ggcagcaccg | gccgtcgtc | ggtgctgcgc | 1320 |
| ggcgccggga | cgcaggccgg | cgggcagtgc | ctgccgcagc | tgaaccgcct | cctggcgtgc | 1380 |
| cgcgcgtacc | tggtgcccgg | cgcgccggac | cccagcgcgg | actgctgcag | cgcgctgagc | 1440 |
| gccgtgtcgc | acgagtgcgc | ctgcagcacc | atgggcatca | tcaacagcct | gcccggccgg | 1500 |
| tgccacctcg | cccaagccaa | ctgctgtaag | cttgtagcca | ggccgcaacg | gcttcgtctc | 1560 |
| ttcatctcgg | tgctatgcta | agcttattaa | tcttatgttt | tcctgcggtt | cgtgttcacc | 1620 |
| atgcagccgc | ttgaagcagg | gacctggcac | gcgtgctgca | atggatggca | ggaggggaga | 1680 |
| ggaataagaa | gtgtttccat | tcacagtgga | gagcagtcga | gctccaacgt | tgtcgtcgtc | 1740 |
| gtcgtcttct | tcttttgata | ttcagactct | gtcttgcggt | ctatatcatc | agcataataa | 1800 |
| taataaaata | agtaaaacca | aaccatgcat | gaccatgcta | tacatgttgc | gagttccagc | 1860 |
| gagacggtta | actataatga | ctgcaacaaa | ggattctgtt | cgttttgaca | cgtgatcacg | 1920 |

```
taagaatacc gctcaggaga ccaacacgga tggtctaaac cactatctcc aaagtaaacc    1980
atactcaagt cttaaaaccg caagagctac agttgttctg aaatctgaat gtagaactgc    2040
ccatctgcac agtcagatcg aaacacctcc gtttcagagc acagaagatg gcgacgggat    2100
ctctagagat cagtaatcat tcaaccgctg cagtattttc atgaacacac gccaggcacg    2160
atctaaatga ccgattttat aagtgcatat actactcgac cataactcca gaaccttgta    2220
ctctacgcag acggttttc taggaacaga gcttcctgct tgctagtgag accgagatcg     2280
ctcagtgaca tctggctctc caattcagtg aaggcacgcc tgggataaga cctcgcctgt    2340
ccaaagaaaa agggcg                                                     2356

<210> SEQ ID NO 14
<211> LENGTH: 103
<212> TYPE: PRT
<213> ORGANISM: Zea mays

<400> SEQUENCE: 14

Met Ala Leu Glu Ala Ala Thr Ala Pro Arg Ala Leu Leu Ala Ala Cys
1               5                   10                  15

Leu Val Leu Leu Val Leu Gly Gly Ser Thr Gly Pro Ser Ser Val Leu
            20                  25                  30

Arg Gly Ala Gly Thr Gln Ala Gly Gly Gln Cys Leu Pro Gln Leu Asn
        35                  40                  45

Arg Leu Leu Ala Cys Arg Ala Tyr Leu Val Pro Gly Ala Pro Asp Pro
    50                  55                  60

Ser Ala Asp Cys Cys Ser Ala Leu Ser Ala Val Ser His Glu Cys Ala
65                  70                  75                  80

Cys Ser Thr Met Gly Ile Ile Asn Ser Leu Pro Gly Arg Cys His Leu
                85                  90                  95

Ala Gln Ala Asn Cys Ser Ala
            100

<210> SEQ ID NO 15
<211> LENGTH: 312
<212> TYPE: DNA
<213> ORGANISM: Zea mays

<400> SEQUENCE: 15
atggcgctag aagcagccac cgccccccgc gcactcctcg ccgcgtgcct cgtcctgctg    60
gtcctcggcg gcagcaccgg cccgtcgtcg gtgctgcgcg gcgccgggac gcaggccggc    120
gggcagtgcc tgccgcagct gaaccgcctc ctggcgtgcc gcgcgtacct ggtgcccggc    180
gcgccggacc ccagcgcgga ctgctgcagc gcgctgagcg ccgtgtcgca cgagtgcgcc    240
tgcagcacca tgggcatcat caacagcctg cccggccggt gccacctcgc ccaagccaac    300
tgctccgctt ga                                                        312

<210> SEQ ID NO 16
<211> LENGTH: 252
<212> TYPE: PRT
<213> ORGANISM: Arabidopsis thaliana

<400> SEQUENCE: 16

Met Glu Thr Val Ala Leu Ser Glu Arg Leu Glu Leu Tyr Ser Ser Glu
1               5                   10                  15

Arg Leu Glu Ala Leu Ala Gly Leu Tyr Ile Leu Glu Leu Glu Val Ala
            20                  25                  30
```

```
Leu Ala Leu Ala Met Glu Thr Pro His Glu Leu Glu Ala Leu Ala Thr
            35                  40                  45

His Arg Gly Leu Tyr Pro Arg Thr His Arg Val Ala Leu Leu Glu Ala
        50                  55                  60

Leu Ala Gly Leu Asn Gly Leu Asn Cys Tyr Ser Ala Arg Gly Ala Ser
65                  70                  75                  80

Pro Gly Leu Leu Glu Ser Glu Arg Ala Ser Asn Val Ala Leu Gly Leu
                85                  90                  95

Asn Val Ala Leu Cys Tyr Ser Ala Leu Ala Pro Arg Leu Glu Leu Glu
                100                 105                 110

Leu Glu Pro Arg Gly Leu Tyr Ala Leu Ala Val Ala Leu Ala Ser Asn
            115                 120                 125

Pro Arg Ala Leu Ala Ala Leu Ala Ala Ser Asn Ser Glu Arg Ala Ser
        130                 135                 140

Asn Cys Tyr Ser Cys Tyr Ser Ala Leu Ala Ala Leu Ala Leu Glu Gly
145                 150                 155                 160

Leu Asn Ala Leu Ala Thr His Arg Ala Ser Asn Leu Tyr Ser Ala Ser
                165                 170                 175

Pro Cys Tyr Ser Leu Glu Cys Tyr Ser Ala Ser Asn Ala Leu Ala Leu
                180                 185                 190

Glu Ala Arg Gly Ala Leu Ala Ala Leu Ala Thr His Arg Thr His Arg
            195                 200                 205

Leu Glu Thr His Arg Ser Glu Arg Leu Glu Cys Tyr Ser Ala Ser Asn
        210                 215                 220

Leu Glu Pro Arg Ser Glu Arg Pro His Glu Ala Ser Pro Cys Tyr Ser
225                 230                 235                 240

Gly Leu Tyr Ile Leu Glu Ser Glu Arg Ala Leu Ala
                245                 250

<210> SEQ ID NO 17
<211> LENGTH: 265
<212> TYPE: PRT
<213> ORGANISM: Oryza sativa

<400> SEQUENCE: 17

Met Glu Thr Ala Leu Ala Ala Leu Ala Ser Glu Arg Leu Tyr Ser Gly
1               5                   10                  15

Leu Tyr Ala Ser Asn Ala Leu Ala Ala Leu Ala Leu Ala Leu Ala Leu
                20                  25                  30

Ala Ala Leu Ala Cys Tyr Ser Ala Leu Ala Leu Glu Val Ala Leu Leu
            35                  40                  45

Glu Val Ala Leu Leu Glu Leu Glu Ala Leu Ala Val Ala Leu Gly Leu
        50                  55                  60

Tyr Ala Leu Ala Gly Leu Ala Leu Ala Gly Leu Asn Gly Leu Tyr Gly
65                  70                  75                  80

Leu Tyr Gly Leu Tyr Gly Leu Tyr Gly Leu Tyr Gly Leu Cys Tyr Ser
                85                  90                  95

Val Ala Leu Pro Arg Gly Leu Asn Leu Glu Ala Ser Asn Ala Arg Gly
            100                 105                 110

Leu Glu Leu Glu Ala Leu Ala Cys Tyr Ser Ala Arg Gly Ala Leu Ala
        115                 120                 125

Thr Tyr Arg Ala Leu Ala Val Ala Leu Pro Arg Gly Leu Tyr Ala Leu
        130                 135                 140

Ala Gly Leu Tyr Ala Ser Pro Pro Arg Ser Glu Arg Ala Leu Ala Gly
```

```
145                 150                 155                 160
Leu Cys Tyr Ser Cys Tyr Ser Ser Glu Arg Ala Leu Ala Leu Glu Ser
                165                 170                 175

Glu Arg Ser Glu Arg Ile Leu Glu Ser Glu Arg Gly Leu Asn Gly Leu
            180                 185                 190

Tyr Cys Tyr Ser Ala Leu Ala Cys Tyr Ser Ser Glu Arg Ala Leu Ala
            195                 200                 205

Ile Leu Glu Ser Glu Arg Ile Leu Glu Met Glu Thr Ala Ser Asn Ser
        210                 215                 220

Glu Arg Leu Glu Pro Arg Ser Glu Arg Ala Arg Gly Cys Tyr Ser His
225                 230                 235                 240

Ile Ser Leu Glu Ser Glu Arg Gly Leu Asn Ile Leu Glu Ala Ser Asn
                245                 250                 255

Cys Tyr Ser Ser Glu Arg Ala Leu Ala
            260                 265

<210> SEQ ID NO 18
<211> LENGTH: 249
<212> TYPE: PRT
<213> ORGANISM: Lilium longiflorum

<400> SEQUENCE: 18

Met Glu Thr Ala Leu Ala Ser Glu Arg Met Glu Thr Leu Tyr Ser Ser
1               5                   10                  15

Glu Arg Leu Glu Ala Leu Ala Thr His Arg Ala Leu Ala Ile Leu Glu
            20                  25                  30

Leu Glu Val Ala Leu Val Ala Leu Glu Leu Glu Leu Glu Ala Leu
        35                  40                  45

Ala Ala Leu Ala Leu Glu Ser Glu Arg Ala Arg Gly Gly Leu Gly Leu
    50                  55                  60

Tyr Ala Arg Gly Ser Glu Arg Gly Leu Asn Ala Ser Asn Cys Tyr Ser
65                  70                  75                  80

Ser Glu Arg Ala Leu Ala Ala Leu Ala Ile Leu Glu Gly Leu Tyr Gly
                85                  90                  95

Leu Leu Glu Met Glu Thr Thr His Arg Cys Tyr Ser Gly Leu Tyr Pro
            100                 105                 110

Arg Thr Tyr Arg Val Ala Leu Leu Glu Pro Arg Gly Leu Tyr Ala Ser
        115                 120                 125

Asn Ala Ser Asn Gly Leu Tyr Ala Leu Ala Pro Arg Ser Glu Arg Gly
    130                 135                 140

Leu Gly Leu Asn Cys Tyr Ser Cys Tyr Ser Ser Glu Arg Ala Leu Ala
145                 150                 155                 160

Leu Glu Ala Arg Gly Ala Leu Ala Val Ala Leu Ala Ser Asn His Ile
                165                 170                 175

Ser Gly Leu Tyr Cys Tyr Ser Leu Glu Cys Tyr Ser Gly Leu Thr His
            180                 185                 190

Arg Ile Leu Glu Ala Ser Asn Ile Leu Glu Ile Leu Glu Ser Glu Arg
        195                 200                 205

Ser Glu Arg Leu Glu Pro Arg Ala Ser Pro His Ile Ser Cys Tyr Ser
    210                 215                 220

Ser Glu Arg Leu Glu Pro Arg Ala Leu Ala Val Ala Leu Ala Ser Asn
225                 230                 235                 240

Cys Tyr Ser Ala Leu Ala Ser Glu Arg
                245
```

<210> SEQ ID NO 19
<211> LENGTH: 325
<212> TYPE: PRT
<213> ORGANISM: Zea mays

<400> SEQUENCE: 19

Met Glu Thr Thr His Arg Ala Leu Ala Thr His Arg Thr His Arg Thr
1               5                   10                  15

His Arg Thr His Arg Ala Leu Ala Ala Leu Ala Gly Leu Tyr Gly Leu
                20                  25                  30

Tyr Gly Leu Tyr Leu Tyr Ser Val Ala Leu Gly Leu Asn Pro Arg Ala
            35                  40                  45

Arg Gly Gly Leu Tyr Leu Glu Pro Arg Ala Leu Ala Ala Leu Ala Leu
        50                  55                  60

Glu Ser Glu Arg Leu Glu Leu Glu Leu Glu Leu Glu Leu Glu Val Ala
65                  70                  75                  80

Leu Leu Glu Ala Leu Ala Ala Leu Ala Gly Leu Tyr Leu Glu Gly Leu
                85                  90                  95

Tyr Gly Leu Tyr Gly Leu Tyr Ala Leu Ala Gly Leu Ala Leu Ala Gly
            100                 105                 110

Leu Asn Gly Leu Asn Thr His Arg Cys Tyr Ser Ala Leu Ala Gly Leu
        115                 120                 125

Tyr Gly Leu Asn Leu Glu Ala Arg Gly Gly Leu Tyr Leu Glu Ala Leu
    130                 135                 140

Ala Pro Arg Cys Tyr Ser Leu Glu Ala Arg Gly Thr Tyr Arg Ser Glu
145                 150                 155                 160

Arg Val Ala Leu Pro Arg Pro Arg Leu Glu Pro Arg Gly Leu Tyr Gly
                165                 170                 175

Leu Asn Val Ala Leu Pro Arg Pro Arg Ala Leu Ala Pro Arg Gly Leu
            180                 185                 190

Tyr Pro Arg Gly Leu Cys Tyr Ser Cys Tyr Ser Ser Glu Arg Ala Leu
        195                 200                 205

Ala Leu Glu Gly Leu Tyr Ala Leu Ala Val Ala Leu Ser Glu Arg Ala
    210                 215                 220

Arg Gly Ala Ser Pro Cys Tyr Ser Ala Leu Ala Cys Tyr Ser Gly Leu
225                 230                 235                 240

Tyr Thr His Arg Pro His Glu Ser Glu Arg Ile Leu Glu Ile Leu Glu
                245                 250                 255

Ala Ser Asn Ser Glu Arg Leu Glu Pro Arg Ala Leu Ala Leu Tyr Ser
            260                 265                 270

Cys Tyr Ser Gly Leu Tyr Leu Glu Pro Arg Pro Arg Val Ala Leu Ser
        275                 280                 285

Glu Arg Cys Tyr Ser Ala Arg Gly Leu Tyr Ser Ala Leu Ala Ser Glu
    290                 295                 300

Arg Ile Leu Glu Ser Glu Arg Ser Glu Arg Thr Tyr Arg Leu Glu Ser
305                 310                 315                 320

Glu Arg Cys Tyr Ser
                325

<210> SEQ ID NO 20
<211> LENGTH: 262
<212> TYPE: PRT
<213> ORGANISM: Hordeum vulgare

<400> SEQUENCE: 20

Met Glu Thr Ala Leu Ala Pro Arg Ser Glu Arg Thr His Arg Val Ala
1               5                   10                  15

Leu Pro Arg Ala Arg Gly Ala Leu Ala Leu Glu Leu Glu Ala Leu Ala
            20                  25                  30

Val Ala Leu Ser Glu Arg Leu Glu Val Ala Leu Leu Glu Leu Glu Val
        35                  40                  45

Ala Leu Ala Leu Ala Gly Leu Tyr Gly Leu Tyr Leu Glu Gly Leu Tyr
    50                  55                  60

Pro Arg Ala Leu Ala Leu Ala Gly Leu Ala Leu Ala Gly Leu Asn
65                  70                  75                  80

Ala Arg Gly Pro Arg Gly Leu Tyr Gly Leu Cys Tyr Ser Val Ala Leu
            85                  90                  95

Pro Arg Gly Leu Asn Leu Glu Ala Ser Asn Ala Arg Gly Leu Glu Leu
            100                 105                 110

Glu Ala Leu Ala Cys Tyr Ser Ala Arg Gly Ala Leu Ala Thr Tyr Arg
            115                 120                 125

Leu Glu Val Ala Leu Pro Arg Gly Leu Tyr Ala Leu Ala Ala Leu Ala
        130                 135                 140

Ala Ser Pro Pro Arg Ser Glu Arg Ala Leu Ala Gly Leu Cys Tyr Ser
145             150                 155                 160

Cys Tyr Ser Gly Leu Tyr Ala Leu Ala Leu Glu Ser Glu Arg Ser Glu
            165                 170                 175

Arg Ile Leu Glu Ser Glu Arg Ala Arg Gly Ala Ser Pro Cys Tyr Ser
            180                 185                 190

Ala Leu Ala Cys Tyr Ser Ser Glu Arg Thr His Arg Met Glu Thr Gly
            195                 200                 205

Leu Tyr Ile Leu Glu Ile Leu Glu Ala Ser Asn Ser Glu Arg Leu Glu
        210                 215                 220

Pro Arg Ser Glu Arg Ala Arg Gly Cys Tyr Ser Ala Ser Asn Ile Leu
225             230                 235                 240

Glu Gly Leu Tyr Gly Leu Asn Val Ala Leu Ala Ser Asn Cys Tyr Ser
            245                 250                 255

Ser Glu Arg Ala Leu Ala
            260

<210> SEQ ID NO 21
<211> LENGTH: 502
<212> TYPE: PRT
<213> ORGANISM: Oryza brachyantha

<400> SEQUENCE: 21

Met Glu Thr Ala Leu Ala Val Ala Leu Thr His Arg Ala Arg Gly Thr
1               5                   10                  15

His Arg Ala Arg Gly Ala Leu Ala Pro Arg Ala Leu Ala Leu Tyr Ser
            20                  25                  30

Thr His Arg Val Ala Leu Ala Arg Gly Ala Leu Ala Val Ala Leu Met
        35                  40                  45

Glu Thr Val Ala Leu Leu Glu Leu Glu Val Ala Leu Val Ala Leu Ala
    50                  55                  60

Leu Ala Val Ala Leu Ala Leu Ala Leu Ala Leu Ala Leu Ala Gly Leu
65                  70                  75                  80

Tyr Met Glu Thr Met Glu Thr Met Glu Thr Thr His Arg Ala Arg Gly
            85                  90                  95

Gly Leu Tyr Ala Leu Ala Gly Leu Ala Leu Ala Gly Leu Asn Gly Leu
            100                 105                 110

Asn Gly Leu Asn Gly Leu Asn Ser Glu Arg Cys Tyr Ser Ala Leu Ala
            115                 120                 125

Ala Leu Ala Gly Leu Asn Leu Glu Thr His Arg Gly Leu Asn Leu Glu
        130                 135                 140

Ala Leu Ala Pro Arg Cys Tyr Ser Ala Leu Ala Ala Arg Gly Pro His
145                 150                 155                 160

Glu Ser Glu Arg Val Ala Leu Pro Arg Pro Arg Ala Leu Ala Pro Arg
                165                 170                 175

Gly Leu Tyr Gly Leu Asn Ala Leu Ala Leu Glu Pro Arg Ala Leu Ala
                180                 185                 190

Pro Arg Gly Leu Tyr Thr His Arg Gly Leu Cys Tyr Ser Cys Tyr Ser
            195                 200                 205

Ser Glu Arg Ala Leu Ala Leu Glu Gly Leu Tyr Ala Leu Ala Val Ala
        210                 215                 220

Leu Ser Glu Arg Ala Arg Gly Ala Ser Pro Cys Tyr Ser Ala Leu Ala
225                 230                 235                 240

Cys Tyr Ser Gly Leu Tyr Thr His Arg Leu Glu Ala Ser Pro Ile Leu
                245                 250                 255

Glu Ile Leu Glu Ala Ser Asn Ser Glu Arg Leu Glu Pro Arg Ser Glu
            260                 265                 270

Arg Leu Tyr Ser Cys Tyr Ser Gly Leu Tyr Leu Glu Pro Arg Ala Arg
            275                 280                 285

Gly Val Ala Leu Thr His Arg Cys Tyr Ser Leu Glu Thr His Arg Ala
            290                 295                 300

Ser Asn Ala Arg Gly Pro His Glu Leu Tyr Ser Thr Tyr Arg Thr His
305                 310                 315                 320

Arg Val Ala Leu Gly Leu Asn Cys Tyr Ser Leu Glu Ser Glu Arg Thr
                325                 330                 335

His Arg Pro His Glu Thr Arg Pro Ala Ser Asn Pro His Glu Leu Tyr
            340                 345                 350

Ser Leu Glu Leu Tyr Ser Thr Arg Pro Gly Leu Asn Pro His Glu Ala
            355                 360                 365

Arg Gly Cys Tyr Ser His Ile Ser Thr Tyr Arg Leu Tyr Ser Ala Ser
            370                 375                 380

Asn Ser Glu Arg Cys Tyr Ser Leu Tyr Ser Ile Leu Glu Ala Arg Gly
385                 390                 395                 400

Ala Ser Asn Leu Glu Thr Tyr Arg Leu Tyr Ser Val Ala Leu Leu Tyr
                405                 410                 415

Ser Val Ala Leu Ser Glu Arg Ala Leu Ala Pro Arg Pro His Glu Ala
                420                 425                 430

Ser Pro Gly Leu Asn Gly Leu Tyr Leu Tyr Ser Thr His Arg Leu Tyr
            435                 440                 445

Ser Ala Arg Gly Gly Leu Tyr Gly Leu Gly Leu Asn Ser Glu Arg Ala
        450                 455                 460

Leu Ala Val Ala Leu Thr Tyr Arg Ile Leu Glu Ala Leu Ala Thr His
465                 470                 475                 480

Arg Ser Glu Arg Gly Leu Leu Glu Ala Leu Ala Gly Leu Asn Gly Leu
                485                 490                 495

Ser Glu Arg Ser Glu Arg
            500

<210> SEQ ID NO 22
<211> LENGTH: 296

<212> TYPE: PRT
<213> ORGANISM: Zea mays

<400> SEQUENCE: 22

Met Glu Thr Thr His Arg Ala Leu Ala Thr His Arg Thr His Arg Thr
1               5                   10                  15

His Arg Thr His Arg Ala Leu Ala Ala Leu Ala Gly Leu Tyr Gly Leu
            20                  25                  30

Tyr Gly Leu Tyr Leu Tyr Ser Val Ala Leu Gly Leu Asn Pro Arg Ala
        35                  40                  45

Arg Gly Gly Leu Tyr Leu Glu Pro Arg Val Ala Leu Ala Leu Ala Leu
    50                  55                  60

Glu Ser Glu Arg Leu Glu Leu Glu Leu Glu Leu Glu Val Ala
65                  70                  75                  80

Leu Leu Glu Ala Leu Ala Ala Leu Ala Gly Leu Tyr Leu Glu Gly Leu
                85                  90                  95

Tyr Gly Leu Tyr Gly Leu Tyr Ala Leu Ala Gly Leu Ala Leu Ala Gly
            100                 105                 110

Leu Asn Gly Leu Asn Thr His Arg Cys Tyr Ser Ala Leu Ala Gly Leu
        115                 120                 125

Tyr Gly Leu Asn Leu Glu Ala Arg Gly Gly Leu Tyr Leu Glu Ala Leu
    130                 135                 140

Ala Pro Arg Cys Tyr Ser Leu Glu Ala Arg Gly Thr Tyr Arg Ser Glu
145                 150                 155                 160

Arg Val Ala Leu Pro Arg Pro Arg Leu Glu Pro Arg Gly Leu Tyr Gly
                165                 170                 175

Leu Asn Val Ala Leu Pro Arg Pro Arg Ala Leu Ala Pro Arg Gly Leu
            180                 185                 190

Tyr Pro Arg Gly Leu Cys Tyr Ser Cys Tyr Ser Ser Glu Arg Ala Leu
        195                 200                 205

Ala Leu Glu Gly Leu Tyr Ala Leu Ala Val Ala Leu Ser Glu Arg Ala
    210                 215                 220

Arg Gly Ala Ser Pro Cys Tyr Ser Ala Leu Ala Cys Tyr Ser Gly Leu
225                 230                 235                 240

Tyr Thr His Arg Pro His Glu Ser Glu Arg Ile Leu Glu Ile Leu Glu
                245                 250                 255

Ala Ser Asn Ser Glu Arg Leu Glu Pro Arg Ala Leu Ala Leu Tyr Ser
            260                 265                 270

Cys Tyr Ser Ala Leu Ala Leu Glu Pro Arg Pro Arg Val Ala Leu Ser
        275                 280                 285

Glu Arg Cys Tyr Ser Gly Leu Asn
    290                 295

<210> SEQ ID NO 23
<211> LENGTH: 284
<212> TYPE: PRT
<213> ORGANISM: Sorghum bicolor

<400> SEQUENCE: 23

Met Glu Thr Ala Leu Ala Ala Leu Ala Leu Glu Gly Leu Ala Leu Ala
1               5                   10                  15

Ala Leu Ala Thr His Arg Thr His Arg Ser Glu Arg Thr His Arg Val
            20                  25                  30

Ala Leu Pro Arg Ala Arg Gly Ala Leu Ala Leu Glu Leu Glu Ala Leu
        35                  40                  45

```
Ala Ala Leu Ala Cys Tyr Ser Leu Glu Val Ala Leu Leu Glu Leu Glu
        50                  55                  60

Val Ala Leu Leu Glu Gly Leu Tyr Gly Leu Tyr Gly Leu Tyr Pro Arg
 65                  70                  75                  80

Ser Glu Arg Ser Glu Ser Glu Arg Val Ala Leu Gly Leu Asn Ala
                85                  90                  95

Leu Ala Gly Leu Asn Gly Leu Tyr Gly Leu Tyr Gly Leu Tyr Gly Leu
                100                 105                 110

Tyr Leu Glu Cys Tyr Ser Leu Glu Pro Arg Gly Leu Asn Leu Glu Ala
            115                 120                 125

Ser Asn Gly Leu Tyr Leu Glu Leu Glu Ala Leu Ala Cys Tyr Ser Ala
        130                 135                 140

Arg Gly Ala Leu Ala Thr Tyr Arg Leu Glu Val Ala Leu Pro Arg Gly
145                 150                 155                 160

Leu Tyr Ala Leu Ala Pro Arg Ala Ser Pro Arg Ser Glu Arg Ala
                165                 170                 175

Leu Ala Ala Ser Pro Cys Tyr Ser Cys Tyr Ser Ser Glu Arg Ala Leu
                180                 185                 190

Ala Leu Glu Ser Glu Arg Ala Leu Ala Val Ala Leu Ser Glu Arg His
            195                 200                 205

Ile Ser Gly Leu Cys Tyr Ser Ala Leu Ala Cys Tyr Ser Ser Glu Arg
        210                 215                 220

Thr His Arg Met Glu Thr Gly Leu Tyr Ile Leu Glu Ile Leu Glu Ala
225                 230                 235                 240

Ser Asn Ser Glu Arg Leu Glu Pro Arg Gly Leu Tyr Ala Arg Gly Cys
                245                 250                 255

Tyr Ser Ala Ser Asn Leu Glu Ala Leu Ala Gly Leu Asn Val Ala Leu
                260                 265                 270

Ala Ser Asn Cys Tyr Ser Ser Glu Arg Ala Leu Ala
            275                 280

<210> SEQ ID NO 24
<211> LENGTH: 249
<212> TYPE: PRT
<213> ORGANISM: Lilium longiflorum

<400> SEQUENCE: 24

Met Glu Thr Ala Leu Ala Ser Glu Arg Met Glu Thr Leu Tyr Ser Ser
 1               5                  10                  15

Glu Arg Leu Glu Ala Leu Ala Thr His Arg Ala Leu Ala Ile Leu Glu
                20                  25                  30

Leu Glu Val Ala Leu Val Ala Leu Leu Glu Leu Glu Leu Glu Ala Leu
            35                  40                  45

Ala Ala Leu Ala Leu Glu Ser Glu Arg Ala Arg Gly Gly Leu Gly Leu
        50                  55                  60

Tyr Ala Arg Gly Ser Glu Arg Gly Leu Asn Ala Ser Asn Cys Tyr Ser
 65                  70                  75                  80

Ser Glu Arg Ala Leu Ala Ala Leu Ala Ile Leu Glu Gly Leu Tyr Gly
                85                  90                  95

Leu Leu Glu Met Glu Thr Thr His Arg Cys Tyr Ser Gly Leu Tyr Pro
                100                 105                 110

Arg Thr Tyr Arg Val Ala Leu Leu Glu Pro Arg Gly Leu Tyr Ala Ser
            115                 120                 125

Asn Ala Ser Asn Gly Leu Tyr Ala Leu Ala Pro Arg Ser Glu Arg Gly
        130                 135                 140
```

```
Leu Gly Leu Asn Cys Tyr Ser Cys Tyr Ser Ser Glu Arg Ala Leu Ala
145                 150                 155                 160

Leu Glu Ala Arg Gly Ala Leu Ala Val Ala Leu Ala Ser Asn His Ile
            165                 170                 175

Ser Gly Leu Tyr Cys Tyr Ser Leu Glu Cys Tyr Ser Gly Leu Thr His
            180                 185                 190

Arg Ile Leu Glu Ala Ser Asn Ile Leu Glu Ile Leu Glu Ser Glu Arg
            195                 200                 205

Ser Glu Arg Leu Glu Pro Arg Ala Ser Pro His Ile Ser Cys Tyr Ser
            210                 215                 220

Ser Glu Arg Leu Glu Pro Arg Ala Leu Ala Val Ala Leu Ala Ser Asn
225                 230                 235                 240

Cys Tyr Ser Ala Leu Ala Ala Leu Ala
            245
```

<210> SEQ ID NO 25
<211> LENGTH: 251
<212> TYPE: PRT
<213> ORGANISM: Lilium longiflorum

<400> SEQUENCE: 25

```
Met Glu Thr Ala Leu Ala Ala Leu Ala Val Ala Leu Leu Tyr Ser Pro
1               5                   10                  15

His Glu Leu Glu Val Ala Leu Cys Tyr Ser Ser Glu Arg Val Ala Leu
            20                  25                  30

Leu Glu Leu Glu Val Ala Leu Val Ala Leu Leu Glu Ala Leu Ala Thr
            35                  40                  45

His Arg Gly Leu Asn Ser Glu Arg Gly Leu Ile Leu Glu Gly Leu Tyr
        50                  55                  60

Leu Glu Ala Leu Ala Gly Leu Asn Ala Ser Asn Cys Tyr Ser Ser Glu
65                  70                  75                  80

Arg Ala Leu Ala Ala Leu Ala Ile Leu Glu Gly Leu Tyr Gly Leu Tyr
                85                  90                  95

Leu Glu Met Glu Thr Ser Glu Arg Cys Tyr Ser Gly Leu Tyr Pro Arg
            100                 105                 110

Thr Tyr Arg Val Ala Leu Leu Glu Pro Arg Gly Leu Tyr Ala Ser Asn
            115                 120                 125

Gly Leu Asn Leu Glu Thr His Arg Pro Arg Ser Glu Arg Thr His Arg
            130                 135                 140

Gly Leu Asn Cys Tyr Ser Cys Tyr Ser Ser Glu Arg Ala Leu Ala Ile
145                 150                 155                 160

Leu Glu Gly Leu Asn Ala Leu Ala Val Ala Leu Ala Ser Asn His Ile
                165                 170                 175

Ser Gly Leu Tyr Cys Tyr Ser Leu Glu Cys Tyr Ser Gly Leu Thr His
            180                 185                 190

Arg Ile Leu Glu Ala Ser Asn Ile Leu Glu Ile Leu Glu Ser Glu Arg
            195                 200                 205

Ser Glu Arg Leu Glu Pro Arg Gly Leu Tyr His Ile Ser Cys Tyr Ser
            210                 215                 220

Ser Glu Arg Leu Glu Pro Arg Pro Arg Val Ala Leu Ser Glu Arg Cys
225                 230                 235                 240

Tyr Ser Gly Leu Tyr Thr His Arg Ala Leu Ala
            245                 250
```

<210> SEQ ID NO 26
<211> LENGTH: 288
<212> TYPE: PRT
<213> ORGANISM: Brassica rapa

<400> SEQUENCE: 26

Met Glu Thr Gly Leu Pro His Glu Leu Glu Leu Tyr Ser Ser Glu Arg
1               5                   10                  15

Pro His Glu Thr His Arg Thr His Arg Ile Leu Glu Leu Glu Pro His
            20                  25                  30

Glu Val Ala Leu Met Glu Thr Pro His Glu Leu Glu Ala Leu Ala Met
        35                  40                  45

Glu Thr Ser Glu Arg Ala Leu Ala Leu Glu Gly Leu Thr His Arg Val
    50                  55                  60

Ala Leu Pro Arg Met Glu Thr Val Ala Leu Ala Arg Gly Ala Leu Ala
65                  70                  75                  80

Gly Leu Asn Gly Leu Asn Cys Tyr Ser Leu Glu Ala Ser Pro Ala Ser
                85                  90                  95

Asn Leu Glu Ser Glu Arg Ala Ser Asn Met Glu Thr Gly Leu Asn Val
            100                 105                 110

Ala Leu Cys Tyr Ser Ala Leu Ala Pro Arg Leu Glu Val Ala Leu Leu
        115                 120                 125

Glu Pro Arg Gly Leu Tyr Ala Leu Ala Val Ala Leu Ala Ser Asn Pro
    130                 135                 140

Arg Ala Leu Ala Pro Arg Ala Ser Asn Ser Glu Arg Ala Ser Asn Cys
145                 150                 155                 160

Tyr Ser Cys Tyr Ser Ile Leu Glu Ala Leu Ala Leu Glu Gly Leu Asn
                165                 170                 175

Ala Leu Ala Thr His Arg Ala Ser Asn Leu Tyr Ser Ala Ser Pro Cys
            180                 185                 190

Tyr Ser Ile Leu Glu Cys Tyr Ser Ala Ser Asn Ala Leu Ala Leu Glu
        195                 200                 205

Ala Arg Gly Ala Leu Ala Ala Leu Ala Thr His Arg Thr His Arg Pro
    210                 215                 220

His Glu Thr His Arg Thr His Arg Thr His Arg Cys Tyr Ser Ala Ser
225                 230                 235                 240

Asn Leu Glu Pro Arg Ser Glu Arg Leu Glu Ala Ser Pro Cys Tyr Ser
                245                 250                 255

Gly Leu Tyr Leu Tyr Ser Ile Leu Glu Thr Arg Pro Ile Leu Glu Ala
            260                 265                 270

Ser Pro Leu Tyr Ser Pro His Glu Pro Arg Pro His Glu Cys Tyr Ser
        275                 280                 285

<210> SEQ ID NO 27
<211> LENGTH: 283
<212> TYPE: PRT
<213> ORGANISM: Silene latifolia

<400> SEQUENCE: 27

Met Glu Thr Ala Leu Ala Ala Ser Asn Ala Ser Asn Met Glu Thr Leu
1               5                   10                  15

Tyr Ser Ser Glu Arg Ala Leu Ala Thr His Arg Pro His Glu Cys Tyr
            20                  25                  30

Ser Leu Tyr Ser Ala Leu Ala Thr His Arg Thr Arg Pro Ala Leu Ala
        35                  40                  45

Ile Leu Glu Pro His Glu Leu Glu Val Ala Leu Ala Leu Ala Leu Glu

```
            50                  55                  60
Ala Leu Ala Ile Leu Glu Leu Glu Val Ala Leu Gly Leu Asn Leu Glu
 65                  70                  75                  80

Leu Tyr Ser Gly Leu Tyr Ser Glu Arg Gly Leu Ala Leu Ala Gly Leu
                 85                  90                  95

Asn Ala Leu Ala Gly Leu Tyr Gly Leu Tyr Cys Tyr Ser Ala Leu Ala
            100                 105                 110

Ser Glu Arg Gly Leu Asn Leu Glu Gly Leu Tyr Ala Ser Asn Leu Glu
            115                 120                 125

Ala Ser Asn Val Ala Leu Cys Tyr Ser Ala Leu Ala Pro Arg Thr Tyr
            130                 135                 140

Arg Val Ala Leu Val Ala Leu Pro Arg Gly Leu Tyr Ala Leu Ala Val
145                 150                 155                 160

Ala Leu Ala Ser Asn Thr His Arg Ala Ser Asn Pro Arg Ser Glu Arg
                165                 170                 175

Gly Leu Asn Gly Leu Cys Tyr Ser Cys Tyr Ser Ala Leu Ala Ala Leu
            180                 185                 190

Ala Leu Glu Ser Glu Arg Gly Leu Tyr Val Ala Leu Ala Ser Asn His
            195                 200                 205

Ile Ser Ala Ser Pro Cys Tyr Ser Met Glu Thr Cys Tyr Ser Ala Ser
210                 215                 220

Asn Thr His Arg Leu Glu Ala Arg Gly Val Ala Leu Ala Leu Ala Ser
225                 230                 235                 240

Glu Arg Gly Leu Asn Leu Glu Pro Arg Ser Glu Arg Ser Glu Arg Cys
                245                 250                 255

Tyr Ser Ala Ser Asn Leu Glu Ala Leu Ala Ala Leu Ala Leu Glu Ala
            260                 265                 270

Ser Asn Cys Tyr Ser Gly Leu Tyr Ala Ser Asn
            275                 280
```

<210> SEQ ID NO 28
<211> LENGTH: 22
<212> TYPE: DNA
<213> ORGANISM: artificial sequence
<220> FEATURE:
<223> OTHER INFORMATION: primer

<400> SEQUENCE: 28
tctacactat ttttgcaaga gg                                          22

<210> SEQ ID NO 29
<211> LENGTH: 20
<212> TYPE: DNA
<213> ORGANISM: artificial sequence
<220> FEATURE:
<223> OTHER INFORMATION: primer

<400> SEQUENCE: 29
cacaaaccaa agagggcatt                                             20

<210> SEQ ID NO 30
<211> LENGTH: 20
<212> TYPE: DNA
<213> ORGANISM: artificial sequence
<220> FEATURE:
<223> OTHER INFORMATION: primer

<400> SEQUENCE: 30
gctcctggtt tgtcaaacag                                             20

<210> SEQ ID NO 31
<211> LENGTH: 19
<212> TYPE: DNA
<213> ORGANISM: artificial sequence
<220> FEATURE:
<223> OTHER INFORMATION: primer

<400> SEQUENCE: 31
tttcgcgtcg cctcctcca                                                  19

<210> SEQ ID NO 32
<211> LENGTH: 22
<212> TYPE: DNA
<213> ORGANISM: artificial sequence
<220> FEATURE:
<223> OTHER INFORMATION: primer

<400> SEQUENCE: 32
cgtcgaggat caagtcatca gg                                              22

<210> SEQ ID NO 33
<211> LENGTH: 22
<212> TYPE: DNA
<213> ORGANISM: artificial sequence
<220> FEATURE:
<223> OTHER INFORMATION: primer

<400> SEQUENCE: 33
cctgcagacg agggtctcac ta                                              22

<210> SEQ ID NO 34
<211> LENGTH: 25
<212> TYPE: DNA
<213> ORGANISM: artificial sequence
<220> FEATURE:
<223> OTHER INFORMATION: primer

<400> SEQUENCE: 34
cttgctctga ataattctgc aggtg                                           25

<210> SEQ ID NO 35
<211> LENGTH: 20
<212> TYPE: DNA
<213> ORGANISM: artificial sequence
<220> FEATURE:
<223> OTHER INFORMATION: primer

<400> SEQUENCE: 35
ttgcaacagc acaaccagca                                                 20

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
ccctgttagc caccatgtcg                                                 20

<210> SEQ ID NO 37
<211> LENGTH: 24
<212> TYPE: DNA
<213> ORGANISM: artificial sequence
<220> FEATURE:

<223> OTHER INFORMATION: primer

<400> SEQUENCE: 37
gggatagtcc tcaacccttta tggc                                        24

<210> SEQ ID NO 38
<211> LENGTH: 21
<212> TYPE: DNA
<213> ORGANISM: artificial sequence
<220> FEATURE:
<223> OTHER INFORMATION: primer

<400> SEQUENCE: 38
ttgttgccac ccttcttgac c                                            21

<210> SEQ ID NO 39
<211> LENGTH: 23
<212> TYPE: DNA
<213> ORGANISM: artificial sequence
<220> FEATURE:
<223> OTHER INFORMATION: primer

<400> SEQUENCE: 39
tgattggatc cgaacacata gga                                          23

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
cttccatggg ccagatgcag                                              20

<210> SEQ ID NO 41
<211> LENGTH: 20
<212> TYPE: DNA
<213> ORGANISM: artificial sequence
<220> FEATURE:
<223> OTHER INFORMATION: primer

<400> SEQUENCE: 41
agaaagaaat gcgagcgtgc                                              20

<210> SEQ ID NO 42
<211> LENGTH: 24
<212> TYPE: DNA
<213> ORGANISM: artificial sequence
<220> FEATURE:
<223> OTHER INFORMATION: primer

<400> SEQUENCE: 42
tgagaaggag aaacatggag ctgg                                         24

<210> SEQ ID NO 43
<211> LENGTH: 20
<212> TYPE: DNA
<213> ORGANISM: artificial sequence
<220> FEATURE:
<223> OTHER INFORMATION: primer

<400> SEQUENCE: 43
acttgcgctc gtacgacagc                                              20

```
<210> SEQ ID NO 44
<211> LENGTH: 20
<212> TYPE: DNA
<213> ORGANISM: artificial sequence
<220> FEATURE:
<223> OTHER INFORMATION: primer

<400> SEQUENCE: 44
atcagcggcg aggcgtaagt                                              20

<210> SEQ ID NO 45
<211> LENGTH: 20
<212> TYPE: DNA
<213> ORGANISM: artificial sequence
<220> FEATURE:
<223> OTHER INFORMATION: primer

<400> SEQUENCE: 45
ggtcttgtca gcccatggac                                              20

<210> SEQ ID NO 46
<211> LENGTH: 23
<212> TYPE: DNA
<213> ORGANISM: artificial sequence
<220> FEATURE:
<223> OTHER INFORMATION: primer

<400> SEQUENCE: 46
tggatacgcc cccactaatt cct                                          23

<210> SEQ ID NO 47
<211> LENGTH: 25
<212> TYPE: DNA
<213> ORGANISM: artificial sequence
<220> FEATURE:
<223> OTHER INFORMATION: primer

<400> SEQUENCE: 47
cgctgtacgt tgtctcttat cgaca                                        25

<210> SEQ ID NO 48
<211> LENGTH: 22
<212> TYPE: DNA
<213> ORGANISM: artificial sequence
<220> FEATURE:
<223> OTHER INFORMATION: primer

<400> SEQUENCE: 48
cgtgtccccc ctaaccaacc tt                                           22

<210> SEQ ID NO 49
<211> LENGTH: 20
<212> TYPE: DNA
<213> ORGANISM: artificial sequence
<220> FEATURE:
<223> OTHER INFORMATION: primer

<400> SEQUENCE: 49
cgcatacgca tgcatggtca                                              20

<210> SEQ ID NO 50
<211> LENGTH: 21
<212> TYPE: DNA
<213> ORGANISM: artificial sequence
<220> FEATURE:
<223> OTHER INFORMATION: primer
```

```
<400> SEQUENCE: 50
cattcggctt gtttcctgtg t                                          21

<210> SEQ ID NO 51
<211> LENGTH: 20
<212> TYPE: DNA
<213> ORGANISM: artificial sequence
<220> FEATURE:
<223> OTHER INFORMATION: primer

<400> SEQUENCE: 51
tctggacgaa gcaaaacggg                                            20

<210> SEQ ID NO 52
<211> LENGTH: 20
<212> TYPE: DNA
<213> ORGANISM: artificial sequence
<220> FEATURE:
<223> OTHER INFORMATION: primer

<400> SEQUENCE: 52
cggccgtaac gctgaacatc                                            20

<210> SEQ ID NO 53
<211> LENGTH: 20
<212> TYPE: DNA
<213> ORGANISM: artificial sequence
<220> FEATURE:
<223> OTHER INFORMATION: primer

<400> SEQUENCE: 53
cggatgaccg acggtaacac                                            20

<210> SEQ ID NO 54
<211> LENGTH: 22
<212> TYPE: DNA
<213> ORGANISM: artificial sequence
<220> FEATURE:
<223> OTHER INFORMATION: primer

<400> SEQUENCE: 54
cgccgggtaa gtctccttgc ta                                         22

<210> SEQ ID NO 55
<211> LENGTH: 20
<212> TYPE: DNA
<213> ORGANISM: artificial sequence
<220> FEATURE:
<223> OTHER INFORMATION: primer

<400> SEQUENCE: 55
tgaggcatgg gagcgagaga                                            20

<210> SEQ ID NO 56
<211> LENGTH: 28
<212> TYPE: DNA
<213> ORGANISM: artificial sequence
<220> FEATURE:
<223> OTHER INFORMATION: primer

<400> SEQUENCE: 56
tgaagcatgt aactccagtc cctgtcca                                   28

<210> SEQ ID NO 57
<211> LENGTH: 26
```

-continued

```
<212> TYPE: DNA
<213> ORGANISM: artificial sequence
<220> FEATURE:
<223> OTHER INFORMATION: primer

<400> SEQUENCE: 57
gcgaggatgc atgtctgtac cctcaa                                          26

<210> SEQ ID NO 58
<211> LENGTH: 28
<212> TYPE: DNA
<213> ORGANISM: artificial sequence
<220> FEATURE:
<223> OTHER INFORMATION: primer

<400> SEQUENCE: 58
tcaaatctgt ccatgggctg acaagacc                                        28

<210> SEQ ID NO 59
<211> LENGTH: 28
<212> TYPE: DNA
<213> ORGANISM: artificial sequence
<220> FEATURE:
<223> OTHER INFORMATION: primer

<400> SEQUENCE: 59
agaaatcaca catccagatg cccgtcag                                        28

<210> SEQ ID NO 60
<211> LENGTH: 22
<212> TYPE: DNA
<213> ORGANISM: artificial sequence
<220> FEATURE:
<223> OTHER INFORMATION: primer

<400> SEQUENCE: 60
ccaacgccaw sgcctcyatt tc                                              22

<210> SEQ ID NO 61
<211> LENGTH: 19
<212> TYPE: DNA
<213> ORGANISM: artificial sequence
<220> FEATURE:
<223> OTHER INFORMATION: primer

<400> SEQUENCE: 61
gcctcyattt cgtcgaatc                                                  19

<210> SEQ ID NO 62
<211> LENGTH: 2754
<212> TYPE: DNA
<213> ORGANISM: Zea mays

<400> SEQUENCE: 62
gtcagcggcg gaagctgcgc tgcgtgcgcg gcgtctcacc gttctcgtcc ctgagcttca     60
ccgccttgta cacgctggcc cccgccaacg cgcccagcgt cggggccagc aggtagatcc    120
agagctgccg gtagttcccc gccgccacgg ccggccccag cgtcctcacc gggttcatgg    180
acccgcccgt cgtcggcctg cccggcccgg agacacgcgc tcacatcagg tcagctcaac    240
caaccacatg cgtgcacgta tgaagatgat caccttatca cgtgctacta caactacaac    300
acatataagc tagcaaggag acttaccegg cgacgaggat gttcagcgtt acggccgctc    360
ccaccgcgat cccggcgagt tcaccccacct gcaagaacga agggcagggc agggcaggag    420
```

```
cagcagaaat tcagatatga atcgatggca acatgcatgc tgtcaatgca ctgaaagaga      480
gagagagaga gagagagaac gcgtactgcg cgggtgtcgg tggcgacggc ggtgacgacg      540
aagaggaggt tgaaggagat gatgaactcg gtgaagaacg cctgggcggt ggagacggtg      600
gcgtcgggca cggtgacgcc gccggagagg aacgggtgga agacgccctt gagcgcgaag      660
gcggcgcaga cggatgccag cgcctggacg gccacgtacg cgggcacctg cagccagggg      720
aagtggcgca cgccgcgaa ggcgatggtg agcgacgggt tcaggtgcgc cccggagatg       780
tgccccgtcg acaggatcac ggtcgccacc gccagccccg cgcacgccgc gttcccgaac      840
gggctgatcg cgccgccgta cttctggttc acgatcggcg ccgccgtcgc gaagaagatg      900
aggatgaacg tgcccacgaa ctccgcgccc agctgcgtgc agcagccacc acgcaaatgt      960
tttcagcgcg cggtcttgtc agcccatgga cagatttgag atgagattgg aatggacgtg     1020
accaatattt cagcgacaca gagagagaga caaaacaacg catgcaagta tgcaaccact     1080
ccagtcacgg acgcctcgat caaactcgag tttgggacgt actgtcgccc ccttttgccg     1140
tgtcacgtcc aagagccgta cttcatcatg aaataattgg agctgggggt accattttc     1200 tttgttccaa aaacgctgta cgttgtctct tatcgacaat ataattaact agacccggtg     1260
tagtttcgat tcaaggctgg ggaacgtgac aggctacccg atctggttca cgtgcacgat     1320
tcttccccat gcatgagctt ttacaagcta agtacatgga gtagacgcag tttattgtca     1380
cgtttcgatc agaacgtcac ttttttttgac agtgcactct agcttttcat tgcctactaa     1440
taaaaacaat attcgaaagt ctactttaat tgtaggccaa aaccattccc attgttaaaa     1500
taaatgttct tgggaacaag cagacatcag ctctctacta cggatcaata taattgatgt     1560
gttcttacgt tgttttggac cttttttcccc cgggatcagc gcgcgaaccc aaatccagca     1620
attcgaaatt cgtcaaccca atgcaaaatt caaacaagcg tgtcgtttat ttcccgggag     1680
cggttaccct ggacctggag aacaacacac aggaaacaag ccgaatgaag gttggttagg     1740
ggggacacga tggcgtggcg tcgcacacgc ctccccggcc cggtttcata cgtgtgtcgt     1800
actgtcgtgt ggtggcaggg gtggggcgcc gcttagccaa gccaaaagtt gcagccacct     1860
gggtgtactt ttgcaggctc acaggtcaca gcagcgccgc gtgtgaagca ggcaggtttc     1920
aggcggcgtg gagtggagat ccatcagccc atcacaccca gcgatgctag caagcctgcc     1980
cactagttgt atttgctgct tcaagctcca aatgtctctc gtcagcatgc aacatcgaga     2040
gatttcaaga acgatgcaaa gagccaaact gagcagtata tataagatca cagaaatgat     2100
caagtgatca tgagatcatc tactgtaagg gatcaattat caacagtcaa caacttatga     2160
catcgatcac gcctacattt ttttttattat ttcttaaagt actagtgctg tcagggctgt     2220
gtcgctacag gctttcagac acaagactgt tgtaacgtta gttttgagcc tttgacctac     2280
acggtataaa attcgcgagg atgcatgtct gtaccctcaa gtaacaatta atagcacaat     2340
acacaaacac aaacacaaaa aaaaaaacaa tgctaaaaga tcatcagacg tgtgaaaata     2400
tgaaaaataa accgcgcact cagaagaaaa aaaaacccac ggaactcagg aaggaaggaa     2460
gaaggagcag aaagaaatgc gagcgtgcat gtgcacgcgc atgtggacgg acggtggcg     2520 gtggcgtacc ttgcgggtga gcgagacgtc cggcgcgggg atctcgacga cgcaggtgtg     2580
cgtcgccacg ccccacccct ccaccgccgg cagcggcagg cacttgcacc gcggcatcga     2640
cttgcgctcg tacgacagcg agtccacccg ggcccgccg ctggagaaca gcggcgccgg     2700
cgtgccgggc gtcgccggcg ccgacccgtt cggggcgtc gaccccggct ccat           2754
```

```
<210> SEQ ID NO 63
<211> LENGTH: 909
<212> TYPE: DNA
<213> ORGANISM: Zea mays

<400> SEQUENCE: 63
atggagccgg ggtcgacgcc cccgaacggg tcggcgccgg cgacgcccgg cacgccggcg      60
ccgctgttct ccagcggcgg gccccgggtg gactcgctgt cgtacgagcg caagtcgatg     120
ccgcggtgca agtgcctgcc gctgccggcg gtggaggggt ggggcgtggc gacgcacacc     180
tgcgtcgtcg agatccccgc gccggacgtc tcgctcaccc gcaagctggg cgcggagttc     240
gtgggcacgt tcatcctcat cttcttcgcg acggcggcgc cgatcgtgaa ccagaagtac     300
ggcggcgcga tcagcccgtt cgggaacgcg gcgtgcgcgg ggctggcggt ggcgaccgtg     360
atcctgtcga cggggcacat ctccggggcg cacctgaacc cgtcgctcac catcgccttc     420
gcggcgctgc gccacttccc ctggctgcag gtgcccgcgt acgtggccgt ccaggcgctg     480
gcatccgtct gcgccgcctt cgcgctcaag ggcgtcttcc acccgttcct ctccggcggc     540
gtcaccgtgc ccgacgccac cgtctccacc gcccaggcgt tcttcaccga gttcatcatc     600
tccttcaacc tcctcttcgt cgtcaccgcc gtcgccaccg acaccgcgc agtgggtgaa      660 ctcgccggga tcgcggtggg agcggccgta acgctgaaca tcctcgtcgc cgggccgacg     720
acgggcgggt ccatgaaccc ggtgaggacg ctggggccgg ccgtggcggc ggggaactac     780
cggcagctct ggatctacct gctggccccg acgctgggcg cgttggcggg ggccagcgtg     840
tacaaggcgg tgaagctcag ggacgagaac ggtgagacgc cgcgcacgca gcgcagcttc     900
cgccgctga                                                             909

<210> SEQ ID NO 64
<211> LENGTH: 1227
<212> TYPE: DNA
<213> ORGANISM: Zea mays

<400> SEQUENCE: 64
cactcggatg tgccgccctt tgcaaaatgc agcgatccct tgttttttt tcttttctt       60 gaggaactgg cttctttggt ttgtatttcc ggtcgggttc atcaggattc ttcaaacaaa     120
aaaaaaattg gtagcaataa tggcttcttg tcacaactca ttcagacaac gaagaaaaac     180
aggaaacacc ccatatcatc tacgtgggct acgggcgtcg gtttcgtcgt cggctgcgca     240
tcaaagccca gtgcgccgg cccaaggtcc gtgaatgcgc ttgctgggct gagctggtcc      300
gggccgcgcg gcccatggtc acgttcttgc tggggtccgg tcaggttccg tcctgtcctg     360
tcctgtcctg cgatgtccac catggcgcgg cggcgcgcac gcgggctgag gagggaacgt     420
gcaccgcgcc gcgacaccac gtgccggcgg ccgctcgcca tgagcaccgc ctcagcccca     480
atgggagtgg gacgccgctg gccagctcgg acggacaagc tccggcggtg gcccaccggt     540
gccgggtgcc gtgatctcct gtgcagcgcg cacgcactac tgcgtgtgca tgcttgcatg     600
gtgtggaggg ggatggaatg gattgcttgc attgcatgcc ccgtgtgcca tgtttagaaa     660
ctactctctc tatttgcgtt gccaaggttt cagtaaacca gctttgtcgg aatccattct     720
cagttctctg tacctagtat acgatgaaat caaaacactc atccggttaa gaatcgcaat     780
cccatctctt ggccttccgt agatgatccg gtaaggagac atgcatgctt actaacgcag     840
cagtttattt atatatgggt gtatctattg tatttaggac tgtttcacga acgacctagc     900
tacctgacct gccacagaca atccgacgcc gtgaagccac gtcagatgtc aaggtgggcc     960
```

| | |
|---|---|
| caaccggaca cagctgtgca ctgcgtatgt ctctgggggt atctgtgctc ctctggcttt | 1020 |
| acggagagat gagatctgtc tgctgtgcct agcttgtgca aagctgcacc agtaagctca | 1080 |
| tggtgtctcc atcttccgtc caccactaca ctgccccaga tactgtgaga tcttttctcc | 1140 |
| accgtccggc cggcgtgatt cttcgtcgct gctggcgatt aacccgaacg atccgacgct | 1200 |
| acagctagct agctagcctt caagctc | 1227 |

<210> SEQ ID NO 65
<211> LENGTH: 1078
<212> TYPE: DNA
<213> ORGANISM: Zea mays

<400> SEQUENCE: 65

| | |
|---|---|
| caggaaacac cccatatcat ctacgtgggc tacgggcgtc ggtttcgtcg tcggctgcgc | 60 |
| atcaaagccc agtgcgcccg gcccaaggtc cgtgaatgcg cttgctgggc tgagctggtc | 120 |
| cgggccgcgc ggcccttggt cacgttcttg ctggggtccg gtcaggttcc gtcctgtcct | 180 |
| gtcctgtcct gcgatgtcca cctaggcgcg gcggcgcgca cgcgggctga ggagggaacg | 240 |
| tgcaccgcgc cgcgacacca cgtgccggcg gccgctcgcc atgagcaccg cctcagcccc | 300 |
| aatgggagtg ggacgccgct ggccagctcg gacgacaag ctccggcggt ggcccaccgg | 360 |
| tgccgggtgc cgtgatctcc tgtgcagcgc gcacgcacta ctgcgtgtgc atgcttgcat | 420 |
| ggtgtggagg gggatggaat ggattgcttg cattgcatgc cccgtgtgcc atgtttagaa | 480 |
| actactctct ctatttgcgt tgccaaggtt tcagtaaacc agctttgtcg gaatccattc | 540 |
| tcagttctct gtacctagta tacgatgaaa tcaaaacact catccggtta agaatcgcaa | 600 |
| tcccatctct tggccttccg tagatgatcc ggtaaggaga catgcatgct tactaacgca | 660 |
| gcagtttatt tatatatggg tgtatctatt gtatttagga ctgtttcacg aacgacctag | 720 |
| ctacctgacc tgccacagac aatccgacgc cgtgaagcca cgtcagatgt caaggtgggc | 780 |
| ccaaccggac acagctgtgc actgcgtatg tctctgggggg tatctgtgct cctctggctt | 840 |
| tacggagaga tgtgatctgt ctgctgtgcc tagcttgtgc aaagctgcac cagtaagctc | 900 |
| atggtgtctc catcttccgt ccaccactac actgccccag atactgtgag aacttttctc | 960 |
| caccgtccgg ccggcgtgat tcttcgtcgc tgctggcgat taacccgaac gatccgacgc | 1020 |
| tacagctagc tagctagcct tcaagctcca tatagctacc actgcgcgcg ccctctgt | 1078 |

<210> SEQ ID NO 66
<211> LENGTH: 1851
<212> TYPE: DNA
<213> ORGANISM: Zea mays

<400> SEQUENCE: 66

| | |
|---|---|
| ttacctagaa ttttcatctg tcttgtcatc agtagccgac gaaagttagt taatttccat | 60 |
| cggtcatacc tgaggccgac gaaaattagc taacttccat cagctacttt tctattggaa | 120 |
| aaagaaatac aaaaaaattc ctcgcttgta catgcacttt cattggtagt acttcgtaag | 180 |
| ctatttttgt agcaagattg taagttctat tgatagaagg tactctctat gttctaaatt | 240 |
| acaagatata ttggcttttt agacagtcaa aatgtcttgt aatttagaa taggaagta | 300 |
| cttggtaaca aatttgtttt ttatgaaata tattacatat ataaatgttt gcatatcctt | 360 |
| cgttatggtc ctacttgttg acaaaaaaac tatccagagt acacaataga ctccatcatc | 420 |
| atgttgttag ttatagtcaa gatagtcaaa aggcatattt ggatcatctt attcgaagtt | 480 |
| cggatatgaa atccattttt cgagaggctt caaagtctag atataaaatc cgttttttgag | 540 |

```
aggatggtcc atcacaaact agtctagccg gccggttcac atgccaattt accaaatttc    600
tcaaatgttt gcatatctat tctattttta taatcttgta caatacatgc atgttaattt    660
gtagcaccta ttttcctatc taccatacca ttgcgtcgaa gcgaaactgt cgagcgccgt    720
accaaagaat gaatcttcat aggatcctaa catatgtcta actgcgtgaa cgaagtttct    780
ctaaattaaa gttattaaat tcatatttgt gttctactgt gacataacaa agacgtattg    840
tttagccaca atagcactca agagtgaagc tttggacaag attgaatata agcatattgt    900
agaatatttt tatttaaaac cctaccaaaa gaatgatgtt attcaaataa aatagatata    960
tttctttata tattatatta cattatatat tattgcaagt tctagattat tattaattat   1020
ttttaataaa acaatataga tgctatagat ttagcatatc acctcaattt ttttccggcc   1080
cgacagcgtg ttcgctggtg cagttcaccc tccacagttt tcagtccgca taaggcgcag   1140
acggtggcgc attgcgtgtt gcaacgaaac gcgcgatcct aagagggta gtagtatatt   1200 tggctaaggc aaagcctttc cctggcggct gggcacacac atggcccaac aaaaaattag   1260
ttttatatcc aattatttat ttcaacgaaa tacaccgtca tatgacccta tcttgcatat   1320 tagttttttcc cataattgta tcaatatttc ctttatcgcc actaagataa gattgtgggt   1380
tcaagtcaca agtcatgcac ttttttttct tctatgttta ctataacaaa tcgtgtcaac   1440
acaatataat acctatttgt cacccaatgc aacaagctct tctttcaata attttgaatc   1500
atgttaatac agtaatattg ttaaatgttt ttaatccaca tcaaaatatg agaaatcaca   1560
tgattaatct acctctttct aatgacattc acttaattca tattctaaat tttgatttaa   1620
actatttttt tatttttttat taggttctat ctctggatct gaagtaattg atgaagaaga   1680
ataaagatat tgctttacaa taacattttt atatgttatt tatctttacc atgcgtcttt   1740
atgtaacttt tgaactacgt tttttagacg tgcttttgtc accggtcggt ccaaggcttt   1800
agcaaatctt gattccacaa ctgtccactg ccaattcttg gcaataaatc c             1851
```

<210> SEQ ID NO 67
<211> LENGTH: 1874
<212> TYPE: DNA
<213> ORGANISM: Zea mays

<400> SEQUENCE: 67

```
ttacctagaa tttccatctg tcttgtcatc agtagccgac gagaattagc taacttccat     60
caactacttt tctattggaa aaagaaatac aaaaaaatcc ctcgcaggta catgcacttt    120
cattagtagt acttcgtaag ctattttctt aacaagattg taagttctat tgatagaagg    180
tactctctct gttctatatt ataagatata ttggcttttt agacagtcaa aatgtcttgt    240
agttttagaa taaggaagta gttggtaata aatttgtttt tatgaaatac attacatata    300
taaatgtttg catatccttc cttatggtcc tacttgttga caaaaaaact atccagagta    360
tacaatagac tccattacca tgttgttact tatagtcaag atagtcaaaa ggcatatttg    420
gatcatctta ttcggagttc ggatatgaaa tccattttt gagaggcttc aaagtctaga    480
tataaaatcc gttttgaga ggatggtcca tcacaaacta gtctagccgg ttcacatgct    540
agattaccaa ctttctcaaa tacatgcwtg ttagttgta gcaccatattt tcctaactac    600 cataccatcg cgtcgaagcg aaactgtcga gcgtcgcacc aaagaatgga tgttcatagg    660
atcctaacat atgtctaatt gcgtgaacga agtttctcta aattaaagtt actaaattca    720
tatttgtgtt ctactatgac ataacaaaga cgtattgttt agccacaata gcactcaaga    780
```

```
gcgaagcttt tggacaagat tgaatataat catatcgtag aatattttat ttaaaaaccc    840
yaccaaaaga acgatgttat ttaaataaaa tagatatatt tctttatata ttatattaca    900
ttatatatta ttgcaagttc tagattatta ttaattattt ttaataaaac aatatagatt    960
ctatagattt agcatatcac ctcaattttt tcccgcccga ccctaagacc atgagcgtgt   1020
tcgctggtgc agttcaccct ccacagtttt cagtccgcat aaggcgcaga cggtggcgca   1080
ttgcgtgttg caacgaaacg cgcgatccta agagggtaa  tagtatattt ggctaaggca   1140
aagcctttcc ctggcggctg gcacacaca  cgacccaaca aaaaatagtt tttatatcca   1200
attatttatt gcaacgaaat acaccgtcat atgaccctat cttgcatatt agttttccc    1260
ataattgtat caagtgtttc tatagggcag catgcaacat gtaaaaaatg ttcttcgatt   1320
ttgacaatag acttgttgta gtacagtgtc aatattcctt tatcgccact aagataagat   1380
aagataagat tgtgggttca agtcacaagt catgcacttt ttttcttcta tttttactat   1440
aacacatcgt gtcaacacaa tacctatttg tcacccaatg caacaagctc ttctttcaat   1500
aattttgaat catgttaata caataatatt gttaaatgtt tttaacccac ctcaaaatat   1560
gataaatcac atgattaatc tacctctttc taatgccatt cacttaattc atattctaaa   1620
ttttgatttg aactatttta tattttatat tttggtatta ggttctatct ctggatctga   1680
agtaattaat tgatgaagaa gaataaaatat attgccttac aataacattt ttatatgtta   1740
tttatcttta ccatgcgtct ttatgtaact tttggactac attttttag acgtgctttt    1800
gtcaccggtc ggtccaaggc tttagcaaat cttgattcca caactgtcca ctgccaattc   1860
ttggcaatta ataa                                                     1874

<210> SEQ ID NO 68
<211> LENGTH: 3000
<212> TYPE: DNA
<213> ORGANISM: Zea mays

<400> SEQUENCE: 68
ttggactggt cagccaattc tttgtgacaa agcgaagaac ttaacagcaa aattcaagta     60
cactagaaag gctctcaaag aatggcagcg gtctctgcca aaaattgata aaacagtgag    120
acaaattaag ttgcttattg agttcattga cataattgag gaggatcgtg accttttcgat  180
tgaagaatgg aatttctggg agcttttgca aaccaaaatt gcgggtctgc ttcaaattca    240
gaaaatttat tggaagcaac gggcttccat caaatgggtc actgatggag atatctgctc    300
tagatttttt tcatgctcat gcaacggtaa agcataggca taatacaatt gtgttgctct    360
ctgatgacag tgggtcaatc ttttcagagc acgatcataa agctaaccttt ctgtggaatg   420
tctttaaatg tcgattgggt tcttctgaat ttttggagaa tgttttatc tctcaggcct     480
gttaattttg caagatggct tgcaatggtt ggatgcgcct ttttcaaggc aagaaattga    540
tagcattgtt gcagctctcc cttcagacaa atccccgggg cctgatggat ttaataccaa    600
ttttatcaaa aaatgctggc cggttatttc tcaggacttc tacgacttat gtgaccaatt    660
ttaccatggg gatgtctgtc ttagaagtat taatggctct tttatcgttc tgatttcgaa    720
gaaggaaaat gctcatttag tgggagattt taggccaatc tcgcttctaa ataatagtat    780
gaaaatcatc actaagttgc tggccaatcg aatgcagaca gtgatgactt cccttgttca    840
caaaaatcaa tatggcttca tcaaaggaag aaccattcat gattgcttgg cctgggcgta    900
tgaatatatc catttatgtc atatctctaa aaaagaaatc atcgtgctca ggttggactt    960
tgaaaaggcc tttgatactg ttgagcatga actgatcctc caagtgttgt ctcatagagg   1020
```

-continued

| | |
|---|---|
| atttgggccc aaatggctgg gctgggttag gaatatcctt cagtctggta cgtcatcggt | 1080 |
| cctacttaat ggcgtcccag ggaaaacttt ccattacaag cgtggggtca gtcaaggaga | 1140 |
| ccccctctcg cctttattat ttgttttagc ggcagatctg cttcaaagta tcatcaataa | 1200 |
| agcgagacaa caagacttac tccagttgcc cctgactaag aactgtggcc aagatttctc | 1260 |
| gattgtctaa tatgttgatg atacattatt gataatggaa gcttgcccca ggcaactatt | 1320 |
| tttcctcaga gcagttctta actcttacgt aacctcgacg gggctcaaag tgaactatat | 1380 |
| aaatcaagta tgtaccccat caatgtttgc ccagcaaaga tggagattct ttctagaaca | 1440 |
| ttcaactgtc agacatgatc aatgcctttc acctaccttg gtgtccctct aggcctgtca | 1500 |
| aaacctagaa tccgtcactt tttatcactt atccaaagga ttgaaggag actgtcttgt | 1560 |
| acatctgctc tcctctccca ggcctgaaga ttggagctag ttaactctgt tttttcagct | 1620 |
| ttcccgactt ttctgatgtg cacgctgaaa attcctgcca ccacagtcca gaagatagat | 1680 |
| gcttaccgga acattgtct ttggagagga acgatgtga actcaaaaaa accaactcta | 1740 |
| gctgcccggt gcatgattac tcagccaaag agcaacgggg gccttggagt ggtcagattg | 1800 |
| gaaacgcaca acaaggcttt gcttttgaaa ttttttaaaca agttcttcaa taatcatgac | 1860 |
| ttaccttggt aaatctcgtt tggaacaact attacaggac agacagacta cctagctgct | 1920 |
| taagtattgg atcttttttgg tggaaaagtc tgcttagtct tgttcaagat ttcaagggat | 1980 |
| tggcagcccc aaccattggc aataggagaa ctatccttt ctgggggat atgtggaata | 2040 |
| agggcattcc agctcagcaa tatccggaat tattttcctt tgtttgcaac agcaaactct | 2100 |
| ctatcaaaga agcaaagcaa aaagatcatc tttttgagat ttttcagctt cctctgtctg | 2160 |
| tgtaggccta cgagcagtat cttgagttaa atgaggcctg gggacaaatc attgtgatca | 2220 |
| acgcaaagga cacttggaaa cacatttggg gatcaaagat tttctctaca aaaaagactt | 2280 |
| acaggcatat gatgggtcat tatcaagttc atcagatttt caaatcgctt tggaaaaata | 2340 |
| aatgtcaacc aaaacataaa gttttttatt gactgtggct aaaaaacaga ttcaacacaa | 2400 |
| gaaatatgct gaggagaaaa aacatgacac ttgagtcata cacttgcgaa aactgcatct | 2460 |
| ggcagaagga gaaaactctt tatcatctct tcctcagatg caacttcgct aaggcctgct | 2520 |
| ggaattcaat tggtttggtg cccctagaa ttgctaatcc agaggaggct gcagcaaatc | 2580 |
| tcaagcagca gctcaatgtt cccttctcca tggagatcat tattctcatg acttggagca | 2640 |
| tttggaagtg tcgtaatgct tggcttttc agaacaaaga tccaacggtg cagcaatgca | 2700 |
| agcatgagtt cacaaaagaa ttactcctgg tcactcatag agctctgggt agatttggtt | 2760 |
| ccgccatccc ggaatggctt cagcaatggc agtagtaact caccctaacc tcctgtaatt | 2820 |
| cgtctacttg tatgttctaa gcactgcttt tttagttata ataaaatttt cagtaggggc | 2880 |
| tccctccttc ttaaaaaaac ttattttaaa ctaaatatta attttaaata acgaatgggc | 2940 |
| cctatgacta ggcatcggca aaatgcaaac gctcacaatc ttctccgcac ccccccccc | 3000 |

<210> SEQ ID NO 69
<211> LENGTH: 2384
<212> TYPE: DNA
<213> ORGANISM: Zea mays

<400> SEQUENCE: 69

| | |
|---|---|
| caaatccccc ggggcctgat ggatttaata ccaattttat caaaaaatgt tggccggtta | 60 |
| tttctcagga cttctacgac ttatgtgacc aattttacca tggggatgt ctgtctcaga | 120 |

| | |
|---|---|
| agtattaatg gctcttttat cgttctgatt tcgagaagga aaatgctcat ttagtgggag | 180 |
| attttaggcc aatctcgctt ctaaataata gtatgaaaat catcactaag ctgctggcca | 240 |
| atcgactgca gacagtgatg acttcccttg ttcacaaaaa tcaatatggc ttcatcaaag | 300 |
| gaagaaccat tcatgattgc ttggcctggg cgtatgaata tatccattta tgtcatatct | 360 |
| actaaaaaag aaatcatcgt gctcaggttg gactttgaaa aggcctttga tactgttgag | 420 |
| catgaactga tcctccaagt gctgtctcat agaggatttg ggcccaaatg ctgggctgg | 480 |
| gttaggaata tccttcagtc tggtacgtca tcggtcctac ttaatggcgt cccagggaaa | 540 |
| actttccatt gcaagcgtgg ggtcagacaa ggagacctcc tctcrcctct attatttgtt | 600 |
| ttagcggcag atctgcttca gagtatcatc aataaagcga gacagcaaga tttactccag | 660 |
| ttgcccctca ctaagaactg tggtcaagat ttcccgattg tccaatatgc tgatgacaca | 720 |
| ttattgataa tggaagcttg ccccaggcaa ctatttttcc tcagagcagt tcttaactct | 780 |
| tacgcaacct cgacggggct caaagtgaat tataataaat caagtatgta ccccatcaat | 840 |
| gtttgccaag caaagatgga gattcttcc agaacattca actgtcagac atgatcaatg | 900 |
| tcctttcacc tacctggtc gtccctctag gcctgtmmaa acctagaatc cgtcacttt | 960 |
| tatcacttat ccaaaggatt gaaaggagac tgtcctgtac atctgctctc ctctcccagg | 1020 |
| ccggaagatt ggagctagtt aactctgttt tctcagcttt cccgactttt ctgatgtgca | 1080 |
| cgctgaaaat tcctgccacc acagtccaga agatagatgc ttaccggaaa cattgtcttt | 1140 |
| ggagaggaaa caatgtgaac tcaaaaaaac cagctctagc tgcctggtgc atgattactc | 1200 |
| agccaaacga gcaacggggg ccttggagtg gtcagattgg aaacgcacaa caaggctttg | 1260 |
| cttttgaaat gtttacacaa gttcttcaat aatcatgact taccttggta aatctcgttt | 1320 |
| ggaacaacta ttacaggaca gatagactac ctagctgctt aagtattgga tccttttggt | 1380 |
| ggaaaagtct gcttagtctt gttcaagatt tcaagggatt gacagcccta accattggca | 1440 |
| atagaactat cctttctgg ggggatatgt ggaataaggg cattccagct cagcaatatc | 1500 |
| cggaattatt ttcctttgtt tgcaacagca aactctctat caaagaagca agcaaaaag | 1560 |
| atcatctttt tgagattttt cagcttcctc tgtctgtgta ggcctacgag cagtatcttg | 1620 |
| agttaaatga ggcctgggga caaatcattg tgatcaacgc aaaggacact tggaaacaca | 1680 |
| tttggggatc agagattttc tctacaaaaa agacttacag gcatctgatg ggtcattatc | 1740 |
| aagttcatca gattttcaaa tcgctttgga aaaataaatg tcaaccaaaa cataaagttt | 1800 |
| tttattggct gtggctaaaa aacagattca acacaagaaa tatgctgagg aggaaaaaca | 1860 |
| tgacacttga gtcatacact tgcgaaaact gcatctggcg gaaggagaaa actctttatc | 1920 |
| atctcttcct caaatgcaac ttcgctaagg cctgctggaa ttcaattggt ttggtgcccc | 1980 |
| ttagaattgc taatccagag gaggctgcgg caaatctcaa gcagcagctc aatgttccct | 2040 |
| tctccatgga gatcattatt ctcatgactt ggagcatttg gaagtgtcgt aatgcttggc | 2100 |
| tttttcagaa caaagatcca acggtgccag caatgcaagc atgagttcac aaaagaatta | 2160 |
| ctcctggtca ctcatagagc tctgggtaga tttggttccg ccatcccgga atggcttcag | 2220 |
| caatggcagt agtaactcac cctaacctcc tgtaattcgt ctacttgtat gttctaagca | 2280 |
| ctgcttttta gttataataa aatttttcagt aggggctccc tcctcctgtt cttaaaaact | 2340 |
| tatttttaaac taaatattaa tttaaaataa cgaatgggcc ctat | 2384 |

<210> SEQ ID NO 70
<211> LENGTH: 3000

<212> TYPE: DNA
<213> ORGANISM: Zea mays

<400> SEQUENCE: 70

```
tttggcaaga gacgtcttgt cgagcacaaa agcgggaggg agaggccaag aacgtccatc    60
ggccatcgcc tccacgtaac ccttcgttta tatgttctgt ggacagtgga cacagctacg   120
tgcacatgga agaccagcgc cgtgggagcc agaggctgca aattcaggaa tgcttaatta   180
cactaacaat acctacatct gttgacaaca gggcatcaga aaatctaact tacaatgttt   240
gaaaaaacac tataactaag tggactaaaa aaagaaaagt aagcacaacc tataaaattc   300
caagatataa acatccaaac tcaaaggcgc caaagctaac cctatcgagt atagtagtag   360
cctaatattc aaaaaataaa agaatacatg atgctatcaa tagccattgt atccacactc   420
tccggatcaa gagcctattg ctagtctcaa tccactaata attaacctaa cctctaaatc   480
acaatgcctc cgaaatggca tagagactaa gacaacacaa aatcaaacga ggcaaaaaaa   540
agatttgaca atccataaac cgtaatacca catcacagct gcacattgaa atccaataac   600
aagccacaaa aacacagatc catcaacgaa caatttcatt tacataaaca tgaataataa   660
tacaaatcca ccgaacaaaa tggaaaaaaa aaatagaaag agataatcac gaacattagc   720
cgaggtgtca ctcactcact caggcactct aatctccaga gctcaacaaa ggctaaagat   780
tcccgctcca cattaaccat ccgtgcaaga tacatgtaaa aatatacaag gttagacaac   840
acaaacaaag ataaaataaa cccacgtaaa acggagaaaa tcaaaatttg aatgatgaac   900
tctagccacg tcggtactca aaggtctgta gctagatgaa gactaaatat taccaaactg   960
gacatcaacg tcgaaattgg atgaacaaaa catacggcca caatgaaaaa caaacgaacg  1020
aactcacgca tgtcgcatat ataggcgtga tcgactgagc aaaaggtgaa accaaagctg  1080
taataatgac taaccctagc tagccacatt gcctctccaa gcttcgcgaa catacacgaa  1140
aatgaagcga tggacagaat tataatagaa aaataagact gtttcctaaa acccaaatag  1200
tcgccgctga tgagcagaac ctacatgtta gtgaaaataa aatcgaagac ttacaagatg  1260
aacagtgcgc tgacagtcat caaatcgagc gtccggagtc cgaactcgag aggaagagat  1320
agtttagtgc acatgatgca catattaaat catcattatc tatatcagaa ctaatatatc  1380
taattgataa ttgtaatttta taaataacat attccaccac tatacccac tacgttagag  1440
ggtgttttta gtaaaattta cctaacaaat agagaagtta tatctaaaat aagtgatgac  1500
gatttaatat gtgcactaaa cttctatgtg catactatat agtcttttg tggatggaaa  1560
cccctgatc cactgcaacc gcatcctgta ataacagtgc aaaatatacg gcggttgaga  1620
cacagcagcc tctcacctcc tcaataatag gaggcaccgc tcacgtcctt ccgggacccg  1680
ccaccaccag ccgcacggcc atcaatagtc caccacgccg ctgtacaaag ctaccagtgg  1740
cagctgctgg cgccggccat ggccatacct gcacgagcgc gcctgcctcc gctggcctgt  1800
ttttctgttc gctctccggt cagccatggt ggcgcgcaca gcgctgcgtg ccacagtgcg  1860
gcctgccggc cgctgccggt gatgctcacg ttccaggcct gggccgggcg gcctactgtt  1920
gcgcgccacc aaccacgtca gcatcgacga cacttggcga ctggcccacc catcatcccc  1980
agttcctgag agtcctcggt gctgtgtctg tgcgcgtgtg atggcctgat gggatcgccg  2040
gaggtagctg cggcttttct aaaagagcca gcaacaattc tcttttctg tctttcactt  2100
ataaactggt tcactatgag gccctgtttg aaagcaagtg gaatgaacgg gattgaaggg  2160
ctaaaatcac ttactatta aaactgaata gtgagaaatt ctagctaggc tactttagaa  2220
```

| | |
|---|---:|
| atctcaaatc ctcttcaaga ttagagagga ttgaggtgaa aatgaactaa tttcctcttc | 2280 |
| aatgtccttt aatcctgaag gggattcgat ttttcaaact agccctcaat ccttctcgtt | 2340 |
| actctcactc ccggcatgtt tggtttgtgg ctaactgtgc cccattttac ctaaggttag | 2400 |
| tcgttcgaat tgaataacta accttaggca gaaaagttag gtaaaatgag gcaaattagg | 2460 |
| catcaatcca aacgggccat agtatggccg ccgtggacg gacggacttt tccaccacca | 2520 |
| cacacgcgcg cgctatataa ggcgcgcagg ccggcgcagc cagcaaggaa accaacaaac | 2580 |
| agagcaagca gttggtggcg catggaacag tagtgtgcgg cgcgagaaaa gaggagcttg | 2640 |
| gtggtgtggg tgcggtggtg gcggccgagc tagcagcagg ctgctgcgac tgggagtggg | 2700 |
| agggagccga gcggaggagg tgcgtgtggt gggaggtggg gacggcagca cagcacacac | 2760 |
| aggcgcacac gcgcgcgcac tgcaccacac acacgccaaa gcgttatttt aagggcggcg | 2820 |
| ccaccactgt tgtcgcctcc ttcctcactg cctcctccta cccttccctc gctgaagccc | 2880 |
| tctcgcgcct cctcccactc ccactggaca gagaggaggt tagtggaagg cgggctagga | 2940 |
| ggctacgccg ccacagacgc gaagcgatag cgtcgggggg aagcaaggaa gcgggtggca | 3000 |

<210> SEQ ID NO 71
<211> LENGTH: 3000
<212> TYPE: DNA
<213> ORGANISM: Zea mays
<400> SEQUENCE: 71

| | |
|---|---:|
| caccgtatat agtaatttca tattaatctt tatgtgagaa ttatatcagt atgatttcat | 60 |
| agtggagatg tgtttcaacc gtcgattgct taatcaggcc taccaattta ttatcactgg | 120 |
| cgcgcgataa tcgaaaccgc ttgtaaaaag ttgaaccacc ataggcttag agctttttt | 180 |
| ctactactgt tgaatttaga tcatatgagt gtcatttgtc gcctaaaaat aaaaaaacag | 240 |
| gagcacgtag tttagcaagt cccatccgca tataatataa ctctagttgg gttatcttga | 300 |
| atagcttgtt tgcaggcttg tctagtgcaa ttcgctcgcg tttcactaca ctaaaatagt | 360 |
| gaacttccta gagcctaaat cctaggaagt tagccataaa ctctagaaag ttagctaaac | 420 |
| tctcagaagt taagtcatcc cgtcagaagt ttggctctca aaattttttt gtcggaagtt | 480 |
| agcttaactt cctagagccc tctagaaagt taactaactt cctatagcca aagcagcatc | 540 |
| tcagaagtta gtaggttctc agaagttagt agcttcacgc cgtcagcgcc gtcagctgac | 600 |
| taacttccta cgactaactt cctatggctg actgtagccc ctaggaagtt agcttacgtc | 660 |
| ccagttggta tctaggaagt taatttggtc agcattataa atgctgttta tttttatttt | 720 |
| acaccatatt tcacaacata acaaatatac caacaactat ataacgcaac atattttcac | 780 |
| ataaaacatc tcacacacaa tcacataaca atatctaaat ccgtagtctc atcaattaca | 840 |
| tcacaaaagt ctcatccata gtcataataa gacacatctc atccagttat aataagagac | 900 |
| aatatctcat acataataaa agtctcaagt atcacaacac ataacatgga agctcacgat | 960 |
| cgccaatcac catcggggta cagtgacgag tgatggtcga tacctccact agcgaagagg | 1020 |
| gtttcgacaa agtctaacac atcttctcgt tgatgagtcg gcaaggtagc tggaggggtc | 1080 |
| taatatacat gtacaaatga tatttgctga gttacatcat aatataacta gcaacaagta | 1140 |
| aatgatgatg aatttgcata cctgatgttc ggtaggtgga tatgtaggtg taggtggagg | 1200 |
| tgaagaccaa agataatgtg cgggaggtat aaacaataaa aaatccatgc taacacacta | 1260 |
| aaagaagtat ataatgccgt aggtcaggtc tgcaagcaaa agaataaaata tccaacatttt | 1320 |
| agatctaaaa cgcctctagg aagttagcgg ctcgcttgac cgaacacacg agtcagcatg | 1380 |

-continued

```
tgaaagctaa ctttctacag cttttataaa atactgtagt aagttatgtt tatttcttag   1440
agctaccagt tgcctctcgg aagttattta tttcctacgg tttgttataa aagttgcagg   1500
aagttaaaaa tagccatagg aactgtatga ttttgtatga ttttagtgta gtgttttttg   1560
gccacctatg ttcttataca tgtttgcaca atgttcaaaa caaaacaaga tggtacatcg   1620
tatttggtca tattagataa tacaggtttc aggtttgtat aagacgacat gcacatagaa   1680
ataaaaaata ttctcatcca ctaaacatag gaccttaata agaatattga ggcgacagat   1740
gagatggatc tcatggatgc atacagcaaa atatgaacaa gagagcaaac ataattttaa   1800
acgtcgctcg cttttgtcaa gagaacgacc gaacattaag actaacgcaa ggaacaacca   1860
caccatactt cgtgactggg ggcagagcaa tggtgtcaaa taaactttt gagcacatac    1920 tttctacata agatcacatg cacctaaaag cattgagcta ctacacccac ccagcctcct   1980
tttctccatc cttgcctttt cccctgccac cacactccac atctctccat gcatgcatgt   2040
gatgcctctg gtatcggtcg taccattgct ccccaagacc atgttaattc agtcgcctgc   2100
acatcagctc gcattgccaa ataagatgg cgatcatgcc ttaacatggt gcctgatcgc    2160
ctgattatct ctttcatgca tgacagtacg acaccactct ctgcccggcc tcagcaaatg   2220
attgcagtag ctctgctgct gcccactttc caaaacatct gttttttaac agaagtactg   2280
ccatcacaga gcaacagtac tagctgatca gtgatccatt aagctgggag agcaagaaaa   2340
gacatccaaa cgcacatgca ggaaaccctaa gcaaatcaa gcttcatggc tttctaacct    2400
taataaactc ctcccacatg catttgctgg tgcgcagata gagccagcag gaaggagaga   2460
gaaaagaaaa gggcagtcaa attcagtagg ccccccactcg atccgggtcc aagacgccca   2520
cagaaaggga ggggagacgt gaggatgaaa aggcaatgca tgcatagagc caaatagatg   2580
ccactttttc ttcttggtcc ttgcattgct atctcaatac gtcatgtgat tctacaatgt   2640
aagcgtgaag tcgaagtagt tcttggtggt acttcagccc tcatgcatct cctcatgcat   2700
gcaatgcaag atcgatgcaa tcctcatcct atataataga tatagcttga tagcttccac   2760
cgacaatggc accacgccta gctagctact gctagctacg gctagcagct aggatacaat   2820
cctcttgtga gatgagatac tagcatggca tcgccatcaa ataatgcact gagtgatcta   2880
tctctcacca tgtctgcctt cccagttggc catttcccac tacaaatagc gagctgattc   2940
atcgatctca gcagtcagca cgtagctcag agctagctag cagtagcacc agcagcagcc   3000
```

`<210>` SEQ ID NO 72
`<211>` LENGTH: 3000
`<212>` TYPE: DNA
`<213>` ORGANISM: Zea mays

`<400>` SEQUENCE: 72

```
ggatttgctg ctgtgtctgt agtagtctcc aaaatccgaa ccagtgtgtg cccctgaaga    60
tagcatgtat aattgacgat ataggtttat gattaaacac cacatcatta cgacaaagcc   120
aaattgacca aaacaacacc gtaacgccaa taagaagcaa ttttttatgc gtgcaacctt   180
tgttggattc tcaatcccct acaatatgat taatattaac gggttggtct aagcaaagta   240
aataattgtc caaacagttt tacctaggta acagtcaaag aaaaggtgtt gtatgccctc   300
gttctggtta caaaagccac acttcaaact tccttgccat ctacgattag ctaagttgtc   360
tttggtgagg gccacacccc tacctagaaa ccaaagaaag atttctacct taaggggtag   420
ttttagcttc caaagcacac aattacgatt ataattgggg ttatttatta aaatatagta   480
```

```
catgatcac gttgagaaag ccctgcccct atgagcttcc cacacgaaag tgtccctcac    540
tggattcagg ttaaccggag ccagcaagtg taccatgttc tgccattcca cgagtttaaa    600
tccaacaatg ggtctccgga agaaagatt tatatttgca tgtgacaaca cttctgcgac    660
cagcaaggtc ttattgcata ttatattaat aagattcggg aattgctctc taagaggagt    720
actgttaagt catttatcct accaaaatct tgttgcttga ccatgcccca cctgaaaacg    780
tccccaccta aggaattgat ccttgatgtt cattaggcca gcccagaaat gagaatcacc    840
cgcttttctg gaaacttggg tgagggattt gcctcccagg tatttatttc ttaggagtcg    900
tggccacata ccaccttcat tgagtaattt atagagccaa ttgctgagta aacaaatgtt    960
ctttatggcc agaatggtga ctcccagccc acctaactct ttaggttggc aaataatctg   1020
ccatttggct actctatatt tctatttatg atgtccacct tgctggaaga atctggaccg   1080
aatagcatct agcttcgcta agaagaagat catgaaaata ggtagtctac ttagaacata   1140
attaatcaaa acaagcctcc ccttggagac aggaatttgg atttccaatt actgagtctc   1200
ttctcaaacc ggttgataaa acaacaccac tcgatgtttc tcaatcttcg atgggtcata   1260
ggaatcccaa ggtacttgaa agacattttg cttattccgc aaccaaagag ccatgagtac   1320
taagtctcac atgccttagc tggcccataa taggaaattc ctcaatcttc gatgctatga   1380
tctaggaaca ccaccgtgtc atctacatat tgaaggatag acaaatctcc tttaatcaag   1440
tgtggtacga tcccaggaaa ttgattctcc tctattgctc tagcaaagag cactaccaac   1500
atatcagcaa caatgttgaa gagtatcggt gagagaggcc ccccttgtc aaaggccctt   1560 gtgtgtcgag aaaaagggtc ctataccatc attaactcta accccacgt gacctcccga   1620 gacgatattt tggatccaag cgcaccactt tggtgagaaa cccttcatgc gcatagcttg   1680
caggagaaaa ttccacttta gcttattata agctttctcg aagtccaact taagaataat   1740
tccatctcat ttttaaccta tgtagctcat gtacagactc atgtaataca attacccctt   1800
caagaatatt acgatcgggc ataaacacag tctaagaggg tttaataatt cgatggacaa   1860
ccacacctat tctgtttgtg agcactttaa taataatgtt aaaagtaaca ctaagcaaac   1920
aaatagatct atatttctgg attttcagat taatctctat cttaggaatt aacataatgg   1980
ctccgaagtt tagtctatac accgagagcg agttattatg gaagtccgcg aacaaaggca   2040
ttaaatcatt tttgttagga tagtggaatg aagttctagc attgtccttg tgatgttaca   2100
tgacacatgg caaaaaaaa actagcagat ggttcgcata ctcgttacta ctaaagctaa   2160
atcatcaatg caatcaagaa tcaaaccgtt cccaatgtgc tgtaacctca gtcaaaggaa   2220
gaagaaaacc accatcatat atgtctccaa cagtgtggct ctaataattt ccctgcagac   2280
aaagtacatt acacctgctg gcaggactac tagtaccacg ccacagtgtt tccagcatta   2340
ttattattat tattattatt attttttacct atgggtactg ccacactgta tccatctttc   2400
tctgcccggc gcttatataa cgcctcccca tgcttctact ccttcccaat ctgtgtttgt   2460
ctttgcttgc cccccttctc cccctcatc tccccctttt tcttgttcct gtgcctgtgc   2520
attggctggc gatggggtcc acttctcctt caggcctgga gctcaccatg ctgtcccgg   2580 gcctcagctc ctcctctggc tcaggtaagc tcaggagacc ccgacctgct agcagagatg   2640
gtattctatc ggtcatacag atacaagtat atatatgtac tcctatgcaa gaatgagacc   2700
atatatcgtt gctgaggttc ttcccacacc tttgccatct gttcaaaata aatatataga   2760
taatcgtcgt catgcatatt tcgatttttc gaatcgtgcg aaactagctt gtctgttgtg   2820
tttacttata tatattctga aagtactccg tattttctgg agtcaagaac agcatactgt   2880
```

```
attttctgtg attttttaaag gagctaactt ggctatatat gaacaaccga tggttgttgc    2940
ttggcggccg cagaggggtt tggatgcaac aacaacaacg ggagcgggaa cgggaacaac    3000
```

<210> SEQ ID NO 73
<211> LENGTH: 2920
<212> TYPE: DNA
<213> ORGANISM: Zea mays

<400> SEQUENCE: 73

```
ctgatgatca gcttgattcg tctagctgag aaggttaaaa ttttaactca taggccgagg      60
taaggcttaa aaaggacagc cgtaatacct gatacaaaga ggattgagat tgctgaacag     120
gccgaagcta tccccttagc ttcggagacg attcctgttg tgacggtcga agttagtgcc     180
gatccagtag aagagtctga gataaagagc tcaaaggcag aagagcaatc aaaactgttg     240
agtcccccaa ccacaactgg gttgccgagg ctaacaactg ctgtaacaat gattcctaag     300
aaaaggagga tggccagtgt tttggatgtt gttttgaagt ctacaaatat tccaactcct     360
gcttctatcg aagctcccaa aaataacgtt gaagagtcga gagaagtacc cactgcaagt     420
gcttctccca cttacactga ggctaaagct tcgagggtta agctagcaga actagcgaag     480
gaaagtcttc atgaaaagcc aacattgcct actcctgaag caccttccca agttgattca     540
aaatatattg ttcgtcatgc ttcggggaag caactatccg aagatcaaat tgccgaagtg     600
caacattatg caaggaatct taaatacctt tggggatcct tagtttatag agggagcgac     660
gaagacgact tcctttactg tctaccagac aggaaggaga ttgatgtttg ccgggaaatg     720
atggacaaca tgggataccct gaagcttgag catggtctgt ctgtaatgac gaaggaccaa     780
cttgtagata gtctcgctta taacagcctg aaagtttgtt tattttgcct tcatatttgg     840
taatttttat tatgatgaac gattttgtgg tgataattat tatcgttatt tgtacattct     900
ttgtttgtca gggtctaatt cttagcaaag ctttaaaggc tcagaaagat gcagaagatg     960
agagcaatca gatggcaatt agaaaccttc gttcggaggt tataactttg agaaacgaag    1020
ctctcgagaa ggataagatc ctgctctctt tggtggaaag attaaaatct agtgaagcta    1080
ggctttctag cctttccgaa gcagagcaga gggtaaaggt gtttgaaatg aagcaacaaa    1140
aaatgtgaag cgcattgctg acttggagta tgcgctattt gttcaagtag aattgcacag    1200
atctgaagtg caaggattga aaaagaaact cgatgaagtg actgaaaatt tcaatgtcga    1260
gcaaataaag cgcgaaatat ctgatactca acggctgaga gttcaaaaaa atgtcgagga    1320
gcttcgtcaa gcaaaagagg aatgctacaa tgttgccctg gaatgttgta ataaattgga    1380
agatagcttt gccaaaattg gtgcgttctc tacggggcaa aattttattc gtggctatcc    1440
tgattgagtt attcggtgga ttagcggcga agccgaaggc tttgaggaga ttctcggtga    1500
taggggagac ttatacgcct tcatcggcgc ctgcggagct gtgtcactcc ttgagaaggt    1560
tggctctgcg agtatgcaaa gactgtggtt tagccaggat tctcgatctc agccaacgac    1620
attaagaacc cttcggccga agccgctgcg ctaagtggaa agttttattc cgaagtctgg    1680
ttgagagatg gccgagaggt agctgacgaa gctatcagaa aaatgagaaa gagtctcatg    1740
ctactttgga agagacccag aaaactgaag aaattgcaga acgtacaaga ctttaagtat    1800
atctatcgtg acctagcagc ttcgtaaatg tacggcaaaa gaagggaggt acatccaaaa    1860
acaagaatga gaaatgtaaa tcatttata tttatataat gtttgggacg gacttggact    1920
ctttgtgcgc gaatcttcta gcgttgtttc attaacatgg ctatagagag atactgcctg    1980
```

```
ctcttttcta tgcaggtgca ggtctaccca cgtcgaaaca tattagcagc tccactacac    2040
atataagctg agggtataat tcgctatggc gtactaaccg gccgggcatt gaaacaggga    2100
tcatcacgaa gatacgttcg tgtgtacagt aataatgatc tacgtactct cttcctttgt    2160
acatatacgt gcgatttacg cgtatcatta cccaaaatag tgcgattcac ccgtatcatt    2220
acccaaaata ctgttttttac tgtaaattgt attgttcgta gaataaagtt tgaatatgat    2280
tacgtggacc actaagagta agttgatgtc aataacctaa tcagtaggcc agcgaggaaa    2340
agagctcgag ccttcagcaa gatcagtaac cccattttaa accgggctgg agccatatcc    2400
caaccgcagc ataaacagga tataaacagg agccaaagcg acaccaccct ttcgctctcg    2460
ctctcgccac agggcgacag gtgcgcgtag ccaggagaca cggctagatt ggtagtagta    2520
gagcgagaag cagagagaga gagagagaga tgtgtttgtg tggctacatc atctccccaa    2580
gggcacaggc acaggcacag cagccgcttg cctgcctgca ggctgctgca ggctgctgcc    2640
gcgcagcagt gccgctgccg atgcgtcaaa attagcagca ggggagtgtg cacagttcac    2700
ggtctgctct ctttctctct cttcccctat tacgagtccc agcagctaga acaacacaaa    2760
ccctctcctg tagctagatg tgtggtagta agctctcgct gttaacctcg gcaaagaacc    2820
tactggaagt cggaagggaa aaagcaaagt aggagtagct agctagtata gcaaacaagc    2880
tcccccgtgt gccgacgagc cgccgactag gtcagccgcc                          2920
```

<210> SEQ ID NO 74
<211> LENGTH: 3000
<212> TYPE: DNA
<213> ORGANISM: Zea mays

<400> SEQUENCE: 74

```
cgcggcagct gtgtgcgccc tcggcccta ccacgagtgc catttccgcg gccctggggg      60
ggatattcct ggcggcgagg ggggtcagca gcgggatgct ggttggcgat gttgtgcact    120
tgctgctggt tgcggccgtc tcgaccggag tctagctgcg gagtccttgt ccacgtgcgg    180
ctggactgtg ggacatcttt cggcttcctt tgggactcaa tcttgcgctg gtggagttct    240
tcggatctgg cgtacttttc aaacagctga tataactcct ggaggctctt tggcggatct    300
ctgatgcaat ggctgtatag gacgccagcg cgaaggccac tgatagcata gtggatggca    360
atctggtcat cgactgaggg cagctgtgat ttgagtgtta aaaatttgcg gtaatactcc    420
ctcagagtct ccttctccag ctgcttgcat agcgagagtt cggccagggc gtcggtgtct    480
gggcggtacc cttggaagtt gagcaggaat ttgtcccgga gactcctcca ggaatcaatg    540
gacagcggag gcaacctggt gaaccaggtg agtgccgggc cctcgagggc gatgatgaaa    600
gacttcgcca ttgtggcgtc gtccctccg gcagatgcaa cggcgacctg ataactcatt    660
atgtattgag ccgggtcggt gatgccgttg tacttgggat aagtccctgc ccggaagtta    720
gctggccaag gcgtcacttg caggtgtggc gccaggggac ttcgctcatc gagatagttg    780
accccttgga acgcgcggc gtgcgggaag gtgaagtcgc gctgggggaa acgcaggtcc    840
tccggttggg cgcggtgttg cagggtggc ccatgatgca ggccgaagtg tccttcgcgc    900
gtgtcttcga gttgtgcgcg ctgctggggg gtgcctcgtg ctgcaggccg gaatggcctt    960
cgcgctgcat cagcgcaatc tcccgctcga gttcttgagc cttctgctct tgtcgcgta   1020 tcatttgccg cactttggct agtgcggaca cacgctggcg cttggcctcc agtatctcct   1080
tctgcctctg gagattgcgg ttcttgaggc gcagggcgcg gagctgtagc tgctcttctg   1140
ctgagacgcc gaggacttca ccgtcctcgg tgaggtctgc gccctccggt ggtgcgaagc   1200
```

```
ctgagggcag ctgcggttgt ccttcagggt cgcaggtgtg gagggttcgt cttcgcaggc   1260
gcgaggaacg ttgtcttcag tggcctcttg gttggtggag tgggtgaggg cgagggcctt   1320 gcccttttctt gcggcgagca gtgctgcctt cgcagcctcg tcagccttcg ggttagctct   1380
cttgggtgcc atcgcgggtg gttttctcgt agcacgaacg gtgggcgcca aatgttggaa   1440
cttgcacacg ggcacaagtc gatccaacag tagggggaat gtaggcacaa acagggtttt   1500
agcgcgtgat ggcaaaagca ctgttcatct ggcctctcac gggcactgta caggggtatt   1560
tataggtacc tgagcacgca gcgccttgag ctaaggacgc atgtgccctc agctacctag   1620
attatccccg gaatattccc ataaagcggg gttacagacc gtaattacag ggatgtcttt   1680
acaaattagg cccgtaacgc acggcggcca cgcggggccc atagcaacgg accggatcac   1740
acgtgggcct ccgagctgga cgaagctgcg ctgtggggtg ccctcgtcg ccagtcttcg   1800 tctgatgcgg tacatgcgaa gggtgtcttc gcctgctttg tctgttggct cagttgctgc   1860
agcgaagaca tcgagcgaag ggaagacttc gagcgaaggg tggcgcctat gccttcgccc   1920
caacagttag caagaactta gtgacctgtt cattttttt ctttatatag ttattttatt   1980
ttgtaccgtg tattgatatg aatcttagat tttatgcaat attagttttt tcgatataaa   2040 tggtttttt gtctcccata gattttcctg ctggctccgc cactactcct cccgtagtcc   2100
cgtgctaacc attaggtaaa atccggccaa cttctgtgct tggttccacc cgagagaaag   2160
gagccgggac aagctggcat tcacagcttc atgcggctcc caccttgtc agagcacaaa   2220 atccggggat ctggcccgtg aagctggtcg tgctcgtggg cacgctgtct ggctgtggct   2280
gattgaaagc tgagaagcag cttgtgaagt ctggtctcga atccgtgcca ttgccaaacg   2340
tcccgtgcaa cagcagagac gtccggtttg tactccaaaa tccactcttc gcttcgcctg   2400
cagtcggcac cgccgttcaa gcaacggcca ccgcacctct tgaaccatga accctaagta   2460
tccttatcca cggtgagctc tgaaatccac gtcgcctcac gtacagtact ccccatagat   2520
ttcagacgga gctggaagaa aaagaaagcc tagccaccga gacgtgcaac gggacacatc   2580
cacgacacga acgccgcgac gggactgggc aatgcaggtg gtgtgggagt atttatcagc   2640
ctcgccgtgt cttctttta tgttccagca cgtaatgtag ggcgcgtaga atctagacta   2700
tcaaatcgcg aggggcgagc gacgacgacg gtgcggtgca gctttctaca ggactagtcg   2760
ttttcacgtc gtagcagagc acgctcgctt ggagcagccg acaaacacca agcgctagta   2820
gactaggact acagtgcagt gcgtctcgca agtccacggg cctcgcattg cattgcaaaa   2880
aaaaaaaaaa aaaacagttg ccgctatata acaggatcca gcgcacggca aggcggcagg   2940
caacagcaac acggagtcaa ggagcacgag ttaggttggc aaccctcgag agtcgagagc   3000
```

<210> SEQ ID NO 75
<211> LENGTH: 3000
<212> TYPE: DNA
<213> ORGANISM: Zea mays

<400> SEQUENCE: 75

```
cgcggcagct gtgtgcgccc tcggcccta ccacgagtgc catttccgcg gccctggggg     60
ggatattcct ggcggcgagg ggggtcagca gcgggatgct ggttggcgat gttgtgcact    120
tgctgctggt tgcggccgtc tcgaccggag tctagctgcg gagtccttgt ccacgtgcgg    180
ctggactgtg ggacatcttt cggcttcctt tgggactcaa tcttgcgctg gtggagttct    240
tcggatctgg cgtactttc aaacagctga tataactcct ggaggctctt tggcggatct    300
```

```
ctgatgcaat ggctgtatag gacgccagcg cgaaggccac tgatagcata gtggatggca    360
atctggtcat cgactgaggg cagctgtgat ttgagtgtta aaaatttgcg gtaatactcc    420
ctcagagtct ccttctccag ctgcttgcat agcgagagtt cggccagggc gtcggtgtct    480
gggcggtacc cttggaagtt gagcaggaat ttgtcccgga gactcctcca ggaatcaatg    540
gacagcggag gcaacctggt gaaccaggtg agtgccgggc cctcgagggc gatgatgaaa    600
gacttcgcca ttgtggcgtc gtcccctccg gcagatgcaa cggcgacctg ataactcatt    660
atgtattgag ccgggtcggt gatgccgttg tacttgggat aagtccctgc ccggaagtta    720
gctggccaag gcgtcacttg caggtgtggc gccaggggac ttcgctcatc gagatagttg    780
accccttgga acggcgcggc gtgcgggaag gtgaagtcgc gctgggggaa acgcaggtcc    840
tccggttggg cgcggtgttg caggggtggc ccatgatgca ggccgaagtg tccttcgcgc    900
gtgtcttcga gttgtgcgcg ctgctggggg gtgcctcgtg ctgcaggccg aatggccttt    960
cgcgctgcat cagcgcaatc tcccgctcga gttcttgagc cttctgctct ttgtcgcgta   1020
tcatttgccg cactttggct agtgcggaca cacgctggcg cttggcctcc agtatctcct   1080
tctgcctctg gagattgcgg ttcttgaggc gcagggcgcg gagctgtagc tgctcttctg   1140
ctgagacgcc gaggacttca ccgtcctcgg tgaggtctgc gccctccggt ggtgcgaagc   1200
ctgagggcag ctgcggttgt ccttcagggt cgcaggtgtg gagggttcgt cttcgcaggc   1260
gcgaggaacg ttgtcttcag tggcctcttg gttggtggag tgggtgaggg cgagggcctt   1320
gcccttctt cggcgagca gtgctgcctt cgcagcctcg tcagccttcg ggttagctct   1380
cttgggtgcc atcgcgggtg gttttctcgt agcacgaacg gtgggcgcca aatgttggaa   1440
cttgcacacg ggcacaagtc gatccaacag taggggaat gtaggcacaa acagggtttt   1500
agcgcgtgat ggcaaaagca ctgttcatct ggcctctcac gggcactgta caggggtatt   1560
tataggtacc tgagcacgca gcgccttgag ctaaggacgc atgtgccctc agctacctag   1620
attatccccg gaatattccc ataaagcggg gttacagacc gtaattacag ggatgtcttt   1680
acaaattagg cccgtaacgc acggcggcca cgcggggccc atagcaacgg accggatcac   1740
acgtgggcct ccgagctgga cgaagctgcg ctgtggggtg ccctcgtcg ccagtcttcg   1800
tctgatgcgg tacatgcgaa gggtgtcttc gcctgctttg tctgttggct cagttgctgc   1860
agcgaagaca tcgagcgaag ggaagacttc gagcgaaggg tggcgcctat gccttcgccc   1920
caacagttag caagaactta gtgacctgtt catttttttt ctttatatag ttattttatt   1980
ttgtaccgtg tattgatatg aatcttagat tttatgcaat attagttttt tcgatataaa   2040
tggttttttt gtctcccata gattttcctg ctggctccgc cactactcct cccgtagtcc   2100
cgtgctaacc attaggtaaa atccggccaa cttctgtgct tggttccacc cgagagaaag   2160
gagccgggac aagctggcat tcacagcttc atgcggctcc caccccttgtc agagcacaaa   2220
atccggggat ctggcccgtg aagctggtcg tgctcgtggg cacgctgtct ggctgtggct   2280
gattgaaagc tgagaagcag cttgtgaagt ctggtctcga atccgtgcca ttgccaaacg   2340
tcccgtgcaa cagcagagac gtccggtttg tactccaaaa tccactcttc gcttcgcctg   2400
cagtcggcac cgccgttcaa gcaacggcca ccgcacctct tgaaccatga accctaagta   2460
tccttatcca cggtgagctc tgaaatccac gtcgcctcac gtacagtact ccccatagat   2520
ttcagacgga gctggaagaa aaagaaagcc tagccaccga gacgtgcaac gggacacatc   2580
cacgacacga acgccgcgac gggactgggc aatgcaggtg gtgtgggagt atttatcagc   2640
ctcgccgtgt cttctttttta tgttccagca cgtaatgtag ggcgcgtaga atctagacta   2700
```

```
tcaaatcgcg aggggcgagc gacgacgacg gtgcggtgca gctttctaca ggactagtcg   2760
ttttcacgtc gtagcagagc acgctcgctt ggagcagccg acaaacacca agcgctagta   2820
gactaggact acagtgcagt gcgtctcgca agtccacggg cctcgcattg cattgcaaaa   2880
aaaaaaaaaa aaaacagttg ccgctatata acaggatcca gcgcacggca aggcggcagg   2940
caacagcaac acggagtcaa ggagcacgag ttaggttggc aaccctcgag agtcgagagc   3000

<210> SEQ ID NO 76
<211> LENGTH: 3000
<212> TYPE: DNA
<213> ORGANISM: Zea mays

<400> SEQUENCE: 76
cgcggcagct gtgtgcgccc tcggcccta ccacgagtgc catttccgcg gccctggggg     60
ggatattcct ggcggcgagg ggggtcagca gcgggatgct ggttggcgat gttgtgcact   120
tgctgctggt tgcggccgtc tcgaccggag tctagctgcg gagtccttgt ccacgtgcgg   180
ctggactgtg ggacatcttt cggcttcctt tgggactcaa tcttgcgctg gtggagttct   240
tcggatctgg cgtacttttc aaacagctga tataactcct ggaggctctt tggcggatct   300
ctgatgcaat ggctgtatag gacgccagcg cgaaggccac tgatagcata gtggatggca   360
atctggtcat cgactgaggg cagctgtgat ttgagtgtta aaaatttgcg gtaatactcc   420
ctcagagtct ccttctccag ctgcttgcat agcgagagtt cggccagggc gtcggtgtct   480
gggcggtacc cttggaagtt gagcaggaat ttgtcccgga gactcctcca ggaatcaatg   540
gacagcggag gcaacctggt gaaccaggtg agtgccgggc cctcgagggc gatgatgaaa   600
gacttcgcca ttgtggcgtc gtcccctccg gcagatgcaa cggcgacctg ataactcatt   660
atgtattgag ccgggtcggt gatgccgttg tacttgggat aagtccctgc ccggaagtta   720
gctggccaag gcgtcacttg caggtgtggc gccaggggac ttcgctcatc gagatagttg   780
accccttgga acgcgcggc gtgcgggaag gtgaagtcgc gctggggaa acgcaggtcc   840 tccggttggg cgcggtgttg caggggtggc ccatgatgca ggccgaagtg tccttcgcgc   900
gtgtcttcga gttgtgcgcg ctgctggggg gtgcctcgtg ctgcaggccg aatggccttt   960
cgcgctgcat cagcgcaatc tcccgctcga gttcttgagc cttctgctct ttgtcgcgta  1020
tcatttgccg cactttggct agtgcggaca cacgctggcg cttggcctcc agtatctcct  1080
tctgcctctg gagattgcgg ttcttgaggc gcagggcgcg gagctgtagc tgctcttctg  1140
ctgagacgcc gaggacttca ccgtcctcgg tgaggtctgc gccctccggt ggtgcgaagc  1200
ctgagggcag ctgcggttgt ccttcagggt cgcaggtgtg gagggttcgt cttcgcaggc  1260
gcgaggaacg ttgtcttcag tggcctcttg gttggtggag tgggtgaggg cgagggcctt  1320 gcccttctt gcggcgagca gtgctgcctt cgcagcctcg tcagccttcg ggttagctct  1380
cttgggtgcc atcgcgggtg gttttctcgt agcacgaacg gtgggcgcca aatgttggaa  1440
cttgcacacg ggcacaagtc gatccaacag taggggaat gtaggcacaa acagggtttt  1500
agcgcgtgat ggcaaaagca ctgttcatct ggcctctcac gggcactgta caggggtatt  1560
tataggtacc tgagcacgca gcgccttgag ctaaggacga atgtgccctc agctacctag  1620
attatccccg gaatattccc ataaagcggg gttacagacc gtaattacag ggatgtcttt  1680
acaaattagg cccgtaacgc acggcggcca gcgcggcccc atagcaacgg accggatcac  1740
acgtgggcct ccgagctgga cgaagctgcg ctgtggggtg cccctcgtcg ccagtcttcg  1800
```

```
tctgatgcgg tacatgcgaa gggtgtcttc gcctgctttg tctgttggct cagttgctgc    1860
agcgaagaca tcgagcgaag ggaagacttc gagcgaaggg tggcgcctat gccttcgccc    1920
caacagttag caagaactta gtgacctgtt cattttttt ctttatatag ttatttattt    1980
ttgtaccgtg tattgatatg aatcttagat tttatgcaat attagttttt tcgatataaa    2040
tggttttttt gtctcccata gattttcctg ctggctccgc cactactcct cccgtagtcc    2100
cgtgctaacc attaggtaaa atccggccaa cttctgtgct tggttccacc cgagagaaag    2160
gagccgggac aagctggcat tcacagcttc atgcggctcc cacccttgtc agagcacaaa    2220
atccggggat ctggcccgtg aagctggtcg tgctcgtggg cacgctgtct ggctgtggct    2280
gattgaaagc tgagaagcag cttgtgaagt ctggtctcga atccgtgcca ttgccaaacg    2340
tcccgtgcaa cagcagagac gtccggtttg tactccaaaa tccactcttc gcttcgcctg    2400
cagtcggcac cgccgttcaa gcaacggcca ccgcacctct tgaaccatga accctaagta    2460
tccttatcca cggtgagctc tgaaatccac gtcgcctcac gtacagtact ccccatagat    2520
ttcagacgga gctggaagaa aaagaaagcc tagccaccga gacgtgcaac gggacacatc    2580
cacgacacga acgccgcgac gggactgggc aatgcaggtg gtgtgggagt atttatcagc    2640
ctcgccgtgt cttctttta tgttccagca cgtaatgtag ggcgcgtaga atctagacta    2700
tcaaatcgcg aggggcgagc gacgacgacg gtgcggtgca gctttctaca ggactagtcg    2760
ttttcacgtc gtagcagagc acgctcgctt ggagcagccg acaaacacca agcgctagta    2820
gactaggact acagtgcagt gcgtctcgca agtccacggg cctcgcattg cattgcaaaa    2880
aaaaaaaaaa aaaacagttg ccgctatata acaggatcca gcgcacggca aggcggcagg    2940
caacagcaac acggagtcaa ggagcacgag ttaggttggc aaccctcgag agtcgagagc    3000

<210> SEQ ID NO 77
<211> LENGTH: 3000
<212> TYPE: DNA
<213> ORGANISM: Zea mays

<400> SEQUENCE: 77
ttgacaagtt ctcaaaatat ggacatttcc ttccattgct tcacccctc actgctccta      60 aggtgactaa gttgttcttg gatcaagtct atcgactaca cggggttgcca accaatatta    120 tttccgatcg ggatcgaatc ttaccagtt tgttttggca acaattgttt cagttgactg     180
atgcacggtt gtgtatgtct ttggcctatc atctgtaata ggggtggaaa tttggctcgg    240
gctcgacgag ccggctcggg ctcggtgagg ctcggctcgg ctcgagccgg ctcgcgagcc    300
aaaacgagcc cgagccgagc ctgattttgt agctcgccag aactgcgagc cgagccgagc    360
cggctcggtc cagctcgcga gccgagctaa caacgtcaag tatactatta taccatatta    420
ttgttatgtt ttgaactatt ttattgaatt tcttaaactt gatatgtgat acacttatat    480
tgtagtctaa aaatatataa tacataattt tttttatctt atatataata aaaaatatat    540
aatttatact ctaaacgtga tttagtgtga ggctcgcgag ctggctcgag ccggctcgcg    600
agccgttacc gagccgagcc gagcctctag gtcgggctcg caaaatgacc gagccgagcc    660
tggctcggct cgcagctgca ccgagccacg tcgagccgag ctcggctcgg tcgtttcca    720 gccctaatct gtaacacctc gtccaatacc tggaccagcg atacttactc ctggcagctc    780
tctaggatca tatactgtcc ccacagacca gcacgagtct tttgtgcaca cttttgtcctt   840 actcatgcgc acccaagaaa aacttcccag tcggtcaccc atcccaaatt gctccaagcc    900
aagcacgctt aacttggagg ttctttcgag ataggcttcc aaaaaagaag atgcaccttg    960
```

```
ttgttatgga tactctatta attctattaa gccttgggcc aggatatcac catcctaggg    1020
gccaggatac cacgtcatcc tcaatcggat ggtcaaaccg agaggttaaa ccaatgtttg    1080
gaaacatttt ttgcgctgtt ttgtgcacgc cttcccagtg aagtggtcta aatggttgtc    1140
tgtcgccgag tattggtata atacttcttt tcactccgta cttgggcgca ccccatttga    1200
ggttttatat ggttatgctc ctcgtcactt tggtatttca tccaaagcag tggttactaa    1260
catggagttg gaggaatggt tgaaggaaag ggagttgatg attcgggtca ttaagttaca    1320
tctgactcgt gcacaggata gaatgaagaa gcaggctgat aaacatcgat cagagaggca    1380
tttcgatgtg ggtgactggg tgtatttgaa attgcaacca tacattcagt cctccgtggc    1440
tacacctgtc aataaaaaac tggcattcaa attctttgga gcttaccaaa tcttggctaa    1500
agtgggacca gtggcttatc tcttgcagct gccttctact agttctaacc atctagtcat    1560
acacgtttct caactgaaga aagcggttgg tcacaaccaa gtgttagttc cttcattgcc    1620
tgatgatctc aggctagttc aggtgcccat ctgagtgctg cagcgcagga tgattgagtg    1680
cggggggtgag ctggtagcac acatcaaagt ggtctggtcc ggtatggatg actctttagc    1740
aacttgggaa gatgttgtgg ctctctgttc tcggtttcct gaagcaccgg cttggggggca   1800
agcagtcttc caaggcgggg gggggggaa atgtggacag cggagcggcg caggctgatg    1860
aaactgaagg caaccacaac ctgaatactg atgaagagaa agcgcgggaa gtttgagttt    1920
aagtgaacag gctgaggcgt gtgaataagc tgaacccaaa atatcttgag ccaacttagg    1980
tcgtgtaata gttgctgtgg cgtttacaat tgggccatgt gccgtgtaat agaacggcgt    2040
cgttgccata taaggagaaa gtcagaccgg aagaggtaac gaagaacata aacctgattc    2100
cttcgcccaa ctcttccctc ttctagttct tcttcttcaa tccaccttct ctctacccgc    2160
taacttaaca gtggagtaca tctaaactag cttgtcagtt gtcacttgga gtagaaccaa    2220
acagactttg atcatgcatg taatcatggc ccggtaatta atgcatggtt gtgtagagcg    2280
accgagcgag cggtttgatt tgatgccggt gaggtgacgt gacgacgcta ggtagctaac    2340
aaggaggtag acgatagctg ctacctgcta gcaggaggtg tgtgatcgag agttgacagc    2400
cggtgcaaaa ggaggaggcc aagagaagaa gagaaagcaa aggaggaggg agtgtgccgg    2460
agaagaggat ccggaagcca aaaccgtgct aaccgttgtg ccaaaagccc ccaccacggc    2520
tgaccgacgg acggcacggt ggattgattg gaaacgcgcc gagatcgacc cagccggccg    2580
gcgcttacac ccacgccgcg tcagatcaca ggggccgggc gcgggcgggc actgcacggc    2640
acccacaata cggcacgcgg gcgggcgggc gggcacggtg ccccacgcct ttcacggatc    2700
gggcagctgt ccccgtccac gccgcgcacc gcgccccgtc ctcgccaccc cgaaatgcac    2760
acgcacacgc cttgtccttg cttgcttcct tggcaccacc gcctcccctc ctctccttat    2820
taccaccacc tagctagcag cggcagcggc agcaccggcc tgttgtgctg ctcgctcaga    2880
cagctctgct agctgcatcc tcctaactct ccaggtctct ctctcctctc ccaactccca    2940
agtcccatcc ggatcgagac gctggaggcg gagcgccccc ccgggacggc ggcggcgacg    3000
```

<210> SEQ ID NO 78
<211> LENGTH: 3000
<212> TYPE: DNA
<213> ORGANISM: Zea mays

<400> SEQUENCE: 78

```
cgcggcagct gtgtgcgccc tcggcccta ccacgagtgc catttccgcg gccctggggg      60
```

```
ggatattcct ggcggcgagg ggggtcagca gcgggatgct ggttggcgat gttgtgcact    120
tgctgctggt tgcggccgtc tcgaccggag tctagctgcg gagtccttgt ccacgtgcgg    180
ctggactgtg ggacatcttt cggcttcctt tgggactcaa tcttgcgctg gtggagttct    240
tcggatctgg cgtactttc aaacagctga tataactcct ggaggctctt tggcggatct    300
ctgatgcaat ggctgtatag gacgccagcg cgaaggccac tgatagcata gtggatggca    360
atctggtcat cgactgaggg cagctgtgat ttgagtgtta aaaatttgcg gtaatactcc    420
ctcagagtct ccttctccag ctgcttgcat agcgagagtt cggccagggc gtcggtgtct    480
gggcggtacc cttggaagtt gagcaggaat ttgtcccgga gactcctcca ggaatcaatg    540
gacagcggag gcaacctggt gaaccaggtg agtgccgggc cctcgagggc gatgatgaaa    600
gacttcgcca ttgtggcgtc gtccctccg gcagatgcaa cggcgacctg ataactcatt    660
atgtattgag ccgggtcggt gatgccgttg tacttgggat aagtccctgc ccggaagtta    720
gctggccaag gcgtcacttg caggtgtggc gccaggggac ttcgctcatc gagatagttg    780
accccttgga acgcgcggc gtgcgggaag gtgaagtcgc gctgggggaa acgcaggtcc    840
tccggttggg cgcggtgttg caggggtggc ccatgatgca ggccgaagtg tccttcgcgc    900
gtgtcttcga gttgtgcgcg ctgctggggg gtgcctcgtg ctgcaggccg aatggcctt    960 cgcgctgcat cagcgcaatc tcccgctcga gttcttgagc cttctgctct ttgtcgcgta    1020
tcatttgccg cactttggct agtgcggaca cacgctggcg cttggcctcc agtatctcct    1080
tctgcctctg gagattgcgg ttcttgaggc gcagggcgcg gagctgtagc tgctcttctg    1140
ctgagacgcc gaggacttca ccgtcctcgg tgaggtctgc gccctccggt ggtgcgaagc    1200
ctgagggcag ctgcggttgt ccttcagggt cgcaggtgtg gagggttcgt cttcgcaggc    1260
gcgaggaacg ttgtcttcag tggcctcttg gttggtggag tgggtgaggg cgagggcctt    1320
gccctttctt gcggcgagca gtgctgcctt cgcagcctcg tcagccttcg ggttagctct    1380
cttgggtgcc atcgcgggtg gttttctcgt agcacgaacg gtgggcgcca aatgttggaa    1440
cttgcacacg ggcacaagtc gatccaacag tagggggaat gtaggcacaa acagggtttt    1500
agcgcgtgat ggcaaaagca ctgttcatct ggcctctcac gggcactgta caggggtatt    1560
tataggtacc tgagcacgca gcgccttgag ctaaggacgc atgtgccctc agctacctag    1620
attatccccg gaatattccc ataaagcggg gttacagacc gtaattacag ggatgtcttt    1680
acaaattagg cccgtaacgc acggcggcca cgcggggccc atagcaacgg accggatcac    1740
acgtgggcct ccgagctgga cgaagctgcg ctgtggggtg ccctcgtcg ccagtcttcg    1800 tctgatgcgg tacatgcgaa gggtgtcttc gcctgctttg tctgttggct cagttgctgc    1860
agcgaagaca tcgagcgaag ggaagacttc gagcgaaggg tggcgcctat gccttcgccc    1920
caacagttag caagaactta gtgacctgtt cattttttt ctttatatag ttattttatt    1980
ttgtaccgtg tattgatatg aatcttagat tttatgcaat attagttttt tcgatataaa    2040
tggttttttt gtctcccata gattttcctg ctggctccgc cactactcct cccgtagtcc    2100
cgtgctaacc attaggtaaa atccggccaa cttctgtgct tggttccacc cgagagaaag    2160
gagccgggac aagctggcat tcacagcttc atgcggctcc cacccttgtc agagcacaaa    2220
atccggggat ctggcccgtg aagctggtcg tgctcgtggg cacgctgtct ggctgtggct    2280
gattgaaagc tgagaagcag cttgtgaagt ctggtctcga atccgtgcca ttgccaaacg    2340
tcccgtgcaa cagcagagac gtccggtttg tactccaaaa tccactcttc gcttcgcctg    2400
cagtcggcac cgccgttcaa gcaacggcca ccgcacctct tgaaccatga accctaagta    2460
```

| | |
|---|---:|
| tccttatcca cggtgagctc tgaaatccac gtcgcctcac gtacagtact ccccatagat | 2520 |
| ttcagacgga gctggaagaa aagaaagcc tagccaccga cacgtgcaac gggacacatc | 2580 |
| cacgacacga acgccgcgac gggactgggc aatgcaggtg gtgtgggagt atttatcagc | 2640 |
| ctcgccgtgt cttctttta tgttccagca cgtaatgtag ggcgcgtaga atctagacta | 2700 |
| tcaaatcgcg aggggcgagc gacgacgacg gtgcggtgca gctttctaca ggactagtcg | 2760 |
| ttttcacgtc gtagcagagc acgctcgctt ggagcagccg acaaacacca agcgctagta | 2820 |
| gactaggact acagtgcagt gcgtctcgca agtccacggg cctcgcattg cattgcaaaa | 2880 |
| aaaaaaaaa aaaacagttg ccgctatata acaggatcca gcgcacggca aggcggcagg | 2940 |
| caacagcaac acggagtcaa ggagcacgag ttaggttggc aaccctcgag agtcgagagc | 3000 |

<210> SEQ ID NO 79
<211> LENGTH: 3000
<212> TYPE: DNA
<213> ORGANISM: Zea mays

<400> SEQUENCE: 79

| | |
|---|---:|
| aaacatcaat tgcaacaaat ttgatttcat attaaagatc tctgaaatga atctcttggt | 60 |
| gcaagctttg taattactag acatgcatat agtttgacta attgttgtcg gattttacga | 120 |
| agactgatgt tttcaaatcc taatacacca agaagaaaag gagggagtcc atggttactg | 180 |
| agaaaagaat cctgtgttat gctgcaggtg gatgtatcac aagttgtgtt atgcgttctt | 240 |
| gcttctcaga ttgcaaatta tgttgagagc tatattgggg ccactttaca agacaaggaa | 300 |
| ggttttgaat gggtcagttt gcatttttac ctgactaaat actgttgctt catctacaga | 360 |
| gtttctttgg acttttttt ttcaattgg tccatttctt cattcagcat gttttgttgg | 420 |
| gttgctaact gttatgctgc ttgcaacttt gcatcaccaa attggcttac atgaagtttt | 480 |
| gtaggagtac cagtggtgta ttaatagggc catcatcatt tatgtgtgcc ataaatacat | 540 |
| ccgctaccct gtggacaact aaccatctta ttcacctcat gacctcctag atcaatttca | 600 |
| gcataatcag ctgaggacat tctcagcatg tggtttaata caaccaagtc tataatccag | 660 |
| atcattttgg tataacccaa tattgatatg gtataatcca aagggcatta tataatttca | 720 |
| tttgctggta tttgtatagc ttttatatgt ttagtaacat tggtgtatgc ctgcatctta | 780 |
| ttgggagtta gagaatatat tagctgctag tctgctacag cacttggcgt ctgttttag | 840 |
| gcatgtaaac taattataag gacgcatcat atatacatag tgcatttgtc aatattgttt | 900 |
| ctggtatcta ttggcggctg agcttctgtt gacaatgatc aacttgaatc catgacatca | 960 |
| cttaaggttt tcttctggat gattttttt agttgcagga agaccattta tattgagctt | 1020 |
| cactgtttct tattccttagt ataccacgct taggcttgta tacttcgtgg attttctct | 1080 |
| ctctctcttg aaactaatgg tgaatattgt tctatgcagc tgaataacga tattgtcaat | 1140 |
| gtactgaata tctctattgg tgccatattg gctgttctaa cgcagcagct gctcgtcagt | 1200 |
| tggagatctt aattttcct tttgacttag gtctgcatcc actattcgaa ttttattctt | 1260 |
| gtagtagctg ccatattttg cccatctgaa atgtaatcat agattcacat ttgggcccat | 1320 |
| cctaactttc tctaggttcc ggtctttgtt atgcctactg tgaaaatgca aaactgtctt | 1380 |
| tccttcagtt acattgagga gttctctaat tatgctgtta acttaggcag atgttgatta | 1440 |
| ggatctgttt gatagagctc tcaaagtgtt tttgggagc tgaaacaat tttttttatt | 1500 |
| aagaagtggg tgatttatg ctaattacgt gaagtaattc ctgaaaataa actaggagat | 1560 |

```
taagagctgc aaaaggtact ttctttaaaa tcattccaca cacagaatta ttttatgtat    1620
agcctagaga ttcattttta tccaaagaac cactttccag aacatactag tttttttcta    1680
tttttttttc tcttgcgtgc gattcttaag ttatgatacc aatcaatttc tatttctagg    1740
gaggttttct tggtaaaaaa atcgatcaca aattaaaact gatgagtgtc agatgccatg    1800
taaaataaaa taaagtaaa cttcagtatc atgtgtactt taatattacc tccattgacg     1860
gtggctagtt cattttgaa ctaaaaatag gtattcatat aagtgacaat gagttctgaa    1920
ttttacatta aagatttaa tggtacgatc ggattctatt tctattaatt tttaaattaa    1980
aatttattta gagtcatgtg aagaagtcat gttaagaatt atttggattg tggttcatta    2040
ccagctctat ctatttatcg ttgagcaaag agccaagctg gcactgtagc aggtggtgat    2100
tgtccggtaa tctcgtaaca ataaacaggg gcttccttta tttgaaggcg tttgatggga    2160
catgtgcgtc gcgaggtgac gcggttgcag gcacctctcc atccttctgc caagcatcac    2220
atggcgcgtg cttttgtaga gaatccggcg ctgatcggtc atctcagtgg ctcagtctgc    2280
agtgcaccac ccaacactat tgccttcggt accagtaatg cctgagtcga acagcttttt    2340
ttttgtcacg tcggctggga cgtgccgacg cacagcccac accagggttg ggatttgggc    2400
ctttgaggtg ttgggcaaag ccagggctcg cgccgacgtg cgggtgcggg gtcgttccac    2460
tgccgcggcg tgtgacacct gaatcctttg gagtcttttt tcatcagtgt tcggatttct    2520
gtcttgcact cttgttcacc gccatcctac ttccacagtt ggcaacggag cacgggaggc    2580
aacggccccc ccccctttta cacttaacca tccagcgatc tcagtgacag tgtgtaggag    2640
tacggctgcg tctcgattta taacattcgc gcttacctaa atctctctaa gaataatgtt    2700
catgtctgca cttctaaatt gatttattat aaaaaaaata aaaattataa tcaactttat    2760
gatatttatt tttattataa agtattggtg ttttattttat aattgattgt tcttaaaata    2820
gtaaagcata atattatgtg ctaaaattgt attctcattc agggtgtagc tagcgcacga    2880
ccagtcaaac tacgtacact gtattactcg atcctgctac tatacagcaa gaaccctcaag   2940 cgtgcggttc cttgtgagtg acccctactg gctactgcta cagcggaggc aagatcctgg    3000
```

<210> SEQ ID NO 80
<211> LENGTH: 3042
<212> TYPE: DNA
<213> ORGANISM: Zea mays

<400> SEQUENCE: 80

```
ctgatgatca gcttgattcg tctagctgag aaggttaaaa ttttaactca taggccgagg     60
taaggcttaa aaaggacagc cgtaataacct gatacaaaga ggattgagat tgctgaacag    120
gccgaagcta tccccttagc ttcggagacg attcctgttg tgacggtcga agttagtgcc    180
gatccagtag aagagtctga gataaagagc tcaaaggcag aagagcaatc aaaactgttg    240
agtcccccaa ccacaactgg gttgccgagg ctaacaactg ctgtaacaat gattcctaag    300
aaaaggagga tggccagtgt tttggatgtt gtttttgaagt ctacaaatat tccaactcct    360
gcttctatcg aagctcccaa aaataacgtt gaagagtcga gagaagtacc cactgcaagt    420
gcttctccca cttacactga ggctaaagct tcgagggtta agctagcaga actagcgaag    480
gaaagtcttc atgaaaagcc aacattgcct actcctgaag caccttccca agttgattca    540
aaatatattg ttcgtcatgc ttcggggaag caactatccg aagatcaaat tgccgaagtg    600
caacattatg caaggaatct taaatacccct tggggatcct tagtttatag agggagcgac    660
gaagacgact tcctttactg tctaccagac aggaaggaga ttgatgtttg ccgggaaatg    720
```

```
atggacaaca tgggatacct gaagcttgag catggtctgt ctgtaatgac gaaggaccaa      780
cttgtagata gtctcgctta taacagcctg aaagtttgtt tattttgcct tcatatttgg      840
taattttat tatgatgaac gattttgtgg tgataattat tatcgttatt tgtacattct       900
ttgtttgtca gggtctaatt cttagcaaag ctttaaaggc tcagaaagat gcagaagatg      960
agagcaatca gatggcaatt agaaaccttc gttcggaggt tataactttg agaaacgaag     1020
ctctcgagaa ggataagatc ctgctctctt tggtggaaag attaaaatct agtgaagcta     1080
ggctttctag ccttccgaa gcagagcaga gggtaaaggt gtttgaaatg aagcaacaaa      1140
aaatgtgaag cgcattgctg acttggagta tgcgctattt gttcaagtag aattgcacag     1200
atctgaagtg caaggattga aaagaaact cgatgaagtg actgaaaatt caatgtcga       1260
gcaaataaag cgcgaaatat ctgatactca acggctgaga gttcaaaaaa atgtcgagga     1320
gcttcgtcaa gcaaaagagg aatgctacaa tgttgccctg aatgttgta ataaattgga      1380
agatagcttt gccaaaattg gtgcgttctc tacggggcaa aatttttattc gtggctatcc    1440
tgattgagtt attcggtgga ttagcggcga agccgaaggt tttgaggaga ttctcggtga     1500
taggggagac ttatacgcct tcatcggcgc ctgcggagct gtgtcactcc ttgagaaggt     1560
tggctctgcg agtatgcaaa gactgtggtt tagccaggat tctcgatctc agccaacgac     1620
attaagaacc cttcggccga agccgctgcg ctaagtggaa agttttattc cgaagtctgg     1680
ttgagagatg gccgagaggt agctgacgaa gctatcagaa aaatgagaaa gagtctcatg     1740
ctactttgga agagacccag aaaactgaag aaattgcaga acgtacaaga ctttaagtat     1800
atctatcgtg acctagcagc ttcgtaaatg tacggcaaaa gaagggaggt acatccaaaa     1860
acaagaatga gaaatgtaa atcatttata tttatataat gtttgggacg gacttggact      1920
ctttgtgcgc gaatcttcta gcgttgtttc attaacatgg ctatagagag atactgcctg     1980
ctctttctcta tgcaggtgca ggtctaccca cgtcgaaaca tattagcagc tccactacac     2040
atataagctg agggtataat tcgctatggc gtactaaccg gccgggcatt gaaacaggga     2100
tcatcacgaa gatacgttcg tgtgtacagt aataatgatc tacgtactct cttcctttgt     2160
acatatacgt gcgatttacg cgtatcatta cccaaaatag tgcgattcac ccgtatcatt     2220
acccaaaata ctgttttac tgtaaattgt attgttcgta gaataaagtt tgaatatgat     2280
tacgtggacc actaagagta agttgatgtc aataacctaa tcagtaggcc agcgaggaaa     2340
agagctcgag ccttcagcaa gatcagtaac cccattttaa accgggctgg agccatatcc     2400
caaccgcagc ataaacagga tataaacagg agccaaagcg acaccaccct ttcgctctcg     2460
ctctcgccac agggcgacag gtgcgcgtag ccaggagaca cggctagatt ggtagtagta     2520
gagcgagaag cagagagaga gagagagaga tgtgtttgtg tggctacatc atctccccaa     2580
gggcacaggc acaggcacag cagccgcttg cctgcctgca ggctgctgca ggctgctgcc     2640
gcgcagcagt gccgctgccg atgcgtcaaa attagcagca gggagtgtg cacagttcac      2700
ggtctgctct ctttctctct cttccctat tacgagtccc agcagctaga acaacacaaa      2760
ccctctcctg tagctagatg tgtggtagta agctctcgct gttaacctcg gcaaagaacc     2820
tactggaagt cggaagggaa aaagcaaagt aggagtagct agctagtata gcaaacaagc     2880
tcccccgtgt gccgacgagc cgccgactag gtcagccgcc atgcggacct ccgtttgtgg     2940
gattacggcg ggcgacacga acgcacggcg aggccttgcc tggacgggcc ccgtgccggt     3000
gccccccccc ctgttctgct tgtatctggc gcgctttctc tc                        3042
```

<210> SEQ ID NO 81
<211> LENGTH: 3000
<212> TYPE: DNA
<213> ORGANISM: Zea mays

<400> SEQUENCE: 81

| | | | | | |
|---|---|---|---|---|---|
| ggataggtat | tgtctaattg | cttttgggtt | tatgttttat | tcttgtgact | tcgaacttat | 60 |
| tcatgtttta | tatcgcagcc | gaattatctc | ctcccccgga | gcccttcggg | tcacaggcca | 120 |
| accccgaagc | aaaaaaggaa | gatgaaatta | ctaagatggc | cgaagctatt | atggataaag | 180 |
| ttgttttttca | actactaaac | gaagctgtgg | aagtagtttt | gaaagaagaa | tagctattgt | 240 |
| tgtaaaaaca | tttagaatat | tgatgtaata | tttgctgaac | aaagtgtgta | atattctata | 300 |
| gttttgaaag | taatatataa | gctgtatgta | attatgttct | ttacgatgca | tgaaacttta | 360 |
| catacatacc | gtttttgagc | ctttggcgaa | aaaacacctt | cccttctttt | catgcttcgt | 420 |
| gaaaaatatc | catattcgtg | aaaatatatg | cttcataagc | aatagatctc | ctctgatact | 480 |
| aaagttgagg | aaactgtact | tcttcaaact | ttattttgtg | ccttggcaca | atttctttga | 540 |
| aacaatttcc | gaagattaac | attgtattcc | cttcttgtgc | cattgatgca | atgtgatgta | 600 |
| tgatgtcatg | ttatacgaat | gatgtgatga | tgctatgata | tgcaaaataa | tatttgtgcg | 660 |
| gaagatacac | atacgttccc | acagtaggac | acagtctctt | tgtcgtttat | ttttcggctt | 720 |
| caccgcttat | ttttggtgc | atcagcgttg | acttttcgct | gtaagcctcc | cttatgagct | 780 |
| tcttcgcctt | ttatttcggc | ggtatcaacg | tttatttttc | gctgtaagcc | tcccttagga | 840 |
| gcttcttcac | cttttatttc | ggcggtatca | gcgtttattt | ttcgttgtaa | gctctgcatt | 900 |
| cccctttggaa | cgacttttga | gcagaaaact | tacactgcgt | tcccttaaga | acgacttttg | 960 |
| ttgctccgac | aaagacttgc | catgcgttcc | ttaaaacgac | ttttttgttgc | ttcgtcaaaa | 1020 |
| cttttggaac | ttcgtcgatt | tatgaggaag | gtatattaca | ttatgataat | gacaaagcta | 1080 |
| ttacaagaaa | ttgaaaacaa | cagaagaact | aagttttcaa | tgattgctct | ttattgaaaa | 1140 |
| aggtaaatga | taacaaatgt | aaaaactgat | tcagaggtag | gatatatctt | agtagatatg | 1200 |
| cttcgattct | ggcacagtat | tgttgactgt | gcgagcttcg | gactgctccc | tgaagtctcg | 1260 |
| ctgctggtga | gtgtgctggc | tcccttctgg | ctgctggcct | tggggataaa | cgggttgcat | 1320 |
| tggtggtgga | ggtggaggct | attgccaaga | tgcctgaggt | tggcttgccg | aagcaacaga | 1380 |
| aactgcagga | tggttaccca | catactctgg | aatgtacggt | gagtggtatg | aagcagtatg | 1440 |
| gataacctgc | ttcagctggc | tctgttgggc | tgcagcttct | gctatctctt | tctgtttctg | 1500 |
| gatggtgaca | tagcacatcc | tggtagtatg | gcccttgtcc | tcaccgcaga | ataggcaata | 1560 |
| aattttcctg | ggatgatccc | caaaccttcc | tccgaagccc | ctggcgcctc | tgcccccttgg | 1620 |
| agctgggggg | cgaggatagc | tccgttgctg | ccccgaagcc | tgagaagaat | actgcggcct | 1680 |
| ctgttgctga | cttcccctgt | cgtcattctg | agtagagtgg | attgatctga | cgtgcctggg | 1740 |
| gtggactctc | cctccgaagc | ccccactaca | cgacggttga | tctttagcga | cccttatttg | 1800 |
| ggaccgacgg | ttggtcgcta | aaaggtatgg | accgacggtt | ggtcgctaaa | tgtgtttata | 1860 |
| gcgacggtct | gtgggtcgct | aaaagtctag | aaatttaacg | acttatggtc | ggtcgctata | 1920 |
| gaggtaactg | tgcgactgat | ggtgggtcgc | tataggggta | tgtgattttt | atgtttctta | 1980 |
| tttactcacc | aaagcccatc | taaaggccta | ctaaacaaac | aaacgaaccc | tattccacgc | 2040 |
| gcgcagccgc | cgtcacttct | cccatggccg | cccctccct | cagccgtgga | gggtgccgcc | 2100 |
| gccacctcac | ccttggtgct | cgccgagctc | gcccttagcc | ctgtcgtgcc | cctgcgctcg | 2160 |

```
gtcctcattg gttccggggg aggtgacgga gcggcggcgg aagaattatc cccgtcaccg   2220
tctatctcct ctcggctctc gccgtctcgc gccatcgaac acccgccttc cagggcgagc   2280
agacgttgcc gggctcgtct ccggtgttcg gcgttggagt ggtaccgatc ttgattccca   2340
ctagaaattt tctcttaccc accgctcaag ctactctcag ccttatcccc actaaaaata   2400
attttggttt aattattatg aatttaggg ttatttaaaa tatgattttg aatttagaaa   2460 aaagaaata gaaaaaaga aaaaaacta acctaactaa cccttggccc attaggccca   2520
tgagccggcc gccccctgcc ccttccctaa ccctaagccg ccgcccctgg ctcctagcag   2580
ccgccgccat cccttctccc tctcctcct ctcctctagc ttctctccct cgcttccctc   2640
ccctgcagct tcctcacgcc atggagtcgc gcccagccgc cgaacaccgc caacacccgc   2700
gcccctgcag ccagccgtgc caccacagcc agcgccccc gctccgcct ggcggccggt   2760 cacaatcggc cagccggtta gcgcgcctgc gcccgaacgc ctcgctccag ccactagccc   2820
acgcccgtcg cccgccgccc acgtcatggc ggcgccagtc gctgccccac tgtgttctag   2880
cagatggtag tctcttctcc ctgcgttttgc ttctcgatct actgccctct ttccatcgtc   2940
tttgccttcc gcggcacaca ggtccttcct tgtactcagg cctcttcgtt tctgagggcc   3000
```

<210> SEQ ID NO 82
<211> LENGTH: 3000
<212> TYPE: DNA
<213> ORGANISM: Zea mays

<400> SEQUENCE: 82

```
ggaccgacca tgtcacaggg gggccatcat tacccctaccc ctagctagct caggctacgg    60
ggaacaagac cggcgtccca tctggctcgc cccggtaaac aaataatgat ggggccccgc   120
atgctccatg acgacgacgg ctctcagccc cttacggaag caaggagacg tcagcaagga   180
ttcgacagcc ccgacagctg tccttccaca gggcccaaac gctcctccga cggccacgac   240
atcacatgaa cagggtgcca aaacctctcc gaatgccacg acagcatgta cttagggctc   300
tagctcctct ctgctagaca cgttagcaca ctgctacacc cccattgtac acctggaccc   360
tctccttacg cctataaaag gaaggtccag ggctctcata cgagaaggtt ggctgcgcgg   420
gagaacggac cgacgcataa ggctctcgct ctctctctct ctcccacgcg aacgcttgta   480
accccctact gcaagcgcat ccatccgccc tgggcgcagg acaacacgaa ggccgcgggt   540 tcccccttact gttctccccc ctttgtgtcc cgtctcgcac cgacccatct gggctgggac   600
acgcaacgac aatttactcg tcggtccagg gaccccccgg ggtcgaaacg ccgacagtat   660
tattaataaa gccaggcatt tgaacctgct tcatctacct ctaccaaaca gatgtggata   720
ggacttctct attgtccaat atgttgatga cactcttttg ataatggaag cttgcccaaa   780
gcagttattc ttcctaaaag gaattctcaa ttcatttgca acatcaaccg gtctcagagt   840
gaactacaac aaatcaagca tgtatccgat caatgttaac tctgagaaaa tggagattct   900
ctcaagaacg ttcaattgtc agaccggacc aatgccattc acctaccttg gtctgccatt   960
gggtctttca agccacgac ttcagcattt tcttcccctg atacatagaa ttgaaaagag  1020
attgtcctat tcctctaaat gttcatattg ttttataagt ggctatggaa aaacaaatgc  1080
caaccaaagc acaaagtttt ctactgattg tggttaaaaa cagacttaac acaaggaata  1140
tgttgagacg aaagaacatg gcacttgagt catattcgtg tgaaaactgc atttgacaaa  1200
aggaggaaac tctatatcac ctgtttctta gatgtaactt tgcaaaggcc tgctggaatt  1260
```

```
ccattgctat gaccoctcct agaattgctc atccggaaga agcctcggct aacctcaggc    1320
aataacttaa tattcctttc tctatggaaa taatcatcct catgacatgg agtatctgga    1380
aatgtcgaaa tgcatggata tttaaaaaca aagacccaac agtgcaacat tgcaaaaata    1440
aattctcaaa ggaattactc ctggtcatct agagagcaag aggaaaatat gacaattcaa    1500
tcccagactg tcttaatcag tggcagtctt aaccctatag ctcattcggt ttaccttctc    1560
aactattcaa ttaggattct cctgtacata cactacgctg taatttacca ttattaatac    1620
aaaatttaca gtaggagtct ctccctcctg atctttaaaa aaccacttga tcaccttctc    1680
cttacgttca aaggacaaca ctattacttc gtttggatgt tggaatttgg tagcaaggaa    1740
tcgaatagat gttgaatacc aaatcgctaa agatatttag cgctccccta tcgatgcaac    1800
gctgctcgct tgagcccctc tatgctctac agtacaaggg ctatacacag gaatccgcga    1860
aattcggcct gaggctatcc gcagcggttc ttcctaattt ttccctctat atcactttt    1920 tgcgtcacat catcaacatt tcaccccta tttttttcat ctcccgcagc ggttccccct    1980
atattatccc ctatacccaa ctaaaaatat aaatatcat tatctaacca tatttatctt    2040
ttattactat ttttatcaat tattaaatag gggagcactg tgcaaggggc gctacagtgc    2100
tccccttgat ctgggggacg tgcgcgccct tccttacgc tgcagcgcgt aggggctctt    2160
tagtgtcagt cgctgcgggc ctagagatcc cgtacgtgag agacagagga ggggtcacgg    2220
cgtcgcaagc gctgcggcca gtctgagcaa accaacccctt tgtctgaaat gtcgtgcgcg    2280
cgcattattt gttagttagg taaaataata ttttatggct gaggtaggga gcggaagaat    2340
ttaggagaaa acccgttgca gaaagagaaa atgtaggaga taaaatctga tgatgttgcg    2400
cgcggtgccg ccacaagccc acaagcttgc gcagcctccc tccgcccgtc cctggcgtct    2460
acaaaaagcc ctcggcaggt ggcgagtgga gacgctccct catacctacc agccaaacca    2520
agcaagcagg gaatccccac aaggcagcag atggaagcga aggtggcgg tggcgcggcg    2580 tggcgcgggc gcgggcgcgg ctagctaggc cggctcgtgt gcgtgcgcga ggagacagcc    2640
acagccatac agggatgctg cctgcttcgt gaccgtgctg gtggtggtgg gctgcagcct    2700
gcagctcgta tcacacgccc acagtgcagg aaggagggag tggaagaaga gagaggaagt    2760 tgttttaaa ggcaacagcg agtcccgctg ctgtccctct ccttcgccac ctccctccct    2820
cactctcttc cctccctctc ggaggaggag agagaagaga gggagccagt ccagctccag    2880
ccagccggac gcccggacca acaccacccc gcctccccct cccccgccc caccggcccg    2940 cccctctcgcg ctgccgtacc cacggccccca cgcacgttca caagtctcgt cgccgccgca    3000
```

<210> SEQ ID NO 83
<211> LENGTH: 3000
<212> TYPE: DNA
<213> ORGANISM: Zea mays

<400> SEQUENCE: 83

```
caactcggtt tccatgctta gcctgactga gtccgtgctt agcatctgat cgacataaca     60 aggcccttc acgatgtcga ctttgagtag gatgccaaga tgtcggtgat agtggaaaca    120
cttgcaatcg agctgtacta gatggggtg caaacacagg ttgctctttt taaacacttg    180
caatcaaagg tccgagagct cttttttaaac caactctctt gtggacccctt ctatgttgct    240 ctactccttt ctttttatagc acaagcgagg agagaatgac atatgcctat tgggtagagg    300
atcttgatta acagattctc aactactcct atattgtcat tgcacatggag tcatacatgg    360 tgactcatct tagatgtgcc acattgttga gtctatcgtg ttgtagcgct agatatgccc    420
```

```
tgtcaaagtg gcaagtacta gagcccacac caccattggg tacgatgtaa ttggtaacta     480
gtgaagcaga ctatacttta taacattgca ggtacgctag cacgttcaag agtgtctata     540
gggatgatgg cacatactat atagtggtct tcagtatgcc tatatagtgc tctaggacgc     600
tccggctcta gagccgaccg ttgcctaaca agacacgttc acaagtgcaa tggctctggc     660
tattccgccg taaattccgc tatcccggtc gacaagctcc ctcctaagag ccgcctaaag     720
gtgactagtc atcgatagag tggcgcgaag agccgaagct ggagcgttcg ggagctctac     780
caaagagacc ctatagtaca aaattatgta gcagtttcca tgccacgtgc acgaccacag     840
aaacgtccgg tgacgctcgt tcactgccca cttggatatg cggcaggaga tggagatgtg     900
tatcggcatt gtcgacatgg ttgtttttgt tgcctacggt cgttacctgc cccgctatca     960
agtgcgcatt ctcgccgtat gtattagggg cagtaatgga tgtgaccaaa tagttctttA    1020 caaaatatc aaggctttaa ataaatttta attgaaaaat aaataaaaat agagttcaat     1080
cctaacttga tctgatactt aattttata gtgtaaaatt tagagctcat tggcacccTt     1140
acgccgcctc aacgcccaaa ccgagtccct atgtatgaga tttatttgaa gcctggctga    1200
cttgggacgg tatacaatag accagacatg tttgatcggt tcatttctc tgttgtgata    1260 ggtccaatac atattttgat tggttgactc gctgaaaaag aagtcgaaaa ataataaata    1320
aaaacttata tagcaagtga gatccgattt tgttcatata aatatcaaaa acacaaaagt    1380
gaaatcagtt tcttaattgg atgaagtcaa gagatataag aagagaatta attaaaaaca    1440
ggtctcggtt tccatgctta ttagcctgac tgagttcgtg cttagcatct gatcggcata    1500
acaaggctcc ttcacgatgt cgactttgag taggatgcca agatgccggt gattgtgcaa    1560
acacttgcaa tcgaggcatc gagctgtact agatggaggt gcaaacccag gttgctcttt    1620
ttaaacactt gcaatcaaag gtccgagagc ttttttttaa accaactctc ttgtggaccc    1680
ttccatgttg ctctatttct ttcttttata gcacaaggga ggagagaatg acatatacct    1740
attgggtaga ggatcttgat taacagaatc tcaactactc ctatattgtc attgacatag    1800
agtcatacat ggtgactcat cttagatgtg ccacattgtt gagtctatcg tgttgtagcg    1860
ctatatatgc cttgtcaaag tggcaagtac tagagcccac gctaccactg ggtacgatat    1920
aattcgtaac tagtgaagta gactatataa catttcaggt acgctagcat gttcaagagt    1980
atctataggg atgatgacac atactatata gtggtcttca atatgcctat actttattat    2040
ttattgttat cttataacgt accattttt ttatcattga ctggctatat aaataacttt     2100
aaattgttaa ttggctttat gtcaacacaa gccatatttt atcggattta tgattttgtt    2160
taatgaaatc tttatttttg gaactgaata ttacggatgg tgcctaacaa ctaaaacaga    2220
ctaaaaatat gattaaagct ccaacgagaa aacatgttga gaagtcgcta taggttgtag    2280
cgacaaagag actcttaaga caatttctat ccgtgttatt tatcttatct tttatttta    2340 aactctactt tgtaaaaaaa tgcaatctat gtgcgtcttt gagagagctc tgggaagctt    2400
cggctctcga ccgatcgttg cctaataaga cacgttcaca agtgtgatgg ttgtggttat    2460
ttcgtaaatt ccgctctccc ggtcgacagc tccctcataa gagccgccta aaggtgactc    2520
gtcatagata gtggcgcgaa gagccgaagc tggagcgttc gggagctcta ccaaagagac    2580
cctatagtat aaaattatgc aaaactgtgt ttcgcaggaa catatatatg gcatgctatc    2640
ctacctccaa gtgccaagt gtcactcact cgcacagcac taagctaaat agcttattaa     2700
ggtgcatgcc caacttcttg ttaaagatat atgcctgcac ctgcattgcg ctgcaaattc    2760
```

```
ttgtcagtac agcttgtgat gtcctgggcg gctggcgcct atatattgga gacccatcat    2820
catagatcac cacaagggca gacgcgcaac gcctcccccc tgtctgtgtg tctcgactag    2880
cttcccgagc tgcactgctc tgtttcgctg actgctgcag ctgacgagcc gagctgagct    2940
cagcctgctc ccacgacgta cacgcaggct caccacacca caccacacca caggccagcc    3000

<210> SEQ ID NO 84
<211> LENGTH: 3000
<212> TYPE: DNA
<213> ORGANISM: Zea mays

<400> SEQUENCE: 84
caactcggtt tccatgctta gcctgactga gtccgtgctt agcatctgat cgacataaca      60
aggcccctcc acgatgtcga ctttgagtag gatgccaaga tgtcggtgat agtggaaaca     120
cttgcaatcg agctgtacta gatggggtg caaacacagg ttgctctttt taaacacttg     180
caatcaaagg tccgagagct cttttttaaac caactctctt gtggacccct ctatgttgct     240
ctactccttt cttttatagc acaagcgagg agagaatgac atatgcctat tgggtagagg     300
atcttgatta acagattctc aactactcct atattgtcat tgacatggag tcatacatgg     360
tgactcatct tagatgtgcc acattgttga gtctatcgtg ttgtagcgct agatatgccc     420
tgtcaaagtg gcaagtacta gagcccacac caccattggg tacgatgtaa ttggtaacta     480
gtgaagcaga ctatacttta taacattgca ggtacgctag cacgttcaag agtgtctata     540
gggatgatgg cacatactat atagtggtct tcagtatgcc tatatagtgc tctaggacgc     600
tccggctcta gagccgaccg ttgcctaaca agacacgttc acaagtgcaa tggctctggc     660
tattccgccg taaattccgc tatcccggtc gacaagctcc ctcctaagag ccgcctaaag     720
gtgactagtc atcgatagag tggcgcgaag agccgaagct ggagcgttcg ggagctctac     780
caaagagacc ctatagtaca aaattatgta gcagtttcca tgccacgtgc acgaccacag     840
aaacgtccgg tgacgctcgt tcactgccca cttggatatg cggcaggaga tggagatgtg     900
tatcggcatt gtcgacatgg ttgttttgt tgcctacggt cgttacctgc cccgctatca     960
agtgcgcatt ctcgccgtat gtattagggg cagtaatgga tgtgaccaaa tagttctta    1020 caaaaatatc aaggctttaa ataaatttta attgaaaaat aaataaaaat agagttcaat    1080
cctaacttga tctgatactt aattttata gtgtaaaatt tagagctcat tggcacccctt    1140 acgccgcctc aacgcccaaa ccgagtccct atgtatgaga tttatttgaa gcctggctga    1200
cttgggacgg tatacaatag accagacatg tttgatcggt ttcatttctc tgttgtgata    1260
ggtccaatac atattttgat tggttgactc gctgaaaaag aagtcgaaaa ataataaata    1320
aaaacttata tagcaagtga gatccgattt tgttcatata aatatcaaaa acacaaaagt    1380
gaaatcagtt tcttaattgg atgaagtcaa gagatataag aagagaatta attaaaaaca    1440
ggtctcggtt tccatgctta ttagcctgac tgagttcgtg cttagcatct gatcggcata    1500
acaaggctcc ttcacgatgt cgactttgag taggatgcca gatgccggt gattgtgcaa    1560 acacttgcaa tcgaggcatc gagctgtact agatggaggt gcaaacccag gttgctcttt    1620
ttaaacactt gcaatcaaag gtccgagagc tttttttaa accaactctc ttgtggaccc    1680
ttccatgttg ctctatttct ttctttata gcacaaggga ggagagaatg acatataccct    1740 attgggtaga ggatcttgat taacagaatc tcaactactc ctatattgtc attgacatag    1800
agtcatacat ggtgactcat cttagatgtg ccacattgtt gagtctatcg tgttgtagcg    1860
ctatatatgc cttgtcaaag tggcaagtac tagagcccac gctaccactg ggtacgatat    1920
```

```
aattcgtaac tagtgaagta gactatataa catttcaggt acgctagcat gttcaagagt   1980
atctataggg atgatgacac atactatata gtggtcttca atatgcctat actttattat   2040
ttattgttat cttataacgt accatttttt ttatcattga ctggctatat aaataacttt   2100 aaaattgttaa ttggctttat gtcaacacaa gccatatttt atcggattta tgattttgtt   2160
taatgaaatc tttattttg gaactgaata ttacggatgg tgcctaacaa ctaaaacaga   2220
ctaaaaatat gattaaagct ccaacgagaa aacatgttga gaagtcgcta taggttgtag   2280
cgacaaagag actcttaaga caatttctat ccgtgttatt tatcttatct tttatttta   2340 aactctactt tgtaaaaaaa tgcaatctat gtgcgtcttt gagagagctc tgggaagctt   2400
cggctctcga ccgatcgttg cctaataaga cacgttcaca agtgtgatgg ttgtggttat   2460
ttcgtaaatt ccgctctccc ggtcgacagc tccctcataa gagccgccta aggtgactc   2520 gtcatagata gtggcgcgaa gagccgaagc tggagcgttc gggagctcta ccaaagagac   2580
cctatagtat aaaattatgc aaaactgtgt tcgcaggaa catatatatg gcatgctatc   2640
ctacctccaa gtggccaagt gtcactcact cgcacagcac taagctaaat agcttattaa   2700
ggtgcatgcc caacttcttg ttaaagatat atgcctgcac ctgcattgcg ctgcaaattc   2760
ttgtcagtac agcttgtgat gtcctgggcg gctggcgcct atatattgga gacccatcat   2820
catagatcac cacaagggca gacgcgcaac gcctccccc tgtctgtgtg tctcgactag   2880
cttcccgagc tgcactgctc tgtttcgctg actgctgcag ctgacgagcc gagctgagct   2940
cagcctgctc ccacgacgta cacgcaggct caccacacca caccacacca caggccagcc   3000

<210> SEQ ID NO 85
<211> LENGTH: 1461
<212> TYPE: DNA
<213> ORGANISM: Zea mays

<400> SEQUENCE: 85
gcacgcatta cagattcgta gtacacagct ctaaggtatt aaaaaatgat gcatcgacat     60
cgtttgttct tttttcactc ataatgcagg aaacagaaat agggcatttg attttttgtgc    120 atatattaag tacaatgata aatcatgcaa tgtgccagtt tttgcccaaa tgatacctat    180
tccgttggct tcattaagcc atatgggaga tgctttgtac atttaggaat aagacaagaa    240
aacatgatta cttctggtat tttgaggaat agacaaaaaa catgattaca tttaggctat    300
gctttgtgcg aggtcaaatg attagtgaat ttctcattat cgatgaaggt attgtttgat    360
ttgttcacca ctgaaaagtg aaaacttggc agtagcagtc tctgagatta atgtgacaat    420
ggtagacatg atcatttgct tcaaaaagcg acggctgctt gtattgatga ataaatctcc    480
tattaacata ttttgaatga agtactttgg ttaccaagtt gattaccaag tttgtcaatt    540
agtattttag tttggatata gagtacgctt atgcatgagc tatttcacaa tgtttattta    600
tgagatatat aatggtaatt tagaatgata tcatcctact ttcatatatt tgatggacat    660
cacatatgca tctcactagc ggtgtggaga gtggcaggga atcctcatcg ttgtactgac    720
ggtacgatat acaacaagta tgtactgtct ttgattgtgc tttcgtttaa aaggtagttt    780
tgtcagttca cattaccctg caacttgtta attactatat ctgttgaaag gagttgtcta    840
ttatctgcaa cttcacatag caggtcaata cagacaagac aaaaaaacta aacaaagcat    900
tgtcaatggt gacctaccac aaaaatatat tcttaactga caataagatt atttcaggct    960
ctgttcatcc tactaacatt ttatttagac atataccgct acgcttgtaa ttattatggt   1020
```

| | |
|---|---|
| gcttatcatc ttctagccca ttggaagttt ccttctcatc tctgttatca gggaagcatt | 1080 |
| tgagccttct ctatcatcaa gctgggatcc cttgagtatt tggagaggta tttaggagat | 1140 |
| catggatgaa gaaatggaag atgtcatagt caaggttctg gactgctcga accaatcaga | 1200 |
| ggtgataaat cagtgctagt tattgcttta tatttctgaa caagacgttt ctgtctgtta | 1260 |
| gaaattgttg cgacatttgc ttagggattc ccatgtgcca tgttactagt tacactgcta | 1320 |
| ttgctggtct catttagttt aacataccac tgttagatct tagaggtata tattgctaaa | 1380 |
| aagaatgcat gatcattgat tcattgtgat accacctgtg ctaacttatt ttgagctcct | 1440 |
| cttattcttg ccggctcccc g | 1461 |

<210> SEQ ID NO 86
<211> LENGTH: 3000
<212> TYPE: DNA
<213> ORGANISM: Zea mays

<400> SEQUENCE: 86

| | |
|---|---|
| gggctaggcc catgggccgg cccggcacgg cccgaaattc aaacgggccg gatcgacccg | 60 |
| aaattcaaac aatacgggcc ttttcgggct tgggccgggc cgggtcgggc ggcccgaatg | 120 |
| tacacctata gataaaggct aacgttgata gatacagatc ggttgataat gttgtgacgg | 180 |
| tagatataga ccctatttag tttactacct aacttgtcat aatttgtcta acttttccta | 240 |
| cataaaaaaa ggtaagttct ttaatttagt caattaacct taaataaatt gtggcacagt | 300 |
| tagccgagaa ccaaatatgt ccatagccca cgattggaac ccgccttaga ataccacatg | 360 |
| tggtaatgaa actgttttga atcataatta taaactaggc ctatgcccgt gcgttgctac | 420 |
| gggtgcatta aaatgcataa caatgttagt gccaatgtgc cattatatag gaactaatcc | 480 |
| ttagtaatat tgcactcttg taaccgaagt atcatcagac caatataagc gagtaaactc | 540 |
| aatagtcgcc caaagcgaaa caacaaattt gccacaagct gcctactgct gggcgcactg | 600 |
| cacccctctgc ccacccgcct ggcacatcat catcctcgtc gtaggcctcc tggtgctgct | 660 |
| gctgccgcct ctgcatctcc tcttcgatgt tcacgtcgta gggcatcgtc tcctcgcact | 720 |
| cgtccagctc catgtcaatg tactgtgata ctggcttggg cgggagaaca gcctccaggg | 780 |
| ccttgcactg ctccgggctc aacgagtccg ggaactccac cgagaagtgg atgtacagct | 840 |
| tgcccttcat gaagggcctc tgatacatgg gcatgccttc atcgttgatt gccttgaaag | 900 |
| aatctgcaca aatttaaaat aaacataatc atacgtcaga atcaaagcca tgagaatgga | 960 |
| attggactgt tgacaactga catggtacaa taattatatt tggtactaac caccagacca | 1020 |
| cacgtatctt agtgtttaaa aataaacaat aattatattt gaataaatat cttaagacct | 1080 |
| atttatatga tatataaaaa ccatagcaaa gcacgggcaa ctggctggta caagattgat | 1140 |
| ggctgaaggt gtccaaatct gtttttagcc ttgcaagttg taactaatat atacataatc | 1200 |
| taatagtaac aagctgaaat agcactcctg attattaaaa actcaaaccg agtatcaata | 1260 |
| agaaaataag cttaatttag cctatgtagc atggatgccc catagtttac catcattcaa | 1320 |
| gaatgaggtc atggaaatac tgcagaacag aaaaaataag aacacacctt cattgacaag | 1380 |
| tctagagact tcctgtacag ctcatttgca ggttcctaca aacagtctgt acagctcatt | 1440 |
| tgcaggttcc tacaaacagc aggtctgaac ttcagtttcc actcaaacca aattggacac | 1500 |
| gacattgcag aaaaaacata aatttttaag gaaaaaggca aaatcttagt tctttcatgg | 1560 |
| aatattcttc cagatgcttg ctgacaacct gactgcatgt ggctcaagcc ccatgggcag | 1620 |
| aggtctgcag gtcagccatt gtcaccagga acatggtaca gagccatgtt ccgtgtccta | 1680 |

-continued

```
ggaatgcagg aacaaaagga aaaactttct caaagagtgt aatgcattcc ttggtcccta   1740
tattccacaa acaaaacgta ccgggaattt tgtgacaatt ggtcagccta gataaaagga   1800
acgatgtaaa tgtgtttgaa attagctaac acaatagcgg cctgcacata ccacatcaac   1860
agccttctgg aaacatccgg ttgcctttgt aaagaactca ttagctattg cattgtctgg   1920
agtgaagaat ccatgagagg tctgagcatt tcccaagcac cagagtgcat cggacttgtt   1980
gggattaatt tgaagtgcct cctccagttt ggcttccaca tctgcaccaa aactcattca   2040
attagtacca ctttcactgt tcattaacat ctacaaagtg gcataaacct agacatactc   2100
gcagcataat gtaatcctat atgcgaactc tgaataatta taaatactc ccacaatttc    2160
aaaatataat ccgttttggc tttttaagcc acaactttga acactcattc ttattcagaa   2220
aattaatgaa aaatgaaaaa taaaataagt catatgtaaa atatatttga taataaacaa   2280
aaccataata aattttattg tttttttac aattttaaa taagttgagt gatcaaaact     2340
ataatttaaa aagtcaaact aattataaat tatgatagag ggagtaatag tttaaggacc   2400
tatatacgtg caatttttat agttggcgaa ataacttag ggagtgtttg gtttctaggg    2460
actaatgttt agtcccttca ttttattctt tttagtgta taaattgcta aatatagaaa    2520
ctaaaataaa gttttagttt ctatatttga caattttgga actaaaatgg aataaaatct   2580
agggactaaa cattagtccc tagaaaccaa acaccccctt aatactttac tcaaagttct   2640
tttatcccgc tacagatgtg gccacctggc catgacggcc atcaatcttc tgatgcgcac   2700
gtgattccga tcgccccatt gtccccctt accctcaacc gtccattcag gatcgtatgg    2760
accaggcggt ggccacgtcc atccactgcc ccgccccacc acgtctggcg ctaggcaaac   2820
cacgcacgca cctgacgggc tcgcatcgca cccgccaccc ccaccgcacg caccctctcg   2880
tcctctctgc gccgacccgg ctcttctccc ccaacacaat cctccttccc cgatccagtc   2940
tcgcggtcgc ggccacgctg agggacagcg agaagagaca gacacagatc gcgcgcggag   3000
```

<210> SEQ ID NO 87
<211> LENGTH: 2062
<212> TYPE: DNA
<213> ORGANISM: Zea mays

<400> SEQUENCE: 87

```
aactatgtga atctgtgaac ttttcatatg cctgtaaact gttcggcttc tttaatatgt     60
gttttacaaa ctgtggttgc atatgaaatt gtggctcttg gttgtctcca tgcagatgtg    120
tgacccttat gaacacacat atgatgatga aatggatgca cacacatctg atgatgaaat    180
ggatgcacac acatctaatg acgaaacaga tggagaaatg cttgttgctc tttatgctgt    240
tgacatttgg ggcaggcatt tcagtcgggc tcctagaaga acattggtcg aatctggtat    300
tcaatgggtt caagaacgt tggagattag taacgactgt tttgacatgt tcggatgcg     360
aagaactgtt tttcgacgat tgcatgcaca gttggtacaa aattatgggc tgcttccaag    420
cagggggtgtc agtactatgg aagctcttgg catattcttg tgggcatgcg ggggtccaca    480
atcgtttagg cagatcagaa ataaatttgg tcactcattg gaaacaatta gcccacaagta  540
tagtgatgtc cttaatgcac tttataagat gtcatctgac acaatcaagc caaaagaccc    600
acattttgtc gagattcatc atcgtttgcg agaggcgagg ttttggccac acttcaagga    660
ttgcataggc gcaatagatg gtagtcactt cccagcggca gtcccggctt cagaacaagc    720
gaaatatatt ggccgacacg gttacacgtc gcagaatgta atgaccgtat gtgacttcga    780
```

```
tatgaggttc acatttgtgg tgacaggatg gccaggttcc gtacatgaca caagagtact    840
acaggatact ttaataactt atgcggacag gttcccccat ccaccggaag gtatataaat    900
attttgttga ttagtataat acagtactat tttatgtcat atgtacgtaa catttgtatt    960
ttgagtttgt gcaggtaaat actatcttgt cgattcgggt tatccaaata gaaaggggta   1020
ccttgcacct tataagggtc agaagtacca cattacggaa tggcaaaatg cgaggcaacc   1080
tattgggagt aaagaagttt tcaactatgc gcactcatcc ctacgaaatg ttattgagcg   1140
atcatttggg gtgctaaaaa tgaagtggag aattctatta agtctccctt catttcgct    1200 tgagaaacaa tcgaagataa ttattgcatg tatgacactg cataacttca ttagagatag   1260
tgctctacac gatagagatt ttgatgaagt aggacctaat agcctaagtc atgatctacc   1320
tgcaggtgag agtagtacta gcacatctga tgagttagac atgagtgatt ttcgagatgc   1380
aattgcaaat gcattagtgt cgtagttaac ttagtgcaat tgtaacggta cttatgatgt   1440
aatcaactcc actaattagt ttgtaatgaa ctttatctgc gttatgggtt tcattttatc   1500
gtttgttcga acagaatctg caatttgaga atctgtatcc aaacacgtag attctgacga   1560
acagcttttc tgcacagctg gcgaaccaaa cacctaaatt ctaaccacca gcttttccca   1620
acagccagct tttccccaca gccagctttt cagataagct ggcagaaaaa aagccgaacc   1680
aaacacgccc catatcttct agaagaagaa tcgagcgcat aacttgggcc tgctcgcggt   1740
tggccccatg tccaccccc accccccaaa ctgtcgacgc cgactcgaca cgaacccaac   1800
cggccaacca cctcccctgc tggtcagaac tccgcaagtc cgcatcaatt cgcactccca   1860
gcttccttta ccttcgcagc aagcaagccg gtagcagcaa gctagatcgc ggggaagcga   1920
ctcgcctcca ccatcggcgc tgctccggcg cggagaagcg tcctctcgcg gcggctggga   1980
agaccagtct ccgccagtcc cggcggctgc ttccgtgagg tgcccttggc tcctgggcga   2040
cgggctcgtg gcggccggcg ag                                            2062
```

```
<210> SEQ ID NO 88
<211> LENGTH: 307
<212> TYPE: DNA
<213> ORGANISM: Zea mays

<400> SEQUENCE: 88
```

```
ctgtccctaa cgccgccacc gcccaccaga gtccctaacg ctgccgccgc ccaccagagt     60
ccagcctcca gcgtccgtcc agaagaccag aactccaaac ctccagtcca gccgtccagg    120
gcaccacgcc cacgctccag tactccacgg accacggctc caactcggca gctcgcaagt    180
cagctgctcg cctgctccaa ctcgcaccac cagtcgtccc agcgcacggg cgggaatcgc    240
gggatcccaa cgcacggact ccccgccgca gtgccgcaca tccacagctc accaggcgtc    300
cggcgtc                                                              307
```

```
<210> SEQ ID NO 89
<211> LENGTH: 1064
<212> TYPE: DNA
<213> ORGANISM: Zea mays
<220> FEATURE:
<221> NAME/KEY: misc_feature
<222> LOCATION: (100)..(100)
<223> OTHER INFORMATION: n is a, c, g, or t

<400> SEQUENCE: 89
```

```
accaattgtt ggaaccagac catcgacaca cagcgcgccc gctaggtcaa tcacacgcac     60
gacacacccg catataccc taggttgtcg cgacgcaacn cacgtgctcg aacgaacaac    120
```

```
aagttttagg gctgttggcc aacactcccc cgtgtgggtt gtaccctcaa ccatataaac      180
catgtttgcc cattcacaac tcacaatgtg ggactaatcc caacgctgtt gtgctttgtg      240
ctggtttaat agtttatctt gttgcttaag catgctactt aagttgatag gatttggaat      300
cctaccgctg ttgcgtaagt tatatgggta ggagatcgat ggtcgcggcg tgcagcccca      360
cggttgtgca cagggagtag gtgaacgaga aagagacgtg gaagatggcc cttgaggcca      420
ggcaagataa ttgccttgct tgatttaatt gatttttttct taaacgcaca aaagagttgt     480
acatctttat atattagaga agagaaaaag tcttacaaaa gaggggaccct tgctaggcaa     540 gatcccctaa atcacacgca caggactatt atatattagg cacatgactc aaccgacaac      600
attaaataga gacttacttt accactaagt gagcaatctt cctaacaaca attaatcatg      660
atcctatttt tatggaaaca atgtaggata tttaaggaag aaaaattcta agcatttcgc      720
ccctaattgt ttgcgtgacg gtctaggtga cgtcggtcat aacataaata gttctcccctt    780 cgtcccaaac tagtagttgt tttagttcta aattttttatg tctatattca tatggatgat    840
ggtggagcta gacatatata gaacacatac attaattatt gtatgaatct aataaaaaga     900
taaaacaaat tttaatttgg gacggaggga gtgttgcata tgttaaggaa cactgatatt     960
gtgctttgac atacatctga aggctcaagc gtgaggtgtt ggctaatatg atgttactgg    1020
ttttctgaag ctgtacccttt atatgtattg aaatgtgaca ggct                     1064

<210> SEQ ID NO 90
<211> LENGTH: 3000
<212> TYPE: DNA
<213> ORGANISM: Zea mays

<400> SEQUENCE: 90
catcaagtgc caccgggagc gggcaggaga tctccattat cttttagaca ggtcctacga      60
cgcgcggcta gggatagctt gctctcccat ccaccaataa tatatgcagt agcacgtatt     120 attcttttc cccagagata atatttgtgc cttatttgtc tgagctaggc gataggaggt      180
gcaacgtgtt cccgatagca cttggatgga tgtgcttgct ttgccaccaa caacaacata     240
tgcatgtcct ttttttttgtc ctgtaattaa attaaaatct atatatctct agcagagcga    300
cgcgctaaaa tacaatctgg tagggcttgg tgggcctcct attggttcgt ggtttaggaa     360
ttagaatgat tcacaaacat atatagacaa aatatataat tagattagtt tcgccatcga    420
tcactttcaa ttcgtacacg cgtagcacga gatgactgtc gcagccggcc ggtcacgtcc    480
gcggcgggtg gagccggcct gatcgatcac gtcacgtgac accgacacgt tgtaccttcg    540
gtgtatgcac gtgacactga cattgtagct ttgctgcatg cgtggcgaca aaacgtgtga    600
gatacgtgca tgatccgccg cgcgtcgcct accttgctat cgatgtatgc tcatccctat    660
tataatttgc acgtgttatt cgtttgatgg gcccttttgat tgaacttgaa cttttttaca   720
agccacattg tttagacctg tgcttgcaat ttgatgatga ttgctgggga tttcttcctt    780
ttcccatcac ggctatatat atagtgttgt gccaagaaga aaaatacttt tttatattcc    840
taattacatt tcaaacttga cgacggttgc ttgggagatc ttcttttccc acttcccgag    900
ctatatatag agggcctaag agcatctcca agagattagt caaatggctt agcaagccaa    960
attttggcta ctcaatagca aaataactct acaacagact agccatccaa cttgtcaagc   1020
tatccggctc ttcaaattgg ctccctctct agccaaattt agctagccgc tgactagcca   1080
aactaaatag agagtctgtt ggagtgagat gctatatata aaatataatc tttatgaaga   1140
```

```
ggtaaataga gtgtcatata gagagtcgaa aatggagtgt ctcttggaga tgctctaaag    1200
acttctaaaa tatagtcctg gccctcccaa taagaaacat gcatcattca tatgtagagg    1260
gcctaaagac ttctaaaata tttatactcc ctccgtttct ttttatttgt cgctggtagt    1320
gcaattttac actatccagc gacaaataaa aagaaacgaa gggagtacca ctttagatca    1380
tctttaacaa ggtgcctcga gcacgacgag gctcgcgata cagtggcaaa ggccactcat    1440
cgataatgct atggtattgt gtgttcccca tgcactagag gtctagaact ctatgggcct    1500
ctcaatctat tctaatccta gtgcgtgtaa tggacgtgca cacgcatgtg tgtgtgcgtg    1560
tggtgtggtg tgtactgaca taagttcatg gcgttcttgt accctctaaa aaacaggact    1620
ttaaaatagt acccaaaaaa taaaatacta catcatttgt agtgtttagg acacttaaaa    1680
attaatatcc aacagttaaa tcctaaatca tatattttta gaaataaaac tatattatta    1740
ttaaaaaaat gttgtagaaa acaagaatat aacacttatc ccagttgacg gttgtagtat    1800
attatggttc ctttatggac tgtcctatat ttattgacaa aaagaataaa gaaaagaag     1860 ttattttta tgagttgaac aatgatttaa ggaactatta gaaatgatct ctttaaggaa     1920
tatatgcgca gggccacacc cacaccacac acaggggtag tcttctcatt cacctgcatg    1980
gacgtcctct catattataa tttgcacgtg ttattcgttt ggtgggccct ttgattgaac    2040
tcgaactttc agaagccatt tagacctgct tgcaatttga tggttgcttg ggatatcttc    2100 ttttccctt cacggtccgg ctttagtgtt gtcccaagaa gaaataatac acttttatat     2160
tcctaattac cttccagagc caaatcgaga tcgagcaaaa catttccatt tacatttcta    2220
acttgatggt tgcttaattg ggagatcttg tcttttcttt ctctttcgtc acaggctata    2280
tatagtcatg tctcttatga atcaatacga cataaaaata gatcaaacac agagaaaaca    2340
tagatttaat ataaaaacac ctccaaagtg aaggaaaaaa aatcacagac gtaggccagc    2400
aacaatatca atattttcg agtagttaca gatcgcagga gatttgcaat gaggtgacga     2460
tctcctgcat attacaattg tatttataga ggcgaaaccc taaggtgagt agggaacgat    2520
ctgtgagggc ggagcccccg caccctaggc gtccctacgc tccgggccaa gcatcccggc    2580
gacgggcctc cgcttcgctc gccaatttag ccgtcttatt cagaatttga atcacaaact    2640
caacaatatc cctccaacaa gaataaatag acatctttta tacgtagagg gcctaaaatt    2700
aaaatgtttg tatagccgcg tgagagaata tatgcgcagc gcatgcaggg ccagacctac    2760
agtcacaccc catacacaga cacagtagtc tcatcattca cctgcagtgt tgtgcccgc     2820 gcgtcctagg ataactctat ataagctaac ccagcgtacg tactaccgaa ccaacagcaa    2880
caccatatac gagctctcta gcacaccata ccgacacaca cagctggtgc ccgcccggtc    2940
gaaccacgct agctgtacac tagctagacg atcaccacgc cagttagtta gcgcagcgcc    3000
```

<210> SEQ ID NO 91
<211> LENGTH: 1896
<212> TYPE: DNA
<213> ORGANISM: Zea mays

<400> SEQUENCE: 91

```
agggcatctc ttgaatttgc taaacttata aaagcaagtt agattatttc ttatgcctta      60
aaatagtacc ttatgagttg tgaacaatgt tgaaagtcat ttacacaatt cttgccattc     120
ttatgtttgg ttaattatct ttgttttttg atgacatcca atcttgccat tatgtacata     180
atatatgtct aaatagttta gccatttca ggattagtct ttgtgccatt acataaataa      240
tatacatgcc taaacacaat gtgccatttt caggactggt ctttgagttg cagcagagcg     300
```

```
ttgtcactag gaacgccatg atacacgagt acgcgtgcga caacgcggag gcgcaggagt      360
gggcgttgga gctgtttagt gcgatgcagg cggaagggtt ggcgcaatag agtgagatta      420
tgttgcccat gttgtgctgt gttgggaygr skccagggcg agactggctg gtggagcttt      480
wtaacgcgat gcaggcggaa ggttagcaca ttttcagagt atggtaacat ctgttggcca      540
ttttggtgct ccactacctt ggtcgtatat taaggctagc ctgatttctt aaccacatac      600
caatgagatg gatacaattt tgtagcatag ttgttttatc ctgatgttat ctttctccat      660
cctgatctta tccattttat ttgcaatagt gtgtccatga ctaatagctg aagttgttgc      720
tggaatgata acagataaaa cggttagtta gcaaagtttg tgcaaatgtg attcaaccca      780
gagtgcaagt aatgatgatg cgaatgccaa aaccattgat cttacatttc cagttaattg      840
tttttgcagt ttgctcggaa ggtgatagca tgtgcatatg ractatacgc gatggattgg      900
ataggtaaga atcactacac taggttttat ataatatgta agtttggagt gtacaagttt      960
gatcagatat aaagttagtt caatggctac cacctaccta tcatcatttg tacccgcaat     1020
gaaaatctta atcccaactt aaacttccac atgtatattt cactgttaat tcaaagtacc     1080
cattgtgata taagtatgca atctctcccc tgctatatat taactgatta cgttcctctt     1140
gctgtagggg ttatagtagt tttatcatca catatggaaa tacaagatga ctgcacacac     1200
taatcaaacc cacaccttaa atcattaata taaacacatt ttgaaaagat acagtccaga     1260
tggttatcta accagaacta ggatgaagat ggtgtttcta aatctcataa acaatcacca     1320
gcaataatag tacacaatta tatagattcc cagaagagat ttactgtaga attatatgaa     1380
tgccatggat agatccacgg ataaatgaat cagtggtttt ctgcaaaagc aatgtcatga     1440
ggcagttacc tttgtagaag tactattata caaatgataa tcctatagct ttagcttttac    1500 cggtacttgg tcttttttggt tagtaatact gtcacgcatt ttcaagaaaa agaatcgaag    1560
ttgtgatcaa tccatggcag ttgtcaatct gacacaattg cttatctcta ggccaagagt     1620
gatgttacac gacgttttag atatggtagg aggtcgacag cctattcaag tgtcgtagga     1680
aggcgacgtt aagcagcagt ggtggctgct agaaagagcc ccacatggcc acatccaatt     1740
ctaagatcga gtcttacttg tagttcacca cagataacga ttatcctctg ttttaacagt     1800
gactattagt ttattaccat gaactgctag atgaatcaat tctgataagt gttggagcac     1860
aagagtggaa ttcaagtgta cacaatgtac wtcaaa                               1896
```

<210> SEQ ID NO 92
<211> LENGTH: 546
<212> TYPE: DNA
<213> ORGANISM: Zea mays

<400> SEQUENCE: 92

```
tataaaaaac actgaaaaat gagaatgcaa aaaacatgag ggcacaaaca catggtacat       60
atctcataaa ccaaaaattg ctaatcaaca aactaataca cactaatgct gcacaattac      120
attagtcctg ggacataatt gcaacatgct acataagcca gttgcaacaa gactgctaaa      180
aaaattacta ctgggacagt tgcaacagtg aatttaaaca aataactagt tgtatacgag      240
cacagttata aaagacagta atgatgtatg tggtctgaaa gtaaaaatta tacagttgca      300
acttatgtca tgaaccagtt gcaacaaaat gtacactgca gttacaataa aagtggaaac      360
atctgagatt ataacctaga acacaaactg cttgttcaaa aatgaaatgt atccgcatta      420
acctagatta taacctagaa tacaacaatt aataattcca atcaacgaat aataatagtt      480
```

```
gcaacacttg gggaaaaaat ggggtttacc tgtctattac cgaaaataac aaaacaaatc    540
caaaaa                                                               546

<210> SEQ ID NO 93
<211> LENGTH: 491
<212> TYPE: DNA
<213> ORGANISM: Zea mays

<400> SEQUENCE: 93
aggccatttt ttgaggtaat ataatagaac ctaatttgtg ttgtcatttt tgtgcatggc     60
tttatggagg tatcgacaac aacgcccaaa ggaacccgtc gcaattttta ttctaggctt    120
tagtacaatt ttttataatt ttattagtat atgcttcctt gataaattat ttcccaattt    180
atctgtttgt gctaatatac atgggtgctc ttttttcttt gtttgtaagc atttttatgg    240
cctctctttt catgatctta ttttttccaga catacaagta caaggattaa cttttcagaa   300
cattctgcag gcactttcac atggatgttt aattaattta ctactttaag aagcaatccc    360
agatccacat ccaattgtgc ctccctgtat tctgtatgat ctatggagat tatgttgtat    420
cttcatggat ccacaacagc tcaacatgta gctaaaaatc agctgcatca gaaatattaa    480
gcaaatcaga c                                                        491

<210> SEQ ID NO 94
<211> LENGTH: 3000
<212> TYPE: DNA
<213> ORGANISM: Zea mays

<400> SEQUENCE: 94
ttactaatat aatcccaatt tgtgatatct tctatgccaa aaaggcttca tgcattatat     60
atcttcgggt tactacgggt aaaactttat gcatgaggag agagcagaga gttaacttat    120
ccatgttctg ttgtatttca atttaatttc ccagattatt caagcactgt agagcttgat    180
atagttgtta tggccacttg gcaatataaa taaatatatg atgccacaca acacaagcaa    240
ataaaatata gagctaaata aaattgttta cgaaggttgc gttatgatgt gacttcaggg    300
gcttgaataa cccaccacaa tctatgcgag tacaagctct agtgtatgtg gcgtcaacgc    360
gtgtgcgacc atcagggcta cgacaacaca acacgccttc gtaataagtg caacaggcaa    420
aattattgct cgataattgg gatacacgat aaatccacgc aacgtgcgca acaggcgcaa    480
ttgtggctcg cggcagacag tgcctacagg gcatgcaaaa aatacgcgat tcagcgatga    540
cggtctgact caacgggagc aatccgatta atggagagcg cgacatagca atcacatgac    600
gcagccaagt tcgaacggca caaatactgc gtcgtgttgc cagggcgcag ccagtgctca    660
accaatgcca taactcggtc gattaataac gtagtctgat cgacgtgttt gaatacccac    720
tatacaattt aatcgctcga cgtgagtcca aaaactcaac atatcataaa tatttagagc    780
gatttaagta tgcacataca gtacgatatt gccttcacat gcattctaat atttctgcta    840
tatatttacc accgagaata gagcaggaag ataaatactag aattaataca tgagcataac    900
acatcatgtg taaaacacaa ttttccatat ttaagtatgc attgtctcaa atatttagtt    960
gtaatcatgc tggcacgagc cactcccatc tcagtttttt ttcaacagct catgttatgt   1020
atggagggta gacagttaga acgcatgcaa aaggaatata tgacaataaa aaaactaaaa   1080
tagaaataaa aatatgacgc tcacagcctg ctgggctggg catccaacga gcatctctcg   1140
cctagtcaaa tcatgcaggg gtgcggccac atacacgtca atcacctcgc acatgtggag   1200
ttagaaacgc ggtagtttgc gttagtttgt gttgcatgcg gacatgcagg acccgctcaa   1260
```

```
ccagcactac ggagttattg gttggcagtt tggcacacga aaataggaac agtagatcta    1320
tatatcaggt cggtacgcgc gatgtggcca gcagagccac cgccggcgta ctgttttttt    1380
caagacgaac agtagatcta tatatttcat accatgtttc ttgattctgc gaatggaaac    1440
gaagcctgtc gcgtaggaca gttcggcaag gccaaagacc tgccggcgtg acgaagagtt    1500
gacgcagatc tgatctcgca gcaacgtcga ggtagagcgt gctgataacg tgttgagaac    1560
tacgttacca cggatcgcca gatccgctcc cttcccttcc gtcagcaaat taggcgcgag    1620
aagctgtaga agacccgtct cccttcccat aagcacgaca gaggaaacac atgagacact    1680
ggatataggg ttgggcctct ggcctctttc tgatctctat tccatatgag gggtacaggt    1740
tctatatata gagacgcgat agccctcagg gctatattcg ttatttgccc gtataaccct    1800
tcattagggt ttttcaacac gaaggaagaa gaataaaaca gaaggctgtt cgattcaaac    1860
tcatgaattt tacaaaacat gatattttat tttactaaaa ttagttcatt cttatactga    1920
aaaacacgga gcaagaaata tatccgcaat ccaaaggcga cctccaaatg tgttcaggta    1980
agaaccagtt attctccccc cccctaaag aatgatgtgt gtaatcaacg cacacgtatc    2040
ggttggcaaa ttatgaagga agaacatacg aagtcggcca agctgaaagg aaaggctcac    2100
gacgaaatcg gcctttcagg ctgtctccag caacgtcctc tatattcatc ctctatatcc    2160
gtcctttaca gtcctctcta aaagattcta tcccctatat ctccttcctc tccaacaacg    2220
tcctctaaat cacgtcctct atactcaaat atctatatta ggaatatttt ttattttat    2280 tttttgtaca tacgtatttg tcatactctc aaatgtattg tacatatttt agttttgcta    2340
aactagttat ttaaagtatt caaatggata gagaaccgtt tagagaaact ctatatatag    2400
agaatccagc agcgtcctct aaatttagag gaccgtttag aggacgctgc tggagggcgt    2460
agaggacctc tatatttagg gtacagaacc ctttagagtt ccttgttgga gctagcctca    2520
gcccactaaa gaaccacagt aactctcttg ggccggacct cttttttctgt cccatggcac    2580 gtgggccaag ttcggcatgc ttgaagtgtt ccacggctcc ttgccccaac ggaaaacttt    2640
gcggccccca ccaccacacc ggcacacctc actcctcagt gccgtctcct ccctcggatt    2700
cccacttgcg gacatctggg gcccacagga gcgctcaacg caggccgcgc acggcgcacc    2760
acccagtctc tctctgccac ctagggtcgt tgcctcgtcg aggagcatct ctgcagtgca    2820
gcggcagctg tgtccaacta ccaagtcaag gtgaccgttg ggctgggcgg cacgagacgc    2880
ggagacgaga cgcaacaaaa cccttgtcag tcgcccgagc ccaaggctc gcacccacgc    2940 cagcggcacc gcaccccccac ccacctcggc ggcgagtccg agcccaggaa acgaagggcg    3000
```

<210> SEQ ID NO 95
<211> LENGTH: 2010
<212> TYPE: DNA
<213> ORGANISM: Zea mays

<400> SEQUENCE: 95

```
atcaagttta aggcatggat ttagcacttg gcggcttaac ctcagttaag ttaaatgaat      60
gcaggcgcca aatatcaccg ttttcctgca atagagtaat aaaccatgca gcgctcgcat     120
gtgtagctgg aggggccaat gatgatgtga tagtgcgttt atgaaccttt gaggtcatca     180
acatctatgt tcatgagaac attgaacctt gggacccaag gggtagtaca gggctacagg     240
catagtaaaa ccgaccacag atgtagcagc ttttagttag atctggatta tttgtgactc     300
atgaatatga aaaattagc cctttcatta tccatccact tggaatagta tccacccttt     360
```

| | |
|---|---|
| ctgcgtttta atatttgtaa cttgtttttt gaaggagcac ctgaccacct ctcgctagaa | 420 |
| gaatctatat agaaagaagc atgttacggt taattggtaa ttttttttcac tctcgaatat | 480 |
| gcaggagagc tgtgtatcat cgcattaaga agaatttaaa tatttacaat aatctcacat | 540 |
| cccacacacc agacaaactt caggttacat actcggtgga gacaaaagat aaacccaacc | 600 |
| aatgctagct taacgtcctt ttagtggcag caacctcaag ttgcattaaa cccctagctc | 660 |
| ctgctaaata ccaatggtgt cttcctcagt tatctaagga ttggctgcat gcttatttgc | 720 |
| tcacaaattt tcaaatgaat tgtagcagaa aactgtggat tactattaca gatttgaatt | 780 |
| tattgagatc tgccatgtgg gcacattcct tctaaggagc cttgttcggg cacgtcatag | 840 |
| gcctacctag tggctaacag ccacagtcaa ttagaggaaa atctgttcag ccttgcctta | 900 |
| gttggttgat tgggttaatt tggaaggttg gaggaatgat agaaaagaag agaggaatta | 960 |
| acttgtatga ggattagaca caagcaggaa ttagacggaa acacttcctc tcttgctcgg | 1020 |
| ccatgggcaa gtccctcggc cggctccggc tccctctttc tctctcccaa ccctagctgc | 1080 |
| caccataaca tctggtatta gagatgttag gttccgatga ggatgacaag caaccaaaga | 1140 |
| aggtgctgcc gctgccaccg gatcccattg ccaaggtatt ggccaacctc acccaacaga | 1200 |
| tggcatctct ctgggcgtgt ctagaggccc tgaaatcctg accgaggcaa gaaggaatta | 1260 |
| gaagcaaaca ccttctctca tgttcaactg tggacaaagc ccggccggtc ccctctctc | 1320 |
| ccaaccccat ccgccaccat aacatctgtt atcatagaca tcagctttcg atgaaggcga | 1380 |
| caagcaacca aggtgctat cgccatcgtc gccggattcc attgccaaag cattggacaa | 1440 |
| cctcacctag tagatggcat ctctctgggc acgcctagag gccatggata tctgaccgtc | 1500 |
| ggtgaccacc accaccatgc cgctagtgtt cccttgtggc ttgctgggct atgggacgcg | 1560 |
| ggacggcagt cgtctccatg ccagattcaa agatgaagga ttgtgtcaat gtagctgagt | 1620 |
| aagaagagtg cccactagtt gtcggtgatg gtgtggctgt aggctgctgc atggcctcct | 1680 |
| agcatgtcgg taggtgcagg agatgtgcga tctgcacctg atttagcccc acccccttc | 1740 |
| gcagcttctc caagttgcgc atcactgcgc cgcattggga gggcatgcgg ttccacatgt | 1800 |
| gggaggcagg caggttcttt cccccgtgga tggcgaactt ggagtttgcg gcagtggcgg | 1860 |
| ttggggaggg tcaccccctcc ctcatcgctg ttctctatcg gaagccctcc tcttttctca | 1920 |
| atccatttca ggttgagaat aataaaatga gccgagatgt aaaaagcttg cttttaggtg | 1980 |
| ttagatcgtt ggttaggttg cagctcgagg | 2010 |

<210> SEQ ID NO 96
<211> LENGTH: 1326
<212> TYPE: DNA
<213> ORGANISM: Zea mays

<400> SEQUENCE: 96

| | |
|---|---|
| gttaatgcga ctagtcattt atggcgggtc agtccggggc cgagcgcgag atccactcga | 60 |
| gtggttccct tccgactcgt ctgtcctccc tcgtcaggct ccgccacgcc tgccccagg | 120 |
| ctcggggtca cgtggttcga ccggggggcga gtccttctag ggtttgcgca cctatctctt | 180 |
| acaactgact aacgggccca gcgatcaggg gctcttccca tagcaccctc actgaccagc | 240 |
| gggtcccagg gaccaggatc atttccccga caacactaga tctgagcatg gaccatccga | 300 |
| catgacccgc ccaatgcaat ggacatacac catagttttc gacacaataa tccacaggct | 360 |
| aggcactagc caatctgaac caactcgaaa aaacctgacc caatatgtct aacggggagg | 420 |
| cacatgtcaa ttcgatcgga ctcgatatca tgtacaagtc agtcgcgagt cgtgcctaag | 480 |

```
tctgtccgca ctcatgtaac ccaaaattta taccactaaa aaatattcta tcatagtcag      540
cgaaattcta tacccatca cacaattctc tacgtcacat tcacctaaat ctctatccta      600
taccaactac catatattct actccctcca tttcaaaata atagtcattt taggtcttta      660
tgtttatgtc tatattgaaa tagataaaga ttaacctata cacatgtaaa acacatacat      720
caattatttt ataaacccac taataatcta aaataaattt taatttagga catagggagg      780
gagtattatt tattttcacc tctcctatcc atacccaacc gtcttctacg gtcctgtcta      840
ggtcacagtg tcacactgct atggattcat attcagtatt tgagattctc tcatctatct      900
gcaagctagt ttttcagtgc atcgatgcaa catatttta ttttattata tattcaccct      960
ataggtttag aattgtcttc aggtatgtga ctgaggatag cctgataact tatgacccga     1020
cctgactcaa tttgaactcg atctgacatt tgagcatgtc taactttaca ctaaggtcgc     1080
gcctttcccg ttcgaaacgt ccaaaccaaa cttcatttt cagtttcgcc aaaatccaaa     1140
tcccgttgcg tacttgcgtg cgtgagcgtt tttccatcgg taccaacccc agcacagtga     1200
cgaaaaggcc caacaacccc ccgacccgtc acctgaccca gccgatcgag aatacccgga     1260
aggccggaac ccacctgctg cgcacctgca agcctcgagt ggagctcttc cacggccgcg     1320
gtggag                                                                1326

<210> SEQ ID NO 97
<211> LENGTH: 494
<212> TYPE: DNA
<213> ORGANISM: Zea mays

<400> SEQUENCE: 97
gaacgtagtg tagacgttca caacatatgg cgcacggttc tgccttgcac ccgcgagacc       60
ctccactccg cgcagcacca gccgccatcc ccgcccgcca tctgcgcgcg tctggcgtct      120
ccctcgcccc cgctctcctc tctgctgtcc acgccctctg ctcgcgtgtc ttccagccac      180
ccgcgagcag agccttcgcc cccggatccc acgcccgcga gcagagctgc tgtccatgcc      240
gtcggatccg ctcctccctc ggaaggagaa tctccaaatc tcgccaccat ccccgcctac      300
catctgcgcg cgttggccgt ctaccggcta cgcgcatgtg actgtcgttg gatcccaggt      360
ctcgcccaat tccaagcgcc cccgcttcga gcgtcgcccc caacaagacg tccggatctg      420
cgctagccct agctcgcgag gtcgacgccg atggatccaa ggacaccagc gtcgcccctc      480
tccgagctcc ccca                                                        494

<210> SEQ ID NO 98
<211> LENGTH: 3133
<212> TYPE: DNA
<213> ORGANISM: Zea mays

<400> SEQUENCE: 98
gtcttgtttt tcagctgatt ttcaaatcgg ttttcgttct aacttgtgtg tgagttctag       60
agtgacacct agcactgtat atgagtgtga ttgtgcacca acactacact agaactctct      120
tggtcaaact actcatcgac aaccctctt tatagtacgg ctaaaagaga ataaagacc       180 taactaaatc gcgagtgtcc acatctcctt gacactcgga ctccgtagac cttcaccttt      240
tgttccgtcg ttttagccgt cgcttcgagt ttcttatttc cgggattgtt ttcaccgttg      300
tagtacttct acctgtcatg cgacctaact taccatttgt ctctgcaaaa acacacgtta      360
gtcacatata atattacgtt gtcattaatc actaaaacca accaggggcc tagatgcttt      420
```

```
caataccatt cagtaactct catttataga tggccaaccg ggccgcacgg cacgacactg    480
acactagcac gactaggcac ggcacgacag ggcacgacac ggctaggcac ggtagaagat    540
ccgtgtcgtg cctgttagtg ccagcgtgct gggccctcgg cccaggcacg gcactatcag    600
tgcttagccg tgccgtgccg tgccaacagg cacgctggca cgccagtgct agtgccagca    660
cgggcactat gcataaaaat accagcagca gcatttaaac actcaaacag ataagtgaa     720 taacagataa ttttattata acttctagca atcaaacaga tacaattta tggtcacaaa     780 gagagtaaga gactaatcaa acaacaattt tatgagctgt agtgcaatgg ctgcctcatt    840
aaaaacctgt ctaggtaaaa ctcacccttg tgagaaaccc tagacaggaa aaagagtac     900 agcccagctc attaaaaagt ttattgtcct tacaacaaag tccagtccag ctgtccaggt    960
gcataatatt acagtcccat tacagaaatg gtcagaaaga gagtaagata ctagagacta   1020
atcaagataa agattttcaa atgtttcttc aagctctttg tcatccacca tgtgttgcat   1080
ccttgcttca gcatcctccc aatctttaat gcatgtcaac atctcaacca catcagactt   1140
caatctcctc ctccgctcgt cgatgatcct gccagttaaa ctaaaagtgg attctgaaga   1200
gatggtagac acaggaacag ttaaaatatc tttagccata attgacagta ctggataagt   1260
gagtttgtgc tgatgccacc agtgcaagat gttgaaatca tcagttaact ggttgacagt   1320
gtcacaatct aagtaagaaa tgagttcaga agcagtagaa gctgaagagc ttgcagcatg   1380
cagtagagca gttgcagagg tatctctagc aatgtttaga gtagaagcaa aagaatgcat   1440
accaacagaa gtacccacat catcagcatc atcataaatt tcatcccaag cagaccgttt   1500
cttaccagac aagttaggag ggacaaccct gttcaatcta acagatccat atttctcttc   1560
atatttatta taaacatcag taagcttagc tctagtggta acctgataaa cagcataatc   1620
tgtacttgtg aggtttcatc gtcggagacg gccatcgacc cacctcggac tcggagtccc   1680
ggttcctcaa cggagtaagc cggagcacca gagctaggag agaggagggg acgaccggtc   1740
cggccaaccg gttcctccac ggatttgaat ccggagcacc agagctagga gagaggagag   1800
ggagaccgga gctaggtgtc aggggccggt aaggagaggg agaccggagc taggagagag   1860
gagagggaga caggagctag gagagaggag agggagacat gagctaggag agaggagagg   1920
ctgagaggga gaccagagca ccgtagctag aagataggag agaggagtcc cggttcctca   1980
acggagtaag ccggagcacc gagatgaatc tccgcagaag cgcagatcac accgagggcc   2040 ggaggggggag agggagaccg gatctgtgtg ccagtgccgg tctgccggac agtaccagag   2100
ggggagaaga agataggaga gggagaccgg agctaggaga gaggagagta ccagtgccag   2160
tgccagtgcc gccgtaccgg accccggagt cccggttcct caacggagta agccggagca   2220
ccgggatctc cgcagaagcg cagatcacac cggaggccgg aggggagaa gaagacagga   2280 gagagtagag aggagaggga gaacggagca ccgggatctc cgcacaagcg cagatcacgc   2340
cggttcacaa atgcgcgtgt aaaccctaat aagccggagc accaggatct ccacagatca   2400
caccggaggg ggagaagaag acaggagatc cgagcgaggg ttatggatct gagttacccg   2460
gttcacaaat gcgcagatcc gagcggggga gagccggaga ggatctccga cgagcgacga   2520
tcgatccgag cggaggcgcc gaggcggaga gccgagacc acagaccgga ggcggagatg   2580
gagaccggag cgcttagcgg aggcggaggg aacgagggag aggagagctc gtcggtcgcc   2640
gccgaatcgc ccgcggctga gagagagcga gtgagtcagt gagcgagagc gagttagggt   2700
ttgagcgaga gcgagtgagg agtgacgccc gcggccgcgg ctggggcggg ttagggttta   2760
cacgcgactc gcggtcgcgg tcacgcggct cgggtgggcc gtgccgacac cgtgccagcc   2820
```

| | |
|---|---|
| cagttagccg tgtcgtgcct gggccgaccc tatgggccca agtggtggcc caggcacgac | 2880 |
| actatgtacg ggccgtgccc ggcactggca ctacaaggac cgtgccgtgc cgtgccagtg | 2940 |
| ccgtgctttt tagtgccgtg tccgggccgg cccgtcgtgt tagtgtcatt tggccaacta | 3000 |
| tactctcatt caccgctctc cacctgccag cctcctcccg cctctattta aacgcgcagg | 3060 |
| cctgatctat ctctcatcat cacacccaac gaccaacakc agcgaaaacg cgcagagaaa | 3120 |
| aatcactgat aca | 3133 |

<210> SEQ ID NO 99
<211> LENGTH: 1802
<212> TYPE: DNA
<213> ORGANISM: Zea mays

<400> SEQUENCE: 99

| | |
|---|---|
| taataaatct gtttcgaaac cctatttcta agagttaaca caagtactat gattaaatct | 60 |
| acaatatgcc gcatgcatat tagttgtctt ctacacacat gccgatggaa ttatctatca | 120 |
| agagatgata tgtcactatg ctcaaattgt taaaacagtc tacaaatttt aggttttggt | 180 |
| gctctattgg caaaggaact atgaatttgt gcaactgggc agatctgtag gatctgaata | 240 |
| ttctattttt ctcacatgtg cattactctt aataaagctt tggatttcgg gcgtgaactt | 300 |
| catttatgtt atatgcttgt gaatgaaatg actacaaact ataataatca gagtatttca | 360 |
| gttattgtga tggattgttc ttgtcttaac tgagaaatcg taataaccaa aaaacaggtt | 420 |
| cgaggtacat tatgaaatca tagtcgagtg tttcaattat atagtccaca tcgtgatatt | 480 |
| aatttgttta gtccataatt aaattcttat gaaccaggcg gtggacaggt gggaacatga | 540 |
| catgactact ggccccccggc aacgggggaa acagaagcga caaggagtgg gcggaacatg | 600 |
| atgacaccac aagcagctcc ttgccgccac ctcctacttc gacatgctca acggcgcctc | 660 |
| tcgcaaccgc gcgtattgcc tcgccatcgg tgccacggtc acggacccca catcccatgt | 720 |
| cctcgacatc gggtgagctg tgcgcctcta ttctccttca gtttcagcgc gtcccaaagg | 780 |
| ttggattgga ttggctccaa ctcccaagga tgataatgct catgtatgat gaatccagaa | 840 |
| ctaggacatg gttactgtcc atgatggttg cacgagcttt gatagctgtt ggaggtgaag | 900 |
| gaaacacaca caatctgtcc atgatggctc cgtgatcgtc gagcgaccca acagcgagcg | 960 |
| tcatgccccc tcgtctgaac gcaggaaggc cgacggtgcc aaacgagggc tgaccccctt | 1020 |
| cttcgcattt ctgtaagcca tacagtccct cttcccgtca tttcgcgtct ccagatctac | 1080 |
| gccatacccct tttaatcttt ttaggatttt gttgaatttt ctgtgttgct gcactgctag | 1140 |
| ggttgatgtc aggccacagt tcctagaggt ccgcgccgcc gtagctaaat aacttagaca | 1200 |
| ccccatgtta tcagcacaac agttggtaca acaacaaaca aagcctctta gtatttact | 1260 |
| gatgtatcaa atttccataa aaatggcctt gtagttcatg aactttatta tttctgttta | 1320 |
| ctatgagtat ggatttttcct tagattagaa aaaaggtgaa tcatttctta gtccactgtc | 1380 |
| tgtcatacac agttctagag agtagagaca ctgtctgtca tacgcactgt tcattatgta | 1440 |
| tgtgaattcg ccaggagggt cagtgacagc ttgtaatacc ttatctaaca tagtatgttt | 1500 |
| gcgttagttg cttcaattag tgctaatgga ttttccattt tctattagga atggctatat | 1560 |
| ttgtgaacat aaaaattagt aatctggaga gggatttaca atattgtact attttaacct | 1620 |
| agacgagcaa aactgaagct aaagtgttct actcgtttag tgcttttatc taacctattt | 1680 |
| tactgatcgt tctggttttct tatggttata caactgttgt gataatgtgg tagtggtgtt | 1740 |

```
ttaatcggga gagcactagc tcaagaaggc caaaggccca agctgatgt tcgggagggg    1800
ag                                                                  1802

<210> SEQ ID NO 100
<211> LENGTH: 2446
<212> TYPE: DNA
<213> ORGANISM: Zea mays

<400> SEQUENCE: 100
tacaggacca catagttaca tacatcccac aactttttta ttctgtattt gtgcttggag     60
ggacacgtga tagtactgct actcttaatg tgtgagtcat attgtatttt taaagactac    120
cgctattccg catttgtaca tattactgtg catagttggt ggttgttcag ctattcatag    180
agctgggtct taatgtacat tgctactgct tgattttttt gcatccttgt aaatttaatt    240
gtgctcccct acagataagc aaaaatgttt ttggtctgaa tgtgcagaac ctacatttag    300
tttttggtct gaatgatgtc ttaaatctcg catgggctct atttcagtcc agatcactgg    360
agcaccctgc agatctgatc accctgcatg tagtattgaa catgtttaca tcaccctgca    420
gttctgatca ctggagctct atttcagttc taaacatgtt tctccatttt atcacctggg    480
tgtctggtga aaggacctt aattgtggta gagtctattt tggttgtggc cctagaacat     540
tgcatcatgt cagctctctg tgtccaaaga cttttttttt atcattatgc aaaacttgcc    600
tctgtttaca ttgttgtact catggtgtac tgtttaattt atcatatgat tctcgaagta    660
agaactacaa tttgatggtt gctgctagct atgaggacct gacaaggcca atgtgcattt    720
gggaagagaa cttgaagagc aaataaatat tgtcttagat tttatgattt tctgaacatg    780
tcgccatgta tcagtgtcag atgctgaatg agttatcttc tgtgatgttg aatcagttgt    840
cttagaatta tttgaacttg tttgcatata ccacttgcat tatgttatca acatcttcag    900
tgatagaaca ctgaatcatg ctcctgctgt tttcaaaagc tgcagtaatg ttatgcacta    960
tggaatgatg ctaaggtttt attgagcagg ttgatctctc agccaccaga caccagacac   1020
gcagccgggg ttggccagcg ccagccacca ggccgccgtg gctccgactt ccaacgtcgt   1080
gccccgcctg gcaaccgacc gcatccaccg cctcctggct ggctgggcag ggtagacaca   1140
aaggtctcat ccagtgctcc actcctccgg tgagcactga tctgatctcc acaatagcaa   1200
ttgcgatttt taattcccaa ttttctaagct ttgcattagt aggtgtttga ctttatttc   1260
ttgtaatgtg gatgcagtag tataataact tcattggatt taattattgc agcatccttt   1320
tctgctccga cacctgct gaagctggaa gtacatggta caaggatgat tactttaatt     1380
gaattggtaa ggaaatgttg gttttctcgt ccaattcaga tattctcgtt tccatttgat   1440
cacacgtgct tcgtacatca cgtggatagt ctgtatgaat cctaaaaaga tctaaatgaa   1500
catcgtcatt taattaatat aggtcggtca ttttgcaacc cttgttaaca ataaccaaac   1560
tgatggattt tctaccgccg taaatttcaa gtaaaattta tgttatgatg ttcaactttt   1620
cttgtcatgt gtggcggaaa cataagtagg ctggataaat agttttgtaa tttttatgcc   1680
taaacatgtt caaacaaact gtttgtaatc taatgtatgc aactttgatg cttagctgtt   1740
atgttaaata ccgaatgtac tataaaatta tatattagat agaattatat ataaaaaaaa   1800
tttgttgtgg cacaccctat acaaaaatcc taggtctgcc actggctgct gccatccact   1860
gcgggctcga tcgccacgcc gacgccatcc ccgtcctcga gcgcgccgtc acagtccggc   1920
acaagaatcg tatgctgaca gcgagcctga ggccggtgca gccgacggcg acgactacca   1980
gcagctgcag cctgtcgagc ccgactagag gggtgagtgg tgctgctcct gatgagatcg   2040
```

| | | | | |
|---|---|---|---|---|
| ctggaggctt | aatggagatt | cctgtaatct | atgaggcact | tggcgatctc | gatgaggccc | 2100 |
| aaaagcttct | tcatagggca | ctcaggcgag | ggctcatcga | gggagtggag | cattgttgcc | 2160 |
| ggtgttgtgg | cacaaatggg | cgttctgtac | tacatggtgg | gaggtatgca | aattcgggga | 2220 |
| actcgttcaa | gggtgcagtt | gcaaagtcta | gggccattgg | tgagaggaag | tcgacatttt | 2280 |
| tcgcattctg | ttgaaccaga | tggggctagc | ttgtgtgtag | ctgttcaaga | tagacgaggt | 2340 |
| tgcatagttg | tttgaggagg | caagggcggt | tctggagcag | gagtgtggca | cttctcatcc | 2400 |
| taatactctt | ggtgtgtaca | caaccttgc | tgcaatctat | aatgcc | | 2446 |

<210> SEQ ID NO 101
<211> LENGTH: 554
<212> TYPE: DNA
<213> ORGANISM: Zea mays

<400> SEQUENCE: 101

| | | | | | | |
|---|---|---|---|---|---|---|
| gattaattac | caagtcagct | tttgagagct | caaaagatgg | tcttcgcatt | gagtagattt | 60 |
| ttgtgaaaca | tttacagatt | taataaagtc | attgttattt | ggttttaaat | taaaaaactt | 120 |
| gagctggcaa | gggaaaataa | catcggacat | catatataga | ggagaaattc | ttagtttctc | 180 |
| acacaggtaa | aaaaaacctt | taacctctgc | ctactcaaac | aaactggtac | cgtagaccat | 240 |
| atgatgaatt | atttactgaa | tttactataa | attattgaat | gttattcctt | cctccttgtt | 300 |
| tagaaagaaa | gataaaaatg | agtatttttt | cctaatgtct | gacgcactct | atctatacat | 360 |
| gcattgtcat | tcccagtttc | tttcgctcag | atacatctcc | attttgttct | gaagctcata | 420 |
| tttgggaata | caaaagaacc | ggggaaaagg | cagagaggat | tgttggtctg | taatctatat | 480 |
| atggatattc | ctattttgca | acaatatgtt | ctgtcagcta | tgtgttttcc | tttttatatt | 540 |
| ttggctttga | atga | | | | | 554 |

<210> SEQ ID NO 102
<211> LENGTH: 1724
<212> TYPE: DNA
<213> ORGANISM: Zea mays
<220> FEATURE:
<221> NAME/KEY: misc_feature
<222> LOCATION: (1609)..(1609)
<223> OTHER INFORMATION: n is a, c, g, or t
<220> FEATURE:
<221> NAME/KEY: misc_feature
<222> LOCATION: (1614)..(1614)
<223> OTHER INFORMATION: n is a, c, g, or t

<400> SEQUENCE: 102

| | | | | | | |
|---|---|---|---|---|---|---|
| aaaggaaaaa | atcataatga | caaaccggtc | aaggagcggc | gaagtgaaga | aggtcatttc | 60 |
| ggctcagccg | ggggggggc | gcgtcaggat | aaggtgtcag | gccacctttg | cgttaaaatg | 120 |
| ctcctgcgac | tcggtcggtc | ggcgcggcga | tttagtcagg | gttgcttctt | agcgaaggca | 180 |
| aggcctcggg | cgagacggaa | accctcggg | gtcggctgcc | cttgtccgag | gctaggctcg | 240 |
| ggcgaggcgt | gatcgagtcg | ctcgtatgga | ctgatccctg | acttaatcgc | acccatcagg | 300 |
| cctctgcagc | tttatgctga | tgggggttac | cagctgagaa | ttaggcgtct | tgagggtacc | 360 |
| cctaattatg | gtccccgaca | ccaagtgcaa | gtatgatttg | tatcagtatc | attgggtgtc | 420 |
| ctcaaatacc | catctacaaa | aagttcaata | ataattgtta | caaaccttct | tagacttttc | 480 |
| agagtttctc | tccaatacgt | acgtactcat | ccataacatc | cactggtact | tcataattta | 540 |
| gcatacataa | tactacagtt | gccttccgca | aggaacttaa | acctttggt | gagatgtgtt | 600 |

| | |
|---|---|
| tatcttctgc caaaagtaat catcatattg tactatacaa agaaatagtg gtcgatgtat | 660 |
| cctaaatcta caataaaaat gaatagggaa actactatta catatactac acatactgaa | 720 |
| tagtaaaaat ggatagacta ttaccttcat cgaaaatact tgggccatac gtgggatgtt | 780 |
| ttgcaaaata atcttgagac agtcttgtgt gcccaacttc tctatctcga tatatatata | 840 |
| tacacaccta ggtacggatc ccttgacatt attcgtgagg cactttgtac gctttgagac | 900 |
| gcgccaatta tgaacttatc gtcgtcatct gaagatgact aatccaaaac acgtgacgaa | 960 |
| taaacaggat gcgaaggcaa tacgatggag cacaatgcca ccagccaaga cctagccact | 1020 |
| gatattgtac taaaaacga aaggcgtcaa atgtactccg ctagacaacg aactgttgaa | 1080 |
| ctgcacactc ggctgtaaac tgttgaactg attgattagt tgcaaaaagg aaaagcttca | 1140 |
| ccattttaaa tctgatcacg tacactagga gggtgtggaa agtcggagat ggctcctgct | 1200 |
| gtagcctagt ccgccttcac tcggttgtcc tcgtagtcca tttagaatga tttaaattta | 1260 |
| ttttagtacc taaatttaaa atctaatgga gaccaatctt tttctcccctt ctaaaacatg | 1320 |
| tttagcaact ttctaaacat atatttagga tcacttttt taaggtaact atgcagatgc | 1380 |
| tcttagctat taggacagtg aaaagacaga gtgaaaaggc gaaaggaata ccataaaact | 1440 |
| ttatccagaa tttgttcaaa taaaggatga aagaaaatg aaaactcgtg ctgaattttc | 1500 |
| tgaaggcttc ttcccctttc tcgtgcactc tagtaatgct gcccacctag ggcgactggg | 1560 |
| cgagtcagta cttcagactt gagtccaccc agccagccaa ggtgctggnc cggnattccc | 1620 |
| gggccgaccc cgcgtccgca gccagccttc aaggcagcac ccaatacacg cagcgcaggc | 1680 |
| gcakcccagc cagattcrac ccgagttcrc gacgagagca cgag | 1724 |

<210> SEQ ID NO 103
<211> LENGTH: 2686
<212> TYPE: DNA
<213> ORGANISM: Zea mays

<400> SEQUENCE: 103

| | |
|---|---|
| ggatggggtc gagaggggtg tggtatggtt gtggcctgtg ggtggaaatt tgcgtccgt | 60 |
| gagggagttt tcgcgtccgc gtgcgcactc gtcagttttg ttgttcacct tttctctagt | 120 |
| ggcacgtgtc aggaggacgg tggctagagg cccacggaat gcggatagcg gttgaatctc | 180 |
| cttcaggttt taatagaagt gattacatga gatgtttgaa tgctaataat gagtattaaa | 240 |
| ttaaatctaa ttgcacaact aatttactcc agtttaacta gatttattga aaaaaataat | 300 |
| aacatttata tatccaaata agtttagtat aaaaatagat ttatggctct atctaatggt | 360 |
| atacataata taaataattt atctatttt agtcaaattt taaatcgctg attctctggg | 420 |
| aaaacaaaaa taaccctcta tttttgagacg gcgaagtact ccactctaat ctccgattgg | 480 |
| gaccggacac tcggacagct ttataaaata tattaaaatc tctactatat ttgggtgaga | 540 |
| atttcttccc gcgtttcctt ctcgcacgta ccgccagaaa aatacaaaaa taaatacaga | 600 |
| acttagagtt taaactctaa ctctctctat tataagctta catgtgttgt acaaaagaga | 660 |
| cacgtggaat ccaccggtat atatctactt ttagggtgtt tggtttgaag aatgagctaa | 720 |
| tccatcatct tctcactcct cactattttt gtttggtttg tggaatggaa tgagttgatc | 780 |
| catcaccacc tcaatcctca tagttaatta gctagtacta atatgaggaa ttgggtcatc | 840 |
| ccaccaaaat tgaggaatga acccatgatg catcacctca atttggatgt agtgattcct | 900 |
| caaaccaaac accctatttta agcttcaacg ggacacgtac actcggacaa ctttataaat | 960 |
| tatattcact gtacgagcta ctctagccgg ctggcatgca cgcactcaca ccgaaatcgt | 1020 |

```
ggcacaaatt tgggaaacca cagccatcgc cgagaccgag aggcagatcg ggcccggggt    1080
catatgaaac tcgtgacgcc ctttattgga tggaaggtcg gagttgactg cttcagcttc    1140
aggtctacag accggccgta ccgtactgtg accaaccta tcagctgaga aaaaagaag     1200 aagaaaagga gccatggcgg catgccggca tggccaatgg ctccatgagc catgaaccat    1260
ccagcggggc gacagggcgt agcccggcgg cgagccgtcg ccatcgccgt cgccgtacgg    1320
gagagcggtg gcgggtcatg tggcgtgacg tgcgacagct gaggtgccac gtcgtcggag    1380
gcgaggcaca catgatgagc gaacgacgtc ggccgttgcc gacagcgtgc gtggcactcc    1440
tgagcccacc ggtgcgcagg gacgctcgat cgttttcgga tctcaccgca cgatcccacg    1500
gtacaggtga taagcgtggc aacagtacc ggaggttgag gcctggatcg tcgtccctga    1560
tgattggacc aaccgatggt accggccgga cagcatgcac gacactaact agtcaatgta    1620 gggggggccat tgccctgcct gtgtatacca cagttcaatg tgaactgttt cgttcgtgta    1680
ccgtctgaag tctacgagat gatggtcttc gtgattgaaa tagaggccgg aggaaacttg    1740
ccggatgaga gagagagaga ggcagttttt atctatagca agcaagtact gcaggccgca    1800
gcaggcgtat cccgccgcgc gcgcgtgacg gcacaggcaa cacgcggtat caccgctgcg    1860
gccctcgggt gacgggtcgc ccgtcacgtc tcgctcgctc agcacaccac accgtcgct    1920 gccatcgcgt cccctcctcg aggccggccg gccggccggc cgccggggga ccgcggagct    1980
gggactggga gacccacacc cagtcaaaga atccccctcg cgcgcgctcc cgcccagatc    2040
acgtgtcgct agcacgcctt tgcgcctgat cggggccgtc acggacccgt ccggccgtcc    2100
ctgtcgcccg caccctcctc ctcctcctcc tcctcctccg tccgatcgcg tcgccaccgc    2160
ggctcctcct ccgacccatc actctcccgc attctcattc cccgaggacc accactcgtt    2220
ccgccggtcc gtcacgtgtt tcatgcgacg cgactcgcct cgcctccgcc ccggcccgg     2280 cccccgacca ggctggcccc gtcccacttg ccggttcatt ggcacgcgct attaaagggg    2340
gggcaaaggg ccatttgcga gaggaggaaa agcacgcgag agcttgtcgg agggctctct    2400
gtctctgtga taaaccgata cgcagaggaa gctgcggaga ggtgtccctg ctctgctggt    2460
gagctgcggc cagcgggtga agtgaagtgg accggacgtg gacgaaggcg agagcttgtc    2520
ggagggctct ctgtctccgt gataaaccga tacgcagagg aagctgcgga gaggtgtccc    2580
tgctctgctg gtgagctgcg gccagcgggt gaagtgaagt ggaccggacg tggacgaagg    2640
agagagrgag agagagagag agagaagaaa gggcgccgcg ggggcc                   2686
```

<210> SEQ ID NO 104
<211> LENGTH: 3518
<212> TYPE: DNA
<213> ORGANISM: Zea mays

<400> SEQUENCE: 104

```
ccgagcacca gatggcacga caaaaagtct cggcaaagaa gtcattgctg atgtacaatt      60
cgtcgacacc tctctaccga gagtcacaat cgacaaagac tttgccgaga gttgtgttcg     120
gtagaggcat acccatttat caatttaagt atatttatat acttattacg agatacatat     180
gcaaatctca caaaaaaaat tatcgtgtca taaacaatca tttcggtcta tggagacaat     240
tatcacaatg atgtggtgca tttggaaata tagaaacgga tggatattcg aaaacactcc     300
tctgaccaca ctgaggtgca aatcatgttt gttcaagaga tgaatcttaa tacctataag     360
atgcgggaga tgatagctaa caatgtcaaa caatggatac aacacattgt aatacgaaaa     420
```

```
gtgtaatctg taaacatata tatagaaaag taataaaaga aatactcttg ggaccctaca    480
gtagaatgct ttattcaaaa aacaatcatt tcggtctcca ccgtatatag taatttcata    540
ttaatcttta tgtgagaatt atatcagtat gatttcatag tggagatgtg tttcaaccgt    600
cgattgctta atcaggccta ccaatttatt atcactggcg cgcgataatc gaaaccgctt    660
gtaaaaagtt gaaccaccat aggcttagag ctttttttct actactgttg aatttagatc    720
atatgagtgt catttgtcgc ctaaaaataa aaaacagga gcacgtagtt tagcaagtcc    780
catccgcata taatataact ctagttgggt tatcttgaat agcttgtttg caggcttgtc    840
tagtgcaatt cgctcgcgtt tcactacact aaaatagtga acttcctaga gcctaaatcc    900
taggaagtta gccataaact ctagaaagtt agctaaactc tcagaagtta agtcatcccg    960
tcagaagttt ggctctcaaa attttttgt cggaagttag cttaacttcc tagagccctc    1020
tagaaagtta actaacttcc tatagccaaa gcagcatctc agaagttagt aggttctcag    1080
aagttagtag cttcacgccg tcagcgccgt cagctgacta acttcctacg actaacttcc    1140
tatggctgac tgtagcccct aggaagttag cttacgtccc agttggtatc taggaagtta    1200
atttggtcag cattataaat gctgtttatt tttattttac accatatttc acaacataac    1260
aaatatacca acaactatat aacgcaacat attttcacat aaaacatctc acacacaatc    1320
acataacaat atctaaatcc gtagtctcat caattacatc acaaaagtct catccatagt    1380
cataataaga cacatctcat ccagttataa taagagacaa tatctcatac ataataaaag    1440
tctcaagtat cacaacacat aacatggaag ctcacgatcg ccaatcacca tcggggtaca    1500
gtgacgagtg atggtcgata cctccactag cgaagagggt ttcgacaaag tctaacacat    1560
cttctcgttg atgagtcggc aaggtagctg gaggggtcta atatacatgt acaaatgata    1620
tttgctgagt tacatcataa tataactagc aacaagtaaa tgatgatgaa tttgcatacc    1680
tgatgttcgg taggtggata tgtaggtgta ggtggaggtg aagaccaaag ataatgtgcg    1740
ggaggtataa acaataaaaa atccatgcta acacactaaa agaagtatat aatgccgtag    1800
gtcaggtctg caagcaaaag aataaatatc caacatttag atctaaaacg cctctaggaa    1860
gttagcggct cgcttgaccg aacacacgag tcagcatgtg aaagctaact ttctacagct    1920
tttataaaat actgtagtaa gttatgttta tttcttagag ctaccagttg cctctcggaa    1980
gttatttatt tcctacggtt tgttataaaa gttgcaggaa gttaaaaata gccataggaa    2040
ctgtatgatt ttgtatgatt ttagtgtagt gttttttggc cacctatgtt cttatacatg    2100
tttgcacaat gttcaaaaca aaacaagatg gtacatcgta tttggtcata ttagataata    2160
caggtttcag gtttgtataa gacgacatgc acatagaaat aaaaaatatt ctcatccact    2220
aaacatagga ccttaataag aatattgagg cgacagatga gatggatctc atggatgcat    2280
acagcaaaat atgaacaaga gagcaaacat aattttaaac gtcgctcgct tttgtcaaga    2340
gaacgaccga acattaagac taacgcaagg aacaaccaca ccatacttcg tgactggggg    2400
cagagcaatg gtgtcaaata aacttttga gcacatactt tctacataag atcacatgca    2460
cctaaaagca ttgagctact acacccaccc agcctccttt tctccatcct tgccttttcc    2520
cctgccacca cactccacat ctctccatgc atgcatgtga tgcctctggt atcggtcgta    2580
ccattgctcc ccaagaccat gttaattcag tcgcctgcac atcagctcgc attgccaaaa    2640
taagatggcg atcatgcctt aacatggtgc ctgatcgcct gattatctct ttcatgcatg    2700
acagtacgac accactctct gcccggcctc agcaaatgat tgcagtagct ctgctgctgc    2760
ccactttcca aaacatctgt ttttaacag aagtactgcc atcacagagc aacagtacta    2820
```

-continued

| | |
|---|---|
| gctgatcagt gatccattaa gctgggagag caagaaaaga catccaaacg cacatgcagg | 2880 |
| aaaccctaag caaatcaagc ttcatggctt tctaacctta ataaactcct cccacatgca | 2940 |
| tttgctggtg cgcagataga gccagcagga aggagagaga aagaaaaagg gcagtcaaat | 3000 |
| tcagtaggcc cccactcgat ccgggtccaa gacgcccaca gaaagggagg ggagacgtga | 3060 |
| ggatgaaaag gcaatgcatg catagagcca aatagatgcc acttttttctt cttggtcctt | 3120 |
| gcattgctat ctcaatacgt catgtgattc tacaatgtaa gcgtgaagtc gaagtagttc | 3180 |
| ttggtggtac ttcagccctc atgcatctcc tcatgcatgc aatgcaagat cgatgcaatc | 3240 |
| ctcatccctat ataatagata tagcttgata gcttccaccg acaatggcac cacgcctagc | 3300 |
| tagctactgc tagctacggc tagcagctag gatacaatcc tcttgtgaga tgagatacta | 3360 |
| gcatggcatc gccatcaaat aatgcactga gtgatctatc tctcaccatg tctgccttcc | 3420 |
| cagttggcca tttcccacta caaatagcga gctgattcat cgatctcagc agtcagcacg | 3480 |
| tagctcagag ctagctagca gtagcaccag cagcagcc | 3518 |

<210> SEQ ID NO 105
<211> LENGTH: 2627
<212> TYPE: DNA
<213> ORGANISM: Zea mays

<400> SEQUENCE: 105

| | |
|---|---|
| tgtaatgtcg ctactctgct actcgtatgt gcatgctcca attctgcaaa gttttggaca | 60 |
| atttgtcatt aacagtcatg aacgttgctt ttcagcagtg cagataatat aacacaagcg | 120 |
| ctcatgttcc tctcgcactt catcagagac atacaccagg tagtacaaac cgcaagcaag | 180 |
| gtttgatgtg ctctatttgg tgtgtttgat cagatcaaca atgtggctga tcgctcatgc | 240 |
| tactgattgc taacacaact actacctgta ctccatagcc acttcactcc gacaaaggag | 300 |
| ggaacaccgt cgacttccac tggtacgcaa ggaagactgt tttacactat gtatgtacat | 360 |
| caaatactgg acatcatcag tcatgatctt gaaatctata ggaacctaga tgctagggca | 420 |
| tgctctgttt tgttcactaa ttgcccggtt tggaacgcca acatcatcta gccgactaaa | 480 |
| gacgacttct atggagacag cgtagccggt tacatcgaca cactgaagaa aaacataatg | 540 |
| atatggaact aggataagag ttttctatag atagagagaa agagagaagc taaatgttaa | 600 |
| ttattcagac ctttattcgc tcggtagcac agagaatggt cggagaagtg tccagctggg | 660 |
| aagcatgcag caagaaccag actgtatgtc cagatatgta tatatgattt gcttcacatt | 720 |
| cagattttt gtgcttgggc atttaattga tctttgtatg ttgttgcatc gagtgttttt | 780 |
| tcgttgatta atacaataat tttcataatt ttctttatgt ttcaaatcct tcgtaaagta | 840 |
| agattactct ctgagttttt gaatggttat aaataaatat cgcaagatat gcgtctgaga | 900 |
| gcatcattgc atcatgccac tgagcataca agggtgttaa ggaagactca accctagaag | 960 |
| gtactactaa tactagcaca ttaaattaat gcctacattc ctgttctgta gtatgcacac | 1020 |
| cggatttgta ttgttgtcgt actattgatg catgatttta acttgagggg gcaagaatac | 1080 |
| gctaattaat ttgtgtttat gttcttggtg cagatcccta tttcttataa atcttatctc | 1140 |
| tactgttcca ttcacctctc tctcctctcc cacatttaaa cggtaaaaat ctaaaattat | 1200 |
| gcaagaataa agattaataa tttgtgagtc gtggcaatgc acgagcacct gactatgttt | 1260 |
| ggttaatgca tgtctgattt ctgttgacga gtgtttcaaa caacagctgt aggtttgggg | 1320 |
| cagtcaactt gtgtaggcat tggtggtgac ccgttcaata tcacatatac acattttgag | 1380 |

-continued

```
attaagacct catattttaa gcaaaagcct tccttttttta aatctattat gaaatatctt    1440
gtcatggatt ttgtactttg ctctgtggaa ttaaaccctt gtctggcatt atctggtact    1500
tgaatactta aagtgtattt ttttattcca aatgctacat acatatgttt ttcagtcaac    1560
acaactccat ctcattttgt agttttctta gtgttcaata ctatttggat tctattaagt    1620
cagaaatagc aaagataaca tagaaaggtg gacttccaaa tgcagaagca attggaaaat    1680
tgtacatctt atgcaacttg atcgaactgt tatattttat atcttttgtt tagcattttt    1740
taatccacat gtaattctct atcatataaa actctatatt gattctttaa aataatttat    1800
atgaatttga taatgtttgt cacaactcac acgaattctg tataccataa tgaattgatg    1860
gttgagagac tatgcacgag gcatgcaaat taacaagact catacaagcg tcgaacaatg    1920
tgctgatgat gatcagagac acaagggcag cacatgatca ggtcttaaca tgtttggctt    1980
ccgaagagcc ttttctccag atccccaagg aagaaaaaga tccggtcaga tatatgtcga    2040
tgctcatccc aacgtacata agctatcaat ggtattatat gttcccgttg caacgcacta    2100
acaacgggcg tcaaacaaac ccaatcctac ctggattcta tacggcaact gcagtatcaa    2160
accaaacacc actgatggta cagtaattac ctctccgacc aacattgctc cccctctgc    2220
ctgcgtgtgg gtcaaatgcg agggaggcac aagctcattc cttttgcacg cctttaaagc    2280
tatccccaca cacattctcg tcgatcactc ttcttcctcc tccgcacacg cgcacatgcg    2340
accagagctt agctcagctt agcttatagc agtatagctt attgcttata ctgtctcccc    2400
ctcggcttcg tcgctcggag gtgtgcacac acacaaaccg aagcccttgc cctcccatcc    2460
ccctccaaac gcgcgcaacc atggagagtg gcggcatcat tgcgccgtgt actccccaat    2520
gattgatctc tcatcgtctc ttcttccaac cacctcctcg tcctcgcact cgcactcgca    2580
ctcgcccttc tctcttccct gcccggctgc ccgcttgtct ccccaaa                  2627
```

<210> SEQ ID NO 106
<211> LENGTH: 2824
<212> TYPE: DNA
<213> ORGANISM: Zea mays

<400> SEQUENCE: 106

```
ttatgtaagc ccatgccata caaaagattt gtagaagcgg ttatcatggc ttcataaaaa     60
tataagattg catacaagaa acgttttaca tggacagatg atattttaa gtgggaacat    120
acaatttgga ctaatgctca aattgactca aaaggtattt tcttcgtacc accttctcag    180
caatttaatt ttttctatga ttttttattat atataatata gttggcaaaa cattagtcta    240
taggagtaac accagctaca tcgttttata agctatggaa tcattttaca agctatagaa    300
atgtggagaa atgatgggcg gatgaaattt gtcaggaaga gtagagtacg tttgttccat    360
gtttaaacat aaaattcaagt tacataacaa aaaataatg ttttgttctc ttatgtttgc    420
ataggttgcg gagattttc ggaggaaatt tgtgattgat ttgttaagtt atgaaggcaa    480
ttcgtatcaa tatgacattt cttcaaacat acaacagaga cttttcaata acgctaaaaa    540
atattaaatt agtgtggtgt tgttgatata tttgcctatc atttaaaatt ctatattgat    600
tctttagaat aatttgtgtg gtattataat atttgttcga catctgttca tttttatttga    660
gtcaacatat ttataataat aacacatatt taaacatcga tataaaatta gtgttaccgt    720
gatgttttgc taaacggatt atatatgtca tagtgatgtt tgttgttttca tatctatgtt    780
tatactaatt tttaactctc gtggcaacgc acgggcacat acctatacat acttaacagt    840
tgtggagagt tgtcgttttc tctcttgttg ctgtccaatt tgctttgtcg gctattgcta    900
```

```
ttgtagcaac aacagtcaca acaagaggcc aagagagata agattgtttt gcgatgctac    960
aactgcaaga gaaagatgtt cactccgtag caacgtacag gtatttacct agtaaataat   1020
taagttaat  agatctctct cgcaaactac tcacggctta tacaattaat ttatatttaa   1080
tcatcctgat taaaatttaa agctcttaaa ctagagaccg aggatcaagc acaccgttat   1140
tttgccagca aagagccatg caatgtatgc gtgaggtata agttttttc  taaaattgca   1200
atttgcaaac cagcaaagaa ccgaagcgtg ccattttgt  gcagaacaca gaacactcga   1260
ggtcgaggcg taggcatagg caccgccagc cataaaaata cggtttgcaa tcactacagt   1320
tctgttaaaa cttttttttt atttggcaat cttgattatt gatgggaaaa gagtgaagga   1380
aggttttcc  tgaccgaagc tttgcctaaa acaaaaggc  gacacctcac atgtttattc   1440
ctttctttca ttttccacca tgtctatgag ctgtattttt ctctatccct taagtcaagc   1500
ttgtcttaac ctgtttctgg tggatcatgt aaaatagagg atgcgatatt ttagataaca   1560
ctgtttatat cgtggagttt gaaatagagg atattataga ggatgtgata agagatctgc   1620
cgaagatgat cttgagcaac tccaaaatga cacttaattt ttttttccca aaaactgatt   1680
attggggctt gactaaaact ttttaggagt aggttatctt gtttactcca acaattccca   1740
aatagaagat taaaacgaaa attgggccag ctaaaagaag cccaaggcat gaatcggcct   1800
attttgcatt agctctgttt tccctcgacg aagggctta  gcccatattt attcaggcga   1860
acatgatttc acgttctaga tcactgcatg ttgtgcgcta aataggatc  agcactccgc   1920
cgtatgtacg acgacatgat gaacggaatc atcaggaga  cgaaggccac cgaggaaggc   1980
aaggacctgc tcgacatgct gctcgactgg atgcgggagc attggccgct agcggaggac   2040
gatgacagca ggatcagtga cactgacatc gccgccaagg agtgcgaggt ggacaggttc   2100
tgaatcaaag gtgtatcccc atttaacact tcaacccttc caccatcagc tcacgtagat   2160
gtatagaaaa ccacataaca agctataatt atgtatatag ttagattgta atttaatgta   2220
ccaagaggct cgtttgcaca tctatactat acttaaaaca ccaatttcaa tagtcgtctc   2280
gcgtcatctt tttcaaataa ccctttataa ctatttcaaa ttaatccgtt gtacgtctat   2340
agatggccaa acagcggcac gacacgggcc agacacccac gggccacaac tctgggccag   2400
gcacgtcatg tcggcatgct gactgtgtcg tgccagcccg ttagcccgtc ggtccatttg   2460
attaaatcag cgtaaaatgt taaaaaatgg tgcaagaggt ggggttcaaa ctcatgtcct   2520
aatagatcga agaagggcag gagacactgg gtgaagctgt ctaacttgta gaacatcatg   2580
ctcaaatgtt tctaataatg aatataaatt gtatatatat atatatatat atatatatat   2640
atatatatat atatatatat atattatata tatatatata tatacatata cgttttttgt   2700
aaaataaaaa aatataatcg tgtcgggccg gaccaacact actggccgag actacaggcc   2760
aagcacgaca cgacgttctt ggctcttgca agtattaggt cgttttgag  accatattgg   2820
cgca                                                               2824
```

<210> SEQ ID NO 107
<211> LENGTH: 844
<212> TYPE: PRT
<213> ORGANISM: Zea mays

<400> SEQUENCE: 107

Met Glu Thr Gly Leu Pro Arg Gly Leu Tyr Ser Glu Arg Thr His Arg
1               5                   10                  15

Pro Arg Pro Arg Ala Ser Asn Gly Leu Tyr Ser Glu Arg Ala Leu Ala

-continued

```
            20                  25                  30

Pro Arg Ala Leu Ala Thr His Arg Pro Arg Gly Leu Tyr Thr His Arg
        35                  40                  45

Pro Arg Ala Leu Ala Pro Arg Leu Glu Pro His Glu Ser Glu Arg Ser
    50                  55                  60

Glu Arg Gly Leu Tyr Gly Leu Tyr Pro Arg Ala Arg Gly Val Ala Leu
65                  70                  75                  80
Ala Ser Pro Ser Glu Arg Leu Glu Ser Glu Arg Thr Tyr Arg Gly Leu
                85                  90                  95
Ala Arg Gly Leu Tyr Ser Ser Glu Arg Met Glu Thr Pro Arg Ala Arg
            100                 105                 110
Gly Cys Tyr Ser Leu Tyr Ser Cys Tyr Ser Leu Glu Pro Arg Leu Glu
        115                 120                 125

Pro Arg Ala Leu Ala Val Ala Leu Gly Leu Gly Leu Tyr Thr Arg Pro
    130                 135                 140

Gly Leu Tyr Val Ala Leu Ala Leu Ala Thr His Arg His Ile Ser Thr
145                 150                 155                 160
His Arg Cys Tyr Ser Val Ala Leu Val Ala Leu Gly Leu Ile Leu Glu
                165                 170                 175
Pro Arg Ala Leu Ala Pro Arg Ala Ser Pro Val Ala Leu Ser Glu Arg
            180                 185                 190
Leu Glu Thr His Arg Ala Arg Gly Leu Tyr Ser Leu Glu Gly Leu Tyr
        195                 200                 205

Ala Leu Ala Gly Leu Pro His Glu Val Ala Leu Gly Leu Tyr Thr His
    210                 215                 220

Arg Pro His Glu Ile Leu Glu Leu Glu Ile Leu Glu Pro His Glu Pro
225                 230                 235                 240

His Glu Ala Leu Ala Thr His Arg Ala Leu Ala Ala Leu Ala Pro Arg
                245                 250                 255

Ile Leu Glu Val Ala Leu Ala Ser Asn Gly Leu Asn Leu Tyr Ser Thr
            260                 265                 270

Tyr Arg Gly Leu Tyr Gly Leu Tyr Ala Leu Ala Ile Leu Glu Ser Glu
        275                 280                 285

Arg Pro Arg Pro His Glu Gly Leu Tyr Ala Ser Asn Ala Leu Ala Ala
    290                 295                 300

Leu Ala Cys Tyr Ser Ala Leu Ala Gly Leu Tyr Leu Glu Ala Leu Ala
305                 310                 315                 320

Val Ala Leu Ala Leu Ala Thr His Arg Val Ala Leu Ile Leu Glu Leu
                325                 330                 335

Glu Ser Glu Arg Thr His Arg Gly Leu Tyr His Ile Ser Ile Leu Glu
            340                 345                 350

Ser Glu Arg Gly Leu Tyr Ala Leu Ala His Ile Ser Leu Glu Ala Ser
        355                 360                 365

Asn Pro Arg Ser Glu Arg Leu Glu Thr His Arg Ile Leu Glu Ala Leu
    370                 375                 380

Ala Pro His Glu Ala Leu Ala Ala Leu Ala Leu Glu Ala Arg Gly His
385                 390                 395                 400

Ile Ser Pro His Glu Pro Arg Thr Arg Pro Leu Glu Gly Leu Asn Val
                405                 410                 415

Ala Leu Pro Arg Ala Leu Ala Thr Tyr Arg Val Ala Leu Ala Leu Ala
            420                 425                 430

Val Ala Leu Gly Leu Asn Ala Leu Ala Leu Glu Ala Leu Ala Ser Glu
        435                 440                 445
```

Arg Val Ala Leu Cys Tyr Ser Ala Leu Ala Leu Ala Pro His Glu
450                 455                 460

Ala Leu Ala Leu Glu Leu Tyr Ser Gly Leu Tyr Val Ala Leu Pro His
465                 470                 475                 480

Glu His Ile Ser Pro Arg Pro His Glu Leu Glu Ser Glu Arg Gly Leu
                485                 490                 495

Tyr Gly Leu Tyr Val Ala Leu Thr His Arg Val Ala Leu Pro Arg Ala
            500                 505                 510

Ser Pro Ala Leu Ala Thr His Arg Val Ala Leu Ser Glu Arg Thr His
        515                 520                 525

Arg Ala Leu Ala Gly Leu Asn Ala Leu Ala Pro His Glu Pro His Glu
    530                 535                 540

Thr His Arg Gly Leu Pro His Glu Ile Leu Glu Ile Leu Glu Ser Glu
545                 550                 555                 560

Arg Pro His Glu Ala Ser Asn Leu Glu Leu Glu Pro His Glu Val Ala
                565                 570                 575

Leu Val Ala Leu Thr His Arg Ala Leu Ala Val Ala Leu Ala Leu Ala
            580                 585                 590

Thr His Arg Ala Ser Pro Thr His Arg Ala Arg Gly Ala Leu Ala Val
    595                 600                 605

Ala Leu Gly Leu Tyr Gly Leu Leu Glu Ala Leu Ala Gly Leu Tyr Ile
    610                 615                 620

Leu Glu Ala Leu Ala Val Ala Leu Gly Leu Tyr Ala Leu Ala Ala Leu
625                 630                 635                 640

Ala Val Ala Leu Thr His Arg Leu Glu Ala Ser Asn Ile Leu Glu Leu
                645                 650                 655

Glu Val Ala Leu Ala Leu Ala Gly Leu Tyr Pro Arg Thr His Arg Thr
            660                 665                 670

His Arg Gly Leu Tyr Gly Leu Tyr Ser Glu Arg Met Glu Thr Ala Ser
        675                 680                 685

Asn Pro Arg Val Ala Leu Ala Arg Gly Thr His Arg Leu Glu Gly Leu
    690                 695                 700

Tyr Pro Arg Ala Leu Ala Val Ala Leu Ala Leu Ala Ala Leu Ala Gly
705                 710                 715                 720

Leu Tyr Ala Ser Asn Thr Tyr Arg Ala Arg Gly Gly Leu Asn Leu Glu
                725                 730                 735

Thr Arg Pro Ile Leu Glu Thr Tyr Arg Leu Glu Leu Glu Ala Leu Ala
            740                 745                 750

Pro Arg Thr His Arg Leu Glu Gly Leu Tyr Ala Leu Ala Leu Glu Ala
        755                 760                 765

Leu Ala Gly Leu Tyr Ala Leu Ala Ser Glu Arg Val Ala Leu Thr Tyr
    770                 775                 780

Arg Leu Tyr Ser Ala Leu Ala Val Ala Leu Leu Tyr Ser Leu Glu Ala
785                 790                 795                 800

Arg Gly Ala Ser Pro Gly Leu Ala Ser Asn Gly Leu Tyr Gly Leu Thr
                805                 810                 815

His Arg Pro Arg Ala Arg Gly Thr His Arg Gly Leu Asn Ala Arg Gly
            820                 825                 830

Ser Glu Arg Pro His Glu Ala Arg Gly Ala Arg Gly
        835                 840

<210> SEQ ID NO 108
<211> LENGTH: 107

```
<212> TYPE: PRT
<213> ORGANISM: Arabidopsis thaliana

<400> SEQUENCE: 108

Met Val Ser Leu Lys Ser Leu Ala Ala Ile Leu Val Ala Met Phe Leu
1               5                   10                  15

Ala Thr Gly Pro Thr Val Leu Ala Gln Gln Cys Arg Asp Glu Leu Ser
            20                  25                  30

Asn Val Gln Val Cys Ala Pro Leu Leu Leu Pro Gly Ala Val Asn Pro
        35                  40                  45

Ala Ala Asn Ser Asn Cys Cys Ala Ala Leu Gln Ala Thr Asn Lys Asp
    50                  55                  60

Cys Leu Cys Asn Arg Leu Arg Ala Ala Thr Thr Leu Thr Ser Leu Cys
65                  70                  75                  80

Asn Leu Pro Ser Phe Asp Cys Gly Lys Met Ile His Arg Leu Lys Pro
                85                  90                  95

Phe Leu Leu Asp Phe Tyr Lys Leu Phe His Gln
            100                 105

<210> SEQ ID NO 109
<211> LENGTH: 95
<212> TYPE: PRT
<213> ORGANISM: Brassica napus

<400> SEQUENCE: 109

Met Glu Phe Leu Lys Ser Phe Thr Thr Ile Leu Phe Val Met Phe Leu
1               5                   10                  15

Ala Met Ser Ala Leu Glu Thr Val Pro Met Val Arg Ala Gln Gln Cys
            20                  25                  30

Leu Asp Asn Leu Ser Asn Met Gln Val Cys Ala Pro Leu Val Leu Pro
        35                  40                  45

Gly Ala Val Asn Pro Ala Pro Asn Ser Asn Cys Cys Ile Ala Leu Gln
    50                  55                  60

Ala Thr Asn Lys Asp Cys Ile Cys Asn Ala Leu Arg Ala Ala Thr Thr
65                  70                  75                  80

Phe Thr Thr Thr Cys Asn Leu Pro Ser Leu Asp Cys Gly Ile Thr
                85                  90                  95

<210> SEQ ID NO 110
<211> LENGTH: 97
<212> TYPE: PRT
<213> ORGANISM: Ricinus communis

<400> SEQUENCE: 110

Met Ala Ala Leu Arg Ser Leu Ile Ala Leu Ser Ser Gln Ala Ala Leu
1               5                   10                  15

Leu Leu Leu Leu Val Ala Leu Ala Met Gln Thr His Leu Val His Ser
            20                  25                  30

Gln Thr Cys Gln Asn Gln Leu Asn Ser Leu Asn Val Cys Ala Pro Phe
        35                  40                  45

Val Val Pro Gly Ala Ala Asn Thr Ser Pro Asn Ala Glu Cys Cys Asn
    50                  55                  60

Ala Leu Glu Ser Val Gln Asn Asp Cys Ile Cys Asn Thr Leu Arg Ile
65                  70                  75                  80

Ala Gly Arg Leu Pro Ser Leu Cys Asn Leu Ser Pro Ile Asn Cys Gly
                85                  90                  95

Asn
```

<210> SEQ ID NO 111
<211> LENGTH: 93
<212> TYPE: PRT
<213> ORGANISM: Ricinus communis

<400> SEQUENCE: 111

Met Ala Ala Pro Lys Phe Leu Gln Ala Ala Leu Leu Leu Leu Ile Ile
1               5                   10                  15

Ala Val Ala Val Gln Thr Gln Glu Ala Gln Ser Gln Thr Cys Pro Ser
            20                  25                  30

Gln Leu Asn Ser Leu Asn Val Cys Ala Pro Phe Val Val Pro Gly Ala
        35                  40                  45

Thr Asn Thr Asn Pro Asn Ala Glu Cys Cys Ser Ala Leu Gln Ser Val
    50                  55                  60

Glu His Asp Cys Leu Cys Asn Thr Leu Arg Ile Ala Ala Arg Leu Pro
65                  70                  75                  80

Ser Gln Cys Asn Leu Ala Pro Val Asn Cys Gly Asn Trp
                85                  90

<210> SEQ ID NO 112
<211> LENGTH: 94
<212> TYPE: PRT
<213> ORGANISM: Populus trichocarpa

<400> SEQUENCE: 112

Met Ala Ala Leu Lys Ser Leu Ser Ser Pro Val Ala Val Leu Leu Leu
1               5                   10                  15

Leu Thr Ala Leu Ala Val Gln Thr Gln Leu Ala His Ser Gln Gln Cys
            20                  25                  30

Thr Ser Gln Leu Asn Asn Leu Asn Val Cys Ala Pro Phe Val Val Pro
        35                  40                  45

Gly Ala Ala Asn Thr Asn Pro Asn Ala Glu Cys Cys Asn Ala Leu Glu
    50                  55                  60

Ala Val Gln His Asp Cys Leu Cys Ser Thr Leu Gln Ile Ser Ser Arg
65                  70                  75                  80

Leu Pro Ser Gln Cys Asn Leu Pro Pro Leu Thr Cys Gly Asn
                85                  90

<210> SEQ ID NO 113
<211> LENGTH: 100
<212> TYPE: PRT
<213> ORGANISM: Silene latifolia

<400> SEQUENCE: 113

Met Ala Asn Asn Met Lys Ser Ala Thr Phe Cys Lys Ala Thr Trp Ala
1               5                   10                  15

Ile Phe Leu Val Ala Leu Ala Ile Leu Val Gln Leu Lys Gly Ser Glu
            20                  25                  30

Ala Gln Ala Gly Gly Cys Ala Ser Gln Leu Gly Asn Leu Asn Val Cys
        35                  40                  45

Ala Pro Tyr Val Val Pro Gly Ala Val Asn Thr Asn Pro Ser Gln Glu
    50                  55                  60

Cys Cys Ala Ala Leu Ser Gly Val Asn His Asp Cys Met Cys Asn Thr
65                  70                  75                  80

Leu Arg Val Ala Ser Gln Leu Pro Ser Ser Cys Asn Leu Ala Ala Leu
                85                  90                  95

```
Asn Cys Gly Asn
            100
```

<210> SEQ ID NO 114
<211> LENGTH: 90
<212> TYPE: PRT
<213> ORGANISM: Lilium longiflorum

<400> SEQUENCE: 114

```
Met Ala Ser Met Lys Ser Leu Ala Thr Ala Ile Leu Val Val Leu Leu
1               5                   10                  15

Leu Ala Ala Leu Ser Arg Glu Gly Arg Ser Gln Asn Cys Ser Ala Ala
            20                  25                  30

Ile Gly Glu Leu Met Thr Cys Gly Pro Tyr Val Leu Pro Gly Asn Asn
        35                  40                  45

Gly Ala Pro Ser Glu Gln Cys Cys Ser Ala Leu Arg Ala Val Asn His
    50                  55                  60

Gly Cys Leu Cys Glu Thr Ile Asn Ile Ile Ser Ser Leu Pro Asp His
65                  70                  75                  80

Cys Ser Leu Pro Ala Val Asn Cys Ala Ala
                85                  90
```

<210> SEQ ID NO 115
<211> LENGTH: 90
<212> TYPE: PRT
<213> ORGANISM: Lilium longiflorum

<400> SEQUENCE: 115

```
Met Ala Ser Met Lys Ser Leu Ala Thr Ala Ile Leu Val Val Leu Leu
1               5                   10                  15

Leu Ala Ala Leu Ser Arg Glu Gly Arg Ser Gln Asn Cys Ser Ala Ala
            20                  25                  30

Ile Gly Glu Leu Met Thr Cys Gly Pro Tyr Val Leu Pro Gly Asn Asn
        35                  40                  45

Gly Ala Pro Ser Glu Gln Cys Cys Ser Ala Leu Arg Ala Val Asn His
    50                  55                  60

Gly Cys Leu Cys Glu Thr Ile Asn Ile Ile Ser Ser Leu Pro Asp His
65                  70                  75                  80

Cys Ser Leu Pro Ala Val Asn Cys Ala Ser
                85                  90
```

<210> SEQ ID NO 116
<211> LENGTH: 90
<212> TYPE: PRT
<213> ORGANISM: Lilium longiflorum

<400> SEQUENCE: 116

```
Met Ala Ala Val Lys Phe Leu Val Cys Ser Val Leu Val Val Leu
1               5                   10                  15

Ala Thr Gln Ser Glu Ile Gly Leu Ala Gln Asn Cys Ser Ala Ala Ile
            20                  25                  30

Gly Gly Leu Met Ser Cys Gly Pro Tyr Val Leu Pro Gly Asn Gln Leu
        35                  40                  45

Thr Pro Ser Thr Gln Cys Cys Ser Ala Ile Gln Ala Val Asn His Gly
    50                  55                  60

Cys Leu Cys Glu Thr Ile Asn Ile Ile Ser Ser Leu Pro Gly His Cys
65                  70                  75                  80

Ser Leu Pro Pro Val Ser Cys Gly Thr Ala
                85                  90
```

<210> SEQ ID NO 117
<211> LENGTH: 94
<212> TYPE: PRT
<213> ORGANISM: Oryza sativa

<400> SEQUENCE: 117

Met Ala Ala Ser Lys Gly Asn Ala Ala Ala Ala Cys Ala Leu Val
1               5                   10                  15

Leu Val Leu Leu Ala Val Gly Ala Glu Ala Gln Gly Gly Gly Gly
                20                  25                  30

Glu Cys Val Pro Gln Leu Asn Arg Leu Leu Ala Cys Arg Ala Tyr Ala
                35                  40                  45

Val Pro Gly Ala Gly Asp Pro Ser Ala Glu Cys Cys Ser Ala Leu Ser
    50                  55                  60

Ser Ile Ser Gln Gly Cys Ala Cys Ser Ala Ile Ser Ile Met Asn Ser
65                  70                  75                  80

Leu Pro Ser Arg Cys His Leu Ser Gln Ile Asn Cys Ser Ala
                85                  90

<210> SEQ ID NO 118
<211> LENGTH: 103
<212> TYPE: PRT
<213> ORGANISM: Sorghum bicolor

<400> SEQUENCE: 118

Met Ala Ala Leu Glu Ala Thr Thr Ser Thr Val Pro Arg Ala Leu
1               5                   10                  15

Leu Ala Ala Cys Leu Val Leu Val Leu Gly Gly Gly Pro Ser Ser
                20                  25                  30

Ser Val Gln Ala Gln Gly Gly Gly Leu Cys Leu Pro Gln Leu Asn
                35                  40                  45

Gly Leu Leu Ala Cys Arg Ala Tyr Leu Val Pro Gly Ala Pro Asp Pro
    50                  55                  60

Ser Ala Asp Cys Cys Ser Ala Leu Ser Ala Val Ser His Glu Cys Ala
65                  70                  75                  80

Cys Ser Thr Met Gly Ile Ile Asn Ser Leu Pro Gly Arg Cys Asn Leu
                85                  90                  95

Ala Gln Val Asn Cys Ser Ala
            100

<210> SEQ ID NO 119
<211> LENGTH: 95
<212> TYPE: PRT
<213> ORGANISM: Hordeum vulgare

<400> SEQUENCE: 119

Met Ala Pro Ser Thr Val Pro Arg Ala Leu Leu Ala Val Ser Leu Val
1               5                   10                  15

Leu Leu Val Ala Gly Gly Leu Gly Pro Ala Ala Glu Ala Gln Arg Pro
                20                  25                  30

Gly Glu Cys Val Pro Gln Leu Asn Arg Leu Leu Ala Cys Arg Ala Tyr
                35                  40                  45

Leu Val Pro Gly Ala Ala Asp Pro Ser Ala Glu Cys Cys Gly Ala Leu
    50                  55                  60

Ser Ser Ile Ser Arg Asp Cys Ala Cys Ser Thr Met Gly Ile Ile Asn
65                  70                  75                  80

-continued

Ser Leu Pro Ser Arg Cys Asn Ile Gly Gln Val Asn Cys Ser Ala
                85                  90                  95

<210> SEQ ID NO 120
<211> LENGTH: 94
<212> TYPE: PRT
<213> ORGANISM: Brachypodium distachyon

<400> SEQUENCE: 120

Met Ala Pro Pro Arg Met Ser Lys Gly Ile Gln Val Met Val Ala Val
1               5                   10                  15

Ala Glu Ala Gln Gln Arg Glu Cys Val Pro Gln Leu Asn Arg Leu Leu
            20                  25                  30

Ala Cys Arg Ala Tyr Leu Ala Ala Pro Gly Ala Ala Ala Ala Ala Pro
        35                  40                  45

Ser Ala Glu Cys Cys Gly Ala Leu Ala Gly Ile Ser Arg Glu Cys Ala
    50                  55                  60

Cys Ser Thr Met Ala Ile Ile Asn Ser Ile Pro Ser Arg Cys Gly Val
65                  70                  75                  80

Ser Gln Val Asn Cys Thr Ala Ser Ser Thr Ser Thr Cys Ala
                85                  90

<210> SEQ ID NO 121
<211> LENGTH: 109
<212> TYPE: PRT
<213> ORGANISM: Zea mays
<220> FEATURE:
<221> NAME/KEY: misc_feature
<222> LOCATION: (13)..(13)
<223> OTHER INFORMATION: Xaa can be any naturally occurring amino acid

<400> SEQUENCE: 121

Met Thr Ala Thr Thr Thr Thr Ala Ala Gly Gly Ala Xaa Val Gln Pro
1               5                   10                  15

Arg Gly Leu Pro Ala Ala Leu Ser Leu Leu Leu Leu Val Leu Ala
            20                  25                  30

Ala Gly Leu Gly Gly Gly Ala Glu Ala Gln Gln Thr Cys Ala Gly Gln
        35                  40                  45

Leu Arg Gly Leu Ala Pro Cys Leu Arg Tyr Ser Val Pro Pro Leu Pro
    50                  55                  60

Gly Gln Val Pro Pro Ala Pro Gly Pro Glu Cys Cys Ser Ala Leu Gly
65                  70                  75                  80

Ala Val Ser Arg Asp Cys Ala Cys Gly Thr Phe Ser Ile Ile Asn Ser
                85                  90                  95

Leu Pro Ala Lys Cys Gly Leu Pro Pro Val Ser Cys Gln
            100                 105

<210> SEQ ID NO 122
<211> LENGTH: 95
<212> TYPE: PRT
<213> ORGANISM: Oryza sativa

<400> SEQUENCE: 122

Met Ala Val Thr Arg Thr Ala Leu Leu Val Leu Val Leu Ala Gly Ala
1               5                   10                  15

Met Thr Met Thr Met Arg Gly Ala Glu Ala Gln Gln Pro Ser Cys Ala
            20                  25                  30

Ala Gln Leu Thr Gln Leu Ala Pro Cys Ala Arg Val Gly Val Ala Pro
        35                  40                  45

```
Ala Pro Gly Gln Pro Leu Pro Ala Pro Pro Ala Glu Cys Cys Ser Ala
        50                  55                  60

Leu Gly Ala Val Ser His Asp Cys Ala Cys Gly Thr Leu Asp Ile Ile
65                  70                  75                  80

Asn Ser Leu Pro Ala Lys Cys Gly Leu Pro Arg Val Thr Cys Gln
                85                  90                  95

<210> SEQ ID NO 123
<211> LENGTH: 99
<212> TYPE: PRT
<213> ORGANISM: Antirrhinum majus

<400> SEQUENCE: 123

Met Ala Ala Met Lys Ser Ile Val Pro Leu Val Met Leu Thr Val Leu
1               5                   10                  15

Val Ala Gln Ser Gln Leu Ile Thr Gln Ser Glu Ala Gln Thr Cys Ser
                20                  25                  30

Ala Ser Leu Ala Asn Leu Asn Ala Cys Ala Pro Phe Val Val Leu Gly
            35                  40                  45

Ala Ala Thr Thr Pro Ser Ser Asp Cys Cys Thr Ala Leu Gln Ser Val
        50                  55                  60

Asp His Glu Cys Leu Cys Asn Thr Leu Arg Ile Ala Ser Arg Val Pro
65                  70                  75                  80

Ala Gln Cys Asn Leu Pro Pro Leu Ser Cys Gly Gly Lys Leu Ser Trp
                85                  90                  95

Thr Asn Cys

<210> SEQ ID NO 124
<211> LENGTH: 94
<212> TYPE: PRT
<213> ORGANISM: Capsicum annuum

<400> SEQUENCE: 124

Met Ala Asp Val Lys Ser Ser Val Val Ser Leu Phe Leu Leu Gly Leu
1               5                   10                  15

Leu Val Val Val Leu Gln Ser Gly Val Ile Glu Cys Gln Pro Gln Ile
                20                  25                  30

Cys Asn Pro Ser Leu Thr Ser Leu Asn Val Cys Ala Pro Phe Val Val
            35                  40                  45

Pro Gly Ala Pro Ser Ala Ser Ala Glu Cys Cys Thr Ala Leu Gln Ser
        50                  55                  60

Ile Asn His Gly Cys Met Cys Asp Thr Met Arg Ile Ala Ala Gln Ile
65                  70                  75                  80

Pro Ala Gln Cys Asn Leu Pro Pro Leu Ser Cys Ala Ala Asn
                85                  90

<210> SEQ ID NO 125
<211> LENGTH: 102
<212> TYPE: PRT
<213> ORGANISM: Solanum lycopersicum

<400> SEQUENCE: 125

Met Ala Ser Val Lys Ser Ser Ser Ser Ser Ser Ser Ser Phe Ile
1               5                   10                  15

Ser Leu Leu Leu Leu Ile Leu Leu Val Ile Leu Gln Ser Gln Val
                20                  25                  30

Ile Glu Cys Gln Pro Gln Gln Ser Cys Thr Ala Ser Leu Thr Gly Leu
```

```
                35                  40                  45
Asn Val Cys Ala Pro Phe Leu Val Pro Gly Ser Pro Thr Ala Ser Thr
 50                  55                  60

Glu Cys Cys Asn Ala Val Gln Ser Ile Asn His Asp Cys Met Cys Asn
 65                  70                  75                  80

Thr Met Arg Ile Ala Ala Gln Ile Pro Ala Gln Cys Asn Leu Pro Pro
                 85                  90                  95

Leu Ser Cys Ser Ala Asn
                100

<210> SEQ ID NO 126
<211> LENGTH: 96
<212> TYPE: PRT
<213> ORGANISM: Arabidopsis thaliana

<400> SEQUENCE: 126

Met Ala Ala Ser Ser Lys Tyr Ser Ser Met Ser Phe Met Lys Val Ala
 1               5                  10                  15

Met Met Val Ala Leu Val Leu Val Ala Ala Thr Val Val Asp Gly
                 20                  25                  30

Gln Ser Cys Asn Ala Gln Leu Ser Thr Leu Asn Val Cys Gly Glu Phe
                 35                  40                  45

Val Val Pro Gly Ala Asp Arg Thr Asn Pro Ser Ala Glu Cys Cys Asn
 50                  55                  60

Ala Leu Glu Ala Val Pro Asn Glu Cys Leu Cys Asn Thr Phe Arg Ile
 65                  70                  75                  80

Ala Ser Arg Leu Pro Ser Arg Cys Asn Ile Pro Thr Leu Ser Cys Ser
                 85                  90                  95

<210> SEQ ID NO 127
<211> LENGTH: 95
<212> TYPE: PRT
<213> ORGANISM: Glycine max

<400> SEQUENCE: 127

Met Ala Ala Ser Pro Lys Ser Leu Leu Ser Leu Ile Leu Leu Leu Leu
 1               5                  10                  15

Val Val Val Ala His Gly Thr Gln Ile Ala Met Ala Gln Ser Ser Thr
                 20                  25                  30

Cys Thr Thr Gln Leu Ser Glu Leu Asn Val Cys Ala Pro Phe Val Val
                 35                  40                  45

Pro Gly Val Asn Thr Asn Pro Ser Ser Arg Cys Cys Asn Ala Leu Gln
 50                  55                  60

Ala Val Asp Arg Asp Cys Leu Cys Ser Thr Ile Arg Ile Ala Ser Gln
 65                  70                  75                  80

Leu Pro Ser Gln Cys Gln Ile Pro Ser Leu Gly Cys Ser Ala Asn
                 85                  90                  95

<210> SEQ ID NO 128
<211> LENGTH: 97
<212> TYPE: PRT
<213> ORGANISM: Medicago truncatula

<400> SEQUENCE: 128

Met Ala Gly Pro Val Ser Met Arg Cys Gln Val Ala Leu Val Leu Val
 1               5                  10                  15

Leu Val Val Ala Leu Gly Thr Lys Met Glu Met Gly Glu Ala Gln Thr
                 20                  25                  30
```

```
Thr Cys Pro Thr Gln Leu Ser Asn Leu Asn Val Cys Ala Pro Phe Val
            35                  40                  45

Val Pro Gly Ser Pro Asn Thr Asn Pro Ser Pro Asp Cys Cys Thr Ala
 50                  55                  60

Leu Gln Ser Thr Asn Pro Asp Cys Leu Cys Asn Thr Leu Arg Ile Ala
 65                  70                  75                  80

Ser Gln Leu Thr Ser Gln Cys Asn Leu Pro Ser Phe Gly Cys Val Leu
                85                  90                  95

Asn

<210> SEQ ID NO 129
<211> LENGTH: 100
<212> TYPE: PRT
<213> ORGANISM: Vitis vinifera

<400> SEQUENCE: 129

Met Ala Ala Ala Arg Ser Leu Phe Ser Leu Arg Phe Arg Ala Thr Leu
 1               5                  10                  15

Leu Leu Val Val Ala Leu Val Ala Arg Thr Gln Met Ala Trp Ser Gln
            20                  25                  30

Pro Ser Ala Cys Ser Thr Gln Leu Asn Asn Leu Ser Val Cys Ala Pro
            35                  40                  45

Phe Val Val Pro Gly Ala Pro Asp Ser Thr Pro Ser Ala Asp Cys Cys
 50                  55                  60

Thr Ala Leu Gln Thr Ile Asp Asp Ala Cys Met Cys Ser Thr Leu Arg
 65                  70                  75                  80

Ile Ala Ser Arg Leu Pro Ser His Cys Asn Leu Thr Pro Val Thr Cys
                85                  90                  95

Asp Val Asn Ala
            100

<210> SEQ ID NO 130
<211> LENGTH: 95
<212> TYPE: PRT
<213> ORGANISM: Triticum sp.

<400> SEQUENCE: 130

Met Ala Pro Ser Thr Phe Pro Arg Ala Leu Leu Ala Val Ser Leu Val
 1               5                  10                  15

Leu Leu Val Val Gly Gly Leu Gly Pro Ala Ala Glu Ala Gln Pro Pro
            20                  25                  30

Gly Arg Cys Val Pro Gln Leu Asn Arg Leu Leu Ala Cys Arg Ala Tyr
            35                  40                  45

Leu Val Pro Gly Ala Ala Asp Pro Ser Ala Asp Cys Cys Ser Ala Leu
 50                  55                  60

Ser Ser Ile Ser Arg Asp Cys Ala Cys Ser Thr Met Gly Ile Ile Asn
 65                  70                  75                  80

Ser Leu Pro Ser Arg Cys Asn Ile Gly Gln Val Asn Cys Ser Ala
                85                  90                  95

<210> SEQ ID NO 131
<211> LENGTH: 489
<212> TYPE: DNA
<213> ORGANISM: Zea mays

<400> SEQUENCE: 131
atgggttgcc ctcgagagcg agctgctgtc gccaatgtgt tcatcgcctc gctcttcctc    60
```

```
ctagctggtc aagcggtgat gcatcaggca gcacacgtcc gcaagctgct caacaacacc    120
agcaccggcg gcggtcactc tcgcggggct gctgctgtgg cgtccgcgga tgacgacgac    180
ccctgctcgg aggaagtggt ggaggtgttc cagggcagcg ccgggagcct gcccaacggc    240
atcccgtcct acagcgtgac catcaccaac acgtgcctgg actgcaccgt gtgcgacgtc    300
catgtctcct gcggcgagtt cgcctccacg gaggtcgtcg accccagcga tttccggcgc    360
ctgtcgtacg gcgattgctt agtcaggaac ggtggaccga tcggcccggg cgagaccatc    420
tccttccagt actccaactc tttcgtttac aaaatggacg tcgctgcggt ctcatgcgtc    480
gacgtatag                                                            489
```

```
<210> SEQ ID NO 132
<211> LENGTH: 162
<212> TYPE: PRT
<213> ORGANISM: Zea mays

<400> SEQUENCE: 132

Met Gly Cys Pro Arg Glu Arg Ala Ala Val Ala Asn Val Phe Ile Ala
1               5                   10                  15

Ser Leu Phe Leu Leu Ala Gly Gln Ala Val Met His Gln Ala Ala His
            20                  25                  30

Val Arg Lys Leu Leu Asn Asn Thr Ser Thr Gly Gly His Ser Arg
        35                  40                  45

Gly Ala Ala Val Ala Ser Ala Asp Asp Asp Pro Cys Ser Glu
    50                  55                  60

Glu Val Val Glu Val Phe Gln Gly Ser Ala Gly Ser Leu Pro Asn Gly
65                  70                  75                  80

Ile Pro Ser Tyr Ser Val Thr Ile Thr Asn Thr Cys Leu Asp Cys Thr
                85                  90                  95

Val Cys Asp Val His Val Ser Cys Gly Glu Phe Ala Ser Thr Glu Val
            100                 105                 110

Val Asp Pro Ser Asp Phe Arg Arg Leu Ser Tyr Gly Asp Cys Leu Val
        115                 120                 125

Arg Asn Gly Gly Pro Ile Gly Pro Gly Glu Thr Ile Ser Phe Gln Tyr
    130                 135                 140

Ser Asn Ser Phe Val Tyr Lys Met Asp Val Ala Ala Val Ser Cys Val
145                 150                 155                 160

Asp Val
```

```
<210> SEQ ID NO 133
<211> LENGTH: 804
<212> TYPE: DNA
<213> ORGANISM: Zea mays

<400> SEQUENCE: 133
atgggttgcc ctcgagagcg agctgctgtc gccaatgtgt tcatcgcctc gctcttcctc     60
ctagctggtc aaggtctgta catgtgctgc atctgtcttc acccctgttg ctgctatcag    120
ctagcccatc aaatataaag cttattatta gccgttgacc ctctctgatc gtctcttgca    180
cgcacgataa tggctggcca aacaattcat gatcacgga gcagctgctg tttcctgtca    240
tcgtccgtct cccaccgtag cggtgatgca tcaggcagca cacgtccgca agctgctcaa    300
caacaccagc agtaagaaac taagactggc accatccatg gtttcttttt cattttttg    360 attcggattc atccctgcta tatgttctat atctacactc ttgtatgtat gcatacatgt    420
```

```
gttgatggat cgagatcagc cggcggcggt cactctcgcg gggctgctgc tgtggcgtcc    480
gcggatgacg acgacccctg ctcggaggaa gtggtggagg tgttccaggg cagcgccggg    540
agcctgccca acggcatccc gtcctacagc gtgaccatca ccaacacgtg cctggactgc    600
accgtgtgcg acgtccatgt ctcctgcggc gagttcgcct ccacggaggt cgtcgacccc    660
agcgatttcc ggcgcctgtc gtacggcgat tgcttagtca ggaacggtgg accgatcggc    720
cccggcgaga ccatctcctt ccagtactcc aactctttcg tttacaaaat ggacgtcgct    780
gcggtctcat gcgtcgacgt atag                                           804
```

<210> SEQ ID NO 134
<211> LENGTH: 10000
<212> TYPE: DNA
<213> ORGANISM: Zea mays
<400> SEQUENCE: 134

```
gagatgattg cagatgtttt ggaaaatttt gagatttatc ttcatcagct gacccctaac     60
gccatcgtta ggcttagcgt gtatatctgg gctctccgaa gccaagggt ggagccgctc    120 gccgaagcct tctgccgagt acatgaactt cactatcata cgaaggctag agaagacgga    180
ctgcatgaga acttcggctg ctataatttt gcttaccgca aagacatgaa gacaccggtt    240
gttagctatc acactaaatg accaactggt tggaaatctg aatggtttta tgttaagatt    300
gatgagaaaa aggagaagct agctagttca gagcctgctg gagctaacct tcgggctgac    360
taggcctcag tgcaacatga cgccaggggc accatgccca gatgctgtga gcgagtttag    420
agttgtgtct gaacatattg gaactaggga tttagttcaa gaatacttag ccaacagagt    480
attcccaacg ctaagggaat ggggtatgcc gaagcttgaa ggagagaaga agaagaatga    540
actcattcgg ctgccctatc attttaaaag aaacacttca agaaccttg ccaagaatgg    600 ttgaatacaa ttgaagttat gtgcaatgag attttgggca aatatacgga aaagaagat    660 cagttgctga ctgcagcctt cggcgcccga ccgaatcgaa gattgaatcg gtaatggat     720 gtcctgaatt ttgaatatcc taactatgag cgattgaaca agggtgccga agggcaaaaa    780 agaaaagaa ttgttagtgt tgtgggcaga caagctgcaa gaatggtgaa agaagatgaa    840
gaaattctga agaagaaaaa attgagccct gagccaaagg cagctgctcc gaagaaaagg    900
aaagctgcgg ctctgaaaca gaaggcgact gatatggatg aagagactcc ttcaacacct    960
tctgctgccg acgtggaaga aattctaaag gtaatgactg aatccttgcc tatcaagcta   1020
agtccactcg ggccacatct gacgaagatt ttacagaaga gaaggagct ctcggcagcg    1080 aagaagtctg ctgggccaaa aaaacgaagg attattactg taactgaagc tattgaagaa   1140
acaccaccgc cagcttcgcc gtcaaaggca ccagctgtcg agagtgctac agctaccaaa   1200
gctgcaccta ctgaagctgc agctgccaaa gctgcaacga ccgaagatgc aaatctagaa   1260
agcacattct ctgatattga taaaatgctt ctggatatgg ccgcagaaga agctgctaca   1320
gccaccgaag agaccatggc cacagcgcct ggaaaagaga aggagatggc cgaagatact   1380
tcagaattgt caaaaacttg ctcggacaag aattgtcaaa agctaaaaaa gaagagttga   1440
gagactatgc catatcctgc gggtatcagc caggggcgct actcttcggc tgtattgacg   1500
atgaaagctt aggttgtctc cgagacagaa ctggagcaaa ggttatcggt actctgtcga   1560
agagtattgg tttcccgaag cttgggaccg atatcagccg ctaccgacga cagcatatcg   1620
tcggtagttt attctattct aatttcaagg taaaacttt cttcgacttt tcattgtttt    1680
taacaacgaa ggtgttttct aacgaaggtt gcttctgcac agagtatgct attaagtaaa    1740
```

-continued

```
gctttgagga tgcaacagga ccttgaagat aaaaaatgtg aagttataat tgaaggttta   1800
gagagcaaaa taaaagatca agcagctgct cttgaaaaga aagatttcga actttagata   1860
gtggagggtt tactggcaga agctgaagcc aaaattacga gattgaatag tgaactcctc   1920
tcaaagtcag aaagcttcga acaagaaaag cagaaatttg attcgaagtt tgaggctgaa   1980
gtcaaaaaaa gttcaaattt gcaaaaatca ttgaaagaga ttcaagataa atgtctagag   2040
ttcagcaatc gatgtgtgca gcggctaaag caggtcttca actcggttgg agccagctct   2100
gagaaattca gtccttcggt tgaagacctt ccagggacct tcgaacacat tgagggcaaa   2160
gttgatgctc ttggtgaagt tatagctaga cacggcaatt tctgtgccct gctagcttct   2220
cagggcacag ctgttgcctt catgaagtct ggttgcacac atgggaaaat tgttaataga   2280
ccaaacttca gtttatcact agcagattta attgatatcc ttgctcgaag cataggaaac   2340
agatttataa agcaaatctg gacgaagggt gggcgaagcc tcgctggtga cgaagctcga   2400
agtcacctca agccggtaat aaaatcatac cttgtgctta ccttttcctt gaaacttgaa   2460
ttttccttat aatgctttaa tatgtacagg atgacgaaga tgaggaacac tgagccgaag   2520
cttagcagat gatccgaagc tcaacagatg gtgaagaagc tcaaatacct agttgtggaa   2580
aaactctaag aaaactcttg tattaacctt tataaagaat attgtaattt aaggattaga   2640
ttctactttg taaatttgtc cataccttgt aatatatttt tacctttcca ccaatgtatg   2700
aagtgctttg atgtggacga aacttgtatt ttttgagccg aaggcgaaaa acaccttccc   2760
ttcttttcgt acacaacgaa gcataaatct gcttttgaag ctgtatcctt atagccgaag   2820
caactatctg tatctgtatg atatgatgat gatgttgatc ctatgtatgt ctaaatgaat   2880
gtttatgaat gcaatgtatg atgtaatgta tcgtgcaaat gaatgcccaa acacacgcat   2940
acgaagcttc atccataacc ttcattccct taggaatgac tgaaatctct ttgccgttta   3000
tttttcggct gcaccgctta ttttttggtg taagttctgc atccccttag gaacatcttt   3060
tgaacttctt cgtcttctat ttaggtggta ttcgcgttga cttttcgtgc ttcgtcttat   3120
atttcggcgg tatttggctc cttaggaacg tcttttgaac ttctttgcct tctatttcgg   3180
cggtattcgc gttggctttt cgtgcttcgt cttatatttc ggcggtattt ggctctgcat   3240
tcccttagga atgacttgtg agcagaaaac ttacgctgcg ctcccttagg aacggctttt   3300
tgtagcttcg tcatgctctg catcccctta gggacgactt tcgagcttct ccctgttttt   3360
ttctttttct ctacactcga tggtgcatac tcagatttta tatttacata ttttgggga    3420
ttttgctctc gtggagctga ataagaaagg aaaaattaca aattatggcc ctattaaaaa   3480
cctttctccc cctttggaaa ggaaaagggt gccatagaaa aataaaaaag attacatcaa   3540
tctatacata ataccgtcga agctcatccg cgttccaaga tctaggaata tcattgtcat   3600
ccatatcttt taatctataa gaaccaggcc ttgacgaaga tactactaga aaaggtcctt   3660
cccacttcag ctgtagtttg cctactgtgt ccgggttagc cactctccga agcactaaat   3720
gccctggctt gatatttttc agtcggactt ttctgtcgcg ccattttatt gtttcaactt   3780
gatatttatt aatattttcc atagtctaaa gtctgacccc ttctatagta tcttttgcca   3840
catgataatc agcttcgtct tcagtcgaag atgttgttct tattgacccc gttttagcct   3900
cttctgggtt atagcttcgt caccaaataa taacttgaat ggagtaaaac ctgttgatct   3960
tgatacggtc gtattgtggc tccacaccac tttaatcaat tcttcttgcc actttcctct   4020
gggctgatta aaaattaact tcattattcc tgtcattata atatcatttg ctctttcgac   4080
```

```
aagtccattt gactctggat gtctgactga cgcaaaatga atctttgtgc cgatttgatc    4140
acagaattcc ttgaaagctt cggcatcaaa ctgtgttctg ttgtccacaa ttatagcctt    4200
tggtacgccg aagcgacaaa caatgttttg ccaaaagaat tctagactta tgaccgaagt    4260
tattgtggcc aaaggcttcg cttcaatcca cttggaaaaa tattctacaa ccaccacaac    4320
atatcttaaa ttgccttgtg ctggtggaag tggacctaac aaatccaggc cccatctttg    4380
caatggccag gttggttgta ttagttgggt taacgatgaa ggttgtttct ggtctcttgc    4440
atatttttga cattttttg cattttttgaa ccagatccgt tgcatccgaa gctgccttcg    4500
gccaataaaa tccttgtctg aagaccttcc ctagcaaagg cctatatcca atgtgagatc    4560
cacacaaacc tgcatgtatt tccttcatca gctctatagc ttcggttctg gataaacact    4620
tgagaagtgg agagctgact ccatgtttgt ataactcccc ttctattatt acatatggtc    4680
ttgttcttgc ctccattctc ttattataag cttcgtcatc tgaaaggcag ttactttgga    4740
ggaaagattt atctcagtcc tccaatcttc actatgaaca ggagatatag tgagcactgc    4800
tctttcgaga agttccaccg aaggtgctct tattgtctca aaaaatactt ccaaaggtag    4860
aggtagcccc tgtgccgctg acttggctag cagatcagcg tgctcatttt ctcctcgtgg    4920
aatattctta atagaaaacc cttcgaaaga ggcttcaagc cttcgaactg tgtccaggta    4980
tttctcaagt ttcggatctc ttgccttgga actcttgtca acatgaccag aaatgacttg    5040
ggagtcggtt ttaaggaccg ccttcttat ccccattgct tttaacttcc gaagccccaa    5100
tagtaaagct tcgtattcag caatattatt tgtacaactg aaatcaagcc ttattgcata    5160
acatgttctg actttggaag gtacaactaa aacagcagcc gcacctgccc cgaaggttcc    5220
ccaggaaccg tcgcagaaca ctatccaagc ttcgacatct ttatttgctt cttcctgagc    5280
ccccggcgtc tagtcaacga tgaagtctgc taacgcctgg gactgaattg aggatctatg    5340
cacataatca atgctgaatt tgttgagttc cgcagcccac tttgcaatcc ttccagtagc    5400
ttctttgttt cttatgatat ccttcagagg ctgtgatgaa ggaacaatta tatagaatgc    5460
ttgaaaataa tgccgaagct tcctggaggc cattaagaca tcatacaaca ccttctccaa    5520
ttctgtatag tttttctttg ataaacttaa aacttcggag acaaagtata ctggggcttg    5580
cttttaatt tgtccttcca gtttctcctg cacaagcgcc gcactcactg cagagtgcga    5640
agctgtcaca tataatagta acggagcccc tggcgcgggt ggagttaatg ttgttagatc    5700
aatcaagtat tgcttcagct cttcaaaggc tttctattga gctgggcccc attgaaagac    5760
ttcggctaac tttagtattt caagaatgg caagtttctt tctgctgatc tagatataaa    5820
tctattcaat gaagccagtc ttcctgccaa ccgttgggc cccttctttg tgcttggtgg    5880
ttccattcga aggatggatt tgatcttgct tgggttagct tcaatcccca tcgttgaaac    5940
tagacagcca aggaacttac ccttcttcac ttcaaagaca cattttcagg atttaattct    6000
aggctagctt gcctgaaatt agcaaatgtt tcttgcagat cagtgatatg cttttctttc    6060
ttcgtgcttt ttactatgat atcatcaaca tatgttagca catttctgcc tatctgggaa    6120
tgaaggactt tggctgtcat tctgctgaaa cttcctccag cattttgag cccctcaggc    6180
atccgaagat aacaataggt gccactggga gttatgaagc tagtcttcgg ttcatcctcc    6240
tttttcatcc aaatttgatg atatcctgag taacaatcca gcagactcat aagttctgaa    6300
gaagctgcta catccacaag agagtctatc cttagtaatg gaaacttgtc cttcggacag    6360
accttgttga gatccgtgaa atcaatacac attctccatt tgccattagc cttcttcacc    6420
ataacagtat tggctagcca ctctggatat tttacttctc taataacacc agcactgaga    6480
```

```
agtcttttga cttcatttcg agcaccttca gctttgtcat cagacatttt ccgaagcctt   6540
tgctttcttg gcctgaaaga cgagtcgaca ttgagtgaat gttcaatgac gtctctgttt   6600
acaccacaaa gatcattggc cgaccaagca aaaacatctt tgttgttgaa taaaaacctt   6660
atcaaggttt tctcctattc ttcagatagc tgagacccca gtagtacctt ctgctctgct   6720
atgtcttcac atagaagcat aggctttggt tgatcagccg aagcagcctt ctctcttctg   6780
tacttgtact gttcacaggc ttcagttcca tctatattgt ggattgcttt tgagtctgtc   6840
cagtttcctt cggcttttct agcagcttcc tgactaccat gaacagcaat gagcccttgt   6900
tccgaaggta tcttcatgca tagatatgct ggatgaagta ttgcttcgaa agcattgagt   6960
gtcccacgac caatgattgc attgtagggg tattccatat caacgatgtc aaacacaact   7020
tgttcagtcc ttgtgttgtg gacgaagccg aaggtcactg gcatcgtgat tttgccgagt   7080
gctgcaatct gcctttctcc gaagccataa agagggtgtg tagcatcatg aatcttgtcc   7140
tctggctctt gcatctgtct gaaggcctta gcaaatatga tgtctgctgc actgcctgta   7200
tcaaccagaa cattatggac caaaaatccc ttgatgacac aagatatgac catagcatca   7260
ttatgaggct aatccttgag ctgaaggtcc tcctaggaga aggtgattgg gatgtgggac   7320
cattttgact tgatgaaggg tccctgcacc ctaacatgtt gtaccttct ctgagcctcc    7380 ttcttctgct tcttgttggc cggttctaag catgaaccgc ttgttatcgg gagcaccagc   7440
ttcgtagccg aagctacttc agcttgattg ttgaacgaag ccatcagctc aacagtggaa   7500
gtaagttcac cggaggtggg cgccaatgtt ggggacttgt tctcaaatgc tatgagttaa   7560
gaacaaggca acacgaagta ttaaatgtca atatccttcg tccttcgaag cattatttcc   7620
cttaggatat aacgatcttc ggacgaaggt caggaagaac gtaccttcat catcatggta   7680
tatgataatg aaagacaaag catatgaaac acaaagata acataaataa tcatataaaa   7740
tcatccacat atcttcatta tataaacttg aataatcaaa gacaaatttt aattacattt   7800
gtaccttcgg tttgatagaa ggcaaaaatc cgagcgttgc gcatgagtga atacaagata   7860
gcgtgaacag tacagggta ctgttcatct atttataggc acaggacaca gcctgtgaga    7920
aattacattc atgccctta caaatgttta caatcataat acaagttttc acgggccgat    7980
tggtcatttc atctttaagt cggtgcatct ggaaatgtac tccgaagctc tctaattgat   8040
agcttcggct ttgtgtcaat cttccgaagg tgtttcttct tatggggcct tcggcggcga   8100
agcagacccc caacactacc ttcgtccgga caggctaggg cgaagaccat caaggactcc   8160
ggagatcgaa caaccagga ctacgaagac catgcaatgt aatcttccac attgtaaaag    8220
ggggtcgtgt atagtcggtc catgtcacag ggtcccgacc gtagaccgcc acactggcaa   8280
ggctgataga gggttggccc atatctgtaa ttgattacgc tgtaatgacc caccataacc   8340
ctccaagggg gaatattccg ggaataacgt agcaaactga gggtgtaatt gtccttggca   8400
aggcagggcc gaccctcggt tacctataaa taccctcgta ctgtaccatt gcggggacg    8460 gaggaaacta gttgccctaa caccttgcgt ctactggcat caaaccgttt tctattctcc   8520
caccgtttga gcttggctga ccacgggtta gcaagtccca atagtcgtca ttgacgagat   8580
cgacgagaag gacgtgagta gtcgcgtgaa gacgcttctc aaaatcctta atcattctct   8640
cctggtgaag gatctcaaag gcgatgggtt ctggagacct gctctctcga ttgcagatgc   8700
acgtcggcac ttaagatgaa gagaactacg ttggcggcgt agctgagcag agaggaaaac   8760
ctaactcgag ttggattggg atggtgtcta gcaagggctg ataggctcct tatatatata   8820
```

```
gggccacatc cacggaccga taagctcgcg atccaatcta attgtgatcc gataaggtcg    8880
tcattggata actatctccc ttgccgtaca taggcttttg cgatttttct agaatttaat    8940
tgaatttctg aattaggtta aacccataaa tccaacatat attatcacga taattgtaga    9000
gtctagtatt gcgaaaccat ggttttataa aacattatta ggccttcttt ggaatgtaga    9060
attggtaaaa tgtagaaata ggaaaaacgt aggaatagag ttgcatgaca attacagtcc    9120
tacaggaatt taaaatacag aaaaacttct aaatagagtg tatggatgca acacaggaaa    9180
acatagcaat tagagaagag acagacacaa atgaaagttt ccaagaaatt ggacctctgg    9240
ttagaattcc tccaaaatct actagaatga gtcatcttat agaaatttta taggatttat    9300
agcttaatca tttatttcaa agagctacat aggaaaattt catatatgga tggttccatc    9360
ccttcaaaat aaaaaaaaac tttttttatg ttcaaagggg gtagcaaacg tgcccatata    9420
tactctacga tcaggctggc ttcgcccctg gcgcaggagg cgaaggtaga gaggaaacgg    9480
cagccgcatg acgaacttgc gcgctactaa ttattacggg agcgcgcata gggaagggaa    9540
gcgggcggac gagcgcgcgc cggggaggcg attttggcgg cggcggcagc agcttcaagt    9600
ctcaacgcat ttcccgtatg aatttaatta gtgcctcgct cggtaactta caaaaggacc    9660
aagactcttc ggaattgcgc tttgacctca aggtaaacg atatgtaagt tcgtgtcact    9720
aaacattaat cacacagagg gatcatcagt tcgtgcacgc acagttaaca gttcacacca    9780
atacaaatac tactacgaga gatccgtata gccaacccgc gcggggtccg tctcagcgtc    9840
ggcctcgact gcgaatggaa gcccagctac cgcagctgga cggcgacgat atctaaggtg    9900
cccatatccc cccagttctg cgccggcgcg gcacccgctg ccgctgcctc ttcttcctcc    9960
agctcgatct gcgccgaacc ttcgtcgatc ggccgcgcgc                         10000
```

<210> SEQ ID NO 135
<211> LENGTH: 1996
<212> TYPE: DNA
<213> ORGANISM: Zea mays

<400> SEQUENCE: 135

```
tgcatctgga aatgtactcc gaagctctct aattgatagc ttcggctttg tgtcaatctt      60
ccgaaggtgt ttcttcttat ggggccttcg gcggcgaagc agaccccccaa cactaccttc    120
gtccggacag gctagggcga agaccatcaa ggactccgga gatcgaacaa accaggacta    180
cgaagaccat gcaatgtaat cttccacatt gtaaagggg gtcgtgtata gtcggtccat    240
gtcacagggt cccgaccgta gaccgccaca ctggcaaggc tgatagaggg ttggcccata    300
tctgtaattg attacgctgt aatgacccac cataaccctc caaggggaa tattccggga    360
ataacgtagc aaactgaggg tgtaattgtc cttggcaagg cagggccgac cctcggatac    420
ctataaatac cctcgtactg taccattgcg ggggacggag gaaactagtt gccctaacac    480
cttgcgtcta ctggcatcaa accgtttct attctcccac cgtttgagct ggctgacca    540
cgggttagca agtcccaata gtcgtcattg acgagatcga cgagaaggac gtgagtagtc    600
gcgtgaagac gcttctcaaa atccttaatc attctctcct ggtgaaggat ctcaaaggcg    660
atgggttctg gagacctgct ctctcgattg cagatgcacg tcggcactta agatgaagag    720
aactacgttg gcggcgtagc tgagcagaga ggaaaaccta actcgagttg gattgggatg    780
gtgtctagca agggctgata ggctcccttat atatatagg ccacatccac ggagcgataa    840
gctcgcgatc caatctaatt gtgatccgat aaggtcgtca ttggataact atctcccttg    900
ccgtacatag gcttttgcga ttttttctaga atttaattga atttctgaat taggttaaac    960
```

```
ccataaatcc aacatatatt atcacgataa ttgtagagtc tagtattgcg aaaccttggt    1020
tttataaaac attattaggc cttctttgga atgtagaatt ggtaaaatgt agaaatagga    1080
aaaacgtagg aatagagttg catgacaatt acagtcctac aggaatttaa aatacagaaa    1140
aacttctaaa tagagtgtat ggatgcaaca caggaaaaca tagcaattag agaagagaca    1200
gacacaaatg aaagtttcca agaaattgga cctctggtta gaattgctcc aaaatctact    1260
agaatgagtc atcttataga aattttatag gatttatagc ttaatcattt atttcaaaga    1320
gctacatagg aaaatttcat atatggatgg ttccatccct tcaaaataaa aaaaaacttt    1380
ttttatgttc aaagggggta gcaaacgtgc ccatatatac tctacgatca ggctggcttc    1440 gccctggcg caggaggcga aggtagagag gaaacggcag ccgcatgacg aacttgcgcg    1500
ctactaatta ttacgggagc gcgcataggg aagggaagcg ggcggacgag cgcgcgccgg    1560
ggaggcgatt ttggcggcgg cggcagcagc ttcaagtctc aacgcatttc ccgtatgaat    1620
ttaattagtg cctcgctcgg taacttacaa aaggaccaag actcttcgga attgcgcttt    1680
gacctcaaag gtaaacgata tgtaagttcg tgtcactaaa cattaatcac acagagggat    1740
catcagttcg tgcacgcaca cttaacagtt cacaccaata caaatactac tacgagagat    1800
ccgtatagcc aacccgcgcg gggtccgtct cagcgtcggc ctcgactgcg aatggaagcc    1860
cagctaccgc agctggacgg cgacgatatc taaggtgccc atatccccccc agttctgcgc    1920 cggcgcggca cccgctgccg ctgcctcttc ttcctccagc tcgatctgcg ccgaaccttc    1980
gtagatctgc cgcgcc                                                   1996

<210> SEQ ID NO 136
<211> LENGTH: 1257
<212> TYPE: DNA
<213> ORGANISM: Zea mays

<400> SEQUENCE: 136
cactcggatg tgccgccctt tgcaaaatgc agcgatccct tgttttttt tcttttctt      60 gaggaactgg cttctttggt ttgtatttcc ggtcgggttc atcaggattc ttcaaacaaa    120
aaaaaaattg gtagcaataa tggcttcttg tcacaactca ttcagacaac gaagaaaaac    180
aggaaacacc ccatatcatc tacgtgggct acgggcgtcg gtttcgtcgt cggctgcgca    240
tcaaagccca gtgcgcccgg cccaaggtcc gtgaatgcgc ttgctgggct gagctggtcc    300
gggccgcgcg gcccatggtc acgttcttgc tggggtccgg tcaggttccg tcctgtcctg    360
tcctgtcctg cgatgtccac catggcgcgg cggcgcgcac gcgggctgag gagggaacgt    420
gcaccgcgcc gcgacaccac gtgccggcgg ccgctcgcca tgagcaccgc ctcagcccca    480
atgggagtgg gacgccgctg gccagctcgg acggacaagc tccggcggtg gcccaccggt    540
gccgggtgcc gtgatctcct gtgcagcgcg cacgcactac tgcgtgtgca tgcttgcatg    600
gtgtggaggg ggatggaatg gattgcttgc attgcatgcc ccgtgtgcca tgtttagaaa    660
ctactctctc tatttgcgtt gccaaggttt cagtaaacca gctttgtcgg aatccattct    720
cagttctctg tacctagtat acgatgaaat caaaacactc atccggttaa gaatcgcaat    780
cccatctctt ggccttccgt agatgatccg gtaaggagac atgcatgctt actaacgcag    840
cagtttattt atatatgggt gtatctattg tatttaggac tgtttcacga acgacctagc    900
tacctgacct gccacagaca atccgacgcc gtgaagccac gtcagatgtc aaggtgggcc    960
caaccggaca cagctgtgca ctgcgtatgt ctctgggggt atctgtgctc ctctggcttt    1020
```

```
acggagagat gagatctgtc tgctgtgcct agcttgtgca aagctgcacc agtaagctca    1080
tggtgtctcc atcttccgtc caccactaca ctgccccaga tactgtgaga tcttttctcc    1140
accgtccggc cggcgtgatt cttcgtcgct gctggcgatt aacccgaacg atccgacgct    1200
acagctagct agctagcctt caagctccat atagctacca ctgcgcgcgc cctctgt       1257
```

<210> SEQ ID NO 137
<211> LENGTH: 1078
<212> TYPE: DNA
<213> ORGANISM: Zea mays

<400> SEQUENCE: 137

```
caggaaacac cccatatcat ctacgtgggc tacgggcgtc ggtttcgtcg tcggctgcgc      60
atcaaagccc agtgcgcccg gcccaaggtc cgtgaatgcg cttgctgggc tgagctggtc     120
cgggccgcgc ggcccttggt cacgttcttg ctggggtccg gtcaggttcc gtcctgtcct     180
gtcctgtcct gcgatgtcca cctaggcgcg gcggcgcgca cgcgggctga ggagggaacg     240
tgcaccgcgc cgcgacacca cgtgccggcg ccgctcgcc atgagcaccg cctcagcccc      300
aatgggagtg ggacgccgct ggccagctcg gacggacaag ctccggcggt ggcccaccgg     360
tgccgggtgc cgtgatctcc tgtgcagcgc gcacgcacta ctgcgtgtgc atgcttgcat     420
ggtgtggagg gggatggaat ggattgcttg cattgcatgc ccgtgtgcc atgtttagaa      480 actactctct ctatttgcgt tgccaaggtt tcagtaaacc agcttgtcg gaatccattc      540 tcagttctct gtacctagta tacgatgaaa tcaaaacact catccggtta agaatcgcaa     600
tcccatctct tggccttccg tagatgatcc ggtaaggaga catgcatgct tactaacgca     660
gcagtttatt tatatatggg tgtatctatt gtatttagga ctgtttcacg aacgacctag     720
ctacctgacc tgccacagac aatccgacgc cgtgaagcca cgtcagatgt caaggtgggc     780
ccaaccggac acagctgtgc actgcgtatg tctctggggg tatctgtgct cctctggctt     840
tacgagagag tgtgatctgt ctgctgtgcc tagcttgtgc aaagctgcac cagtaagctc     900
atggtgtctc catcttccgt ccaccactac actgccccag atactgtgag aacttttctc     960
caccgtccgg ccggcgtgat tcttcgtcgc tgctggcgat taacccgaac gatccgacgc    1020
tacagctagc tagctagcct tcaagctcca tatagctacc actgcgcgcg ccctctgt     1078
```

<210> SEQ ID NO 138
<211> LENGTH: 833
<212> TYPE: DNA
<213> ORGANISM: Zea mays

<400> SEQUENCE: 138

```
catatagcta ccactgcgcg cgccctctgt gaagagcgct agctcgatct ggactggacc      60
tctccctcgg cgacaacggc tataaatacc tgctgctcgc caaccctca tccatcaacc      120 atagcagcta agctagtgat ttccgagctt cacatcacca gtagagctcc acacgtactg     180
ctcacccagc cagtcttgtt gctgctgcta gctgctagct tgctcgagct agttaggtcg     240
agcgagggcg cagtgagcca acttagctag tgaggcatat ggcggccatg gccaggtctg     300
atgatcagtg cgaccgtctt gtgtgggcat tgcccatgga gcgtccgctc agggactgcc     360
gcggcaccgg cgacgacgac gacgacgact acgacgtcgc cccggctgct taataattaa     420
ctaacggatc aaaatctgca gtatgcatgg catgtgatct agagttagag attgtacaag     480
cgatgacgat gagtgagtat gtgtgtgccg aacgaggtct cgagatgata gatgtatatc     540
atcatttctt gcctccaagc tagctagcta ataataactt agggcttgtt tgggagcaag     600
```

```
ccottagttt actctcttgt agtagtaata ttaattaatg tgtagcttgc ctagctagtt     660
agaaataaaa aaggcgttca tgacgaatga gcagctaatg atgtactaga gttgataagt     720
caggataatt gctgactcca tgtatttata tggatgcatg ttaattggtg taacaaaggt     780
tatgtgttgt ttactattac aacgactttg taaaggaaat aaattgaagg acg            833

<210> SEQ ID NO 139
<211> LENGTH: 680
<212> TYPE: DNA
<213> ORGANISM: Zea mays

<400> SEQUENCE: 139
gggtggagcg cacgagtgat atttgggtgg agcaggaaat tcatgaattt tggggtgctt      60
aacacgacct tcgttactct tattccaaag aaagaagggg tgatgaggtg aaggatttta    120
ggccaattag catagttcat aactttgcca agattttagc taagcttttg gctatttggt    180
tggctagcat actacacgac atggtccaac aaaatctcac tatctacatc agcaaaaaca    240
gttacgtgtg cttctcagac ttgatatttc tgatgtgttc gattcaatct cttggccttt    300
tctcattgaa gtcttgtaag ggtttggact ttggacagat ttagagggat ttgaatcagt    360
ggtcttcttt agacttcatc gactaggttc tccttaacgg ctcccaagga cagcccattt    420
gcaccggcga gggctcggac gggaggatcc gctctcttca atgtcgttca tcttggttat    480
ggactttctt gggtttttg ctacaaaggc aggaaattaa ggatttcttc aacctcttga    540
ggctaggatg gtgcagcacc atatctctat tatgtggatg atgtggtcat tttcctttga    600
ccaattacga ttcttcatct tttggggctg cttttggttt gcgtaccaat atgaataaaa    660
gtagtatctt tcccattaga                                                 680

<210> SEQ ID NO 140
<211> LENGTH: 144
<212> TYPE: DNA
<213> ORGANISM: Zea mays

<400> SEQUENCE: 140
atggtccaac aaaatctcac tatctacatc agcaaaaaca gttacgtgtg cttctcagac     60
ttgatatttc tgatgtgttc gattcaatct cttggccttt tctcattgaa gtcttgtaag    120
ggtttggact ttggacagat ttag                                            144

<210> SEQ ID NO 141
<211> LENGTH: 47
<212> TYPE: PRT
<213> ORGANISM: Zea mays

<400> SEQUENCE: 141

Met Val Gln Gln Asn Leu Thr Ile Tyr Ile Ser Lys Asn Ser Tyr Val
1               5                  10                  15

Cys Phe Ser Asp Leu Ile Phe Leu Met Cys Ser Ile Gln Ser Leu Gly
            20                  25                  30

Leu Phe Ser Leu Lys Ser Cys Lys Gly Leu Asp Phe Gly Gln Ile
        35                  40                  45

<210> SEQ ID NO 142
<211> LENGTH: 10000
<212> TYPE: DNA
<213> ORGANISM: Zea nays

<400> SEQUENCE: 142
```

```
gtccccaagg ttttcgaatt ctaggagggt ttcctcatca ctgcttttcc ctgatcctat      60
tggcgaagtt catggcggca gaattcgtga ctgttacaaa tttcaaaatt cgaattttaa     120
ctggtctcgg actcgcaacc ttcaatggcg tcccgttcgg gttcgagggc ctgctgggcc     180
actgggccca cctgtcttcc gctgtcattt ctgtaaggtg aggggcact tggaattatt      240
ttgtccctct aagaaatctt ctttcggttt tcctttagcc tcgttccctg cctttgggag     300
tcgtgccatt ttggtgggaa atcgaaaatc tctggaccac agtacctggt ttcgctcccc     360
cgtggtgtct ctgatcggtg acccctagc tatagttgct tcgaggagtt cgcccgggag      420
gtattaaaaa atccgaatcg tcacctctcc agtccctgac gctttctttg ggtgtcactt     480
catcaaaacc ccaaactgct ccttcttcga ctgctggttg gcgatcctcg cttccttctc     540
cgatggcgta taggtgtgtt gatcccgagc ccttcttcc gccgggcttc agcgcttcga      600
tggtcctgca ctgggaggtt atggccaggt cagtgactag gcgtctcccg ccaatgcatg     660
aggattgggc tattatcaat attcaacctt tacctgatca tgaggtcact ttccgacggt     720
gagggatgtg gttagagaat atttggtgga gcaccggtgg gttggggtgc gggatatcca     780
gcggtcgcac ctgggtcagg ttctggttca gtttagcagt gtgcttgaaa gagacaatct     840
tgtcttgctt ggtccgcagc aatacctcga tgccaccttc actgctcagc gacataatga     900
tgcttggaac cgcagggcgc ttttttttaa tcgcgaatgc tggcttatgt tgttgggatt     960
cccccttgat tatcgttcct cagagtactt gcaggctgct attggctcct ttggtagatt    1020
aatcttgtgg gaggaagaca gacacaatgt ttataggact atgcttaggg ttcgggtcac    1080
gtctctcgag gaggtcccgc agttcattgt tttttcggag gctgatggtt ttatcggtga    1140
ctcgtggaca gtgcagtgtg aaatcattca acaaaccctt gctgggggc cagccccaag     1200
atgaagatct ggtgccggtg gtcccggaag atggtcagca gctccctctc gcgttctttg    1260
gtctgggtca gcctatgcct gctgcggggt gggatctcaa tttcccgcca gaaggcaatg    1320
ttcaagttca gccagcagac aatattcaag gggattggga ccagtggatt gttaatgacc    1380
cacctacgca gtagccccag gaggacctgc cacctgacga gcagcaagtc aacaatcagc    1440
attcgggcct gtcctcggat agttcttcta gtcccattca tggtgttccg gtgcagaatg    1500
ggcagattct tgatgacctg gacgtggttg ggccggtgct acgctttaat gcccctgccc    1560
tccctgcttt gggtgatgct cctatgaatg ggctccagga ggttgacggc ccaccaaacc    1620
agggagatct ccatgtgccg ggggatattc ttatccctga tgcccagcca gaggaacaaa    1680
tcaacaatgg tcccaacaat atggtgttga actatatgtt ctcccaggat tggcagccag    1740
accctgtttt actgagtcac ttggaaagga aaggaatgc ccaattctat aggatctggg     1800
ctaactattt tgctcccgct ggtaagccag aattctctgt gcagatccct aagaagtggt    1860
ctcctttctt catgtctaac ctgctacatg aagattcttt caactggtcg aaatctttct    1920
tgtcttcaga tattccttct gctttgctgg agcctgagtc tgagactcac ccttttgcca    1980
tccccaagaa atgtcctaat ggcaagttcc ttgaatctgt cctctcagaa gaatctactg    2040
gcaacgtctc tgctccgtca gactcggcct cttcccccctc caagcctaca gttgtggaat    2100
ctgacctgag gagaagtaag agactgcgtg atgctcgggc tgggttcagg caggactctt    2160
gccagaaaaa gaactgtctg atgtgtcaac ataagtttga gggccctcct tccttatcag    2220
ccaaggccat caaaaaccta ggggaaaat tttgcaatct gtcagaagtg gatctgtctg     2280
ataaagctct gaagaagaag aagaatccct ctggatgtgt tggccccaat aagccaggga    2340
```

```
aaaaagacaa tgaggataag aaacaggact ctgcagatga agacaactaa tttgatggtg    2400
ttgctccggg tgggggatt ttgcaggact ttacttcgtc gggcttttg gctgtttctg      2460 ccccggcgta tttgttttgt tgttgcggtg tcaaactttg tggtttctgg ttatttcgtt    2520
gtgccctgtt ctaacagata cttgtttgcc cacccagtaa ttgggtttgg gtttcctttc    2580
gtcgacaaac ctgattatgc ccccgatgaa tagtcacaac gcagttattt tttctgaatg    2640
gtctgtttta agcttaatg tctgtgggat caattcagtg gttaaagtga atggtattca     2700
ttgtgcgatt agggaatcca gatgtgatat tatctgcttg caggaaacca agaaggaatt   2760
tttcgacagg gctgatctca gaaagttttg tcccaactcc tttgactcac tcgcttttgt    2820
ccccttggtg ggaaattcgg gtggtttcat tattgtttgg aatagctcga agttggtggg    2880
cagtgttatt taccagaatg attatgctct ttcggttgaa ttttctgcta attcgtcgaa    2940
tgaatcctgg attgtcacga atatttacgc gccctgttct ccgcatggga aaattgaatt    3000
cctaaattgg ttctccaata taaatatgcc ctcggaaaaa cttttggctga ttgttgggga   3060 atttaatctt actcgtaggc ccgaaaacag gaatatcgct gggggccctt agcctgatgt    3120
tgaaatttaa tgagtcaatt agccagcttg atctgatgga aattcctctc catggtctgt    3180
cctttacttg gtcgaatagg caaagagagc cccttcttca gagactcgat tggttttca    3240 tctcgcaaga atggtcagtt ttctaccccg acactcacgc aactacgctg cctagggaca    3300
tctccgacca tgttccttgt ctgatttctt tcaagtcaaa ggtccccaag cctaagcttt    3360
ttaggtttga aaattctggg ctgcaatttg aagatttat gtctgtcttt caaaattctt     3420
ggactggtca gccaattctt tgtgacaaag cgaagaactt aacagcaaaa ttcaagtaca    3480
ctagaaaggc tctcaaagaa tggcagcggt ctctgccaaa aattgataaa acagtgagac    3540
aaattaagtt gctattgag ttcattgaca taattgagga ggatcgtgac ctttcgattg      3600
aagaatggaa tttctgggag cttttgcaaa ccaaaattgc gggtctgctt caaattcaga    3660
aaatttattg gaagcaacgg gcttccatca aatgggtcac tgatggagat atctgctcta    3720
gatttttttc atgctcatgc aacggtaaag cataggcata atacaattgt gttgctctct    3780
gatgacagtg ggtcaatctt ttcagagcac gatcataaag ctaaccttct gtggaatgtc    3840
tttaaatgtc gattgggttc ttctgaattt ttggagaatg ttttttatctc tcaggcctgt   3900 taattttgca agatggcttg caatggttgg atgcgccttt ttcaaggcaa gaaattgata    3960
gcattgttgc agctctccct tcagacaaat ccccggggcc tgatggattt aataccaatt    4020
ttatcaaaaa atgctggccg gttatttctc aggacttcta cgacttatgt gaccaatttt    4080
accatgggga tgtctgtctt agaagtatta atggctcttt tatcgttctg atttcgaaga    4140
aggaaaatgc tcatttagtg ggagatttta ggccaatctc gcttctaaat aatagtatga    4200
aaatcatcac taagttgctg gccaatcgaa tgcagacagt gatgacttcc cttgttcaca    4260
aaaatcaata tggcttcatc aaaggaagaa ccattcatga ttgcttggcc tgggcgtatg    4320
aatatatcca tttatgtcat atctctaaaa aagaaatcat cgtgctcagg ttggactttg    4380
aaaaggcctt tgatactgtt gagcatgaac tgatcctcca agtgttgtct catagaggat    4440
ttgggcccaa atgctgggc tgggttagga atatccttca gtctggtacg tcatcggtcc    4500
tacttaatgg cgtcccaggg aaaactttcc attacaagcg tggggtcagt caaggagacc    4560
ccctctcgcc tttattattt gttttagcgg cagatctgct tcaaagtatc atcaataaag    4620
cgagacaaca agacttactc cagttgcccc tgactaagaa ctgtggccaa gatttctcga    4680
ttgtctaata tgttgatgat acattattga taatggaagc ttgccccagg caactatttt    4740
```

```
tcctcagagc agttcttaac tcttacgtaa cctcgacggg gctcaaagtg aactatataa    4800
atcaagtatg taccccatca atgtttgccc agcaaagatg gagattcttt ctagaacatt    4860
caactgtcag acatgatcaa tgcctttcac ctaccttggt gtccctctag gcctgtcaaa    4920
acctagaatc cgtcactttt tatcacttat ccaaaggatt gaaaggagac tgtcttgtac    4980
atctgctctc ctctcccagg cctgaagatt ggagctagtt aactctgttt tttcagcttt    5040
cccgactttt ctgatgtgca cgctgaaaat tcctgccacc acagtccaga agatagatgc    5100
ttaccggaaa cattgtcttt ggagaggaaa cgatgtgaac tcaaaaaaac caactctagc    5160
tgcccggtgc atgattactc agccaaagag caacgggggc cttggagtgg tcagattgga    5220
aacgcacaac aaggctttgc ttttgaaatt tttaaacaag ttcttcaata atcatgactt    5280
accttggtaa atctcgtttg gaacaactat tacaggacag acagactacc tagctgctta    5340
agtattggat cttttttggtg gaaaagtctg cttagtcttg ttcaagattt caagggattg    5400
gcagccccaa ccattggcaa taggagaact atccttttct gggggatat gtggaataag    5460 ggcattccag ctcagcaata tccggaatta ttttcctttg tttgcaacag caaactctct    5520
atcaaagaag caaagcaaaa agatcatctt tttgagattt ttcagcttcc tctgtctgtg    5580
taggcctacg agcagtatct tgagttaaat gaggcctggg gacaaatcat tgtgatcaac    5640
gcaaaggaca cttggaaaca catttgggga tcaaagattt tctctacaaa aaagacttac    5700
aggcatatga tgggtcatta tcaagttcat cagattttca aatcgctttg gaaaaataaa    5760
tgtcaaccaa aacataaagt ttttttattga ctgtggctaa aaaacagatt caacacaaga    5820
aatatgctga ggagaaaaaa catgacactt gagtcataca cttgcgaaaa ctgcatctgg    5880
cagaaggaga aaactcttta tcatctcttc ctcagatgca acttcgctaa ggcctgctgg    5940
aattcaattg gtttggtgcc ccctagaatt gctaatccag aggaggctgc agcaaatctc    6000
aagcagcagc tcaatgttcc cttctccatg gagatcatta ttctcatgac ttggagcatt    6060
tggaagtgtc gtaatgcttg ctttttcag aacaaagatc caacggtgca gcaatgcaag    6120
catgagttca caaagaatt actcctggtc actcatagag ctctgggtag atttggttcc    6180
gccatcccgg aatggcttca gcaatggcag tagtaactca ccctaacctc ctgtaattcg    6240
tctacttgta tgttctaagc actgcttttt tagttataat aaaattttca gtagggctc    6300 cctccttctt aaaaaaactt attttaaact aaatattaat tttaaataac gaatgggccc    6360
tatgactagg catcggcaaa atgcaaacgc tcacaatctt ctccgcaccc ccccccccc    6420 ccccctccgt acatgtcgcc tctatagcca aacgggccgc gcttgcatgg gtagacggta    6480
gactcggcac ggcagcaatg gtacacctag gctggagcac aggcagttgc aagaggaaga    6540
gcacgaagaa agatcttggt gccgcatggc cagcttcccg ccgccgcctc catcgttggc    6600
gatgacagca gcgtctgggc ctatccgaga gtttccgcta ggccattctc tctcttccca    6660
tctacttgat tgctaattgt gctcatggtt tgtcttttttt ttaatcgtgg aaggaggagg    6720
aggcgataga ggacgacgtg cgtccctgcc gagatctgga gagcaagaag ccggaggcgg    6780
ctaggactgc caagcgttgg gaagtggtaa gatccttgga gttctctggt cagccgacgt    6840
caccggcgtg tcctcactgg tgtgttatag ccacgcctgt tccttactag ggattgtttt    6900
tttccaaata tgcaagaaaa tgtgatgtcc acactagaat ataaggatga tgcttgctat    6960
atatgagtag ggtcctgacc acatggctaa ttttcttgat attcatgtta aatttggaga    7020
atttcttatg ggtttcatga agcttgtttg tagttaatta aacagcctcc tggtatatag    7080
```

```
gacaacgaat gtatattgtt atgtatttgt atttattatc ctgaagcgta gtttgtactt   7140
tgtagaatga tattttgcag caccgtagtc tgaacttggt gttggtgtca tattgaatgt   7200
ttttccttcc catttttttt acctaaaaat ggtgaatgag tgcaaatttg tcttgatgtt   7260
cagacaattc tgcgacaatg aactgaagct tatgctgatt gctgactgat tattcaacta   7320
gttgtcactt gtggctacta cctctttctt gattagctac tggatctttt tttgttcagc   7380
ttgtgcatgg taagttaggc aaatatcaat caattgcatt caccagcatg tggccatatt   7440
tgcaggacat caattaggct cacattgatt agcttattgg aaattatatc cctcatggtt   7500
gctctcaaat gtggactagt gttcctaact gcatttaaac tttgagttcc tacaagtatg   7560
tatctgatcg ttttttgaaa tctcattata atgttatatt tttgaacctg aacatctggt   7620
tgtaatgcag gatatcaact agtgggatta caaattattc aaatggcaac gctgtttaac   7680
ttaagctctt tactttaagc atgctcttaa gtatatattt ctcactttga tgcctgaaaa   7740
ttctgattct ttgttttgtg aagctacatt gagtcatgag gtcaccagtc tctccgcaat   7800
tgctagggaa agatttgctt tgatttatca cttccccaga ccctactcat gtgggagccc   7860
cttcggcatt aggtctgcca ttttttcttg atttgtgaag ttacaaccaa ttaacatgtg   7920
atctgcagac ctgaaatact aaatgaagtt tgttattaac tattaaaatt tcatttgaaa   7980
caatcataac gattttgtt gacgttattt ctctacctca aatgtggctt gtgcagcctt   8040
cagcatagtt gttacttcaa atttcattcc aattacataa aaggtaggcc ttatcttctt   8100
cttttatgct gattggtttg taccagtgat agaagttcta attttggta tctgatcctt    8160
tctcagctgc tgaaaagttg cccacgcagc aacatgtctt tttataagcg gttacctaat   8220
gattttgtc acataggtcc catctccct tttacactta catggtttcg acttatttt     8280
catttataca tggttgattt ggtggcccat accatttta gtccaatatg atattttgta   8340
tatatgcagt aattggttta aaatttata tttctaatga tcaattatta cattttcctg   8400
gaagatattt ttttgtattg aactctaatt ttcaaatgcc aatttaatta tggtgaaaat   8460
attcctgtga taaaatcatg taacctggac atatgattgt cccccagata tatgttctcc   8520
gtttatcagg gattttgcat ctgttgcctg gacttgattc cctgtcgctg atctgtgtta   8580
agtgtctact ctggaaccat agacttgatt ccctgtcgct gatctgcgtt agatgtctac   8640
tcggcacccc tgatgtgttg ttgtgcttcg aattccacta cattgcaatg taaagatcca   8700
ttctttacta aaactatttc cagcagttta tccatattca tcctcatatt caaacttcac   8760
tctgcaaaca atacagtcta tattacaaaa cagtgctagc atggtagttt acaagtgtga   8820
ccatatgtga actgctggag gcggtctaat atattaactg ctagcatggt agtttacaag   8880
tgtcatgcat catcagtgaa ctggccaacc tggtgaatca aataaactga actcaaagta   8940
aattagtaaa ttaccacacc aagactgcta gtctgctagt gattatagtg ctgattgctg   9000
aaagtggtag tattttatgt accaggctca gttatctata taccattgac taggtgttta   9060
attgcttact tgcttagcta agggcatgta cagtggagag acaccaaaac ggttctctaa   9120
gcacaggaga caactaagag actctattgt acaatggagt gtctataaac gtagtctatt   9180
aataaataca taattaaatg tatttgtata gcatcagatc gatagaacag acgacaaatt   9240
ggtacagtgg gaagtgaggc gtctgttgtt acttggttta cgagccagag gcgtctcttc   9300
acggagagac ggctctaaga tttttttgca ataacccccc taaacaccct taagagccct   9360
ccacattaaa caccactgta catgcccctaa tactccctct gtttcgtttt agttgtcgct   9420
ggatagtgca aaattgaact attcaatgac aactaaaaag aaacggagag agtattactg   9480
```

| | |
|---|---:|
| gagatgcaca cttttcatc ttggatctct tggtgctcgc aggatttggt aagtcctccc | 9540 |
| catagtttat atttatgtgg ccttaatcta ttaaccagtc taatgatttt gattccagct | 9600 |
| tcaaatctat catttcggtg ttctagtttc acctactgat ttgatgtttg ggtctattac | 9660 |
| atatgcttat caacatgtga tttacatatc ctgcagttcc tgtgccaata acatatcctt | 9720 |
| atcaacatgt attttaccat gtcgctgtac tgtgcatata ccaatattaa tggttctttt | 9780 |
| taggaggaag ctagagtttg gggtggagcg cacgagtgat atttgggtgg agcaggaaat | 9840 |
| tcatgaattt tggggtgctt aacacgacct tcgttactct tattccaaag aaagaagggg | 9900 |
| tgatgaggtg aaggattta ggccaattag catagttcat aactttgcca agattttagc | 9960 |
| taagcttttg gctatttggt tggctagcat actacacgac | 10000 |

<210> SEQ ID NO 143
<211> LENGTH: 1996
<212> TYPE: DNA
<213> ORGANISM: Zea mays

<400> SEQUENCE: 143

| | |
|---|---:|
| ctaactgcat ttaaactttg agttcctaca agtatgtatc tgatcgtttt ttgaaatctc | 60 |
| attataatgt tatatttttg aacctgaaca tctggttgta atgcaggata tcaactagtg | 120 |
| ggattacaaa ttattcaaat ggcaacgctg tttaacttaa gctctttact ttaagcatgc | 180 |
| tcttaagtat atatttctca ctttgatgcc tgaaaattct gattctttgt tttgtgaagc | 240 |
| tacattgagt catgaggtca ccagtctctc cgcaattgct agggaaagat ttgctttgat | 300 |
| ttatcacttc cccagaccct actcatgtgg gagccccttc ggcattaggt ctgccatttt | 360 |
| ttcttgattt gtgaagttac aaccaattaa catgtgatct gcagacctga atactaaat | 420 |
| gaagtttgtt attaactatt aaaatttcat ttgaaacaat cataacgatt tttgttgacg | 480 |
| ttatttctct acctcaaatg tggcttgtgc agccttcagc atagttgtta cttcaaattt | 540 |
| cattccaatt acataaaagg taggccttat cttcttcttt tatgctgatt ggtttgtacc | 600 |
| agtgatagaa gttctaattt ttggtatctg atcctttctc agctgctgaa aagttgccca | 660 |
| cgcagcaaca tgtcttttta taagcggtta cctaatgatt tttgtcacat aggtcccatc | 720 |
| tccccttta cacttacatg gtttcgactt attttcatt tatacatggt tgatttggtg | 780 |
| gcccatacca tttttagtcc aatatgatat tttgtatata tgcagtaatt ggtttaaaat | 840 |
| tttatatttc taatgatcaa ttattacatt ttcctggaag atatttttt gtattgaact | 900 |
| ctaatttca aatgccaatt taattatggt gaaaatattc ctgtgataaa atcatgtaac | 960 |
| ctggacatat gattgtcccc cagatatatg ttctccgttt atcagggatt ttgcatctgt | 1020 |
| tgcctggact tgattcctg tcgctgatct gtgttaagtg tctactctgg aaccatagac | 1080 |
| ttgattccct gtcgctgatc tgcgttagat gtctactcgg cacccctgat gtgttgttgt | 1140 |
| gcttccaatt ccactacatt gcaatgtaaa gatccattct ttactaaaac tatttccagc | 1200 |
| agtttatcca tattcatcct catattcaaa cttcactctg caaacaatac agtctatatt | 1260 |
| acaaaacagt gctagcatgg tagttacaa gtgtgaccat atgtgaactg ctggaggcgg | 1320 |
| tctaatatat taactgctag catggtagtt tacaagtgtc atgcatcatc agtgaactgg | 1380 |
| ccaacctggt gaatcaaata aactgaactc aaagtaaatt agtaaattac cacaccaaga | 1440 |
| ctgctagtct gctagtgatt atagtgctga ttgctgaaag tggtagtatt ttatgtacca | 1500 |
| ggctcagtta tctatatacc attgactagg tgtttaattg cttacttgct tagctaaggg | 1560 |

| | |
|---|---|
| catgtacagt ggagagacac caaaacggtt ctctaagcac aggagacaac taagagactc | 1620 |
| tattgtacaa tggagtgtct ataaacgtag tctattaata aatacataat taaatgtatt | 1680 |
| tgtatagcat cagatcgata gaacagacga caaattggta cagtgggaag tgaggcgtct | 1740 |
| gttgttactt ggtttacgag ccagaggcgt ctcttcacgg agagacggct ctaagatttt | 1800 |
| tttgcaaata accccctaaa acaccttaag agccctccac attaaacacc actgtacatg | 1860 |
| ccctaatact ccctctgttt cgttttagtt gtcgctggat agtgcaaaat tgaactattc | 1920 |
| aatgacaact aaaagaaac ggagagagta ttactggagt tgcacacttt ttcatcttgg | 1980 |
| atctcttggt gctcgc | 1996 |

<210> SEQ ID NO 144
<211> LENGTH: 10000
<212> TYPE: DNA
<213> ORGANISM: Zea mays

<400> SEQUENCE: 144

| | |
|---|---|
| gctgacgtct cctttgcttc cgtaggggc tgagaaccgc cgtcatcatg ggagcacgcg | 60 |
| gggtgccatc attacttgtt tacctgggcg agccagatgg gacgccggtc ttgttccccg | 120 |
| tagcctgagc tagctagggg tagggtaatg atgtaccccc tgtggcgtgg tcggtccgag | 180 |
| cccaaggtcg ggcgaggcgg tgactcctct gaggtcgagg ttgaggccga gccctggggt | 240 |
| tgggcgaggc ggagaccgtc ttccgaggtc gaggttgagc ccgagccctg ggtcgggcg | 300 |
| aagcggagat cgtcttccga ggtcgaggcg ggggccgagc cctagggtcg ggcgaggcgg | 360 |
| agaccgtctt ccgaggtcga ggttgagtcc gaacccctagg gtcgggcgag gcggagaccg | 420 |
| tcttccgagg tcgaggcggg ggccgagccc cggggtcagg cgagggagct tcctatggcg | 480 |
| cctgaggctg gactcggctg ctgtcagcct caccctagcg agtggcacag cagtcggagc | 540 |
| agggcaggcg gccctgtttt cctgtcaggt aagtcagtgg aggggcgaag tgactgcggt | 600 |
| cacttcggcc ctgccgactg aggaacgcgt gtcaggataa ggtgtcaggc gatccttgca | 660 |
| ttgaatgctc ctgcgatacg gtcggttggc gaggcgatct ggccaaggtt gcttcactgc | 720 |
| gaaacctgcc cgagctgggc ctcgggcgag tcgaaggtgc gcccgttgct tggggaggcc | 780 |
| ctcgggcggg gcgtgaatcc acttgggtct actgttcctg ctcggcggcg acgacaagat | 840 |
| ctgcgtcggc ggcgttgcgt ttcgctagcg acttcttctt gcccttcttc ttcgtgccgc | 900 |
| gctgagcgga cgcctcgggg acgtcttcct gctgacgccc ctgaggctgc ttatccttcc | 960 |
| ggaagatggc ctcgaccgcc tcctgaccag aggcgaactt ggtggcgatg tccatcagct | 1020 |
| cgctcgccct agtgggagtc ttgcgaccca gcttgctcac caggtcgcgg caagtggtgc | 1080 |
| cggcgaggaa cgcaccgatg acatacgtgc ttcggaaatc gccggatgta gtcccgcagg | 1140 |
| gattctcctg gctgctggcg gcagctttgg agaccccagg agttcccagg gcgcacgtat | 1200 |
| gtgccctgga agtttccggc gaaggctttg actaggtcgt cccagttgga gatctacgca | 1260 |
| ggaggcagat gctccagcca ggctcaggcg gcgtcggaaa gggacagggg gaggttgcgg | 1320 |
| atgatgaggt tgtcatcgtc cgttccaccc agctggcagg ccaaccggta gtccgcgagc | 1380 |
| cacagttccg gccttgtttc ccccgagtac ttggtgatgg tagtcggggc tcagaaccgg | 1440 |
| gtcgggaacg gctcccatcg tatggcccgg ctgaaagctt gcggaccggg tggttcgggc | 1500 |
| gagggggctct gatcctcccc gctgtcgtag cgtcccccac gcctggggtg gtagcctcgg | 1560 |
| cgcaccttct cgtcgaggtg ggctcgacgg tcgcggcggt ggtgctcgtt gccgaggcaa | 1620 |
| cacggggctg caggcgttgc gtcccgcgtg cgcccggtgt ggactgaggc ttcccgcatg | 1680 |

```
aattgggaag tcatggcgcg atgctccggg gggtacccct gccttcggga ggcagagctt    1740
tcggcccgtc ggaccgcggc atcctctagg agattcttga gttctccctg gatacgccgc    1800
ccctcggagg tggatggctc tagcatcgct cggagtagta ttgctgctgc agccaggttc    1860
tggccgaccc cactagaagt cgggggcagc cttgccctgg catcgtcagc gacgcggtgc    1920
tggacgtcct gggccagatg acgcgcttct ccggctagtg ctcggcctgc ccactcctgc    1980
ccgatgtttt gctggagctg cacaagttgt cctgcttcct cgtcgagctt ggcctacatc    2040
tcgcggattt gctcgagctg tgtgtcctga ccccccacag ggaccgggac cacagctagc    2100
tcccgaagga tgtcaatgcg aggcgcagac ctaagggatc gtcgtcctcc ggcataccaa    2160
ggtggttgcc ttcgtcgaaa ccccctagat cgacgtggaa acattcgtga cttgggccac    2220
agtcctcgtc gtcaaggctg tggccaccat cggagtaatc ggagaggcag tagtcacatg    2280
cggccatgaa gtctcgcatg gcactgggt  taccgagcct ggagaaatcc caaccagagt    2340
cgggcttgtc atcttcctcg gaacccgggg gccgtaggt  cgacgcggtc gtcagtcggt    2400
cccaggttga ccacatatgg tacccggaa  ggttaggata tgcctttatg aaagcgtcca    2460
ccgaagcggg gtcgcttggt gggtcgaagc tgaatctaaa aggcacaggg tggaaaacgg    2520
acggtacctc ttgatcgacg gatggtgacg aagtcgcgtc ggggacggac tgcaccgtta    2580
tcttaggcac gaggctaacg cccagcaagt ccttcgcgag cgtgctggcg tcatccgtcc    2640
gcttggggtt ggcgtgttgc ggggaaacga tgctcgtctt cgtctcagaa gcgaggtcaa    2700
cgcccgacgt gtccccgct  ggggcgccgg cgtcatcgac tcgctcgaca gccaacgagg    2760
tgccgcctcc tgcttgtcca tggttgcccc gcctcctcct cctgcggcgg ggaaggtgac    2820
aggacaggcc cggatgctgc tcttccgcca tgggggaaaa acgtcgttga ttccgccgcc    2880
gtcgggcggg ctgacggccg tcgttgtcgt tgtcgcgcgg cggaggaagg agtaccatgt    2940
cgtagctgct gtcgagggac atgaactcga gactcccgaa acggagcagc gtcccaggct    3000
ggagaggttg ctggagacta cccatctgga gcttgacggg aagctgttcg tcaacacgca    3060
gcaggcccct acctggcgcg ccaactgtcg gcgtttcgac cccggggggt ccctggaccg    3120
acgagtaaat tgtcgctgca tgcccctgcc cagatgggtc ggcgcgagac gaaacacaag    3180
gggggggggg gagaaccgcg gcttcgtgtt gtcctacgcc cagggtggat gcgcttgcag    3240
tagggggtta caagcgtccg cgagggagag agagagagag agagcctgcc cgtcagcccg    3300
tcctccctcg cggccacctc ctcgtacgag ggccctggac cttcctttta tagatgtaag    3360
gagagggtcc aggtgtacaa tggggggtgt agcaatatgc taacgtgtcc ggcagagagg    3420
agccagagcc ctatgtacat gccgacgtgg ctgtcggaga ggtgctagtg ccctgtgcat    3480
gtgatgtcat ggccgtcgga ggagcgcttg agccctgtag aagcacagct gtcgggctg     3540
tcgggacctt gctgacgtct ccttgcttcc gtaggggct  gagaaccgcc gtcgtcatgg    3600
gagcacgcgg ggtgccatca ttacttgttt acccggcga  ccagatgggg acgccggtct    3660
tgttccccgt agcctgagct agctaggggt agggtaatga tgtacccccc tgtggcgtgg    3720
ttggtccgag cccaaggtcg ggcgaggcgg tgactcctct gaggtcgagg ttgaggccga    3780
gccctagggt cgggcgaggc ggagaccgtc ttcgaggtc  gaggttgagg ccgagccctg    3840
gggtcgggc  gaggcggaga tcgtcttccg aggtcgaggc ggggggccgag ccctagggtc    3900
aggcgaggcg gagaccgtct tccgaggtcg aggtcgaggc ggggggccgag ccccggggtc    3960
gggcgaggcg gagcttccta tggcacctga ggctggactc ggctgctgtc agcctcagcc    4020
```

```
tggcgggtgg cacagcagtc ggagcagggc aggcgacact gttttcctat caggtcagtt    4080
agtggagggg cgaagtgact gcggtcactt cggccctgcc gactgaggaa cgcgcgtccg    4140
gataaggtgt caggcgatcc ttgcattgaa tgctcctgcg atacggtcgg ttggcgaggc    4200
gatctggcca aggttgcttc actgcgaaac ctgcccgagc tgggcctcgg gcgagtcgaa    4260
ggtgcacctg ttgcttgggg aggccctcgg gcgaggcgtg aatccacctg ggtctactgt    4320
tcctgcccga ggctgggctc agggcgaggc gagatcgtgt cccttgagtg gacgagcct     4380 tgacctgaat tgcgcccatc aggcttttgc agcttgtgct gatggtgatt accagccgag    4440
tttaggagtc ttggggggtac ccctaattat ggtcgccgac actatttgaa ttgcgcacaa   4500
atttcatgtc attagtgtca atttgtgaga tatggggttg atgatatata tgttgttcgt    4560
tctcatgtaa ttattgtgca ttaatattta tcgaataatt tatacgccgt cgcaacgcac    4620
gggcacatac ctatatatgt ttaattcttg gacgaagaga gattgaacga gcccatcagc    4680
aaacgatcga ggacggaata gtagtccctg agatgaacat ttgtctcaaa ttctagacat    4740
tcatatacta cacaaacaaa cgaagcgatg gctacgatac ctctttaact atatatgttt    4800
aaatggacgg accgggctaa cattacctga gcacgactat gcctgatacg aattgcgtgt    4860
cagtccagtc cggcctgatc aaattaagga ccataaaat gagttatatg ggccgtgtcg    4920
tgattgtagc ccataagaga actagaacaa gacaacacga ttaaggtaat atgattcctt    4980
ctccttctga tataccaagt gataacgtaa gtaaattaca aggagaaggt taagatagat    5040
acaaatattt tacgaggatc catagaaatg caacaataca tgaatagtga ttcatatttc    5100 ttatatttt taccattcac atgagtttac aaagatacct tcggatactt aaaggtgata    5160
caagaatgtc ttggattcaa gagcttcgga tgcagagcaa ttcaacaata tttcagtcaa    5220
ttgctcgggg cccctataca tggacattgt actactattt atagagacga catgacgtac    5280
accttcgtat aaaattacat ttatattccc aaatcatata catatgatct ataaagactg    5340
atgagggtgt agttgtcttt tcctcatgga agcgtgttgc gcacgtcgct tgggcttccc    5400
tttgtcctct gggttatgtg cttcggattt cgggcgcttc atcacgcttc gtccaagttg    5460
taatgccgaa gctgccacct tcttcttata cactacggat gctttcatga cgaagattaa    5520
tttattactc ctgaaacaaa cccaaagatg gctatgattt tattattttg agggccttcg    5580
cacaagtaga ccctcaacaa gcccggtggg cttaaccagg ccatgtcgcc tatgggctcg    5640
atagacacat tgtcactgta tatataagta gacaaaaatc tcaaacattt catatgaaga    5700
tcacaagagt cgaaaagcaa gatcaagtag tgaaaactta ttcaactcaa taattattgg    5760 agttttagt gcaatgctgc ctcattaaaa accttactag ataaaatccc acacctcatg    5820
agaagatcct agcaagaata agagtacatc caactcccaa atgttcaagt gtcaatagac    5880
tcatgaagtt cattacatca atagtttagt aaacatatga gtaaacaacc ccttttcaa    5940 gctcttccag ctcatgttgc cccttcttc tccttgtcct tgttcttgct actcacttca     6000
acaccaaggt acatgttctc aaaggttgat tgaagcttcc cggtctctag tgttttgcat    6060
atgcttgtct ataagctccc aatccttgat gtagcataag acatcaacca tatctgttgt    6120
aagcgttgtt gttgctcctc gagcaacctg gcaataagac taaaggtata ttatgaagat    6180
atggtgaaat aaggaacaat caaaacatct ttagcaagga gagaaaggac atcataagtg    6240
agcttatgcc tctgccacca attaagaatg aagtctactc caagttaggt gacaatatca    6300
ctgtctaggt atgaagagag ctcagagatg gatgcgatag tagatacaac aggagcagga    6360
ctacctggtc cccttcaaag aggagaagct agagacccac cacaatatca tcatcaccat    6420
```

```
aaatgtcatc ccatgcctct ttagccttac cctcacctcc acttgttggt acatgttgtc    6480
cacacaagag tgcttcacca aacttggatt catgcaacta aaatgtcttt attaacttag    6540
tacaaacaaa ttatggaaat ctagagtaat cattactagt tagactagtc aattacataa    6600
aaagtttatg aaaccccctc atcttagctc tatgatccaa aatgaaagaa aatacatata    6660
caatgggtat attcctcgag tattatagaa aattagttct cataggaata taacatgttt    6720
taggagtgga tcattctcaa aagcatttag atgtctacac attttcaata tatgatgcat    6780
cattaatgga gatgtggggt agtaaacact agaccgtgca atagttgaat catagaacag    6840
ttcaagaaaa gataacaact tatcaataat ataccaatga tctttagtta ataaaggaga    6900
accatctaat ctcaaaggat ggttgcttta gataaagata gaaaatgtgt ttttataagg    6960
aagaatatgt ttaaggatca agtagaattc catctaacat cgatgtcaac accaaacttg    7020
cgagggcgaa caccttgact caaacaaacc atcttgtatg ttggtttgaa gcattgacga    7080
atgtaatagt agttctaaac tcattaagat aagtcttcaa gtgcttcaaa ccaaatttaa    7140
ctcaaaatta atagtgtggc aagcacatcg ttgatgaaaa atactagtta aattttattc    7200
ttcatcatct atattaacat gatcaataga tgcaaagtca aggtaattag agaaaatagg    7260
tttaaggaga gagtaattat gtttgacgaa gcattgtcca gggtgatagc aaaaaattat    7320
ttgttatgtc ataatcatct actaccatgc aacatgttta gcaatattga accagtatg    7380 tgcgtcttca ataggcctta aaccaagtag cctttttttc caaacctcaa tcataattca    7440
cataatgagc aacaatacta atgcaatcct ctttgtccct accagaccaa atatcataag    7500
taagtgtcat agatgaaaca aagaatttca aagtttcaat tagactttcc atttggccac    7560
tgtaatgttt agttaagtct ctagtcattg tttgcatagg ggacttaata aatctaggat    7620
tatgcaaatg agtgatatac tcttgaaaag catcagactc accaaagcat agaggcagat    7680
cctcccagct atcaagtgac atagctcaat tcgtacaatt gaagcagaat aatcccattg    7740
ttgcatagaa ccattgggtt tgtacttaag tattgactga acaatgcccg cttgatcaag    7800
ttcgatctta gaattacaat attcttggtg ctagagcaag tgttcgttac tagagcaaga    7860
tctagtagac aagcttgcag tgtttgtaga tagaagagat ctttacctag aattttcatc    7920
tgtcttgtca tcagtagccg acgaaagtta gttaatttcc atcggtcata cctgaggccg    7980
acgaaaatta gctaacttcc atcagctact tttctattgg aaaagaaat acaaaaaaat    8040 tcctcgcttg tacatgcact ttcattggta gtacttcgta agctattttt gtagcaagat    8100
tgtaagttct attgatagaa ggtactctct atgttctaaa ttacaagata tattggcttt    8160
ttagacagtc aaaatgtctt gtaatttag aataaggaag tacttggtaa caaatttgtt    8220
ttttatgaaa tatattacat atataaatgt ttgcatatcc ttcgttatgg tcctacttgt    8280
tgacaaaaaa actatccaga gtacacaata gactccatca tcatgttgtt agttatagtc    8340
aagatagtca aaaggcatat ttggatcatc ttattcgaag ttcggatatg aaatcccattt    8400 ttcgagaggc ttcaaagtct agatataaaa tccgttttg agaggatggt ccatcacaaa    8460
ctagtctagc cggccggttc acatgccaat ttaccaaatt tctcaaatgt ttgcatatct    8520
attctatttt tataatcttg tacaatacat gcatgttaat ttgtagcacc tatttttccta    8580 tctaccatac cattgcgtcg aagcgaaact gtcgagcgcc gtaccaaaga atgaatcttc    8640
ataggatcct aacatatgtc taactgcgtg aacgaagttt ctctaaatta aagttattaa    8700
attcatattt gtgttctact gtgacataac aaagacgtat tgtttagcca caatagcact    8760
```

```
caagagtgaa gctttggaca agattgaata taagcatatt gtagaatatt tttatttaaa    8820
accctaccaa aagaatgatg ttattcaaat aaaatagata tatttcttta tatattatat    8880
tacattatat attattgcaa gttctagatt attattaatt attttaata aaacaatata    8940
gatgctatag atttagcata tcacctcaat tttttccgg cccgacagcg tgttcgctgg    9000
tgcagttcac cctccacagt tttcagtccg cataaggcgc agacggtggc gcattgcgtg    9060
ttgcaacgaa acgcgcgatc ctaagagggg tagtagtata tttggctaag gcaaagcctt    9120
tccctggcgg ctgggcacac acatggccca acaaaaaatt agttttatat ccaattattt    9180
atttcaacga aataccgt catatgaccc tatcttgcat attagttttt cccataattg    9240
tatcaatatt tcctttatcg ccactaagat aagattgtgg gttcaagtca caagtcatgc    9300
acttttttt cttctatgtt tactataaca aatcgtgtca acacaatata atacctattt    9360
gtcacccaat gcaacaagct cttctttcaa taattttgaa tcatgttaat acagtaatat    9420
tgttaaatgt ttttaatcca catcaaaata tgagaaatca catgattaat ctacctcttt    9480
ctaatgacat tcacttaatt catattctaa attttgattt aaactatttt tttattttt    9540
attaggttct atctctggat ctgaagtaat tgatgaagaa gaataaagat attgctttac    9600
aataacattt ttatatgtta tttatctta ccatgcgtct ttatgtaact tttgaactac    9660
gttttttaga cgtgcttttg tcaccggtcg gtccaaggct ttagcaaatc ttgattccac    9720
aactgtccac tgccaattct tggcaataaa tcctttattg atgcaacacc accgccttac    9780
aatttcattg caacacatca accttttat aataatcctt ccataataa tatggtgagc    9840
tcatctcaac cacctactgt tccattgcaa taacatcagc atactgcacc aaaaattaag    9900
attgtttgtc gtgcatgact tgaccatctc agtgcgcacg acgccactta tcatttgacc    9960
tctccatcat gaatttgcat caacatgtaa gatgtaacct                          10000
```

<210> SEQ ID NO 145  
<211> LENGTH: 222  
<212> TYPE: DNA  
<213> ORGANISM: Zea mays

<400> SEQUENCE: 145

```
atgaaatata ctatgatatt gtacattggt ctgactacta tctgtattcc actcaactgt     60
ctatatatat actctgtatt ccacttcaaa cgactcaata accacagtat atataaccac    120
aataaatgcc ttcattattt acagaagttt ctattagtat atatggtgtc actaataact    180
tctattccct cgttgcagaa atggatcatt gagaacatat ga                        222
```

<210> SEQ ID NO 146  
<211> LENGTH: 73  
<212> TYPE: PRT  
<213> ORGANISM: Zea mays

<400> SEQUENCE: 146

```
Met Lys Tyr Thr Met Ile Leu Tyr Ile Gly Leu Thr Thr Ile Cys Ile
1               5                   10                  15

Pro Leu Asn Cys Leu Tyr Ile Tyr Ser Val Phe His Phe Lys Arg Leu
            20                  25                  30

Asn Asn His Ser Ile Tyr Asn His Asn Lys Cys Leu His Tyr Leu Gln
        35                  40                  45

Lys Phe Leu Leu Val Tyr Met Val Ser Leu Ile Thr Ser Ile Pro Ser
    50                  55                  60

Leu Gln Lys Trp Ile Ile Glu Asn Ile
```

<210> SEQ ID NO 147
<211> LENGTH: 689
<212> TYPE: DNA
<213> ORGANISM: Zea mays

<400> SEQUENCE: 147

```
tcttgattcc acaactgtcc actgccaatt cttggcaata atcctttat tgatgcaaca      60
ccaccgcctt acaatttcat tgcaacacat caaccttttt ataataatcc ttccaataat     120
aatatggtga gctcatctca accacctact gttccattgc ataacatca gcatactgca     180
ccaaaaatta agattgtttg tcgtgcatga cttgaccatc tcagtgcgca cgacgccact     240
tatcatttga cctctccatc atgaatttgc atcaacatgt aagatgtaac ctatgaaata     300
tactatgata ttgtacattg gtctgactac tatctgtatt ccactcaact gtctatatat     360
atactctgta ttccacttca aacgactcaa taaccacagt atatataacc acaataaatg     420
ccttcattat ttacagaagt ttctattagt atatatggtg tcactaataa cttctattcc     480
ctcgttgcag aaatggatca ttgagaacat atgaaggccg ataaaatgga aaaagaaaac     540
ttatttgaaa aaaatcata tgtagaaatt tcttactgtc atatttcatg ttatctctga     600
tgtcttaatt catatacggt gcagagaaat caaattgcaa gtcacacatc ttaccactca     660
tgcatggctc agtgtcagtg aggttcaca                                        689
```

<210> SEQ ID NO 148
<211> LENGTH: 1846
<212> TYPE: DNA
<213> ORGANISM: Zea mays

<400> SEQUENCE: 148

```
ggagaagaga gagagtacag ccttgttgcc atgtacacac tcagatatca acagtctctt      60
atatttgctg ttactacctg ttattagtgt ccagtgatga tgaaggctgt accctctctc     120
ttcttctctt agcttcttga tgcaaagaaa gttgcatact acacacacct ggggagctct     180
tgtgatgaag caagcgttag atctggatca cgtacgtact acacagcagc cacgcatcag     240
aagttcagaa ctcggtgcaa ctctaacttt tggccagttt cgttttctt ttcgtttctt     300
tcaaacagct cctcatagca catgcatgca tcctatagct acattctctg tcagcttatt     360
aattagtaca tatttcgtgt atatatatat ggcgtatgtg ttaatcattt gcacgtacag     420
gtaggcacac cgtatatgta ggcagaacta aatgcttcaa atttgcaaat ttcaagtttt     480
ccgcgaaaga aactaatttc tccattcaga taaagtaaga tgtctcctct agttaccgtt     540
tgttttagt catcatgcac tgttttcttc tatctagtta tcctttgccg agttttttt     600
accggttgtt ttttttgtt agacactcgg caatgaactt ttttgtcaag tgtccgaaaa     660
aaacactcga caacttgttt gacactcggt aaagagccag attctgatag tgaaccattg     720
cttgctgagt cgtctcaatc cactttcact atcaaaacta agcaaaatgg gatgagattg     780
aatgaacatg atggacgact atatatcagt cagttatcat ataccaattg ctcatcacct     840
tggcaaaata tacagagcgg agcttttgc ttggctgcgt aactccgttt cacatttaat     900
ctatagatag atagatggat tgaccagtat ggagtgcagc ggcgtttgga tttcagacac     960
acaaatatcg agtccccaca aacgactccg gctgctgaat ggctgtgtca ctgtgtgaca    1020
tagctgacac acatccccta acacggccca gaagcgaacc tgacctcggc ctgtttatat    1080
tcttttatac aagcaaaaag cccaatacgt tagcccgccc atggtatatc tatagtatgt    1140
```

```
taacttttt  atatataaga  tgatgtgaac  ctcactgaca  ctgagccatg  catgagtggt    1200
aagatgtgtg  acttgcaatt  tgatttctct  gcaccgtata  tgaattaaga  catcagagat    1260
aacatgaaat  atgacagtaa  gaaatttcta  catatgattt  ttttttcaaat  aagttttctt    1320 tttccatttt  atcggccttc  atatgttctc  aatgatccat  ttctgcaacg  agggaataga    1380
agttattagt  gacaccatat  atactaatag  aaacttctgt  aaataatgaa  ggcatttatt    1440
gtggttatat  atactgtggt  tattgagtcg  tttgaagtgg  aatacagagt  atatatatag    1500
acagttgagt  ggaatacaga  tagtagtcag  accaatgtac  aatatcatag  tatatttcat    1560
aggttacatc  ttcatgttg   atgcaaattc  atgatggaga  ggtcaaatga  taagtggcgt    1620
cgtgcgcact  gagatggtca  agtcatgcac  gacaaacaat  cttaattttt  ggtgcagtat    1680
gctgatgtta  ttgcaatgga  acagtaggtg  gttgagatga  gctcaccata  ttattattgg    1740
aaggattatt  ataaaaaggt  tgatgtgttg  caatgaaatt  gtaaggcggt  ggtgttgcat    1800
caataaagga  tttattgcca  agaattggca  gtggacagtt  gtggaa                   1846

<210> SEQ ID NO 149
<211> LENGTH: 1999
<212> TYPE: DNA
<213> ORGANISM: Zea mays

<400> SEQUENCE: 149
acttcttgta  tatgtttata  tgtgcacata  ttaattaaat  ttgtatatgt  agaaaataaa      60
aattcacttt  agtgcatgtc  aagagctagt  actaaaagtc  acccttattt  agtagcggtt     120
taattttagc  caacgaccgg  tactaaagag  ggagcttaat  ttataccagt  tttaaataag     180
aaccatcact  tttagtacca  actcatgcaa  tcgggactaa  agatcgatgt  ctttagtcaa     240
gattgtgtag  taccgattgg  aaatctagta  ttgtagttag  ttctcaaccg  atacttgttt     300
catgttttct  cgtagtggtc  tagctatagt  ctaactaact  ctagtagcct  ttttcatgcg     360
tagagaagag  ctctaagcct  gtaataggtt  taatttactg  gcggtttcgg  ttatcaagcg     420
tcagtgatat  ttctagtgac  ggtttttaa   ggctatctct  agcggatctc  ttatcttatc     480
ccctatttaa  aacttttctc  tgcaaacagt  gtcaaacaat  atcatctaca  gtctgtgtcc     540 cctattttc   acggtctatt  gacgacagtc  taagaaaact  accactagaa  atccatgatt     600
tctacatgcg  gttttcttaa  gaaatcgcca  ctacaaatca  ctctacccta  attttttga      660 gttttttaaaa  tgacctcata  tgaaaaaaca  accaacataa  agttgtaga   tcactaaaag    720 ttatgaaact  ttgtagttga  caactttttt  atttgaaatc  atttcggctc  tcaaaaattg    780
catctaaatt  tgtaaaattt  aaaatgcaaa  ttttgcaaac  gacttcggat  aagaaaata     840 ccaaataaa   agttgtataa  cttcaaaagt  tataaaactt  tgtagttgac  aatcttttta    900
gaaccgctag  tgcaaatata  tttacaacca  catgtataga  gcttctatgt  aatagtgtac    960
attgcttctt  aatttctaaa  gtgtaatcgt  tacacgttga  aacaacttta  tcagaggtat   1020
atagataatt  tcactgtacg  tttggtcccc  atatctgtat  ttcttttggg  agagagaaag   1080
aggcagcaga  caggaagtga  acacatacag  tggatcggag  ttgatatatt  gtagtatata   1140
actgcggcca  cttgcaggcc  atatatatat  ccacactact  gggtagtggg  gaacgtacac   1200
gggggcccgg  ccagctgctg  cgggctcgag  accgatcaga  tcatcatatg  caacgccagt   1260
gcaagttgat  ctgatgccct  cgctcgatca  gcaggcgccc  tgggacgggc  tcatgcactg   1320
aacttcgccg  acacccagct  agctctagct  agtagtcagt  cgtctcctca  taataatatt   1380
```

-continued

| | |
|---|---|
| atgatgatta tccaggggca ataatatat ctatagtgta tcataatttg taactgtcgt | 1440 |
| ctcctcataa taacttagtc taatatacag cagtatattt ttttattata taccatcagt | 1500 |
| gaccggtttt taactgtgga ctccttttc caactatact caactgagag gagagacggg | 1560 |
| aaagtaattc attgttccat acttttagg gttccaaggc atgcatggtc aaaaattaaa | 1620 |
| gtgtggctct agatgcacat gcatggatct gtctctaaat tttaagcata aactatagta | 1680 |
| ccttgacaag ccaaccattt tgggtggctg tgtgacaaca catcaggctg ggatggccta | 1740 |
| cgttatcacc actgccgccg gaaggttcaa cttgcacacc ccccaggtga attattgtct | 1800 |
| ctgtcctttg ctaatggtca tgtgcagtcg agcatctata taagaggag ggagggggc | 1860 |
| gatccaggag cgacgaaatg gagcacgagg acactgacat ggactgaagg agtagaaaac | 1920 |
| aagtccccag tggtagtagg agctagcact ggagctgata gatcgaagag gagagagaga | 1980 |
| gagagagaga tagagaggg | 1999 |

<210> SEQ ID NO 150
<211> LENGTH: 6333
<212> TYPE: DNA
<213> ORGANISM: Zea mays

<400> SEQUENCE: 150

| | |
|---|---|
| atgggggcac ttccatatag gatttaagaa acccagaaac cgcacaacat ttttaaatta | 60 |
| taggaacaac tctccaacca ctacctatta ccataaccat cgccctatca tttttcacta | 120 |
| ttatttaat ttaaatcaaa tttacatgtt ttgtgagtgg cactactgga atcaatagct | 180 |
| ttaccgagtg cctgaagcac tcggcgaaac cttaaaaaca ctcggcaaag cctttgccga | 240 |
| gtgtaacact cggcaaagaa ggctcggcaa acagtgcatc ggcaaagcct cctttgccga | 300 |
| gtgctttttg tcgggcactc ggcaaaactc tttgccgagt gccagagagc actcggcaaa | 360 |
| gctaccgtct ccgtcacccg cgccgtaac ggccactttt ctttgccgag tgctctctgg | 420 |
| cactcggcaa agagttttgc cgagtgcccg acaaaaagca ctcggcaaag gaggctttgc | 480 |
| cgatgcactg tttgccgagc cttctttgcc gagtgttaca ctcggcaaag gctttgccga | 540 |
| gtgttttaa ggtttcgccg agtgcttcag gcactcggta aagctattga ttccagtagt | 600 |
| gccactcaca aaacatgtaa atttgattta aattaaaata atagtgaaaa atgatagggc | 660 |
| gatggttatg gtaataggta gtggttggag agttgttcct ataatttaaa aaatgttttg | 720 |
| cagtttttg gattttttc aattcttaat ttgtcgagtg cttttcgaca ctcgacaaag | 780 |
| tctttgccaa gtgcccgaaa aaagtactca gcaaagaacc cttttgccga taaaattttt | 840 |
| gctgagtatt ctttgctgag tgtaaaatgg catttgtcga gtgtcttaga cactccgagt | 900 |
| gtcttagaca ctcgataaag aacgtgattc cggtagtgac aacaccacta ccaactccgt | 960 |
| agctcatgcc gactactacc acgctacggg ccttggttgt ccaatatctc agacctggac | 1020 |
| tcatcattgt caatataatc taagtgtggc aggcgccatc gtgtcctcct cggtggcacg | 1080 |
| aacggatcgg agaaagtcca ggagcaagat tgactcgccc cgtacccgcg tcgacgagcg | 1140 |
| tcggtcggct cgtggctgca atcatgggtg ggggcagtag gttggggagg aagaataggg | 1200 |
| cgaaggtcgg gaagacaaac gggacgaatg acgacggcga aaatgatggt gcacgcatct | 1260 |
| gggaaacgtc ctcgtggacg tgcaatagcc actgcgcggg tcgtgttgg ggctggtgtc | 1320 |
| ggatgaaatac ggggaggagg cgcctactcc cacgccctct gccgagaatg gggtggcatg | 1380 |
| gaggtggagg catgtgagaa gagagaaaag aagcaggatg cgaacaagg tggcgacaac | 1440 |
| tgatcgagtc gagggccatc attatcgtgc agaggtatga atgaccaaat ggaccgtgtc | 1500 |

```
tggcgagccg gcccgaggca cgacgcattt aatagtgcct aggccagccc ggcacgagca    1560
tcgtgtcgtg cttgggccgt agcctcggcc cgacacgatt atattttta ttttacaaaa    1620 aaatcgtata tacatatgta caatttatat taaatattaa aaacacctga gcataatgta    1680
ctactggtta gacggcttca ctcagtgtct cccgcccttc ttccatcagg gcgtgggttt    1740 gaacccccacc tttcgtctcg cttttttaaca ttttacactg atttaaccaa atgggtcgac   1800
gggctaatgg gccagcccga cacggtcaac aggccggcat gtcattccta ggccggagct    1860
atggcccgcg tgtgtcgggc ctaatgggcc cgtactgggc cgccgtttga ccatctatat    1920
gcgaaggtgt ggtttgggac gtgtagtttg gttgcgtgca acaggttaat ttgaattaga    1980
tgtgagagat tatttataaa tagataacac ggaaagaccg ttgaaagaaa ctggtgcttt    2040
aatatagtaa agactttctg atagtttttt ttcctagcta gctgccattg caacacgtgc    2100
atgtgttcgc tgattattta tatgaattat aaaaaaaaaa gagcagacga aaaacatata    2160
tagtggccac acaccagcta gcgtagtgtg tgtgacaacc agccggcagc ctatatatct    2220
acctaccttt cccgatttcg accctgttgc tcttagattt ggcccctact tttgtacgta    2280
tgacatatct tgccaaactt gaaaggcggg gcgcgcgcgc gcgcgtacac acaagacatt    2340
cttggattca catggaataa tgcacaccct gtttttctac tttaacttgt acacagtaca    2400
caagacaatg caacaggaga gcaatcagct gcaggacaca cagcgcgaga attgacgcac    2460
aaaagcacga gaaaagcacc gccgctgcca tgcactgtac tacgtagcag gccccagctg    2520
cacatggcga aggcgaagag ggccttgctg tagtgcatga aatatagcca tgcattcgtt    2580
ctatgggcgt ggcgccaagg ctagcccata gacctcctgt ccatcaccag tactgcgtgc    2640
tcaatcgacc atgtgcagtg ctgtgctgtg cgtacaactg tagtgcatgc accttacgct    2700
ctcttttttc tttgtcccac gcttaggttc tgtttgtttc cttttatttc gagaaattga    2760
aatcttacta atagaatagg ttattttttt aatatgatat tccagcattt tctaaagtta    2820
tcatataagc ctacctcaaa ttcatgaggt gagagatgga aattgattgt atagatttac    2880
atgctatttt tctgatgtat aacttatagc acattcttct acttgcgcct ctataacata    2940
aatatagtat ataactatct ctctcatatg atttaggata atatacaaat atattacata    3000
tataaatata taaacttaat tagttttgtc taaattataa ttattaaaat ggaattcaat    3060
tccaacgaaa taaatgggcc tttacagaat tcaaaatttg tctctgaata aatatatgtc    3120
cactatacta gagaatgagg tttcctccat caatatttgt ttcggttgtt ttaaaaatcg    3180
gtacagatac aagcatcagt agcacttttta aatgttgagt ccacgcgaaa aatattagta    3240
ccggttggtg tcccaaaccg atactaataa tatcaagtct ttagtaccga ttgaagacac    3300
accaactgat actaaagtgc aaagatatct ttaataccga ttcttacaaa gaaccgatac    3360
taaaaggcta ttttacattc ccgctagaag tttagggttc atgtccaaat tacttagcaa    3420
cggtgtttaa aaagaaccgg tactaagagt gaagggttta gtaccagttc tttgatggaa    3480
tcggcactaa agatattccg cttcttgtca gaactttcaa ctcttctatc tagcacatcc    3540
ttactacggt tcttagttag aaccggtact aaagttttcc ctataaaccc agtctttttc    3600
aagccttttt cattcgtgat cagtctgagt catgaggaga catcacaagc aacagtgatg    3660
tctcgtcccc ctggtgagca cattagaaac tcttatgcat tattcttatg tatctttgct    3720
ataaagtttg tatttttcat acaccagtaa aatgatgttt gttcatgttt ttcttttttg    3780
tttgttgtcc ataatgctta catcatttat tttaaactct aatttttctt gtttaatatg    3840
```

```
tttttcattc ataggaattg tgctaacatt gatctccttg aaatggagaa gaacttggat    3900
catgaactag ttcttaggta ggaaataaaa atactttcaa ctatcaacta gtccttagtt    3960
aaatatattt ttttatttcc tgcactaagg gttagttgtc agataagaac atcttcatcc    4020
ttagccagag acccatggcc aaagatgaaa aagagctgc ccgaaaaagg aactagagcc     4080
gaagaatgac aaaggcaaag aaggaactga tatgaaaaat aagggtcaaa taagaaatcg    4140
agacgaaaaa atattcttgt ctatttatac agaaaaacac gtaatactcg ttttgaattt    4200
agtaaatatc ttgactttaa gaagaaaaaa agaactccct gtacattttt atgtgcacag    4260
aaaaaggacg aaatctcttt agtttagtcc attaaaaaga acttcttgta tatgttttata   4320
tgtgcacata ttaattaaat ttgtatatgt agaaaataaa aattcacttt agtgcatgtc    4380
aagagctagt actaaaagtc acccttattt agtagcggtt taattttagc caacgaccgg    4440
tactaaagag ggagcttaat ttataccagt tttaaataag aaccatcact tttagtacca    4500
actcatgcaa tcgggactaa agatcgatgt ctttagtcaa gattgtgtag taccgattgg    4560
aaatctagta ttgtagttag ttctcaaccg atacttgttt catgttttct cgtagtggtc    4620
tagctatagt ctaactaact ctagtagcct ttttcatgcg tagagaagag ctctaagcct    4680
gtaataggtt taatttactg gcggtttcgg ttatcaagcg tcagtgatat ttctagtgac    4740
ggttttttaa ggctatctct agcggatctc ttatcttatc ccctatttaa aacttttctc    4800
tgcaaacagt gtcaaacaat atcatctaca gtctgtgtcc cctattttc acggtctatt     4860
gacgacagtc taagaaaact accactagaa atccatgatt tctacatgcg gttttcttaa    4920
gaaatcgcca ctacaaatca ctctacccta atttttttga gtttttaaaa tgacctcata    4980
tgaaaaaaca accaacataa aagttgtaga tcactaaaag ttatgaaact ttgtagttga    5040
caactttttt atttgaaatc atttcggctc tcaaaaattg catctaaatt tgtaaaattt    5100
aaaatgcaaa ttttgcaaac gacttcggat aagaaaaata ccaaaataaa agttgtataa    5160
cttcaaaagt tataaaactt tgtagttgac aatcttttta gaaccgctag tgcaaatata    5220
tttacaacca catgtataga gcttctatgt aatagtgtac attgcttctt aatttctaaa    5280
gtgtaatcgt tacacgttga aacaacttta tcagaggtat atagataatt tcactgtacg    5340
tttggtcccc atatctgtat ttcttttggg agagagaaag aggcagcaga caggaagtga    5400
acacatacag tggatcggag ttgatatatt gtagtatata actgcggcca cttgcaggcc    5460
atatatatat ccacactact gggtagtggg gaacgtacac gggggcccgg ccagctgctg    5520
cgggctcgag accgatcaga tcatcatatg caacgccagt gcaagttgat ctgatgccct    5580
cgctcgatca gcaggcgccc tgggacgggc tcatgcactg aacttcgccg acacccagct    5640
agctctagct agtagtcagt cgtctcctca taataatatt atgatgatta tccaggggca    5700
aataatatat ctatagtgta tcataatttg taactgtcgt ctcctcataa taacttagtc    5760
taatatacag cagtatattt ttttattata taccatcagt gaccggtttt taactgtgga    5820
ctccttttc caactatact caactgagag gagagacggg aaagtaattc attgttccat     5880
actttttagg gttccaaggc atgcatggtc aaaaattaaa gtgtggctct agatgcacat    5940
gcatggatct gtctctaaat tttaagcata aactatagta ccttgacaag ccaaccattt    6000
tgggtggctg tgtgacaaca catcaggctg ggatggccta cgttatcacc actgccgccg    6060
gaaggttcaa cttgcacacc ccccaggtga attattgtct ctgtcctttg ctaatggtca    6120
tgtgcagtcg agcatctata taagaggag ggagggggggc gatccaggag cgacacaagt    6180
ccccagtggt agtaggagct agcactggag ctgatagatc gaagaggaga gagagagaga    6240
```

```
gagagataga gagggaaaat gtacatggag tgctgtcggt aacagataga gagagggaga    6300
gggagaaact atgatatttc atcaaggcta aag                                6333

<210> SEQ ID NO 151
<211> LENGTH: 127
<212> TYPE: DNA
<213> ORGANISM: Zea mays

<400> SEQUENCE: 151
ggagaagaga gagagtacag ccttgttgcc atgtacacac tcagatatca acagtctctt     60
atatttgctg ttactacctg ttattagtgt ccagtgatga tgaaggctgt accctctctc    120
ttcttct                                                             127

<210> SEQ ID NO 152
<211> LENGTH: 312
<212> TYPE: DNA
<213> ORGANISM: Zea mays

<400> SEQUENCE: 152
atggcgctag aagcagccac cgccccccgc gcactcctcg ccgcgtgcct cgtcctgctg     60
gtcctcggcg gcggcaccgg cccgtcgtcg gtgctgcgcg gcgccggggt gcaggccggc    120
gggcagtgcc tgccgcagct gaaccgcctc ctggcgtgcc gcgcgtacct ggtgcccggc    180
gcgccggacc ccagcgcgga ctgctgcagc gcgctgagcg ccgtgtcgca cgagtgcgcc    240
tgcagcacca tgggcatcat caacagcctg cccggccggt gccacctcgc ccaagccaac    300
tgctccgctt ga                                                       312

<210> SEQ ID NO 153
<211> LENGTH: 103
<212> TYPE: PRT
<213> ORGANISM: Zea mays

<400> SEQUENCE: 153

Met Ala Leu Glu Ala Ala Thr Ala Pro Arg Ala Leu Leu Ala Ala Cys
1               5                   10                  15

Leu Val Leu Leu Val Leu Gly Gly Ser Thr Gly Pro Ser Ser Val Leu
                20                  25                  30

Arg Gly Ala Gly Val Gln Ala Gly Gly Gln Cys Leu Pro Gln Leu Asn
            35                  40                  45

Arg Leu Leu Ala Cys Arg Ala Tyr Leu Val Pro Gly Ala Pro Asp Pro
        50                  55                  60

Ser Ala Asp Cys Cys Ser Ala Leu Ser Ala Val Ser His Glu Cys Ala
65                  70                  75                  80

Cys Ser Thr Met Gly Ile Ile Asn Ser Leu Pro Gly Arg Cys His Leu
                85                  90                  95

Ala Gln Ala Asn Cys Ser Ala
            100

<210> SEQ ID NO 154
<211> LENGTH: 304
<212> TYPE: PRT
<213> ORGANISM: Arabidopsis thaliana

<400> SEQUENCE: 154

Met Ala Pro Pro Glu Ala Glu Val Gly Ala Val Met Val Met Ala Pro
1               5                   10                  15
```

Pro Thr Pro Gly Thr Pro Gly Thr Pro Gly Pro Leu Ile Thr Gly
            20                  25                  30

Met Arg Val Asp Ser Met Ser Phe Asp His Arg Lys Pro Thr Pro Arg
        35                  40                  45

Cys Lys Cys Leu Pro Val Met Gly Ser Thr Trp Gly Gln His Asp Thr
50                  55                  60

Cys Phe Thr Asp Phe Pro Ser Pro Asp Val Ser Leu Thr Arg Lys Leu
65                  70                  75                  80

Gly Ala Glu Phe Val Gly Thr Phe Ile Leu Ile Phe Thr Ala Thr Ala
                85                  90                  95

Gly Pro Ile Val Asn Gln Lys Tyr Asp Gly Ala Glu Thr Leu Ile Gly
            100                 105                 110

Asn Ala Ala Cys Ala Gly Leu Ala Val Met Ile Ile Ile Leu Ser Thr
        115                 120                 125

Gly His Ile Ser Gly Ala His Leu Asn Pro Ser Leu Thr Ile Ala Phe
    130                 135                 140

Ala Ala Leu Arg His Phe Pro Trp Ala His Val Pro Ala Tyr Ile Ala
145                 150                 155                 160

Ala Gln Val Ser Ala Ser Ile Cys Ala Ser Phe Ala Leu Lys Gly Val
                165                 170                 175

Phe His Pro Phe Met Ser Gly Val Thr Ile Pro Ser Val Ser Leu
            180                 185                 190

Gly Gln Ala Phe Ala Leu Glu Phe Ile Ile Thr Phe Ile Leu Leu Phe
        195                 200                 205

Val Val Thr Ala Val Ala Thr Asp Thr Arg Ala Val Gly Glu Leu Ala
210                 215                 220

Gly Ile Ala Val Gly Ala Thr Val Met Leu Asn Ile Leu Val Ala Gly
225                 230                 235                 240

Pro Ser Thr Gly Gly Ser Met Asn Pro Val Arg Thr Leu Gly Pro Ala
                245                 250                 255

Val Ala Ser Gly Asn Tyr Arg Ser Leu Trp Val Tyr Leu Val Ala Pro
            260                 265                 270

Thr Leu Gly Ala Ile Ser Gly Ala Ala Val Tyr Thr Gly Val Lys Leu
        275                 280                 285

Asn Asp Ser Val Thr Asp Pro Pro Arg Pro Val Arg Ser Phe Arg Arg
290                 295                 300

<210> SEQ ID NO 155
<211> LENGTH: 311
<212> TYPE: PRT
<213> ORGANISM: Oryza sativa

<400> SEQUENCE: 155

Met Glu Met Ala Ala Pro Asn Gly Gly Gly Ala Ala Gly Met Ser Ser
1               5                   10                  15

Pro Val Asn Gly Ala Ser Ala Pro Ala Thr Pro Gly Thr Pro Ala Pro
            20                  25                  30

Leu Phe Ala Gly Pro Arg Val Asp Ser Leu Ser Tyr Glu Arg Lys Ser
        35                  40                  45

Met Pro Arg Cys Lys Cys Leu Pro Ala Ala Val Ala Glu Ala Trp Ala
    50                  55                  60

Pro Ser Ala His Gly Cys Val Glu Ile Pro Ala Pro Asp Val Ser
65                  70                  75                  80

Leu Thr Arg Lys Leu Gly Ala Glu Phe Val Gly Thr Phe Ile Leu Ile
                85                  90                  95

```
Phe Phe Ala Thr Ala Ala Pro Ile Val Asn Gln Lys Tyr Gly Gly Ala
                100                 105                 110

Ile Ser Pro Phe Gly Asn Ala Ala Cys Ala Gly Leu Ala Val Thr Thr
            115                 120                 125

Ile Ile Leu Ser Thr Gly His Ile Ser Gly Ala His Leu Asn Pro Ser
130                 135                 140

Leu Thr Ile Ala Phe Ala Ala Leu Arg His Phe Pro Trp Leu Gln Val
145                 150                 155                 160

Pro Ala Tyr Val Ala Val Gln Val Leu Gly Ser Ile Cys Ala Gly Phe
                165                 170                 175

Ala Leu Lys Gly Val Phe His Pro Phe Leu Ser Gly Val Thr Val
            180                 185                 190

Pro Asp Pro Thr Ile Ser Thr Ala Gln Ala Phe Phe Thr Glu Phe Ile
            195                 200                 205

Ile Thr Phe Asn Leu Leu Phe Val Val Thr Ala Val Ala Thr Asp Thr
210                 215                 220

Arg Ala Val Gly Glu Leu Ala Gly Ile Ala Val Gly Ala Ala Val Thr
225                 230                 235                 240

Leu Asn Ile Leu Ile Ala Gly Pro Thr Thr Gly Gly Ser Met Asn Pro
                245                 250                 255

Val Arg Thr Leu Gly Pro Ala Val Ala Ala Gly Asn Tyr Arg Gln Leu
            260                 265                 270

Trp Ile Tyr Leu Ile Ala Pro Thr Leu Gly Ala Val Ala Gly Ala Gly
            275                 280                 285

Val Tyr Thr Ala Val Lys Leu Arg Asp Glu Asn Gly Glu Thr Pro Arg
            290                 295                 300

Pro Gln Arg Ser Phe Arg Arg
305                 310

<210> SEQ ID NO 156
<211> LENGTH: 302
<212> TYPE: PRT
<213> ORGANISM: Zea mays

<400> SEQUENCE: 156

Met Glu Pro Gly Ser Thr Pro Pro Asn Gly Ser Ala Pro Ala Thr Pro
1               5                   10                  15

Gly Thr Pro Ala Pro Leu Phe Ser Ser Gly Gly Pro Arg Val Asp Ser
            20                  25                  30

Leu Ser Tyr Glu Arg Lys Ser Met Pro Arg Cys Lys Cys Leu Pro Leu
        35                  40                  45

Pro Ala Val Glu Gly Trp Gly Val Ala Thr His Thr Cys Val Val Glu
50                  55                  60

Ile Pro Ala Pro Asp Val Ser Leu Thr Arg Lys Leu Gly Ala Glu Phe
65                  70                  75                  80

Val Gly Thr Phe Ile Leu Ile Phe Phe Ala Thr Ala Ala Pro Ile Val
                85                  90                  95

Asn Gln Lys Tyr Gly Gly Ala Ile Ser Pro Phe Gly Asn Ala Ala Cys
            100                 105                 110

Ala Gly Leu Ala Val Ala Thr Val Ile Leu Ser Thr Gly His Ile Ser
            115                 120                 125

Gly Ala His Leu Asn Pro Ser Leu Thr Ile Ala Phe Ala Ala Leu Arg
            130                 135                 140

His Phe Pro Trp Leu Gln Val Pro Ala Tyr Val Ala Val Gln Ala Leu
```

-continued

```
145                 150                 155                 160
Ala Ser Val Cys Ala Ala Phe Ala Leu Lys Gly Val Phe His Pro Phe
                165                 170                 175

Leu Ser Gly Gly Val Thr Val Pro Asp Ala Thr Val Ser Thr Ala Gln
            180                 185                 190

Ala Phe Phe Thr Glu Phe Ile Ile Ser Phe Asn Leu Leu Phe Val Val
        195                 200                 205

Thr Ala Val Ala Thr Asp Thr Arg Ala Val Gly Glu Leu Ala Gly Ile
    210                 215                 220

Ala Val Gly Ala Ala Val Thr Leu Asn Ile Leu Val Ala Gly Pro Thr
225                 230                 235                 240

Thr Gly Gly Ser Met Asn Pro Val Arg Thr Leu Gly Pro Ala Val Ala
                245                 250                 255

Ala Gly Asn Tyr Arg Gln Leu Trp Ile Tyr Leu Leu Ala Pro Thr Leu
            260                 265                 270

Gly Ala Leu Ala Gly Ala Ser Val Tyr Lys Ala Val Lys Leu Arg Asp
            275                 280                 285

Glu Asn Gly Glu Thr Pro Arg Thr Gln Arg Ser Phe Arg Arg
    290                 295                 300
```